US012043655B2

(12) United States Patent
Lin et al.

(10) Patent No.: US 12,043,655 B2
(45) Date of Patent: Jul. 23, 2024

(54) CONSTITUTIVELY ACTIVE CHIMERIC CYTOKINE RECEPTORS

(71) Applicant: Allogene Therapeutics, Inc., South San Francisco, CA (US)

(72) Inventors: Regina Junhui Lin, San Mateo, CA (US); Thomas John Van Blarcom, Oakland, CA (US); Siler Panowski, Berkeley, CA (US); Barbra Johnson Sasu, San Francisco, CA (US)

(73) Assignee: Allogene Therapeutics, Inc., South San Francisco, CA (US)

( * ) Notice: Subject to any disclaimer, the term of this patent is extended or adjusted under 35 U.S.C. 154(b) by 668 days.

(21) Appl. No.: 16/804,917

(22) Filed: Feb. 28, 2020

(65) Prior Publication Data

US 2020/0291090 A1    Sep. 17, 2020

Related U.S. Application Data

(60) Provisional application No. 62/980,823, filed on Feb. 24, 2020, provisional application No. 62/812,911, filed on Mar. 1, 2019.

(51) Int. Cl.
| | | |
|---|---|---|
| C07K 14/715 | (2006.01) | |
| A61K 35/17 | (2015.01) | |
| A61K 39/00 | (2006.01) | |
| A61P 35/00 | (2006.01) | |
| C07K 16/40 | (2006.01) | |
| C12N 5/0783 | (2010.01) | |
| C12N 7/00 | (2006.01) | |
| C12N 15/86 | (2006.01) | |

(52) U.S. Cl.
CPC ........... *C07K 14/715* (2013.01); *A61K 35/17* (2013.01); *A61P 35/00* (2018.01); *C07K 16/40* (2013.01); *C12N 5/0636* (2013.01); *C12N 7/00* (2013.01); *C12N 15/86* (2013.01); *C07K 2317/24* (2013.01); *C07K 2317/73* (2013.01); *C07K 2319/02* (2013.01); *C07K 2319/03* (2013.01); *C07K 2319/30* (2013.01); *C07K 2319/33* (2013.01); *C12N 2740/15043* (2013.01)

(58) Field of Classification Search
None
See application file for complete search history.

(56) References Cited

U.S. PATENT DOCUMENTS

| | | |
|---|---|---|
| 6,866,998 B1 | 3/2005 | Kitamura |
| 8,389,282 B2 | 3/2013 | Sadelain et al. |
| 9,434,935 B2 | 9/2016 | Spencer et al. |
| 9,913,882 B2 | 3/2018 | Slawin et al. |
| 9,944,690 B2 | 4/2018 | Spencer et al. |
| 10,287,354 B2 | 3/2019 | Brogdon et al. |
| 10,336,810 B2 | 7/2019 | Tanaka |
| 10,548,921 B2 | 2/2020 | Leen et al. |
| 2014/0050709 A1 | 2/2014 | Leen et al. |
| 2014/0087468 A1 | 3/2014 | Spencer et al. |
| 2015/0111294 A1 | 4/2015 | Spencer et al. |
| 2016/0175359 A1 | 6/2016 | Spencer et al. |
| 2016/0297884 A1 | 10/2016 | Kuo et al. |
| 2018/0037630 A1 | 2/2018 | Tanaka et al. |
| 2019/0000881 A1 | 1/2019 | Sadelain et al. |

FOREIGN PATENT DOCUMENTS

| | | | |
|---|---|---|---|
| CA | 2842368 A1 | 2/2013 | |
| WO | WO1996004389 A1 | 2/1996 | |
| WO | 199802558 A1 | 1/1998 | |
| WO | WO9802558 A2 | 1/1998 | |
| WO | WO2007075899 A2 | 7/2007 | |
| WO | WO-2011069004 A1 * | 6/2011 | ........... C12Q 1/6883 |
| WO | WO2011069004 A1 | 6/2011 | |
| WO | WO2012138858 A1 | 10/2012 | |
| WO | WO2014151960 A2 | 9/2014 | |
| WO | WO2016055551 A1 | 4/2016 | |
| WO | 2016127257 A1 | 8/2016 | |
| WO | 2017/029512 A1 | 2/2017 | |
| WO | WO2017029512 A1 | 2/2017 | |
| WO | 2017068360 A1 | 4/2017 | |
| WO | WO2017103596 A1 | 6/2017 | |
| WO | 2018/038945 A1 | 3/2018 | |
| WO | WO2018038945 A1 | 3/2018 | |
| WO | WO-2018038945 A1 * | 3/2018 | ............. A61K 35/12 |
| WO | WO2018094244 A1 | 5/2018 | |
| WO | WO2018104473 A1 | 6/2018 | |
| WO | WO-2018150187 A1 * | 8/2018 | ............. A61K 35/17 |
| WO | 2018/161064 A1 | 9/2018 | |
| WO | WO2018161064 A1 | 9/2018 | |
| WO | 2019055946 A1 | 3/2019 | |
| WO | 2019/102207 A1 | 5/2019 | |
| WO | 2019102207 A1 | 5/2019 | |
| WO | WO2019118508 A1 | 6/2019 | |

(Continued)

OTHER PUBLICATIONS

Suthaus et al (Molecular Biology of the Cell, 2010, 21:2797-2807).*
Metcalfe et al (Frontiers in Immunology, Jul. 2020, vol. 11, article 1424, internet pp. 1-25).*
Behncken et al (Journal of Biological Chemistry, 2000, 276:17000-17007).*
Morris et al (Protein Science, 2018, 27:1984-2009).*
Ding et al (Blood, 2009, 114:3325-3328).*
Lee et al (Plos One, 2011, 6:e23396, internet pp. 1-7).*
Defour et al (Leukemia, 2016, 30:1177-1228).*

(Continued)

*Primary Examiner* — Laura B Goddard

(57) ABSTRACT

Provided herein are constitutively active chimeric cytokine receptors (CACCRs). When present on chimeric antigen receptor (CAR)-bearing immune cells, such CACCRs allow for increased immune cell activation, proliferation, persistence, and/or potency. Also provided are methods of making and using the CACCRs described herein.

39 Claims, 42 Drawing Sheets

Specification includes a Sequence Listing.

(56) References Cited

FOREIGN PATENT DOCUMENTS

| WO | 2019169290 A1 | 9/2019 | |
| WO | WO-2019169290 A1 * | 9/2019 | ............ A61K 35/17 |
| WO | 2019/246563 A1 | 12/2019 | |
| WO | 2019246563 A1 | 12/2019 | |
| WO | 2020044055 A1 | 3/2020 | |
| WO | WO2020180664 A1 | 9/2020 | |
| WO | WO2016168612 A1 | 10/2020 | |

OTHER PUBLICATIONS

Bajgain, Pradip, "CAR T Cell Therapy for Breast Cancer: Harnessing the Tumor Milieu to Drive T Cell Activation", Research Article, J Immunother Cancer. May 10, 2018;6(1):34. doi: 10.1186/s40425-018-0347-5.

Behrmann, Iris, et al., "A single STAT recruitment module in a chimeric cytokine receptor complex is sufficient for STAT activation.", J Biol Chem.;272(8):5269-74., 1997.

Boger, Dale L., et al., "Cytokine receptor dimerization and activation: prospects for small molecule agonists.", Bioorg Med Chem. ;9(3):557-62., 2001.

Boyerinas, B., et al., "Abstract 602: A novel TGF-B/IL-12R signal conversion platform that protects Car T cells from TGF-B-mediated immune suppression and concurrently amplifies effector function", Proceedings of the American Association for Cancer Research Annual Meeting 2017; Apr. 1-5, 2017; Washington, DC. Philadelphia (PA): AACR; Cancer Res 2017;77(13 Suppl):Abstract 602, 4 total pages.

Cherkassky, L., et al., "Human CAR T cells with cell-intrinsic PD-1 checkpoint blockade resist tumor-mediated Inhibition", J. Clin. Invest. 126:3130-3144, 2016.

Defour, J P, et al., "Oncogenic activation of MPL/thrombopoietin receptor by 17 mutations at W515: implications for myeloproliferative neoplasms", Leukemia 30, 1214-1216; doi:10.1038/leu.2015.271, 2016.

Defour, J P, et al., "Tryptophan at the transmembrane-cytosolic junction modulates thrombopoietin receptor dimerization and activation", PNAS 110:2540-2545, 2013.

EPO, "International Search Report & Written Opinion", mailed on May 29, 2020 for PCT Application No. PCT/US2020/020415; 17 pages.

EPO, "International Search Report and Written Opinion", mailed on Jun. 4, 2020 for PCT Application No. PCT/US2020/020340; 15 pages.

EPO, "International Search Report and Written Opinion", mailed on May 31, 2019 for PCT Application No. PCT/US2019/020340; 18 pages.

Friedmann, Michael C., et al., "Different interleukin 2 receptor beta-chain tyrosines couple to at least two signaling pathways and synergistically mediate interleukin 2-induced proliferation", Immunology; Proc. Natl. Acad. Sci. USA, vol. 93, pp. 2077-2082, Mar. 1996.

Hoyos, V., et al., "Engineering CD19-specific T lymphocytes with interleukin-15 and a suicide gene to enhance their anti-lymphoma/leukemia effects and safety", Leukemia 24:1160-1170, 2010.

Hurton, L. V., et al., "Tethered IL-15 augments antitumor activity and promotes a stem-cell memory subset in tumor-specific T cells", PNAS E7788-E7797, 2016.

Johnson, L.A., et al., "Rational development and characterization of humanized anti-EGFR variant III chimeric antigen receptor T cells for glioblastoma", Science Translational Medicine, vol. 7, No. 275, Feb. 18, 2015, pp. 1-16, XP055362795, US ISSN: 1946-6234, DOI: 10.1126/scitranslmed.aaa4963.

Kagoya, Yuki, et al., "A Novel Chimeric Antigen Receptor Containing a JAK-STAT Signaling Domain Mediates Superior Antitumor Effects", Nat Med. Feb. 2018; 24(3): 352-359; doi: 10.1038/nm.4478, Feb. 5, 2018.

Kloss, C., "TGFBeta signaling blockade within PSMA targeted CAR human T cells for the eradication of metastatic prostate cancer", Abstract 638, Molucular Therapy vol. 24, Supplement 1, 2 total pages, 2016.

Leen, Ann M, et al., "Reversal of Tumor Immune Inhibition Using a Chimeric Cytokine Receptor", Molecular Therapy vol. 22 No. 6, 1211-1220 Jun. 2014, Mar. 2014.

Leroy, Emilie, et al., "His 499 Regulates Dimerization and Prevents Oncogenic Activation by Asparagine Mutations of the Human Thrombopoietin Receptor", Journal of Biological Chemistry, vol. 291, No. 6, pp. 2974-2987, XP055696813, US ISSN: 0021-9258, DOI: 10.1074/jbc.M115.696534, 2015.

Liu, X., et al., "A chimeric switch-receptor targeting PD1 augments the efficacy of second-generation CAR T cells in advanced solid tumors", Cancer Res. 76:1578-1590, 2016.

U, Xiaohui, et al., "Dimerization by a Cytokine Receptor Is Necessary for Constitutive Activation of JAK2V617F", J Biol Chem; . Feb. 29, 2008;283(9):5258-66. doi: 10.1074/jbc.M707125200; Epub Dec. 23, 2007.

Malek, Thomas R., et al., "Interleukin-2 Receptor Signaling: At the Interface between Tolerance and Immunity", Immunity. Aug. 27, 2010; 33(2): 153-165. doi:10.1016/j.immuni.2010.08.004, 2010.

Matthews, E E, et al., "Thrombopoietin receptor activation: Transmembrane helix dimerization, rotation, and allosteric modulation", FASEB J. 25:2234-2244, 2011.

Maute, R L, "Engineering high-affinity PD-1 variants for optimized immunotherapy and immuno-PET imaging", PNAS 112:E6506-E6514, 2015.

Murray, P J, "The JAK-STAT signaling pathway: input and output integration.", J Immunol. Mar. 1, 2007;178(5):2623-9., Feb. 2007.

Nakamura, T, et al., "A selective switch-on system for self-renewal of embryonic stem cells using chimeric cytokine receptors.", Biochem Biophys Res Commun. Jul. 9, 1998;248(1):22-7., Jul. 1998.

Shum, T, et al., "Constitutive signaling from an engineered IL7 receptor promotes durable tumor elimination by tumor-redirected T cells", Cancer Discovery 7:1-10, 2017.

Sukumaran, S., "Enhancing the potency and specificity of engineered T cells for cancer treatment", Cancer Discovery 8:972-987, 2018.

Tokarew, Nicholas, et al., "Teaching an old dog new tricks: next-generation CAR T cells", British Journal Cancer, Nature Publishing Group; 120, 26-37. https://doi.org/10.1038/s41416-018-0325-1, Nov. 6, 2018.

Varghese, Lelia N., et al., "The Thrombopoietin Receptor: Structural Basis of Traffic and Activation by Ligand, Mutations, Agonists, and Mutated Calreticulin", Frontiers in Endocrinology, Mar. 2017, vol. 8, Article 59; doi: 10.3389/fendo.2017.00059.

Vong, Q, et al., "Inhibiting TGFbeta signaling in CAR T-cells may significantly enhance efficacy of tumor immunotherapy", Blood 130:1791, 5 total pages, 2017.

Wu, C-Y, et al., "Remote control of therapeutic T cells through a small molecule-gated chimeric receptor", Science 350:aab4077, 21 total pages, 2015.

EPO, "International Search Report & Written Opinion", Mailed on Jun. 21, 2021 for International Application No. PCT/US2021/019362.

Morris, Rhiannon, et al., "The molecular details of cytokine signaling via the JAK/STAT pathway", Protein Science 2018 ; vol. 27; pp. 1984-2009;, Dec. 1, 2018.

EPO, "International Search Report & Written Opinion", mailed for PCT/US2020/048402 on Nov. 27, 2020; 23 pages.

Saur, Sebastian J., et al., "Ubiquitination and degradation of the thrombopoietin receptor c-Mpl", Blood, Feb. 11, 2010 vol. 115, No. 6, pp. 1254-1263.

Zenatti P.P. et al., Oncogenic IL7R gain-of-function mutations in childhood T-cell acute lymphoblastic leukemia. Nat Genet, vol. 43, Issue No. 10, pp. 932-939 (Oct. 2011).

Shochat C. et al., Gain-of-function mutations in interleukin-7 receptor-? (IL7R) in childhood acute lymphoblastic leukemias. J Exp Med, vol. 208, Issue No. 5, pp. 901-908 (May 2011).

Ajina, Adam, et al., "Strategies to Address Chimeric Antigen Receptor Tonic Signaling", Mol Cancer Ther, . Sep. 2018;17(9):1795-1815. doi: 10.1158/1535-7163.MCT-17-1097.

Gacerez, Albert T., et al., "How Chimeric Antigen Receptor Design Affects Adoptive T Cell Therapy", J Cell Physiol; Dec. 2016;231(12):2590-8. doi: 10.1002/jcp.25419. Epub Jun. 2, 2016.

(56) References Cited

OTHER PUBLICATIONS

Grotzinger, Joachim, "Molecular mechanisms of cytokine receptor activation", Biochim Biophys Acta; Nov. 11, 2002;1592(3):215-23.

Hu, Yuan, et al., "Chimeric antigen receptor (CAR)-transduced natural killer cells in tumor immunotherapy", Acta Pharmacol Sin; Feb. 2018;39(2):167-176. doi: 10.1038/aps.2017.125. Epub Sep. 7, 2017.

Kim, Jin Hee, et al., "High cleavage efficiency of a 2A peptide derived from porcine teschovirus-1 in human cell lines, zebrafish and mice", PLoS One; 2011;6(4):e18556. doi: 10.1371/journal.pone.0018556. Epub Apr. 29, 2011.

Shao, Huang, et al., "Structural requirements for signal transducer and activator of transcription 3 binding to phosphotyrosine ligands containing the YXXQ motif", J Biol Chem; Apr. 30, 2004;279(18):18967-73. doi: 10.1074/jbc.M314037200. Epub Feb. 13, 2004.

Shochat Chen, et al., "Gain-of-function mutations in interleukin-7 receptor-α (IL7R) in childhood acute lymphoblastic leukemias", Journal of Experimental Medicine; 2(2011) 208 (5): 901-908; https://doi.org/10.1084/jem.20110580.

Zenatti, Priscila, et al., "Oncogenic IL7R gain-of-function mutations in childhood T-cell acute lymphoblastic leukemia", Nature Genetics; Sep. 4, 2011;43(10):932-9. doi: 10.1038/ng.924.

Zhang, Cheng, et al., "Engineering CAR-T cells", Biomarker Research, vol. 5: 22 (2017).

Xie, Jiasen, et al., "Construction of an anti-programmed death-ligand 1 chimeric antigen receptor and determination of its antitumor function with transduced cells", Oncology Letters; Jul. 2018; vol. 16 Issue 1; DOI: https://doi.org/10.3892/ol.2018.8617.

Itaya, Miki, "Regulation of Dimerization and Activation of the Thrombopoietin Receptor", PHD Thesis, Dec. 1, 2012; Stony Brook University; https://dspace.sunyconnect.suny.edu/bitstream/handle/1951/59699/Itaya_grad.sunysb_0771E_11150.pdf?sequence=1&isAllowed=y.

Plo, Isabelle, et al., "Genetic Alterations of the Thrombopoietin/MPL/JAK2 Axis Impacting Megakaryopoiesis", Frontiers in Endocrinology; Review; Sep. 12, 2017; doi: 10.3389/fendo.2017.00234.

Intellectual Property Office of Singapore, Written Opinion mailed for Singaporean application No. 11202107984R on Jul. 4, 2023.

* cited by examiner

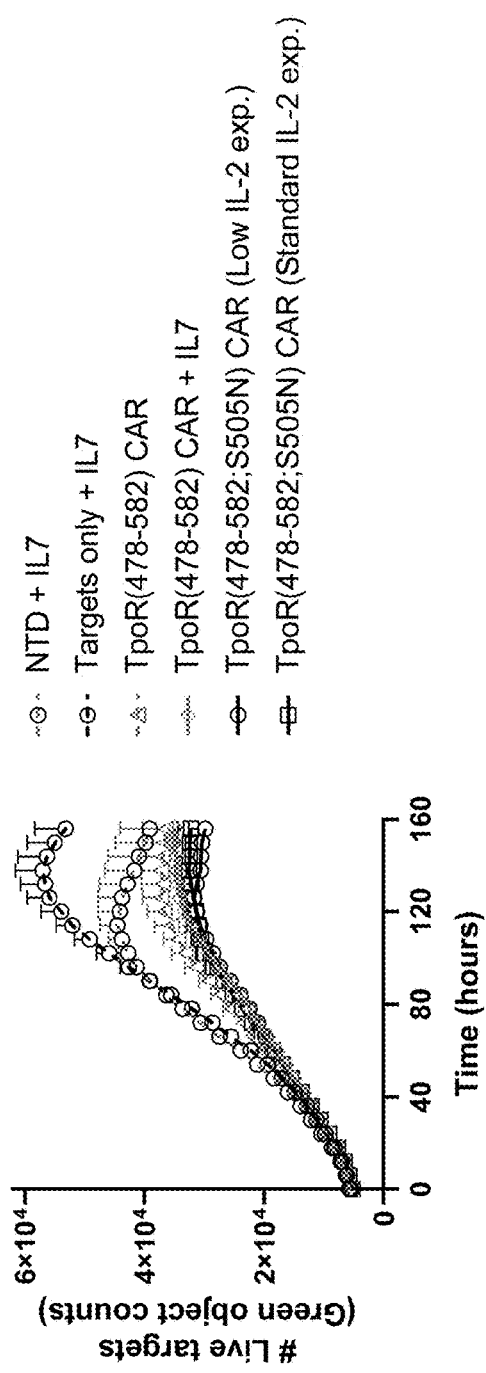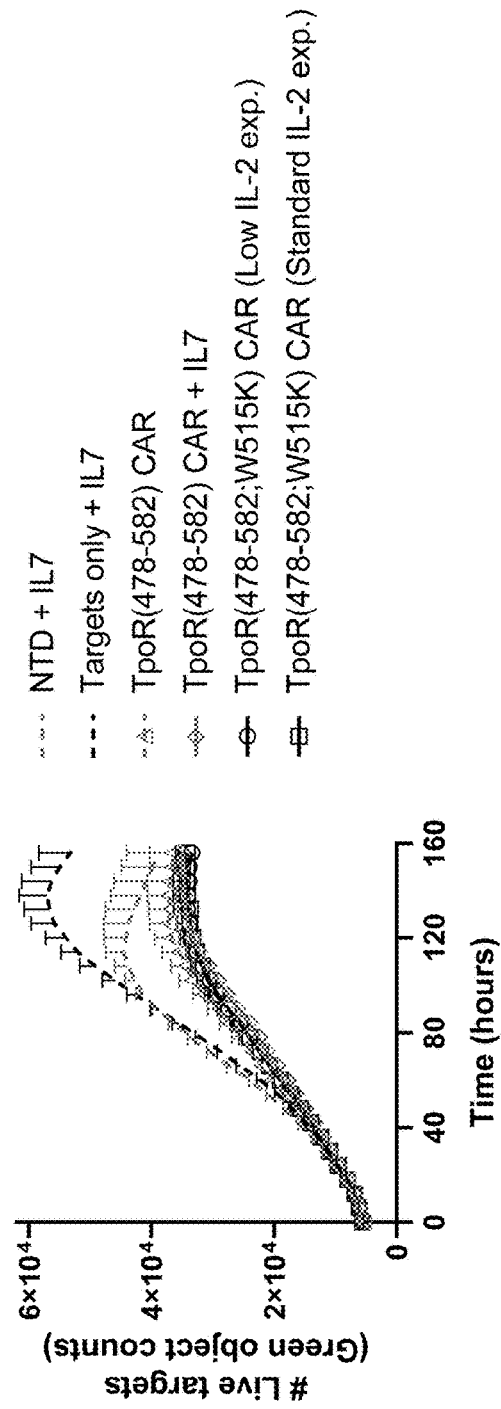

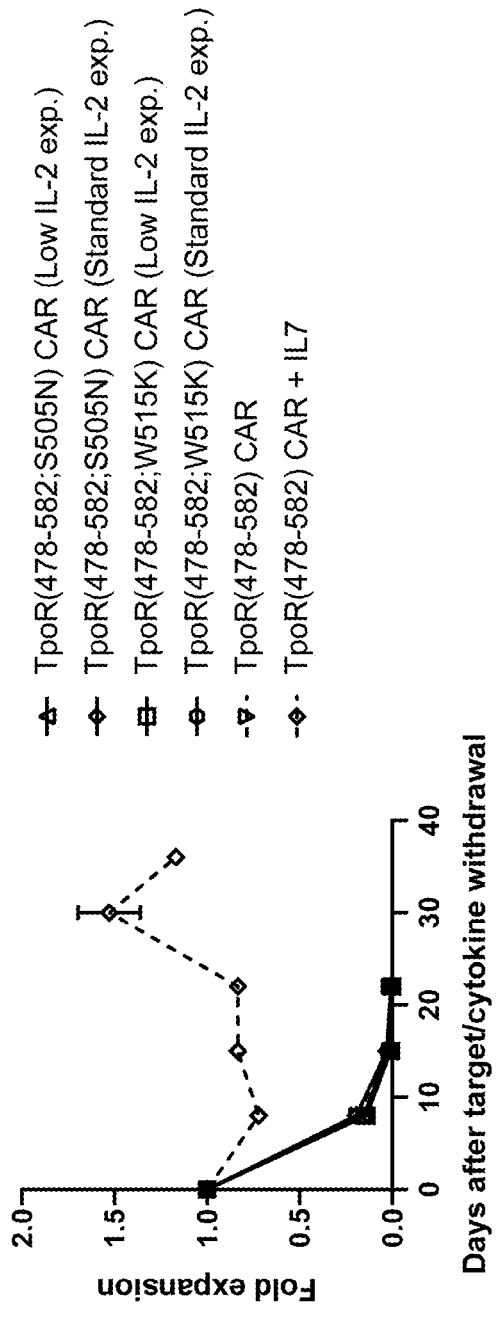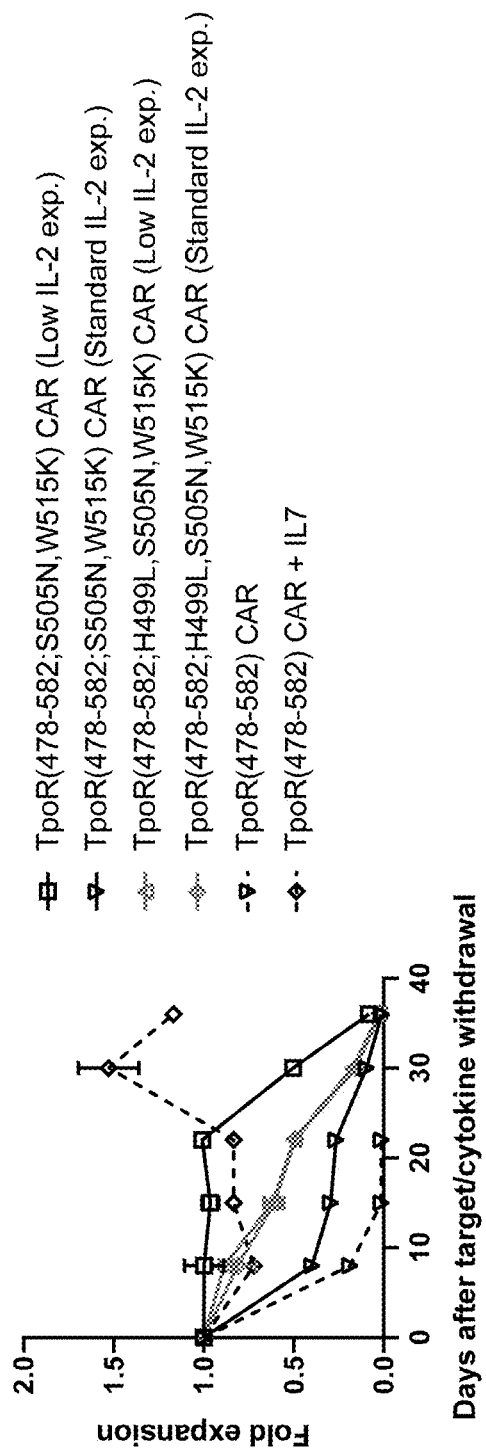

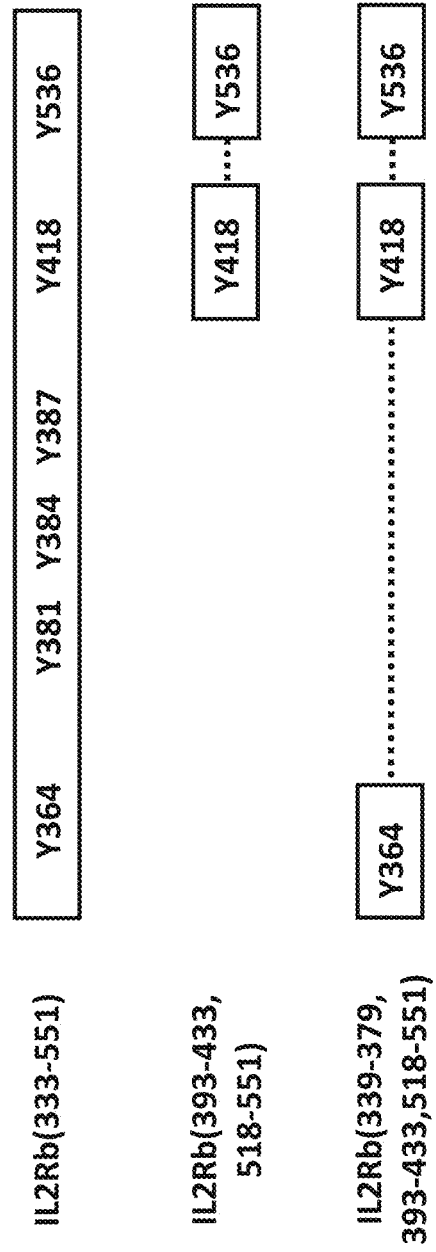

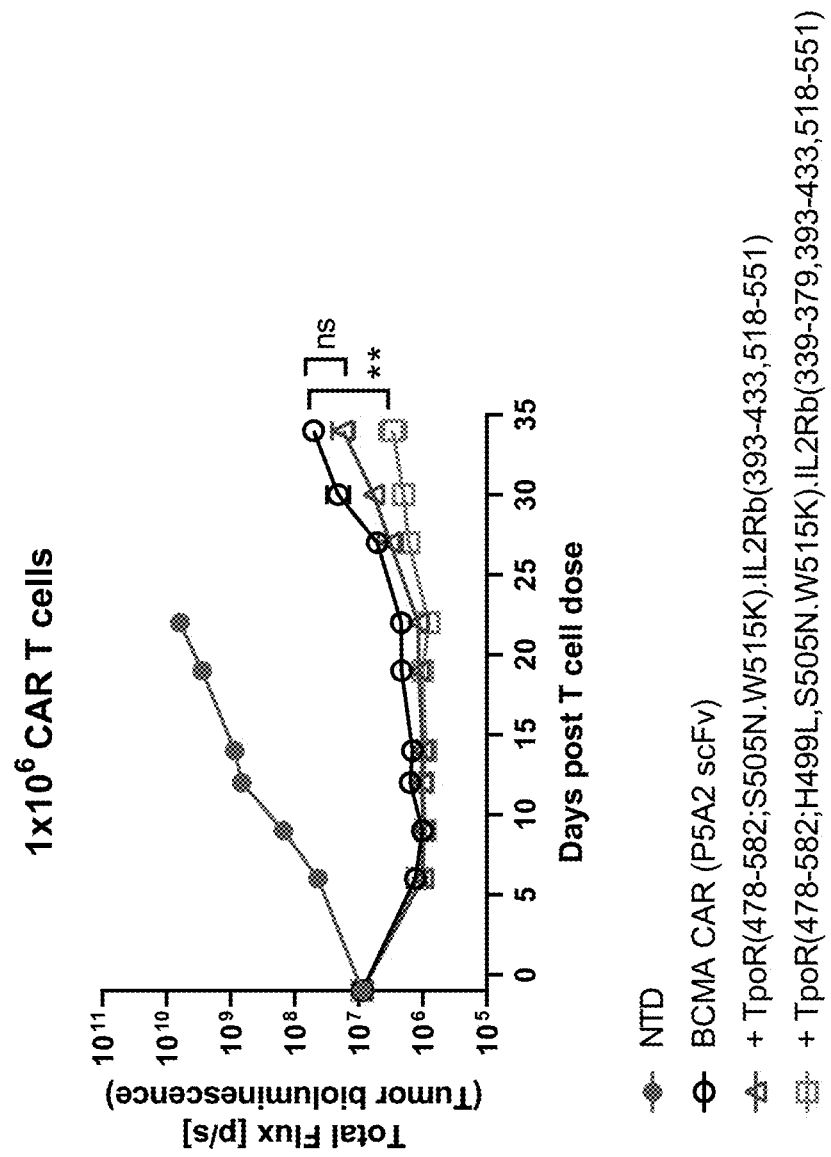

CONSTITUTIVELY ACTIVE CHIMERIC CYTOKINE RECEPTORS

CROSS REFERENCE TO RELATED APPLICATIONS

The present application claims the benefit of priority to U.S. Provisional Application No. 62/812,911, filed on Mar. 1, 2019; and U.S. Provisional Application No. 62/980,823, filed on Feb. 24, 2020, the contents of all of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Feb. 25, 2020, is named AT-023_03US-_SL.txt and is 248,684 bytes in size.

BACKGROUND

Adoptive transfer of immune cells (e.g. T-cells) genetically modified to recognize malignancy-associated antigens is showing promise as a new approach to treating cancer. For example, T-cells can be genetically modified to express chimeric antigen receptors (CARs), which are fusion proteins comprised of an antigen recognition moiety and T-cell activation domains.

T-cell proliferation, cytotoxic potency and persistence is driven by signal transduction pathways. Conventional CAR designs provide two signals—CD3zeta activation (Signal 1) and co-stimulation (Signal 2, e.g. via 4-1BB, OX40, and/or CD28 expression). In some contexts, a third signal (Signal 3), cytokine-induced cytokine receptor signaling (e.g. cytokine support for immune potentiation), may be desirable. Approaches to provide Signal 3 have however been met with significant limitations.

One approach to provide cytokine support includes combining CAR-T-cell therapy with systemic infusions of recombinant cytokines/cytokine mimetics, and engineering CAR-T-cells to secrete/express cytokines extracellularly. As cytokines have pleiotropic effects and can also impact the function of other cell types, the systemic administration or production of immune-potentiating cytokines by CAR-T-cells have at least two major drawbacks: (i) these approaches can cause systemic toxicity in humans, and (ii) in the context of allogeneic CAR-T-cell therapy, these approaches may cause bystander host immune-activation that could accelerate the rejection of allogeneic CAR-T-cells, thereby compromising therapeutic efficacy. Another approach to provide cytokine support was based on introducing a constitutively activated dimerized cytokine receptor, an IL-7Ra—this limits the nature (IL-7 signaling only) and magnitude of signaling output. Yet another approach to provide cytokine support involved incorporating Signal 3 directly into the CAR molecule (Nat Med. 2018 March; 24(3):352-359). A limitation of this approach is that the strength of Signal 3 depends on the strength of CAR activation. In the absence of target (and CAR activation), Signal 3 would not be transduced.

Needed are solutions to circumvent these drawbacks by targeting cytokine signals specifically to CAR-T cells in a tunable way, thus allowing for an improved safety profile and therapeutic efficacy. Provided herein are compositions and methods that address this need.

SUMMARY

The present disclosure provides constitutively active chimeric cytokine receptors (CACCRs). When present on chimeric antigen receptor (CAR)-bearing immune cells (CAR-I cells, e.g. CAR-T-cells), such CACCRs allow for increased immune cell activation, proliferation, persistence, and/or potency. Also provided are methods of making and using the CACCRs described herein.

Accordingly, in one aspect, provided herein is a CACCR composed of two monomers, each monomer comprising: (a) a transmembrane domain; (b) a Janus Kinase (JAK)-binding domain; and (c) a recruiting domain, wherein the monomers are constitutively dimerized. In some embodiments, the CACCR does not comprise an extracellular domain ligand binding domain.

In some embodiments, the transmembrane domain and/or the JAK-binding domain is derived from the TPOR/MPLR receptor. In some embodiments, the transmembrane domain and/or the JAK binding domain is derived from amino acids 478-582 of the naturally occurring TPOR/MPLR receptor of SEQ ID NO: 6. In some embodiments, the TPOR/MPLR receptor comprises one or more of the amino acid substitutions selected from H499L, S505N, W515K, and G509N. In some embodiments, the TPOR/MPLR receptor comprises the H499L, S505N and W515K substitutions, or the S505N and W515K substitutions. In some embodiments, the recruiting domain is a STAT-recruiting domain. In some embodiments, the recruiting domain comprises the STAT-recruiting domain from IL7Ra, for example, IL7Ra(316-459). In some embodiments, the recruiting domain comprises the STAT-recruiting domain from IL2Rb, for example, IL2Rb (333-551), IL2Rb(393-433, 518-551), IL2Rb(339-379, 393-433, 518-551), IL2Rb(333-551, Y381S, Y384S, Y387S), IL2Rb(333-551, Y364S, Y381S, Y384S, Y387S). In some embodiments, the recruiting domain comprises the STAT-recruiting domain from IL12Rb1, for example, IL12Rb1(622-662). In some embodiments, the recruiting domain comprises the STAT-recruiting domain from IL12Rb2, for example, IL12Rb2(714-862) or IL12Rb2(775-825). In some embodiments, the recruiting domain comprises the STAT-recruiting domain from IL21R, for example, IL21R(322-538).

In a related aspect provided herein is a polynucleotide encoding any one of the CACCRs of the disclosure, and an expression vector comprising such polynucleotide. In some embodiments, the polynucleotide further encodes for a chimeric antigen receptor (CAR), wherein the CAR binds to BCMA, EGFRvIII, Flt-3, WT-1, CD20, CD23, CD30, CD38, CD70, CD33, CD133, LeY, NKG2D, CS1, CD44v6, ROR1, CD19, Claudin-18.2 (Claudin-18A2, or Claudin18 isoform 2), DLL3 (Delta-like protein 3, Drosophila Delta homolog 3, Delta3), Muc17 (Mucin17, Muc3, Muc3), FAP alpha (Fibroblast Activation Protein alpha), Ly6G6D (Lymphocyte antigen 6 complex locus protein G6d, c6orf23, G6D, MEGT1, NG25), and/or RNF43 (E3 ubiquitin-protein ligase RNF43, RING finger protein 43).

In another aspect, provided herein is an engineered immune cells comprising at least one chimeric antigen receptor (CAR) and at least one CACCR of the disclosure. In some embodiments the immune cell is a T-cell. In some embodiments the immune cell is an allogeneic immune cell. In other embodiments, the immune cell is an autologous immune cell. The immune cell may be selected from the group consisting of: T-cell, dendritic cell, killer dendritic cell, mast cell, NK-cell, macrophage, monocyte, B-cell and an immune cell derived from a stem cell. In a related aspect, provided herein is a pharmaceutical composition comprising any of the engineered immune cells of the disclosure, and a kit comprising such a pharmaceutical composition.

In another aspect, provided herein is a method of treating a cancer in a subject, comprising administering to the subject a therapeutically effective amount of any of the engineered immune cells described herein.

BRIEF DESCRIPTION OF THE DRAWINGS

FIGS. 7A-7D show the cytotoxic activity of TpoR TM mutants, indicating that constitutive cytokine receptor signaling enhances CAR-T-cell potency.

FIGS. 10A-10B show the fold expansion of CAR-T-cells over time in a growth factor-independent assay.

FIGS. 13A-13B and FIGS. 14A-14B show optimization of CACCR signaling strength shown in a reporter assay in HEK293 T cells expressing full-length or truncated cytotails.

FIGS. 22A-22C show that CACCRs improved the in vivo anti-tumor activity and persistence of BCMA CAR-T cells against orthotopic multiple myeloma.

DETAILED DESCRIPTION

Figure 1:
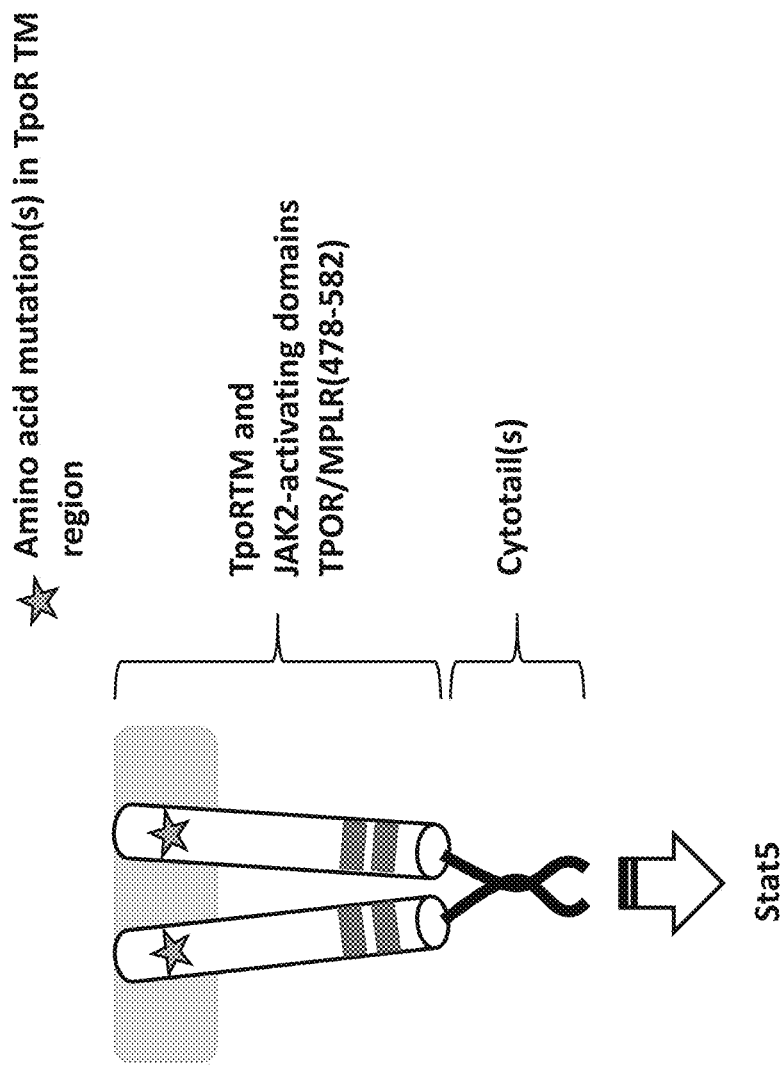
FIG. 1 shows a schematic of an engineered CACCR of the disclosure.

The present disclosure provides constitutively active chimeric cytokine receptors (CACCRs). The presence of a constitutively active, tunable chimeric cytokine receptor allows for the immune potentiation of Signal 3 to meet the need for immune potentiation. Accordingly, when present on chimeric antigen receptor (CAR)-bearing immune cells (CAR-I cells, e.g. CAR-T-cells), such CACCRs allow for increased immune cell activation, proliferation, persistence, and/or potency. Also provided herein are methods of making and using the CACCRs described herein.

The CACCRs of the disclosure are tunable, and have flexible cytokine signaling outputs for the enhancement of CAR-T cell activity, persistence, and the like. The components, methods of making and use are described in turn below.

I. Constitutively Active Chimeric Cytokine Receptors (CACCRs)

The CACCRs of the disclosure are composed of two monomers, each monomer comprising: (a) transmembrane domain; (b) a JAK-binding domain; and (c) a recruiting domain, wherein the monomers are constitutively dimerized. In some embodiments, the CACCR of the disclosure does not comprise a extracellular ligand-binding domain.

In some embodiments, the monomers are identical, giving rise to a constitutively active homodimer. In such embodiments, the number of proteins that need to be expressed in a vector are reduced. In some embodiments, the monomers are not identical, giving rise a constitutively active heterodimer, which may be desirable under certain circumstances.

The monomers of the CACCRs of the disclosure are capable of spontaneously dimerizing, and can activate signaling in the absence of any exogenous stimulation or ligand (ligand-independent dimerization). The level of activity can be controlled by mutations introduced into the transmembrane domain of the CACCRs. A skilled artisan will appreciate that the monomers of the CACCRs are not dimerized 100% of the time, and may exist as a monomer.

A. Transmembrane Domains

The CACCRs of the disclosure comprise transmembrane domains. The transmembrane domains of the disclosure contain sequences such that they allow for constitutive dimerization with the monomer pair, thus allowing constitutive JAK activation on the intracellular portion, and constitutive recruitment and phosphorylation of, for example, STAT on the cytoplasmic region of the receptor.

The transmembrane domains are on the N-terminus and are coupled to intracellular/cytoplasmic domains on the C-terminus. In some embodiments, the coupling is achieved optionally through a linker.

As used herein, the transmembrane domains are capable of insertion into the membrane of a cell in which it is expressed. In some embodiments, the transmembrane domains of the disclosure span a cellular membrane, and comprise an extracellular portion, and/or an intracellular portion.

In some embodiments, the transmembrane domains of the disclosure are engineered (synthetic) and do not resemble any naturally occurring transmembrane domain, e.g. they are non-naturally occurring.

In other embodiments, the transmembrane domains of the disclosure are derived from naturally occurring receptors.

In some embodiments, the transmembrane domains and/or JAK-activating domains of the disclosure are derived from, for example, one or more of the following receptors: erythropoietin receptor (EpoR), Interleukin 6 signal transducer (GP130 or IL6ST), prolactin receptor (PrlR), growth hormone receptor (GHR), granulocyte colony-stimulating factor receptor (GCSFR), and thrombopoietin receptor/myeloproliferative leukemia protein receptor (TPOR/MPLR). When derived from naturally occurring receptors, the entire receptor, or the entire transmembrane sequence of the receptor may not be necessary to effectuate constitutive activation and constitutive JAK binding/activation on the intracellular portion. Accordingly fragments of naturally occurring receptors may be utilized. Furthermore, certain mutations may be introduced into the transmembrane domains derived from naturally occurring receptors, to further tune the downstream signaling.

In some embodiments, the transmembrane domain and/or JAK-activating domain of the disclosure is derived from the naturally occurring EpoR receptor.

In some embodiments, the transmembrane domain and/or JAK-activating domain of the disclosure is derived from the naturally occurring GP130 receptor.

In some embodiments, the transmembrane domain and/or JAK-activating domain of the disclosure is derived from the naturally occurring PrlR receptor.

In some embodiments, the transmembrane domain and/or JAK-activating domain of the disclosure is derived from the naturally occurring GHR receptor.

In some embodiments, the transmembrane domain and/or JAK-activating domain of the disclosure is derived from the naturally occurring GCSF receptor.

In some embodiments, the transmembrane domain and/or JAK-activating domain of the disclosure is derived from the naturally occurring TPOR receptor.

Table 1a provides exemplary full-length sequences of naturally occurring receptors provided in the disclosure, from which the transmembrane proteins are derived. The sequences provided in Table 1a are reference sequences, in relation to which later mutations are expressed, for example in Tables 1b and 1c.

TABLE 1a

Exemplary Naturally Occurring Receptors

| Naturally Occurring Receptor Name | SEQ ID NO: |
|---|---|
| >AAI12154.1 Erythropoietin receptor [Homo sapiens]<br>MDHLGASLWPQVGSLCLLLAGAAWAPPPNLPDPKFESKAALLAARGPEELLCFTERLEDLV<br>CFWEEAASA<br>GVGPGNYSFSYQLEDEPWKLCRLHQAPTARGAVRFWCSLPTADTSSFVPLELRVTAASGAP<br>RYHRVIHIN<br>EVVLLDAPVGLVARLADESGHVVLRWLPPPETPMTSHIRYEVDVSAGNGAGSVQRVEILEG<br>RTECVLSNL<br>RGRTRYTFAVRARMAEPSFGGFWSAWSEPVSLLTPSDLDPLILTLSLILVVILVLLTVLALLS<br>HRRALKQ<br>KIWPGIPSPESEFEGLFTTHKGNFQLWLYQNDGCLWWSPCTPFTEDDPPASLEVLSERCWGT<br>MQAVEPGTD<br>DEGPLLEPVGSEHAQDTYLVLDKWLLPRNPPSEDLPGPGGSVDIVAMDEGSEASSCSSALA<br>SKPSPEGAS<br>AASFEYTILDPSSQLLRPWTLCPELPPTPPHLKYLYLVVSDSGISTDYSSGDSQGAQGGLSDG<br>PYSNPYE<br>NSLIPAAEPLPPSYVACS | 1 |
| >AAI17403.1 Interleukin 6 signal transducer (GP130, oncostatin M receptor) [Homo sapiens]<br>MLTLQTWLVQALFIFLTTESTGELLDPCGYISPESPVVQLHSNFTAVCVLKEKCMDYFHVN<br>ANYIVWKTN<br>HFTIPKEQYTIINRTASSVTFTDIASLNIQLTCNILTFGQLEQNVYGITIISGLPPEKPKNLSCIV<br>NEGK<br>KMRCEWDRGRETHLETNFTLKSEWATHKFADCKAKRDTPTSCTVDYSTVYFVNIEVWVE<br>AENALGKVTSD<br>HINFDPVYKVKPNPPHNLSVINSEELSSILKLTWTNPSIKSVIILKYNIQYRTKDASTWSQIPPE<br>DTAST<br>RSSFTVQDLKPFTEYVFRIRCMKEDGKGYWSDWSEEASGITYEDRPSKAPSFWYKIDPSHT<br>QGYRTVQLV<br>WKTLPPFEANGKILDYEVTLTRWKSHLQNYTVNATKLTVNLTNDRYVATLTVRNLVGKSD<br>AAVLTIPACD<br>FQATHPVMDLKAFPKDNMLWVEWTTPRESVKKYILEWCVLSDKAPCITDWQQEDGTVHR<br>TYLRGNLAESK<br>CYLITVTPVYADGPGSPESIKAYLKQAPPSKGPTVRTKKVGKNEAVLEWDQLPVDVQNGFI<br>RNYTIFYRT<br>IIGNETAVNVDSSHTEYTLSSLTSDTLYMVRMAAYTDEGGKDGPEFTFTTPKFAQGEIEAIV<br>VPVCLAFL<br>LTTLLGVLFCFNKRDLIKKHIWPNVPDPSKSHIAQWSPHTPPRHNFNSKDQMYSDGNFTDV<br>SVVEIEAND<br>KKPFPEDLKSLDLFKKEKINTEGHSSGIGGSSCMSSSRPSISSSDENESSQNTSSTVQYSTVVH<br>SGYRHQ<br>VPSVQVFSRSESTQPLLDSEERPEDLQLVDHVDGGDGILPRQQYFKQNCSQHESSPDISHFER<br>SKQVSSV<br>NEEDFVRLKQQISDHISQSCGSGQMKMFQEVSAADAFGPGTEGQVERFETVGMEAATDEG | 2 |

TABLE 1a-continued

Exemplary Naturally Occurring Receptors

| Naturally Occurring Receptor Name | SEQ ID NO: |
|---|---|
| MPKSYLPQTV<br>RQGGYMPQ | |
| >XP_011512371.1 prolactin receptor isoform X2 [Homo sapiens]<br>MKENVASATVFTLLLFLNTCLLNGQLPPGKPEIFKCRSPNKETFTCWWRPGTDGGLPTNYS<br>LTYHREGET<br>LMHECPDYITGGPNSCHFGKQYTSMWRTYIMMVNATNQMGSSFSDELYVDVTYIVQPDPP<br>LELAVEVKQP<br>EDRKPYLWIKWSPPTLIDLKTGWFTLLYEIRLKPEKAAEWEIHFAGQQTEFKILSLHPGQKY<br>LVQVRCKP<br>DHGYWSAWSPATFIQIPSDFTMNDTTVWISVAVLSAVICLIIVWAVALKGYSMVTCIFPPVP<br>GPKIKGFD<br>AHLLEKGKSEELLSALGCQDFPPTSDYEDLLVEYLEVDDSEDQHLMSVHSKEHPSQGMKPT<br>YLDPDTDSG<br>RGSCDSPSLLSEKCEEPQANPSTFYDPEVIEKPENPETTHTWDPQCISMEGKIPYFHAGGSKC<br>STWPLPQ<br>PSQHNPRSSYHNITDVCELAVGPAGAPATLLNEAGKDALKSSQTIKSREEGKATQQREVESF<br>HSETDQDT<br>PWLLPQEKTPFGSAKPLDYVEIHKVNKDGALSLLPKQRENSGKPKKPGTPENNKEYAKVSG<br>VMDNNILVL<br>VPDPHAKNVACFEESAKEAPPSLEQNQAEKALANFTATSSKCRLQLGGLDYLDPACFTHSF<br>H | 3 |
| >NP_000154.1 growth hormone receptor isoform 1 precursor<br>[Homo sapiens]<br>MDLWQLLLTLALAGSSDAFSGSEATAAILSRAPWSLQSVNPGLKTNSSKEPKFTKCRSPERE<br>TFSCHWTD<br>EVHHGTKNLGPIQLFYTRRNTQEWTQEWKECPDYVSAGENSCYFNSSFTSIWIPYCIKLTSN<br>GGTVDEKC<br>FSVDEIVQPDPPIALNWTLLNVSLTGIHADIQVRWEAPRNADIQKGWMVLEYELQYKEVNE<br>TKWKMMDPI<br>LTTSVPVYSLKVDKEYEVRVRSKQRNSGNYGEFSEVLYVTLPQMSQFTCEEDFYFPWLLIII<br>FGIFGLTV<br>MLFVFLFSKQQRIKMLILPPVPVPKIKGIDPDLLKEGKLEEVNTILAIHDSYKPEFHSDDSWV<br>EFIELDI<br>DEPDEKTEESDTDRLLSSDHEKSHSNLGVKDGDSGRTSCCEPDILETDFNANDIHEGTSEVA<br>QPQRLKGE<br>ADLLCLDQKNQNNSPYHDACPATQQPSVIQAEKNKPQPLPTEGAESTHQAAHIQLSNPSSLS<br>NIDFYAQV<br>SDITPAGSVVLSPGQKNKAGMSQCDMHPEMVSLCQENFLMDNAYFCEADAKKCIPVAPHI<br>KVESHIQPSL<br>NQEDIYITTESLTTAAGRPGTGEHVPGSEMPVPDYTSIHIVQSPQGLILNATALPLPDKEFLSS<br>CGYVST<br>DQLNKIMP | 4 |
| >XP_016855859.1 granulocyte colony-stimulating factor receptor<br>isoform X1 [Homo sapiens]<br>MARLGNCSLTWAALIILLLPGSLEECGHISVSAPIVHLGDPITASCIIKQNCSHLDPEPQILWR<br>LGAELQ<br>PGGRQQRLSDGTQESIITLPHLNHTQAFLSCCLNWGNSLQILDQVELRAGYPPAIPHNLSCL<br>MNLTTSSL<br>ICQWEPGPETHLPTSFTLKSFKSRGNCQTQGDSILDCVPKDGQSHCCIPRKHLLLYQNMGIW<br>VQAENALG<br>TSMSPQLCLDPMDVVKLEPPMLRTMDPSPEAAPPQAGCLQLCWEPWQPGLHINQKCELRH<br>KPQRGEASWA<br>LVGPLPLEALQYELCGLLPATAYTLQIRCIRWPLPGHWSDWPSLELRTTERAPTVRLDTW<br>WRQRQLDPR<br>TVQLFWKPVPLEEDSGRIQGYVVSWRPSGQAGAILPLCNTTELSCTFHLPSEAQEVALVAY<br>NSAGTSRPT<br>PVVFSESRGPALTRLHAMARDPHSLWVGWEPPNPWPQGYVIEWGLGPPSASNSNKTWRM<br>EQNGRATGFLL<br>KENIRPFQLYEIIVTPLYQDTMGPSQHVYAYSQEMAPSHAPELHLKHIGKTWAQLEWVPEP<br>PELGKSPLT<br>HYTIFWTNAQNQSFSAILNASSRGFVLHGLEPASLYHIHLMAASQAGATNSTVLTLMTLTPE<br>GSELHIIL<br>GLFGLLLLLTCLCGTAWLCCSPNRKNPLWPSVPDPAHSSLGSWVPTIMEELPGPRQGQWLG<br>QTSEMSRAL<br>TPHPCVQDAFQLPLGTPPITKLTVLEEDEKKPVPWESHNSSETCGLPTLVQTYVLQGDPRA<br>VSTQPQSQ<br>SGTSDQVLYGQLLGSPTSPGPGHYLRCDSTQPLLAGLTPSPKSYENLWFQASPLGTLVTPAP<br>SQEDDCVF<br>GPLLNFPLLQGIRVHGMEALGSF | 5 |
| >NP_005364.1 thrombopoietin receptor precursor [Homo sapiens]<br>MPSWALFMVTSCLLLAPQNLAQVSSQDVSLLASDSEPLKCFSRTFEDLTCFWDEEEAAPSG | 6 |

TABLE 1a-continued

Exemplary Naturally Occurring Receptors

| Naturally Occurring Receptor Name | SEQ ID NO: |
|---|---|
| TYQLLYAYP REKPRACPLSSQSMPHFGTRYVCQFPDQEEVRLFFPLHLWVKNVFLNQTRTQRVLFVDSVG LPAPPSIIK AMGGSQPGELQISWEEPAPEISDFLRYELRYGPRDPKNSTGPTVIQLIATETCCPALQRPHSA SALDQSP CAQPTMPWQDGPKQTSPSREASALTAEGGSCLISGLQPGNSYWLQLRSEPDGISLGGSWGS WSLPVTVDL PGDAVALGLQCFTLDLKNVTCQWQQQDHASSQGFFYHSRARCCPRDRYPIWENCEEEEKT NPGLQTPQFS RCHFKSRNDSIIHILVEVTTAPGTVHSYLGSPFWIHQAVRLPTPNLHWREISSGHLELEWQHP SSWAAQE TCYQLRYTGEGHQDWKVLEPPLGARGGTLELRPRSRYRLQLRARLNGPTYQGPWSSWSDP TRVETATETA WISLVTALHLVLGLSAVLGLLLLRWQFPAHYRRLRHALWPSLPDLHRVLGQYLRDTAALS PPKATVSDTC EEVEPSLLEILPKSSERTPLPLCSSQAQMDYRRLQPSCLGTMPLSVCPPMAESGSCCTTHIAN HSYLPLS YWQQP | |

In some embodiments, the transmembrane domain of the disclosure is derived from a truncated version of the naturally occurring TPOR/MPLR (myeloproliferative leukemia protein) receptor show in Table 1a.

In some embodiments, the transmembrane domain of the CACCR comprises amino acids 478-582 of the TPOR receptor of Table 1a.

Table 1b provides exemplary transmembrane domain amino acid sequences of the disclosure, wherein the transmembrane domain is derived from the naturally occurring TPOR receptor.

TABLE 1b

Exemplary transmembrane domain amino acid sequences

| Transmembrane Domain | Amino acid sequence | SEQ ID |
|---|---|---|
| TPOR/MPLR(478-582) | SDPTRVETATETAWISLVTALHL VLGLSAVLGLLLLRWQFPAHYRR LRHALWPSLPDLHRVLGQYLRDT AALSPPKATVSDTCEEVEPSLLE ILPKSSERTPLPL | 7 |
| TPOR/MPLR(478-582; H499L, S505N) | SDPTRVETATETAWISLVTALLL VLGLNAVLGLLLLRWQFPAHYRR LRHALWPSLPDLHRVLGQYLRDT AALSPPKATVSDTCEEVEPSLLE ILPKSSERTPLPL | 8 |
| TPOR/MPLR(478-582; S505N) | SDPTRVETATETAWISLVTALHL VLGLNAVLGLLLLRWQFPAHYRR LRHALWPSLPDLHRVLGQYLRDT AALSPPKATVSDTCEEVEPSLLE ILPKSSERTPLPL | 9 |
| TPOR/MPLR(478-582; H499L, W515K) | SDPTRVETATETAWISLVTALLL VLGLSAVLGLLLLRKQFPAHYRR LRHALWPSLPDLHRVLGQYLRDT AALSPPKATVSDTCEEVEPSLLE ILPKSSERTPLPL | 10 |
| TPOR/MPLR(478-582; W515K) | SDPTRVETATETAWISLVTALHL VLGLSAVLGLLLLRKQFPAHYRR LRHALWPSLPDLHRVLGQYLRDT AALSPPKATVSDTCEEVEPSLLE ILPKSSERTPLPL | 11 |
| TPOR/MPLR(478-582; H499L, S505N, W515K) | SDPTRVETATETAWISLVTALLL VLGLNAVLGLLLLRKQFPAHYRR LRHALWPSLPDLHRVLGQYLRDT AALSPPKATVSDTCEEVEPSLLE ILPKSSERTPLPL | 12 |
| TPOR/MPLR(478-582; S505N, W515K) | SDPTRVETATETAWISLVTALHL VLGLNAVLGLLLLRKQFPAHYRR LRHALWPSLPDLHRVLGQYLRDT AALSPPKATVSDTCEEVEPSLLE ILPKSSERTPLPL | 13 |
| TPOR/MPLR(478-582; H499L, G509N) | SDPTRVETATETAWISLVTALLL VLGLSAVLNLLLLRWQFPAHYRR LRHALWPSLPDLHRVLGQYLRDT AALSPPKATVSDTCEEVEPSLLE ILPKSSERTPLPL | 14 |

In some embodiments, the transmembrane domain of the CACCR comprises amino acids 478-582 of the TPOR receptor, and an amino acid substitution at least at H499. In some embodiments, the transmembrane domain of the CACCR comprises amino acids 478-582 of the TPOR receptor, and the amino acid substitution H499L.

In some embodiments, the transmembrane domain of the CACCR comprises amino acids 478-582 of the TPOR receptor, and an amino acid substitution at least at S505. In some embodiments, the transmembrane domain of the CACCR comprises amino acids 478-582 of the TPOR receptor, and the amino acid substitution S505N.

In some embodiments, the transmembrane domain of the CACCR comprises amino acids 478-582 of the TPOR receptor, and an amino acid substitution at least at G509. In some embodiments, the transmembrane domain of the CACCR comprises amino acids 478-582 of the TPOR receptor, and the amino acid substitution G509N.

In some embodiments, the transmembrane domain of the CACCR comprises amino acids 478-582 of the TPOR receptor, and an amino acid substitution at least at W515.

In some embodiments, the transmembrane domain of the CACCR comprises amino acids 478-582 of the TPOR receptor, and the amino acid substitution W515K.

In some embodiments, the transmembrane domain of the CACCR comprises amino acids 478-582 of the TPOR receptor, and an amino acid substitution at H499 and S505 (sequence provided in Table 1b).

In some embodiments, the transmembrane domain of the CACCR comprises amino acids 478-582 of the TPOR receptor, and an amino acid substitution at H499 and W515 (sequence provided in Table 1b).

In some embodiments, the transmembrane domain of the CACCR comprises amino acids 478-582 of the TPOR receptor, and an amino acid substitution at H499, S505, and W515 (sequence provided in Table 1b).

In some embodiments, the transmembrane domain of the CACCR comprises amino acids 478-582 of the TPOR receptor, and an amino acid substitution at S505, and W515 (sequence provided in Table 1b).

In some embodiments, the transmembrane domain of the CACCR comprises amino acids 478-582 of the TPOR receptor, and an amino acid substitution at H499 and G509 (sequence provided in Table 1b).

In some embodiments, the transmembrane domain of the CACCR comprises amino acids 478-582 of the TPOR receptor, and the amino acid substitutions H499L and S505N (sequence provided in Table 1b).

In some embodiments, the transmembrane domain of the CACCR comprises amino acids 478-582 of the TPOR receptor, and the amino acid substitutions H499L and W515K (sequence provided in Table 1b).

In some embodiments, the transmembrane domain of the CACCR comprises amino acids 478-582 of the TPOR receptor, and the amino acid substitutions H499L and G509N (sequence provided in Table 1b).

In some embodiments, the transmembrane domain of the CACCR comprises amino acids 478-582 of the TPOR receptor, and the amino acid substitutions S505N and W515K (sequence provided in Table 1b).

In some embodiments, the transmembrane domain of the CACCR comprises amino acids 478-582 of the TPOR receptor, and the amino acid substitutions H499L, S505N, and W515K (sequence provided in Table 1b).

In some embodiments, the transmembrane domain of the CACCR comprises amino acids 478-582 of the TPOR receptor, and an amino acid substitution at H499 and S505 (sequence provided in Table 1b).

The CACCRs of the disclosure are tunable, to achieve the level of Signal 3/immune potentiation required in a CAR-bearing immune cell (e.g. CAR-T-cell) and desired in a particular context or condition.

In some embodiments, a low level of STAT5 activation is desired in a CAR-bearing immune cell (e.g. CAR-T-cell). By way of example, in such embodiments, the transmembrane domain of the CACCR comprising amino acids 478-582 of the TPOR receptor, and the amino acid substitution S505N, W515K, or H499L/G509N may be introduced.

In some embodiments, an increased level of STAT5 activation is desired in a CAR-bearing immune cell (e.g. CAR-T-cell). By way of example, in such embodiments, the transmembrane domain of the CACCR comprising amino acids 478-582 of the TPOR receptor, and the amino acid substitutions H499L, S505N, and W515K may be introduced. By way of another example, in such embodiments, the transmembrane domain of the CACCR comprising amino acids 478-582 of the TPOR receptor, and the amino acid substitutions S505N and W515K may be introduced.

In some embodiments, increased differentiation into memory T cells is desired in a CAR-bearing immune cell (e.g. CAR-T-cell). By way of example, in such embodiments, the transmembrane domain of the CACCR comprising amino acids 478-582 of the TPOR receptor, and the amino acid substitutions W515K, or H499L/G509N may be introduced.

In some embodiments, increased differentiation into memory T cells is desired in a CAR-bearing immune cell (e.g. CAR-T-cell). By way of example, in such embodiments, the transmembrane domain of the CACCR comprising amino acids 478-582 of the TPOR receptor, and the amino acid substitutions S505N/W515K and H499L/S505N/W515K may be introduced.

Also substitutions to increase cytotoxic potency, durability of response, and increased persistence are provided herein, for example S505N/W515K and H499L/S505N/W515K substitutions.

TABLE 1c

Exemplary Transmembrane + JAK2 Binding Domain Sequences

| Transmembrane and JAK2 binding domain | Amino acid sequence | SEQ ID NO: |
|---|---|---|
| GCSFR(614-710) | LTLMTLTPEGSELHIILGLFGLLLLLTCLCGTAWL CCSPNRKNPLWPSVPDPAHSSLGSWVPTIMEEDA FQLPGLGTPPITKLTVLEEDEKKPVPWE | 15 |
| GP130(609-700) | TTPKFAQGEIEAIVVPVCLAFLLTTLLGVLFCFNK RDLIKKHIWPNVPDPSKSHIAQWSPHTPPRHNFN SKDQMYSDGNFTDVSVVEIEAND | 16 |
| TPOR/MPLR(478-582) | SDPTRVETATETAWISLVTALHLVLGLSAVLGLL LLRWQFPAHYRRLRHALWPSLPDLHRVLGQYLR DTAALSPPKATVSDTCEEVEPSLLEILPKSSERTPL PL | 17 |
| TPOR/MPLR(N-1) | SDPTRVETATETWISLVTALHLVLGLSAVLGLLL LRWQFPAHYRRLRHALWPSLPDLHRVLGQYLRD TAALSPPKATVSDTCEEVEPSLLEILPKSSERTPLP L | 18 |

TABLE 1c-continued

Exemplary Transmembrane + JAK2 Binding Domain Sequences

| Transmembrane and JAK2 binding domain | Amino acid sequence | SEQ ID NO: |
|---|---|---|
| TPOR/MPLR(N-2) | SDPTRVETATETISLVTALHLVLGLSAVLGLLLLR WQFPAHYRRLRHALWPSLPDLHRVLGQYLRDT AALSPPKATVSDTCEEVEPSLLEILPKSSERTPLPL | 19 |
| TPOR/MPLR(N-2 + 1) | SDPTRVETATETLISLVTALHLVLGLSAVLGLLLL RWQFPAHYRRLRHALWPSLPDLHRVLGQYLRDT AALSPPKATVSDTCEEVEPSLLEILPKSSERTPLPL | 20 |
| TPOR/MPLR(N-3) | SDPTRVETATETSLVTALHLVLGLSAVLGLLLLR WQFPAHYRRLRHALWPSLPDLHRVLGQYLRDT AALSPPKATVSDTCEEVEPSLLEILPKSSERTPLPL | 21 |
| TPOR/MPLR(N-4) | SDPTRVETATETLVTALHLVLGLSAVLGLLLLRW QFPAHYRRLRHALWPSLPDLHRVLGQYLRDTAA LSPPKATVSDTCEEVEPSLLEILPKSSERTPLPL | 22 |
| TPOR/MPLR(N-4 + 1) | SDPTRVETATETILVTALHLVLGLSAVLGLLLLR WQFPAHYRRLRHALWPSLPDLHRVLGQYLRDT AALSPPKATVSDTCEEVEPSLLEILPKSSERTPLPL | 23 |
| TPOR/MPLR(N-5) | SDPTRVETATETVTALHLVLGLSAVLGLLLLRW QFPAHYRRLRHALWPSLPDLHRVLGQYLRDTAA LSPPKATVSDTCEEVEPSLLEILPKSSERTPLPL | 24 |
| TPOR/MPLR(N-6) | SDPTRVETATETTALHLVLGLSAVLGLLLLRWQF PAHYRRLRHALWPSLPDLHRVLGQYLRDTAALS PPKATVSDTCEEVEPSLLEILPKSSERTPLPL | 25 |
| TPOR/MPLR(N-7) | SDPTRVETATETALHLVLGLSAVLGLLLLRWQFP AHYRRLRHALWPSLPDLHRVLGQYLRDTAALSP PKATVSDTCEEVEPSLLEILPKSSERTPLPL | 26 |
| TPOR/MPLR(N-8) | SDPTRVETATETLHLVLGLSAVLGLLLLRWQFPA HYRRLRHALWPSLPDLHRVLGQYLRDTAALSPP KATVSDTCEEVEPSLLEILPKSSERTPLPL | 27 |
| TPOR/MPLR(N-9) | SDPTRVETATETHLVLGLSAVLGLLLLRWQFPAH YRRLRHALWPSLPDLHRVLGQYLRDTAALSPPK ATVSDTCEEVEPSLLEILPKSSERTPLPL | 28 |
| TPOR/MPLR(N-10) | SDPTRVETATETLVLGLSAVLGLLLLRWQFPAHY RRLRHALWPSLPDLHRVLGQYLRDTAALSPPKA TVSDTCEEVEPSLLEILPKSSERTPLPL | 29 |
| TPOR/MPLR(N-11) | SDPTRVETATETVLGLSAVLGLLLLRWQFPAHYR RLRHALWPSLPDLHRVLGQYLRDTAALSPPKAT VSDTCEEVEPSLLEILPKSSERTPLPL | 30 |
| TPOR/MPLR(N-12) | SDPTRVETATETLGLSAVLGLLLLRWQFPAHYRR LRHALWPSLPDLHRVLGQYLRDTAALSPPKATV SDTCEEVEPSLLEILPKSSERTPLPL | 31 |
| TPOR/MPLR(N-13) | SDPTRVETATETGLSAVLGLLLLRWQFPAHYRRL RHALWPSLPDLHRVLGQYLRDTAALSPPKATVS DTCEEVEPSLLEILPKSSERTPLPL | 32 |
| TPOR/MPLR(N-14) | SDPTRVETATETLSAVLGLLLLRWQFPAHYRRLR HALWPSLPDLHRVLGQYLRDTAALSPPKATVSD TCEEVEPSLLEILPKSSERTPLPL | 33 |
| TPOR/MPLR(N-15) | SDPTRVETATETSAVLGLLLLRWQFPAHYRRLRH ALWPSLPDLHRVLGQYLRDTAALSPPKATVSDT CEEVEPSLLEILPKSSERTPLPL | 34 |
| TPOR/MPLR(N-16) | SDPTRVETATETAVLGLLLLRWQFPAHYRRLRH ALWPSLPDLHRVLGQYLRDTAALSPPKATVSDT CEEVEPSLLEILPKSSERTPLPL | 35 |
| TPOR/MPLR(N-17) | SDPTRVETATETVLGLLLLRWQFPAHYRRLRHA LWPSLPDLHRVLGQYLRDTAALSPPKATVSDTCE EVEPSLLEILPKSSERTPLPL | 36 |

TABLE 1c-continued

Exemplary Transmembrane + JAK2 Binding Domain Sequences

| Transmembrane and JAK2 binding domain | Amino acid sequence | SEQ ID NO: |
|---|---|---|
| TPOR/MPLR(N-18) | SDPTRVETATETLGLLLLRWQFPAHYRRLRHAL WPSLPDLHRVLGQYLRDTAALSPPKATVSDTCEE VEPSLLEILPKSSERTPLPL | 37 |
| TPOR/MPLR(N + 1) | SDPTRVETATETAWLISLVTALHLVLGLSAVLGL LLLRWQFPAHYRRLRHALWPSLPDLHRVLGQYL RDTAALSPPKATVSDTCEEVEPSLLEILPKSSERTP LPL | 38 |
| TPOR/MPLR(N + 2) | SDPTRVETATETAWVLISLVTALHLVLGLSAVLG LLLLRWQFPAHYRRLRHALWPSLPDLHRVLGQY LRDTAALSPPKATVSDTCEEVEPSLLEILPKSSER TPLPL | 39 |
| TPOR/MPLR(N + 3) | SDPTRVETATETAWLVLISLVTALHLVLGLSAVL GLLLLRWQFPAHYRRLRHALWPSLPDLHRVLGQ YLRDTAALSPPKATVSDTCEEVEPSLLEILPKSSE RTPLPL | 40 |
| TPOR/MPLR(N + 4) | SDPTRVETATETAWILVLISLVTALHLVLGLSAVL GLLLLRWQFPAHYRRLRHALWPSLPDLHRVLGQ YLRDTAALSPPKATVSDTCEEVEPSLLEILPKSSE RTPLPL | 41 |
| TPOR/MPLR(N + 5) | SDPTRVETATETAWLILVLISLVTALHLVLGLSAV LGLLLLRWQFPAHYRRLRHALWPSLPDLHRVLG QYLRDTAALSPPKATVSDTCEEVEPSLLEILPKSS ERTPLPL | 42 |
| TPOR/MPLR(N + 6) | SDPTRVETATETAWLLILVLISLVTALHLVLGLSA VLGLLLLRWQFPAHYRRLRHALWPSLPDLHRVL GQYLRDTAALSPPKATVSDTCEEVEPSLLEILPKS SERTPLPL | 43 |
| TPOR/MPLR(N + 7) | SDPTRVETATETAWVLLILVLISLVTALHLVLGLS AVLGLLLLRWQFPAHYRRLRHALWPSLPDLHRV LGQYLRDTAALSPPKATVSDTCEEVEPSLLEILPK SSERTPLPL | 44 |
| TPOR/MPLR(N + 8) | SDPTRVETATETAWLVLLILVLISLVTALHLVLGL SAVLGLLLLRWQFPAHYRRLRHALWPSLPDLHR VLGQYLRDTAALSPPKATVSDTCEEVEPSLLEILP KSSERTPLPL | 45 |

B. Janus Kinase (JAK)-Binding Domains

The CACCRs of the disclosure comprise intracellular JAK-binding domains. The JAK-binding domain is coupled to the C-terminus of the transmembrane domain, either directly, or via a linker. The JAK-binding domain is coupled to the transmembrane domain on the intracellular side of the chimeric cytokine receptor.

In some embodiments, the JAK-binding domain is a JAK-1-binding domain, a JAK-2 binding domain, a JAK-3 binding domain, or a TYK2 binding domain.

In some embodiments, the JAK-binding domains of the CACCRs of the disclosure are naturally occurring, and derived from a naturally occurring receptor.

In some embodiments, the JAK-binding domains of the CACCRs of the disclosure are synthetic.

Table 1b and Table 1c provide exemplary amino acid sequences for transmembrane and JAK2 binding domains of the disclosure. In some embodiments, the CACCR of the disclosure comprises a transmembrane and JAK2 binding domain comprising an amino acid sequence selected from the sequences in Tables 1b and 1c. In some embodiments, the CACCR of the disclosure comprises a transmembrane and JAK2 binding domain comprising an amino acid sequence that is at least 80%, 85%, 90%, 95%, 98%, 99%, or 100% identical to any one the sequences in Tables 1b and 1c.

C. Recruiting Domains

The CACCRs of the disclosure comprise cytoplasmic recruiting domains. The recruiting domain can be a STAT-recruiting domain, an AP1-recruiting domain, a Myc/Max-recruiting domain; or an NFkB-recruiting domain. In some embodiments, the recruiting domain is a Signal Transducer and Activator of Transcription (STAT)-recruiting (STAT-activating) domains. e/g/ from receptor tails (cytotails) or from cytokine receptor tails. These intracellular recruiting domains of the CACCRs of the disclosure allow for the propagation of Signal 3 in an immune cell comprising a CAR and a chimeric cytokine receptor (e.g. a CAR-T-cell with a chimeric cytokine receptor of the disclosure). Cytokine signaling propagated through the Stat-recruiting domain allows for the cytokine-based immune potentiation of the cell. In some embodiments, the immune-potentiation is homeostatic, e.g. signaling gives rise to increase in immune cells bearing the CAR. In some embodiments, the immune-potentiation is inflammatory, e.g. signaling gives rise to increase in the potency of the immune cells bearing the CAR. In some embodiments, the immune-potentiation prevents exhaustion, e.g. signaling maintains the long-term functionality of immune cells bearing the CAR.

In some embodiments, the recruiting domains of the disclosure are synthetic, and do not resemble any naturally occurring receptor fragment. In some embodiments, the immune-potentiation prevents exhaustion, e.g. signaling maintains the long-term functionality of immune cells bearing the CAR.

In some embodiments, the Stat-recruiting domains of the disclosure are synthetic, and do not resemble any naturally occurring receptor fragment.

In other embodiments, the Stat-recruiting domains of the disclosure are derived from cytoplasmic tails of naturally occurring receptors, e.g. derived from naturally occurring cytokine receptors. These cytoplasmic tails of naturally occurring receptors may be the regions downstream of the JAK-activating domains of the transmembrane domain of the receptor. The Stat-recruiting domains of the chimeric cytokine receptors comprise at least one STAT-recruiting domain from at least one receptor. In some embodiments, the Stat-recruiting domain comprises at least one STAT1-recruiting domain. In some embodiments, the Stat-recruiting domain comprises at least one STAT2-recruiting domain. In some embodiments, the Stat-recruiting domain comprises at least one STAT3-recruiting domain. In some embodiments, the Stat-recruiting domain comprises at least one STAT4-recruiting recruiting domain. In some embodiments, the Stat-recruiting domain comprises at least one STAT5-recruiting domain. In some embodiments, the Stat-recruiting domain comprises at least one STAT6-recruiting domain. In some embodiments, the Stat-recruiting domain comprises at least one STAT7-recruiting domain.

In some embodiments, the naturally occurring receptor from which the Stat-recruiting domain is derived, is not a cytokine receptor.

In some embodiments, the naturally occurring receptor from which the Stat-recruiting domain is derived, is a cytokine receptor. Exemplary cytokine receptors through which T-cell-immune potentiating cytokines signal include, but are not limited to IL-2 receptor, IL-7 receptor, IL-15 receptor and IL-21 receptor. In alternative embodiments, the receptor from which the Stat-recruiting domain is derived, is not a cytokine receptor. By choosing the Stat-recruiting domain of the CACCR, the receptor can be redirected to signaling of choice.

In some embodiments, the CACCR of the disclosure comprises a recruiting domain connected to the C-terminus of the transmembrane/JAK2 binding domain, with or without a linker. In some embodiments, the linker comprises one or more amino acid residues.

Table 2a provides exemplary receptors from which recruiting domains of the CACCRs of the disclosure are derived. Table 2b provides exemplary amino acid sequences of recruiting domains of the disclosure. In some embodiments, the CACCR of the disclosure comprises a recruiting domain comprising the amino acid sequence selected from one or more of the receptor sequences in Table 2b. In some embodiments, the CACCR of the disclosure comprises a recruiting domain comprising an amino acid sequence that is at least 80%, 85%, 90%, 95%, 98%, 99%, or 100% identical to any one of the sequences in Table 2b.

TABLE 2a

| Source of Recruiting Domains |
| --- |
| BLNK |
| IL2RG |
| EGFR |
| EpoR |
| GHR |
| IFNAR1 |
| IFNAR2 |
| IFNAR1/2 |
| IFNLR1 |
| IL10R1 |
| IL12Rb1 |
| IL12Rb2 |
| IL21R |
| IL2Rb |
| IL2small |
| IL7R |
| IL7Ra |
| IL9R |
| IL15R |
| IL21R |

TABLE 2b

Recruiting Domain (Cytotail) Sequences

| Cytotail sequences | Amino acid sequence | SEQ ID NO: |
| --- | --- | --- |
| IL7R(316-459) | ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ | 46 |
| IL2Rb(333-551) | VTQLLLQQDKVPEPASLSSNHSLTSCFTNQGYFF FHLPDALEIEACQVYFTYDPYSEEDPDEGVAGAP TGSSPQPLQPLSGEDDAYCTFPSRDDLLLFSPSLL GGPSPPSTAPGGSGAGEERMPPSLQERVPRDWDP QPLGPPTPGVPDLVDFQPPPELVLREAGEEVPDA GPREGVSFPWSRPPGQGEFRALNARLPLNTDAYL SLQELQGQDPTHLV | 47 |
| IFNAR1(508-557) | ISTIATVEETNQTDEDHKKYSSQTSQDSGNYSNE DESESKTSEELQQDFV | 48 |
| IFNAR2(310-515) | KKKVWDYNYDDESDSDTEAAPRTSGGGYTMHG LTVRPLGQASATSTESQLIDPESEEEPDLPEVDVE LPTMPKDSPQQLELLSGPCERRKSPLQDPFPEEDY SSTEGSGGRITFNVDLNSVFLRVLDDEDSDDLEA | 49 |

TABLE 2b-continued

Recruiting Domain (Cytotail) Sequences

| Cytotail sequences | Amino acid sequence | SEQ ID NO: |
|---|---|---|
| | PLMLSSHLEEMVDPEDPDNVQSNHLLASGEGTQ PTFPSPSSEGLWSEDAPSDQSDTSESDVDLGDGYI MR | |
| IFNAR1/2(IFNAR1 residues 508-557-IFNAR2 residues 310-515) | ISTIATVEETNQTDEDHKKYSSQTSQDSGNYSNE DESESKTSEELQQDFVKKKVWDYNYDDESDSDT EAAPRTSGGGYTMHGLTVRPLGQASATSTESQLI DPESEEEPDLPEVDVELPTMPKDSPQQLELLSGPC ERRKSPLQDPFPEEDYSSTEGSGGRITFNVDLNSV FLRVLDDEDSDDLEAPLMLSSHLEEMVDPEDPD NVQSNHLLASGEGTQPTFPSPSSEGLWSEDAPSD QSDTSESDVDLGDGYIMR | 50 |
| IFNLR1(300-520) | RGVRPTPRVRAPATQQTRWKKDLAEDEEEEDEE DTEDGVSFQPYIEPPSFLGQEHQAPGHSEAGGVD SGRPRAPLVPSEGSSAWDSSDRSWASTVDSSWD RAGSSGYLAEKGPGQGPGGDGHQESLPPPEFSKD SGFLEELPEDNLSSWATWGTLPPEPNLVPGGPPV SLQTLTFCWESSPEEEEEARESEIEDSDAGSWGAE STQRTEDRGRTLGHYMAR | 51 |
| IL2RG(335-369) | IPPKGGALGEGPGASPCNQHSPYWAPPCYTLKPE T | 52 |
| IL9R(356-521) | TALLTCGPARPWKSVALEEEQEGPGTRLPGNLSS EDVLPAGCTEWRVQTLAYLPQEDWAPTSLTRPA PPDSEGSRSSSSSSSSNNNNYCALGCYGGWHLSA LPGNTQSSGPIPALACGLSCDHQGLETQQGVAW VLAGHCQRPGLHEDLQGMLLPSVLSKARSWTF | 53 |
| IL21R(322-538) | PRSPAKRLQLTELQEPAELVESDGVPKPSFWPTA QNSGGSAYSEERDRPYGLVSIDTVTVLDAEGPCT WPCSCEDDGYPALDLDAGLEPSPGLEDPLLDAG TTVLSCGCVSAGSPGLGGPLGSLLDRLKPPLADG EDWAGGLPWGGRSPGGVSESEAGSPLAGLDMD TFDSGFVGSDCSSPVECDFTSPGDEGPPRSYLRQ WVVIPPPLSSPGPQAS | 54 |
| GHR(353-638) | PDEKTEESDTDRLLSSDHEKSHSNLGVKDGDSGR TSCCEPDILETDFNANDIHEGTSEVAQPQRLKGE ADLLCLDQKNQNNSPYHDACPATQQPSVIQAEK NKPQPLPTEGAESTHQAAHIQLSNPSSLSNIDFYA QVSDITPAGSVVLSPGQKNKAGMSQCDMHPEM VSLCQENFLMDNAYFCEADAKKCIPVAPHIKVES HIQPSLNQEDIYITTESLTTAAGRPGTGEHVPGSE MPVPDYTSIHIVQSPQGLILNATALPLPDKEFLSS CGYVSTDQLNKIMP | 55 |
| EpoR(339-508) | WGTMQAVEPGTDDEGPLLEPVGSEHAQDTYLVL DKWLLPRNPPSEDLPGPGGSVDIVAMDEGSEASS CSSALASKPSPEGASAASFEYTILDPSSQLLRPWT LCPELPPTPPHLKYLYLVVSDSGISTDYSSGDSQG AQGGLSDGPYSNPYENSLIPAAEPLPPSYVACS | 56 |
| murine IL2Rb(337-539) | AVQLLLLQKDSAPLPSPSGHSQASCFTNQGYFFF HLPNALEIESCQVYFTYDPCVEEEVEEDGSRLPE GSPHPPLLPLAGEQDDYCAFPPRDDLLLFSPSLST PNTAYGGSRAPEERSPLSLHEGLPSLASRDLMGL QRPLERMPEGDGEGLSANSSGEQASVPEGNLHG QDQDRGQGPILTLNTDAYLSLQELQAQDSVHLI | 57 |
| murine IL7Ra(316-459) | ARDEVESFLPNDLPAQPEELETQGHRAAVHSAN RSPETSVSPPETVRRESPLRCLARNLSTCNAPPLL SSRSPDYRDGDRNRPPVYQDLLPNSGNTNVPVPV PQPLPFQSGILIPVSQRQPISTSSVLNQEEAYVTMS SFYQNK | 58 |
| EGFR(955-1186) | VIQGDERMHLPSPTDSNFYRALMDEEDMDDVVD ADEYLIPQQGFFSSPSTSRTPLLSSLSATSNNSTVA CIDRNGLQSCPIKEDSFLQRYSSDPTGALTEDSID DTFLPVPEYINQSVPKRPAGSVQNPVYHNQPLNP APSRDPHYQDPHSTAVGNPEYLNTVQPTCVNSTF DSPAHWAQKGSHQISLDNPDYQQDFFPKEAKPN GIFKGSTAENAEYLRVAPQSSEFIGA | 59 |

TABLE 2b-continued

Recruiting Domain (Cytotail) Sequences

| Cytotail sequences | Amino acid sequence | SEQ ID NO: |
|---|---|---|
| EGFR(955-1186; Y974F, d1045-1057) | VIQGDERMHLPSPTDSNFFRALMDEEDMDDVVD ADEYLIPQQGFFSSPSTSRTPLLSSLSATSNNSTVA CIDRNGLQSCPIKEDSFLQRIDDTFLPVPEYINQSV PKRPAGSVQNPVYHNQPLNPAPSRDPHYQDPHS TAVGNPEYLNTVQPTCVNSTFDSPAHWAQKGSH QISLDNPDYQQDFFPKEAKPNGIFKGSTAENAEY LRVAPQSSEFIGA | 60 |
| EGFR(955-1009; Y974F) | VIQGDERMHLPSPTDSNFFRALMDEEDMDDVVD ADEYLIPQQGFFSSPSTSRTP | 61 |
| EGFR(1019-1085) | NNSTVACIDRNGLQSCPIKEDSFLQRIDDTFLPVP EYINQSVPKRPAGSVQNPV | 62 |
| EGFR(1037-1103; Y1068/1101F, d1045-1057) | KEDSFLQRIDDTFLPVPEFINQSVPKRPAGSVQNP VYHNQPLNPAPSRDPHFQD | 63 |
| EGFR(1066-1118; Y1068/1086F) | VPEFINQSVPKRPAGSVQNPVFHNQPLNPAPSRD PHYQDPHSTAVGNPEYLNTV | 64 |
| EGFR(1122-1165) | PEYLNTVQPTCVNSTFDSPAHWAQKGSHQISLDN PDYQQDFFPKEAKPNGIFKG | 65 |
| EGFR(1133-1186; Y1148F) | WAQKGSHQISLDNPDFQQDFFPKEAKPNGIFKGS TAENAEYLRVAPQSSEFIGA | 66 |
| IL12Rb2(775-825) | SDPKPENPACPWTVLPAGDLPTHDGYLPSNIDDL PSHEAPLADSLEELEPQ | 67 |
| IL7Ra(376-416) | ACDAPILSSSRSLDCRESGKNGPHVYQDLLLSLG TTNSTLP | 68 |
| IL7Ra(424-459) | GILTLNPVAQGQPILTSLGSNQEEAYVTMSSFYQ NQ | 69 |
| IL7Ra(376-416, 424-459) | ACDAPILSSSRSLDCRESGKNGPHVYQDLLLSLG TTNSTLPQGQPILTSLGSNQEEAYVTMSSFYQNQ | 70 |
| IL7Ra(424-459; Y456F) | GILTLNPVAQGQPILTSLGSNQEEAYVTMSSFFQN Q | 71 |
| IL7R(376-416, 424-459, Y456F) | ACDAPILSSSRSLDCRESGKNGPHVYQDLLLSLG TTNSTLPQGQPILTSLGSNQEEAYVTMSSFFQNQ | 72 |
| IL2Rbsmall(393-433) | DEGVAGAPTGSSPQPLQPLSGEDDAYCTFPSRDD LLLFSPSGQGEFRALNARLPLNTDAYLSLQELQG QDPTHLV | 73 |
| IL2Rbsmall(518-551) | GQGEFRALNARLPLNTDAYLSLQELQGQDPTHL V | 74 |
| IL2Rbsmall(339-379, 393-433) | QQDKVPEPASLSSNHSLTSCFTNQGYFFFHLPDA LEIEACQDEGVAGAPTGSSPQPLQPLSGEDDAYC TFPSRDDLLLFSPS | 75 |
| IL2Rbsmall(339-379, 518-551) | QQDKVPEPASLSSNHSLTSCFTNQGYFFFHLPDA LEIEACQ GQGEFRALNARLPLNTDAYLSLQELQGQDPTHL V | 76 |
| IL2Rbsmall(393-433, 518-551) | DEGVAGAPTGSSPQPLQPLSGEDDAYCTFPSRDD LLLFSPSGQGEFRALNARLPLNTDAYLSLQELQG QDPTHLV | 77 |
| IL2Rbsmall(339-379, 393-433, 518-551) | QQDKVPEPASLSSNHSLTSCFTNQGYFFFHLPDA LEIEACQDEGVAGAPTGSSPQPLQPLSGEDDAYC TFPSRDDLLLLFSPSGQGEFRALNARLPLNTDAYLS LQELQGQDPTHLV | 78 |
| IFNAR2small(310-352) | KKKVWDYNYDDESDSDTEAAPRTSGGGYTMHG LTVRPLGQASA | 79 |
| IFNAR2small(486-515) | EGLWSEDAPSDQSDTSESDVDLGDGYIMR | 80 |
| IFNAR2small(310-352, | KKKVWDYNYDDESDSDTEAAPRTSGGGYTMHG | 81 |

TABLE 2b-continued

Recruiting Domain (Cytotail) Sequences

| Cytotail sequences | Amino acid sequence | SEQ ID NO: |
|---|---|---|
| 486-515) | LTVRPLGQASA EGLWSEDAPSDQSDTSESDVDLGDGYIMR | |
| BLNK(53-208) | ASESPADEEEQWSDDFDSDYENPDEHSDSEMYV MPAEENADDSYEPPPVEQETRPVHPALPFARGEY IDNRSSQRHSPPFSKTLPSKPSWPSEKARLTSTLP ALTALQKPQVPPKPKGLLEDEADYVVPVEDNDE NYIHPTESSSPPPEKAPMVNR | 82 |
| BLNK(53-208; Y72F) | ASESPADEEEQWSDDFDSDFENPDEHSDSEMYV MPAEENADDSYEPPPVEQETRPVHPALPFARGEY IDNRSSQRHSPPFSKTLPSKPSWPSEKARLTSTLP ALTALQKPQVPPKPKGLLEDEADYVVPVEDNDE NYIHPTESSSPPPEKAPMVNR | 83 |
| BLNK(53-208; Y72F, Y96F) | ASESPADEEEQWSDDFDSDFENPDEHSDSEMYV MPAEENADDSFEPPPVEQETRPVHPALPFARGEY IDNRSSQRHSPPFSKTLPSKPSWPSEKARLTSTLP ALTALQKPQVPPKPKGLLEDEADYVVPVEDNDE NYIHPTESSSPPPEKAPMVNR | 84 |
| EpoR(339-508) | WGTMQAVEPGTDDEGPLLEPVGSEHAQDTYLVL DKWLLPRNPPSEDLPGPGGSVDIVAMDEGSEASS CSSALASKPSPEGASAASFEYTILDPSSQLLRPWT LCPELPPTPPHLKYLYLVVSDSGISTDYSSGDSQG AQGGLSDGPYSNPYENSLIPAAEPLPPSYVACS | 85 |
| IL12Rb2(714-862) | VTPVFRHPPCSNWPQREKGIQGHQASEKDMMHS ASSPPPPRALQAESRQLVDLYKVLESRGSDPKPE NPACPWTVLPAGDLPTHDGYLPSNIDDLPSHEAP LADSLEELEPQHISLSVFPSSSLHPLTFSCGDKLTL DQLKMRCDSLML | 86 |
| IL12Rb1(622-662) | WDKGERTEPLEKTELPEGAPELALDTELSLEDGD RCKAKM | 87 |
| IL10R1(304-578) | VSPELKNLDLHGSTDSGFGSTKPSLQTEEPQFLLP DPHPQADRTLGNREPPVLGDSCSSGSSNSTDSGIC LQEPSLSPSTGPTWEQQVGSNSRGQDDSGIDLVQ NSEGRAGDTQGGSALGHHSPPEPEVPGEEDPAA VAFQGYLRQTRCAEEKATKTGCLEEESPLTDGL GPKFGRCLVDEAGLEIPPALAKGYLKQDPLEMTL ASSGAPTGQWNQPTEEWSLLALSSCSDLGISDWS FAHDLAPLGCVAAPGGLLGSFNSDLVTLPLISSLQ SSE | 88 |
| IL2Rb(333-551, Y381S, Y384S, Y387S) | VTQLLLQQDKVPEPASLSSNHSLTSCFTNQGYFF FHLPDALEIEACQVSFTSDPSSEEDPDEGVAGAPT GSSPQPLQPLSGEDDAYCTFPSRDDLLLFSPSLLG GPSPPSTAPGGSGAGEERMPPSLQERVPRDWDPQ PLGPPTPGVPDLVDFQPPPELVLREAGEEVPDAG PREGVSFPWSRPPGQGEFRALNARLPLNTDAYLS LQELQGQDPTHLV | 106 |
| IL2Rb(333-551, Y364S, Y381S, Y384S, Y387S) | VTQLLLQQDKVPEPASLSSNHSLTSCFTNQGSFFF HLPDALEIEACQVSFTSDPSSEEDPDEGVAGAPTG SSPQPLQPLSGEDDAYCTFPSRDDLLLFSPSLLGG PSPPSTAPGGSGAGEERMPPSLQERVPRDWDPQP LGPPTPGVPDLVDFQPPPELVLREAGEEVPDAGP REGVSFPWSRPPGQGEFRALNARLPLNTDAYLSL QELQGQDPTHLV | 143 |

In some embodiments, the Stat-recruiting domain of a CACCR of the disclosure comprises a STAT-recruiting domain from one receptor.

In order to generate multiple outputs, two or more STAT-recruiting domains may be joined in tandem to mimic signaling from one or more cytokines.

In some embodiments, two or more STAT-recruiting domains may be joined in tandem with or without a linker. In some embodiments, the linker comprises one or more amino acid residues.

In some embodiments, the STAT-recruiting domain comprises portions of more than one receptor, e.g. comprising more than one STAT-recruiting domain. In such embodiments, a tandem cytokine signaling domain is provided, allowing for enhanced signaling. Accordingly, in some embodiments, the STAT-recruiting domain of a monomer of the CACCR of the disclosure comprises the STAT-recruiting domains from more than one receptor, e.g. comprises the STAT-recruiting domains from two, three, four, five, or even six receptors. For example, in some embodiments, STAT-recruiting domains can be linked in tandem to stimulate multiple pathways (e.g., the IL7R(316-459)-IL12Rb2(775-825) fragment fusion for pro-persistence STAT5 and pro-inflammatory STAT4; IL7R(316-459)-IL2Rbsmall(393-433,518-551) for pro-persistence; IL7R(316-459)-EGFR (1122-1165) for pro-persistence and anti-exhaustion; IL2Rbsmall(393-433,518-551)-EGFR(1122-1165) for pro-persistence and anti-exhaustion).

When generating multiple outputs, the proximity of individual STAT-recruiting domains to the cell membrane can influence the strength of their respective signaling outputs. Table 2c shows examples of CACCRs with the dual outputs, where each output can be placed either proximal or distal to the cell membrane. In some embodiments, the CACCRs of the disclosure comprise a recruiting domain with dual outputs selected from Table 2c.

TABLE 2c

Examples of CACCRs with dual outputs

| Dual output STAT-recruiting domain | Membrane proximal | Membrane distal |
|---|---|---|
| IL2Rbsmall (393-433, 518-551)/IL21R (322-538) | IL2Rbsmall (393-433, 518-551) | IL21R (322-538) |
| IL2Rb (333-551)/IL21R (322-538) | IL2Rb (333-551) | IL21R (322-538) |
| IL21R (322-538)/IL2Rbsmall (393-433, 518-551) | IL21R (322-538) | IL2Rbsmall (393-433, 518-551) |
| IL21R (322-538)/IL2Rb (333-551) | IL21R (322-538) | IL2Rb (333-551) |
| IL2Rbsmall (339-379, 393-433, 518-551)/IL21R (322-538) | IL2Rbsmall (339-379, 393-433, 518-551) | IL21R (322-538) |
| IL21R (322-538)/IL2Rbsmall (339-379, 393-433, 518-551) | IL21R (322-538) | IL2Rbsmall (339-379, 393-433, 518-551) |
| IL2Rb (333-551)/IL12Rb1 (622-662) | IL2Rb (333-551) | IL12Rb1 (622-662) |
| IL2Rbsmall (393-433, 518-551)/IL12Rb1 (622-662) | IL2Rbsmall (393-433, 518-551) | IL12Rb1 (622-662) |
| IL2Rbsmall (339-379, 393-433, 518-551)/IL12Rb1 (622-662) | IL2Rbsmall (339-379, 393-433, 518-551) | IL12Rb1 (622-662) |
| IL12Rb1 (622-662)/IL2Rb (333-551) | IL12Rb1 (622-662) | IL2Rb (333-551) |
| IL12Rb1 (622-662)/IL2Rbsmall (393-433, 518-551) | IL12Rb1 (622-662) | IL2Rbsmall (393-433, 518-551) |
| IL12Rb1 (622-662)/IL2Rbsmall (339-379, 393-433, 518-551) | IL12Rb1 (622-662) | IL2Rbsmall (339-379, 393-433, 518-551) |
| IL2Rb (333-551)/IL12Rb2 (714-862) | IL2Rb (333-551) | IL12Rb2 (714-862) |
| IL2Rbsmall (393-433, 518-551)/IL12Rb2 (714-862) | IL2Rbsmall (393-433, 518-551) | IL12Rb2 (714-862) |
| IL2Rbsmall (339-379, 393-433, 518-551)/IL12Rb2 (714-862) | IL2Rbsmall (339-379, 393-433, 518-551) | IL12Rb2 (714-862) |
| IL2Rb (333-551)/IL12Rb2 (775-825) | IL2Rb (333-551) | IL12Rb2 (775-825) |
| IL2Rbsmall (393-433, 518-551)/IL12Rb2 (775-825) | IL2Rbsmall (393-433, 518-551) | IL12Rb2 (775-825) |
| IL2Rbsmall (339-379, 393-433, 518-551)/IL12Rb2 (775-825) | IL2Rbsmall (339-379, 393- | IL12Rb2 (775-825) |

TABLE 2c-continued

Examples of CACCRs with dual outputs

| Dual output STAT-recruiting domain | Membrane proximal | Membrane distal |
|---|---|---|
| | | 433, 518-551) |
| IL12Rb2 (714-862)/IL2Rb (333-551) | IL12Rb2 (714-862) | IL2Rb (333-551) |
| IL12Rb2 (714-862)/IL2Rbsmall (393-433, 518-551) | IL12Rb2 (714-862) | IL2Rbsmall (393-433, 518-551) |
| IL12Rb2 (714-862)/IL2Rbsmall (339-379, 393-433, 518-551) | IL12Rb2 (714-862) | IL2Rbsmall (339-379, 393-433, 518-551) |
| IL12Rb2 (775-825)/IL2Rb (333-551) | IL12Rb2 (775-825) | IL2Rb (333-551) |
| IL12Rb2 (775-825)/IL2Rbsmall (393-433, 518-551) | IL12Rb2 (775-825) | IL2Rbsmall (393-433, 518-551) |
| IL12Rb2 (775-825)/IL2Rbsmall (339-379, 393-433, 518-551) | IL12Rb2 (775-825) | IL2Rbsmall (339-379, 393-433, 518-551) |
| IL7Ra (316-459)/IL21R (322-538) | IL7Ra (316-459) | IL21R (322-538) |
| IL7Ra (376-416, 424-459, Y456F)/IL21R (322-538) | IL7Ra (376-416, 424-459, Y456F) | IL21R (322-538) |
| IL21R (322-538)/IL7Ra (316-459) | IL21R (322-538) | IL7Ra (316-459) |
| IL21R (322-538)/IL7Ra (376-416, 424-459, Y456F) | IL21R (322-538) | IL7Ra (376-416, 424-459, Y456F) |
| IL7Ra (316-459)/IL12Rb1 (622-662) | IL7Ra (316-459) | IL12Rb1 (622-662) |
| IL7Ra (376-416, 424-459, Y456F)/IL12Rb1 (622-662) | IL7Ra (376-416, 424-459, Y456F) | IL12Rb1 (622-662) |
| IL7Ra (316-459)/IL12Rb2 (714-862) | IL7Ra (316-459) | IL12Rb2 (714-862) |
| IL7Ra (376-416, 424-459, Y456F)/IL12Rb2 (714-862) | IL7Ra (376-416, 424-459, Y456F) | IL12Rb2 (714-862) |
| IL7Ra (316-459)/IL12Rb2 (775-825) | IL7Ra (316-459) | IL12Rb2 (775-825) |
| IL7Ra (376-416, 424-459, Y456F)/IL12Rb2 (775-825) | IL7Ra (376-416, 424-459, Y456F) | IL12Rb2 (775-825) |
| IL12Rb1 (622-662)/IL7Ra (316-459) | IL12Rb1 (622-662) | IL7Ra (316-459) |
| IL12Rb1 (622-662)/IL7Ra (376-416, 424-459, Y456F) | IL12Rb1 (622-662) | IL7Ra (376-416, 424-459, Y456F) |
| IL12Rb2 (714-862)/IL7Ra (316-459) | IL12Rb2 (714-862) | IL7Ra (316-459) |
| IL12Rb2 (714-862)/IL7Ra (376-416, 424-459, Y456F) | IL12Rb2 (714-862) | IL7Ra (376-416, 424-459, Y456F) |
| IL12Rb2 (775-825)/IL7Ra (316-459) | IL12Rb2 (775-825) | IL7Ra (316-459) |
| IL12Rb2 (775-825)/IL7Ra (376-416, 424-459, Y456F) | IL12Rb2 (775-825) | IL7Ra (376-416, 424-459, Y456F) |
| IL7Ra (316-459)/IL2Rb (333-551) | IL7Ra (316-459) | IL2Rb (333-551) |

TABLE 2c-continued

Examples of CACCRs with dual outputs

| Dual output STAT-recruiting domain | Membrane proximal | Membrane distal |
|---|---|---|
| IL7Ra (376-416, 424-459, Y456F)/IL2Rb (333-551) | IL7Ra (376-416, 424-459, Y456F) | IL2Rb (333-551) |
| IL7Ra (316-459)/IL2Rbsmall (393-433, 518-551) | IL7Ra (316-459) | IL2Rbsmall (393-433, 518-551) |
| IL7Ra (376-416, 424-459, Y456F)/IL2Rbsmall (393-433, 518-551) | IL7Ra (376-416, 424-459, Y456F) | IL2Rbsmall (393-433, 518-551) |
| IL7Ra (316-459)/IL2Rbsmall (339-379, 393-433, 518-551) | IL7Ra (316-459) | IL2Rbsmall (339-379, 393-433, 518-551) |
| IL7Ra (376-416, 424-459, Y456F)/IL2Rbsmall (339-379, 393-433, 518-551) | IL7Ra (376-416, 424-459, Y456F) | IL2Rbsmall (339-379, 393-433, 518-551) |
| IL2Rb (333-551)/IL7Ra (316-459) | IL2Rb (333-551) | IL7Ra (316-459) |
| IL2Rb (333-551)/IL7Ra (376-416, 424-459, Y456F) | IL2Rb (333-551) | IL7Ra (376-416, 424-459, Y456F) |
| IL2Rbsmall (393-433, 518-551)/IL7Ra (316-459) | IL2Rbsmall (393-433, 518-551) | IL7Ra (316-459) |
| IL2Rbsmall (393-433, 518-551)/ IL7Ra (376-416, 424-459, Y456F) | IL2Rbsmall (393-433, 518-551) | IL7Ra (376-416, 424-459, Y456F) |
| IL2Rbsmall (339-379, 393-433, 518-551)/IL7Ra (316-459) | IL2Rbsmall (339-379, 393-433, 518-551) | IL7Ra (316-459) |
| IL2Rbsmall (339-379, 393-433, 518-551)/ IL7Ra (376-416, 424-459, Y456F) | IL2Rbsmall (339-379, 393-433, 518-551) | IL7Ra (376-416, 424-459, Y456F) |
| IL12Rb1 (622-662)/IL21R (322-538) | IL12Rb1 (622-662) | IL21R (322-538) |
| IL12Rb2 (714-862)/IL21R (322-538) | IL12Rb2 (714-862) | IL21R (322-538) |
| IL12Rb2 (775-825)/IL21R (322-538) | IL12Rb2 (775-825) | IL21R (322-538) |
| IL21R (322-538)/IL12Rb1 (622-662) | IL21R (322-538) | IL12Rb1 (622-662) |
| IL21R (322-538)/IL12Rb2 (714-862) | IL21R (322-538) | IL12Rb2 (714-862) |
| IL21R (322-538)/IL12Rb2 (775-825) | IL21R (322-538) | IL12Rb2 (775-825) |

Without being bound to theory or mechanism, in some embodiments, a JAK-protein (JAK1, JAK2, JAK3, or TYK2) is bound to a dimerized CACCR of the disclosure. The two bound JAK-proteins are activated, which are capable of phosphorylating tyrosine residues on the recruiting domain of the CACCR. The phosphorylated recruiting domains are then capable of binding the recruited proteins (e.g. a phosphorylated STAT-recruiting domain binds a STAT-protein), which in turn effectuate transcription events in the nucleus.

D. Exemplary CACCRs

Table 3 shows exemplary CACCR sequences of the disclosure. The receptors may be expressed with a signal sequence, e.g. a CD8SS of sequence (SEQ ID NO: 89)
MALPVTALLLPLALLLHAARP.

In some embodiments, the CACCR of the disclosure comprises any one of the sequences in Table 3. In some embodiments, the CACCR comprises an amino acid sequence that is at least about 80%, 85%, 90%, 95%, 96%, 98%, 99% or 100% identical to any one of the amino acid sequences of SEQ ID NO: 90-98, and 107-139. In some embodiments, the TPOR/MPLR receptor comprises any one of the amino acid sequences of SEQ ID NO: 90-98, and 107-139.

In some embodiments, the CACCR comprises the transmembrane domain and/or JAK-binding domain derived from the TPOR/MPLR receptor. In some embodiments, the CACCR of the disclosure comprises amino acids 478-582 of the naturally occurring TPOR/MPLR receptor of SEQ ID NO: 6. In some embodiments, the CACCR of the disclosure comprises the amino acid sequence that is at least about 80%, 85%, 90%, 95%, 96%, 98%, 99% or 100% identical to the amino acid sequence of SEQ ID NO: 17. In some embodiments, the CACCR of the disclosure comprises the amino acid sequence of SEQ ID NO: 17. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 143. In some embodiments, the STAT-recruiting domain from IL2Rb comprises the amino acid sequence of SEQ ID NO: 47, 73, 74, 75, 76, 77, 78, 106 or 143. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 90 or 119, with or without a signal sequence. In some embodiments, the CACCR comprises the amino acid sequence of SEQ ID NO: 90 or 119, with or without a signal sequence.

In some embodiments, the CACCR of the disclosure comprises the transmembrane domain and/or JAK-binding domain from a TPOR/MPLR receptor that comprises one or more amino acid substitutions at H499, S505, G509 or W515. In some embodiments, the TPOR/MPLR receptor comprises a H499L substitution. In some embodiments, the TPOR/MPLR receptor comprises a S505N substitution. In some embodiments, the TPOR/MPLR receptor comprises a G509N substitution. In some embodiments, the TPOR/MPLR receptor comprises a W515K substitution. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 143. In some embodiments, the STAT-recruiting domain from IL2Rb comprises the amino acid sequence of SEQ ID NO: 47, 73, 74, 75, 76, 77, 78, 106 or 143. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 92, 94, 121, or 123, with or without a signal sequence. In some embodiments, the CACCR comprises the amino acid sequence of SEQ ID NO: 92, 94, 121, or 123, with or without a signal sequence.

In some embodiments, the CACCR of the disclosure comprises the transmembrane domain and/or JAK-binding domain from a TPOR/MPLR receptor that comprises the H499L and S505N substitutions. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 143. In some embodiments, the STAT-recruiting domain from IL2Rb comprises the amino acid sequence of SEQ ID NO: 47, 73, 74, 75, 76, 77, 78, 106 or 143. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 91, 98, 120, or 127, with or without a signal sequence. In some embodiments, the CACCR comprises the amino acid sequence of SEQ ID NO: 91, 98, 120, or 127, with or without a signal sequence.

In some embodiments, the CACCR of the disclosure comprises the transmembrane domain and/or JAK-binding domain from a TPOR/MPLR receptor that comprises the H499L and W515K substitutions or the H499L and G509N substitutions. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 143. In some embodiments, the STAT-recruiting domain from IL2Rb comprises the amino acid sequence of SEQ ID NO: 47, 73, 74, 75, 76, 77, 78, 106 or 143. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 97, or 126, with or without a signal sequence. In some embodiments, the CACCR comprises the amino acid sequence of SEQ ID NO: 97, or 126, with or without a signal sequence.

In some embodiments, the CACCR of the disclosure comprises the transmembrane domain and/or JAK-binding domain from a TPOR/MPLR receptor that comprises the S505N and W515K substitutions. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 143. In some embodiments, the STAT-recruiting domain from IL2Rb comprises the amino acid sequence of SEQ ID NO: 47, 73, 74, 75, 76, 77, 78, 106 or 143. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 96, 107, 109, 111, 113, 115, 117, 125, 128, 129, 132, 134, 136, or 138, with or without a signal sequence. In some embodiments, the CACCR comprises the amino acid sequence of SEQ ID NO: 96, 107, 109, 111, 113, 115, 117, 125, 128, 129, 132, 134, 136, or 138, with or without a signal sequence.

In some embodiments, the CACCR of the disclosure comprises the transmembrane domain and/or JAK-binding domain from a TPOR/MPLR receptor that comprises the H499L and W515K substitutions. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 143. In some embodiments, the STAT-recruiting domain from IL2Rb comprises the amino acid sequence of SEQ ID NO: 47, 73, 74, 75, 76, 77, 78, 106 or 143. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 93, with or without a signal sequence. In some embodiments, the CACCR comprises the amino acid sequence of SEQ ID NO: 93, with or without a signal sequence.

In some embodiments, the CACCR of the disclosure comprises the transmembrane domain and/or JAK-binding domain from a TPOR/MPLR receptor that comprises the H499L, S505N and W515K substitutions. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 143. In some embodiments, the STAT-recruiting domain from IL2Rb comprises the amino acid sequence of SEQ ID NO: 47, 73, 74, 75, 76, 77, 78, 106 or 143. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 95, 108, 110, 112, 114, 116, 118, 124, 130, 131, 133, 135, 137, or 139, with or without a signal sequence. In some embodiments, the CACCR comprises the amino acid sequence of SEQ ID NO: 95, 108, 110, 112, 114, 116, 118, 124, 130, 131, 133, 135, 137, or 139, with or without a signal sequence.

TABLE 3

| Receptor | Amino acid sequence | SEQ ID NO: |
| --- | --- | --- |
| TPOR/MPLR(478-582). IL7Ra(316-459) | SDPTRVETATETAWISLVTALHLVLGLSAVLGLL LLRWQFPAHYRRLRHALWPSLPDLHRVLGQYLR DTAALSPPKATVSDTCEEVEPSLLEILPKSSERTPL PL ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ | 90 |
| TPOR/MPLR(478-582; H499L, S505N). IL7Ra(316-459) | SDPTRVETATETAWISLVTALLLVLGLNAVLGLL LLRWQFPAHYRRLRHALWPSLPDLHRVLGQYLR DTAALSPPKATVSDTCEEVEPSLLEILPKSSERTPL PL ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ | 91 |
| TPOR/MPLR(478-582; S505N). IL7Ra(316-459) | SDPTRVETATETAWISLVTALHLVLGLNAVLGLL LLRWQFPAHYRRLRHALWPSLPDLHRVLGQYLR DTAALSPPKATVSDTCEEVEPSLLEILPKSSERTPL PL ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ | 92 |
| TPOR/MPLR(478-582; H499L, W515K). IL7Ra(316-459) | SDPTRVETATETAWISLVTALLLVLGLSAVLGLL LLRKQFPAHYRRLRHALWPSLPDLHRVLGQYLR DTAALSPPKATVSDTCEEVEPSLLEILPKSSERTPL PL ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ | 93 |
| TPOR/MPLR(478-582; W515K). IL7Ra(316-459) | SDPTRVETATETAWISLVTALHLVLGLSAVLGLL LLRKQFPAHYRRLRHALWPSLPDLHRVLGQYLR DTAALSPPKATVSDTCEEVEPSLLEILPKSSERTPL PL ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ | 94 |
| TPOR/MPLR(478-582; H499L, S505N, W515K). IL7Ra(316-459) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PL ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ | 95 |
| TPOR/MPLR(478-582; S505N, W515K). IL7Ra(316-459) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL | 96 |

TABLE 3-continued

| Receptor | Amino acid sequence | SEQ ID NO: |
|---|---|---|
| | PL ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ | |
| TPOR/MPLR(478-582; H499L, G509N). IL7Ra(316-459) | SDPTRVETATETAWISLVTALLLVLGLSAVLNLL LLRWQFPAHYRRLRHALWPSLPDLHRVLGQYLR DTAALSPPKATVSDTCEEVEPSLLEILPKSSERTPL PL ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ | 97 |
| TPOR/MPLR(478-582, H499L, S505N). IL7Ra(316-459) | SDPTRVETATETAWISLVTALLLVLGLNAVLGLL LLRWQFPAHYRRLRHALWPSLPDLHRVLGQYLR DTAALSPPKATVSDTCEEVEPSLLEILPKSSERTPL PL ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ | 98 |
| CD8SS-TPOR/MPLR(478-582; S505N, W515K). IL12Rb2(714-862) | MALPVTALLLPLALLLHAARP SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PL VTPVFRHPPCSNWPQREKGIQGHQASEKDMMHS ASSPPPPRALQAESRQLVDLYKVLESRGSDPKPE NPACPWTVLPAGDLPTHDGYLPSNIDDLPSHEAP LADSLEELEPQHISLSVFPSSSLHPLTFSCGDKLTL DQLKMRCDSLML | 107 |
| CD8SS-TPOR/MPLR(478-582; H499L, S505N, W515K). IL12Rb2(714-862) | MALPVTALLLPLALLLHAARP SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PL VTPVFRHPPCSNWPQREKGIQGHQASEKDMMHS ASSPPPPRALQAESRQLVDLYKVLESRGSDPKPE NPACPWTVLPAGDLPTHDGYLPSNIDDLPSHEAP LADSLEELEPQHISLSVFPSSSLHPLTFSCGDKLTL DQLKMRCDSLML | 108 |
| CD8SS-TPOR/MPLR(478-582; S505N, W515K). IL12Rb2(775-825) | MALPVTALLLPLALLLHAARP SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PL SDPKPENPACPWTVLPAGDLPTHDGYLPSNIDDL PSHEAPLADSLEELEPQ | 109 |
| CD8SS-TPOR/MPLR(478-582; H499L, S505N, W515K). IL12Rb2(775-825) | MALPVTALLLPLALLLHAARP SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PL SDPKPENPACPWTVLPAGDLPTHDGYLPSNIDDL PSHEAPLADSLEELEPQ | 110 |
| CD8SS-TPOR/MPLR(478-582; S505N, W515K). IL2Rb(333-551) | MALPVTALLLPLALLLHAARP SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PL VTQLLLQQDKVPEPASLSSNHSLTSCFTNQGYFF FHLPDALEIEACQVYFTYDPYSEEDPDEGVAGAP TGSSPQPLQPLSGEDDAYCTFPSRDDLLLFSPSLL GGPSPPSTAPGGSGAGEERMPPSLQERVPRDWDP QPLGPPPTPGVPDLVDFQPPPELVLREAGEEVPDA GPREGVSFPWSRPPGQGEFRALNARLPLNTDAYL SLQELQGQDPTHLV | 111 |

TABLE 3-continued

| Receptor | Amino acid sequence | SEQ ID NO: |
|---|---|---|
| CD8SS-TPOR/MPLR(478-582; H499L, S505N, W515K). IL2Rb (333-551) | MALPVTALLLPLALLLHAARP SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PL VTQLLLQQDKVPEPASLSSNHSLTSCFTNQGYFF FHLPDALEIEACQVYFTYDPYSEEDPDEGVAGAP TGSSPQPLQPLSGEDDAYCTFPSRDDLLLFSPSLL GGPSPPSTAPGGSGAGEERMPPSLQERVPRDWDP QPLGPPTPGVPDLVDFQPPPELVLREAGEEVPDA GPREGVSFPWSRPPGQGEFRALNARLPLNTDAYL SLQELQGQDPTHLV | 112 |
| CD8SS-TPOR/MPLR(478-582; S505N, W515K). IL2Rb(393-433, 518-551) | MALPVTALLLPLALLLHAARP SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PL DEGVAGAPTGSSPQPLQPLSGEDDAYCTFPSRDD LLLFSPSGQGEFRALNARLPLNTDAYLSLQELQG QDPTHLV | 113 |
| CD8SS-TPOR/MPLR(478-582; H499L, S505N, W515K) IL2Rb(393-433, 518-551) | MALPVTALLLPLALLLHAARP SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PL DEGVAGAPTGSSPQPLQPLSGEDDAYCTFPSRDD LLLFSPSGQGEFRALNARLPLNTDAYLSLQELQG QDPTHLV | 114 |
| CD8SS-TPOR/MPLR(478-582; S505N, W515K). IL2Rb(339-379, 393-433, 518-551) | MALPVTALLLPLALLLHAARP SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PL QQDKVPEPASLSSNHSLTSCFTNQGYFFFHLPDA LEIEACQDEGVAGAPTGSSPQPLQPLSGEDDAYC TFPSRDDLLLFSPSGQGEFRALNARLPLNTDAYLS LQELQGQDPTHLV | 115 |
| CD8SS-TPOR/MPLR(478-582; H499L, S505N, W515K). IL2Rb (339-379,393-433, 518-551) | MALPVTALLLPLALLLHAARP SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PL QQDKVPEPASLSSNHSLTSCFTNQGYFFFHLPDA LEIEACQDEGVAGAPTGSSPQPLQPLSGEDDAYC TFPSRDDLLLFSPSGQGEFRALNARLPLNTDAYLS LQELQGQDPTHLV | 116 |
| CD8SS-TPOR/MPLR(478-582; S505N, W515K). IL7Ra(316-459). IL12Rb2 (775-825) | MALPVTALLLPLALLLHAARP SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PL ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ SDPKPENPACPWTVLPAGDLPTHDGYLPSNIDDL PSHEAPLADSLEELEPQ | 117 |
| CD8SS-TPOR/MPLR(478-582; H499L, S505N, W515K). IL7Ra(316-459). IL12Rb2(775-825) | MALPVTALLLPLALLLHAARP SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PL ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ SDPKPENPACPWTVLPAGDLPTHDGYLPSNIDDL PSHEAPLADSLEELEPQ | 118 |

TABLE 3-continued

| Receptor | Amino acid sequence | SEQ ID NO: |
|---|---|---|
| TPOR/MPLR(478-582). IL7Ra(316-459) | SDPTRVETATETAWISLVTALHLVLGLSAVLGLL LLRWQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 119 |
| TPOR/MPLR(478-582; H499L, S505N). IL7Ra(316-459) | SDPTRVETATETAWISLVTALLLVLGLNAVLGLL LLRWQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 120 |
| TPOR/MPLR(478-582; S505N). IL7Ra(316-459) | SDPTRVETATETAWISLVTALHLVLGLNAVLGLL LLRWQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 121 |
| TPOR/MPLR(478-582; H499L, W515K). IL7Ra(316-459) | SDPTRVETATETAWISLVTALLLVLGLSAVLGLL LLRKQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 122 |
| TPOR/MPLR(478-582; W515K). IL7Ra(316-459) | SDPTRVETATETAWISLVTALHLVLGLSAVLGLL LLRKQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 123 |
| TPOR/MPLR(478-582; H499L, S505N, W515K). IL7Ra(316-459) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 124 |
| TPOR/MPLR(478-582; S505N, W515K). IL7Ra(316-459) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 125 |
| TPOR/MPLR(478-582, H499L, G509N). IL7Ra(316-459) | SDPTRVETATETAWISLVTALLLVLGLSAVLNLL LLRWQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 126 |
| TPOR/MPLR(478-582; H499L, S505N). IL7Ra(316-459) | SDPTRVETATETAWISLVTALLLVLGLNAVLGLL LLRWQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ | 127 |

TABLE 3-continued

| Receptor | Amino acid sequence | SEQ ID NO: |
|---|---|---|
| | SPNCPSEDVVITPESFGRDSSLTCLAGNVSACDAP ILSSSRSLDCRESGKNGPHVYQDLLLSLGTTNSTL PPPPFSLQSGILTLNPVAQGQPILTSLGSNQEEAYV TMSSFYQNQ | |
| TPOR/MPLR(478-582; S505N, W515K). IL2Rb(333-551) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEVTQLLLQQDKVPEPASLSSNHSLTSCFTNQ GYFFFHLPDALEIEACQVYFTYDPYSEEDPDEGV AGAPTGSSPQPLQPLSGEDDAYCTFPSRDDLLLFS PSLLGGPSPPSTAPGGSGAGEERMPPSLQERVPRD WDPQPLGPPTPGVPDLVDFQPPPELVLREAGEEV PDAGPREGVSFPWSRPPGQGEFRALNARLPLNTD AYLSLQELQGQDPTHLV | 128 |
| TPOR/MPLR(478-582; S505N, W515K). IL12Rb2(714-862) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEVTPVFRHPPCSNWPQREKGIQGHQASEKD MMHSASSPPPPRALQAESRQLVDLYKVLESRGS DPKPENPACPWTVLPAGDLPTHDGYLPSNIDDLP SHEAPLADSLEELEPQHISLSVFPSSSLHPLTFSCG DKLTLDQLKMRCDSLML | 129 |
| TPOR/MPLR(478-582; H499L, S505N, W515K). IL2Rb(333-551) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEVTQLLLQQDKVPEPASLSSNHSLTSCFTNQ GYFFFHLPDALEIEACQVYFTYDPYSEEDPDEGV AGAPTGSSPQPLQPLSGEDDAYCTFPSRDDLLLFS PSLLGGPSPPSTAPGGSGAGEERMPPSLQERVPRD WDPQPLGPPTPGVPDLVDFQPPPELVLREAGEEV PDAGPREGVSFPWSRPPGQGEFRALNARLPLNTD AYLSLQELQGQDPTHLV | 130 |
| TPOR/MPLR(478-582; H499L, S505N, W515K). IL12Rb2(714-862) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEVTPVFRHPPCSNWPQREKGIQGHQASEKD MMHSASSPPPPRALQAESRQLVDLYKVLESRGS DPKPENPACPWTVLPAGDLPTHDGYLPSNIDDLP SHEAPLADSLEELEPQHISLSVFPSSSLHPLTFSCG DKLTLDQLKMRCDSLML | 131 |
| TPOR/MPLR(478-582, S505N, W515K). IL12Rb2(775-825) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLESDPKPENPACPWTVLPAGDLPTHDGYLPSN IDDLPSHEAPLADSLEELEPQ | 132 |
| TPOR/MPLR(478-582; H499L, S505N, W515K). IL12Rb2(775-825) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLESDPKPENPACPWTVLPAGDLPTHDGYLPSN IDDLPSHEAPLADSLEELEPQ | 133 |
| TPOR/MPLR(478-582; S505N, W515K). IL7Ra(316-459). IL12Rb2 (775-825) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPPFSLQSGILTLNPVAQGQPILTSLGSNQEEAYV TMSSFYQNQSRSDPKPENPACPWTVLPAGDLPTH DGYLPSNIDDLPSHEAPLADSLEELEPQ | 134 |
| TPOR/MPLR(478-582; H499L, S505N, W515K). IL7Ra(316-459). IL12Rb2(775-825) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPPFSLQSGILTLNPVAQGQPILTSLGSNQEEAYV TMSSFYQNQSRSDPKPENPACPWTVLPAGDLPTH DGYLPSNIDDLPSHEAPLADSLEELEPQ | 135 |

TABLE 3-continued

| Receptor | Amino acid sequence | SEQ ID NO: |
|---|---|---|
| TPOR/MPLR(478-582; S505N, W515K). IL2Rb (333-551; Y381S, Y384S, Y387S) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEVTQLLLQQDKVPEPASLSSNHSLTSCFTNQ GYFFFHLPDALEIEACQVSFTSDPSSEEDPDEGVA GAPTGSSPQPLQPLSGEDDAYCTFPSRDDLLLFSP SLLGGPSPPSTAPGGSGAGEERMPPSLQERVPRD WDPQPLGPPTPGVPDLVDFQPPPELVLREAGEEV PDAGPREGVSFPWSRPPGQGEFRALNARLPLNTD AYLSLQELQGQDPTHLV | 136 |
| TPOR/MPLR(478-582; H499L, S505N, W515K). IL2Rb(333-551; Y381S, Y384S, Y387S) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEVTQLLLQQDKVPEPASLSSNHSLTSCFTNQ GYFFFHLPDALEIEACQVSFTSDPSSEEDPDEGVA GAPTGSSPQPLQPLSGEDDAYCTFPSRDDLLLFSP SLLGGPSPPSTAPGGSGAGEERMPPSLQERVPRD WDPQPLGPPTPGVPDLVDFQPPPELVLREAGEEV PDAGPREGVSFPWSRPPGQGEFRALNARLPLNTD AYLSLQELQGQDPTHLV | 137 |
| TPOR/MPLR(478-582; S505N, W515K). IL2Rb(333-551; Y364S, Y381S, Y384S, Y387S) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEVTQLLLQQDKVPEPASLSSNHSLTSCFTNQ GSFFFHLPDALEIEACQVSFTSDPSSEEDPDEGVA GAPTGSSPQPLQPLSGEDDAYCTFPSRDDLLLFSP SLLGGPSPPSTAPGGSGAGEERMPPSLQERVPRD WDPQPLGPPTPGVPDLVDFQPPPELVLREAGEEV PDAGPREGVSFPWSRPPGQGEFRALNARLPLNTD AYLSLQELQGQDPTHLV | 138 |
| TPOR/MPLR(478-582; H499L, S505N, W515K). IL2Rb(333-551; Y364S, Y381S, Y384S, Y387S) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEVTQLLLQQDKVPEPASLSSNHSLTSCFTNQ GSFFFHLPDALEIEACQVSFTSDPSSEEDPDEGVA GAPTGSSPQPLQPLSGEDDAYCTFPSRDDLLLFSP SLLGGPSPPSTAPGGSGAGEERMPPSLQERVPRD WDPQPLGPPTPGVPDLVDFQPPPELVLREAGEEV PDAGPREGVSFPWSRPPGQGEFRALNARLPLNTD AYLSLQELQGQDPTHLV | 139 |

*The underlined LE and SR are exemplary optional linker that may be inserted between two domains.

E. Expression of CACCRs

Provided herein are polynucleotides encoding any one of the CACCRs provided herein. Likewise, provided herein are expression vectors comprising such polynucleotides. In some embodiments, the vector is a viral vector. In some embodiments, the vector is not a viral vector.

In some embodiments, the expression vector comprises a CACCR and a polynucleotide expressing a chimeric antigen receptor (CAR).

Figure 2:
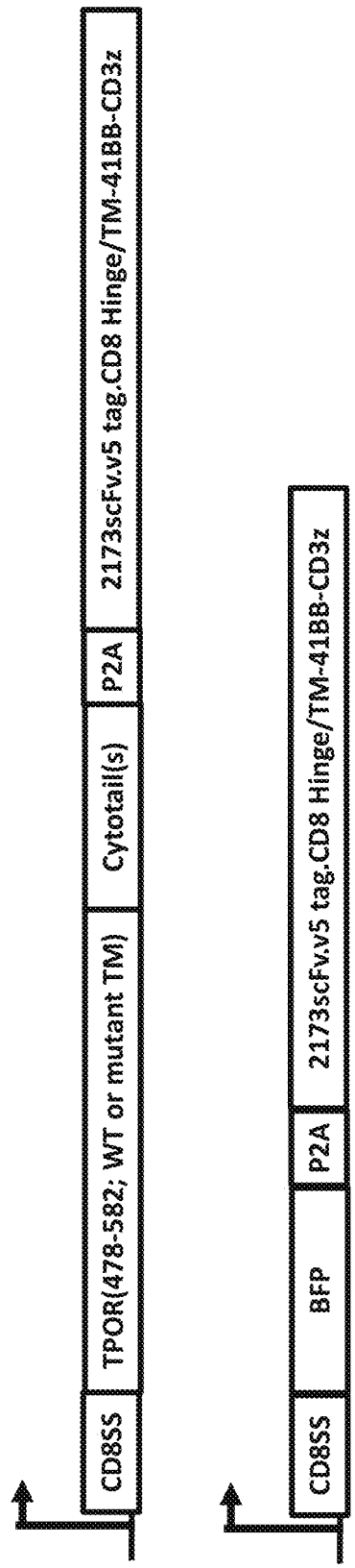
FIG. 2 shows a schematic of a vector of the disclosure that can be used to co-express the CACCR and CAR of the disclosure. One or more cytotails may be joined in tandem to mimic signaling from one or more cytokines. A schematic diagram of the vector expressing the control BFP (blue fluorescent protein) CAR is also shown.

In some embodiments, expression of the CACCR and the CAR are expressed as a single polypeptide chain, separated by a linker. FIG. 2 shows a schematic of a vector that can be used to co-express the CACCR and CAR of the disclosure. One or more recruiting domains may be joined in tandem to mimic signaling from one or more cytokines.

II. CAR-Bearing Immune Cells

Provided herein are engineered immune cells comprising a polynucleotide encoding a chimeric antigen receptor (CAR) and a CACCR of the disclosure; and provided herein are engineered immune cells expressing a chimeric antigen receptor (CAR-I cell) and a CACCR of the disclosure. Examples of immune cells include T-cells, e.g., alpha/beta T-cells and gamma/delta T-cells, B cells, natural killer (NK) cells, natural killer T (NKT) cells, invariant NKT cells, mast cells, myeloic-derived phagocytes, dendritic cells, killer dendritic cells, macrophages, and monocytes. Immune cells also refer to cells derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells.

Accordingly in some embodiments, provided herein are CAR-T-cells comprising a CACCR of the disclosure.

In some embodiments, a CAR can comprise an extracellular ligand-binding domain (e.g., a single chain variable fragment (scFv)), a transmembrane domain, and an intracellular signaling domain. In some embodiments, the extracellular ligand-binding domain, transmembrane domain, and intracellular signaling domain are in one polypeptide, i.e., in a single chain. Multichain CARs and polypeptides are also provided herein. In some embodiments, the multichain CARs comprise: a first polypeptide comprising a transmembrane domain and at least one extracellular ligand-binding domain, and a second polypeptide comprising a transmembrane domain and at least one intracellular signaling domain, wherein the polypeptides assemble together to form a multichain CAR.

The extracellular ligand-binding domain of a CAR specifically binds to a target of interest. The target of interest can be any molecule of interest, including, for example without limitation BCMA, EGFRvIII, Flt-3, WT-1, CD20, CD23, CD30, CD38, CD70, CD33, CD133, LeY, NKG2D, CS1, CD44v6, ROR1, CD19, Claudin-18.2 (Claudin-18A2, or Claudin18 isoform 2), DLL3 (Delta-like protein 3, Drosophila Delta homolog 3, Delta3), Muc17 (Mucin17, Muc3, Muc3), FAP alpha (Fibroblast Activation Protein alpha), Ly6G6D (Lymphocyte antigen 6 complex locus protein G6d, c6orf23, G6D, MEGT1, NG25), and/or RNF43 (E3 ubiquitin-protein ligase RNF43, RING finger protein 43).

In some embodiments, the extracellular ligand-binding domain of a CAR comprises an scFv comprising the light chain variable (VL) region and the heavy chain variable (VH) region of a target antigen specific monoclonal antibody joined by a flexible linker. Single chain variable region fragments are made by linking light and/or heavy chain variable regions by using a short linking peptide (Bird et al., Science 242:423-426, 1988) (e.g. glycine-serine containing linkers). In general, linkers can be short, flexible polypeptides and are generally comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The intracellular signaling domain of a CAR according to the invention is responsible for intracellular signaling following the binding of extracellular ligand-binding domain to the target resulting in the activation of the immune cell and immune response (Signals 1 and/or 2). The intracellular signaling domain has the ability to activate of at least one of the normal effector functions of the immune cell in which the CAR is expressed. For example, the effector function of a T cell can be a cytolytic activity or helper activity including the secretion of cytokines.

In some embodiments, an intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability. Intracellular signaling domains comprise two distinct classes of cytoplasmic signaling sequences: those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRζ, FcRγ, FcRβ, FcRε, CD3γ, CD3δ, CD3ε, CD5, CD22, CD79a, CD79b and CD66d. In some embodiments, the intracellular signaling domain of the CAR can comprise the CD3ζ signaling domain. In some embodiments the intracellular signaling domain of the CAR of the invention comprises a domain of a co-stimulatory molecule.

In some embodiments, the intracellular signaling domain of a CAR of the invention comprises a part of co-stimulatory molecule selected from the group consisting of fragment of 41BB (GenBank: AAA53133.) and CD28 (NP_006130.1).

CARs are expressed on the surface membrane of the cell. Thus, the CAR comprises a transmembrane domain. Suitable transmembrane domains for a CAR disclosed herein have the ability to (a) be expressed at the surface of a cell, preferably an immune cell such as, for example without limitation, lymphocyte cells or Natural killer (NK) cells, and (b) interact with the ligand-binding domain and intracellular signaling domain for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T cell receptor such as α,β, γ or δ, polypeptide constituting CD3 complex, IL-2 receptor p55 (α chain), p75 (β chain) or γ chain, subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8α chain (e.g., NP_001139345.1). The transmembrane domain can further comprise a stalk domain between the extracellular ligand-binding domain and said transmembrane domain. A stalk domain may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4, or CD28, or from all or part of an antibody constant region. Alternatively the stalk domain may be a synthetic sequence that corresponds to a naturally occurring stalk sequence, or may be an entirely synthetic stalk sequence. In some embodiments said stalk domain is a part of human CD8α chain (e.g., NP_001139345.1). In another particular embodiment, said transmembrane and hinge domains comprise a part of human CD8α chain. In some embodiments, the intracellular signaling domain comprises a CD3ζ signaling domain. In some embodiments, the intracellular signaling domain comprises a CD3 ζ signaling domain and additionally a second signaling domain. In some embodiments, the intracellular signaling domain comprises a CD3ζ signaling domain and a 4-1BB signaling domain. In some embodiments, CARs disclosed herein can comprise an extracellular ligand-binding domain that specifically binds BCMA or EGFRvIII, CD8α human hinge and transmembrane domains, the CD3ζ signaling domain, and 4-1BB signaling domain. In some embodiments, the EGFRvIII specific CAR comprises the amino acid sequence of SEQ ID NO: 140. In some embodiments, the BCMA specific CAR comprises the amino acid sequence of SEQ ID NO: 141 or 142, with or without a signal sequence.

In some aspects, the CAR-immune cell is a BCMA CAR-T cell comprising a CACCR of the disclosure. In some embodiments, the CACCR of the BCMA CAR-T cell comprises a transmembrane/JAK-binding domain of amino acids 478-582 of the naturally occurring TPOR/MPLR receptor of SEQ ID NO: 6, with H499L, S505N, and W515K triple substitutions, or S505N and W515K double substitutions (e.g., SEQ ID NO: 12 or 13). In some embodiments, the CACCR further comprises a recruiting domain from IL2Rb. In some embodiments, the CACCR of the BCMA CAR-T cell further comprises a recruiting domain from IL2Rb (393-433,518-551) or IL2Rb (339-379,393-433,518-551) (e.g., SEQ ID NO: 77 or 78). In some embodiments, the BCMA specific CAR comprises the amino acid sequence of SEQ ID NO: 141 or 142, with or without a signal sequence. In some embodiments, the BCMA CAR-T cells comprise a CACCR that comprises the amino acid sequence of SEQ ID NO: 113, 114, or 116, with or without a signal sequence.

In some embodiments, a CAR can be introduced into an immune cell as a transgene via a plasmid vector. In some embodiments, the plasmid vector can also contain, for example, a selection marker which provides for identification and/or selection of cells which received the vector.

Table 4 provides exemplary sequences of CAR components that can be used in the CARs disclosed herein and the antibody and/or CAR sequences exemplified herein.

TABLE 4

| Domain | Amino acid sequence | SEQ ID |
|---|---|---|
| V5 epitope tag | IPNPLLGLDST | 99 |
| 2173 scFv | EIQLVQSGAEVKKPGESLRISCKGSGFNIEDYYIH WVRQMPGKGLEWMGRIDPENDETKYGPIFQGH VTISADTSINTVYLQWSSLKASDTAMYYCAFRG GVYWGQGTTVTVSSGGGGSGGGGSGGGGSGGG GSDVVMTQSPDSLAVSLGERATINCKSSQSLLDS DGKTYLNWLQQKPGQPPKRLISLVSKLDSGVPD RFSGSGSGTDFTLTISSLQAEDVAVYYCWQGTHF PGTFGGGTKVEIK | 100 |
| CD8 hinge and transmembrane | TTTPAPRPPTPAPTIASQPLSLRPEACRPAAGGAV HTRGLDFACDIYIWAPLAGTCGVLLLSLVITLYC | 101 |
| 4-1BB intracellular signaling | KRGRKKLLYIFKQPFMRPVQTTQEEDGCSCRFPE EEEGGCEL | 102 |
| CD3z intracellular signaling | RVKFSRSADAPAYQQGQNQLYNELNLGRREEYD VLDKRRGRDPEMGGKPRRKNPQEGLYNELQKD KMAEAYSEIGMKGERRRGKGHDGLYQGLSTAT KDTYDALHMQALPPR | 103 |
| BFP | MSELIKENMHMKLYMEGTVDNHHFKCTSEGEG KPYEGTQTMRIKVVEGGPLPFAFDILATSFLYGS KTFINHTQGIPDFFKQSFPEGFTWERVTTYEDGG VLTATQDTSLQDGCLIYNVKIRGVNFTSNGPVM QKKTLGWEAFTETLYPADGGLEGRNDMALKLV GGSHLIANIKTTYRSKKPAKNLKMPGVYYVDYR LERIKEANNETYVEQHEVAVARYCDLPSKLGHK LN | 104 |
| P2A | GSGATNFSLLKQAGDVEENPGP | 105 |
| 2173 anti-EGFRvIII scFv | MALPVTALLLPLALLLHAARPEIQLVQSGAEVKK PGESLRISCKGSGFNIEDYYIHWVRQMPGKGLEW MGRIDPENDETKYGPIFQGHVTISADTSINTVYLQ WSSLKASDTAMYYCAFRGGVYWGQGTTVTVSS GGGGSGGGGSGGGGSGGGGSDVVMTQSPDSLA VSLGERATINCKSSQSLLDSDGKTYLNWLQQKP GQPPKRLISLVSKLDSGVPDRFSGSGSGTDFTLTIS SLQAEDVAVYYCWQGTHFPGTFGGGTKVEIKTT TPAPRPPTPAPTIASQPLSLRPEACRPAAGGAVHT RGLDFACDIYIWAPLAGTCGVLLLSLVITLYCKR GRKKLLYIFKQPFMRPVQTTQEEDGCSCRFPEEE EGGCELRVKFSRSADAPAYKQGQNQLYNELNLG RREEYDVLDKRRGRDPEMGGKPRRKNPQEGLY NELQKDKMAEAYSEIGMKGERRRGKGHDGLYQ GLSTATKDTYDALHMQALPPR | 140 |
| P5A2 anti-BCMAscFv | EVQLLESGGGLVQPGGSLR LSCAASGFTFSSYAMNWVR QAPGKGLEWVSAISDSGGS TYYADSVKGRFTISRDNSK NTLYLQMNSLRAEDTAVYY CARYWPMDIWGQGTLVTVS SGGGGSGGGGSGGGGSEIV LTQSPGTLSLSPGERATLS CRASQSVSSSYLAWYQQKP GQAPRLLMYDASIRATGIP DRFSGSGSGTDFTLTISRL EPEDFAVYYCQQYGSWPLT FGQGTKVEIK | 141 |

TABLE 4-continued

Sequences relating to CARs

| Domain | Amino acid sequence | SEQ ID |
|---|---|---|
| P5A2 anti-BCMACAR | (M A L P V T A L L L P L A L L L H A A<br>R P)E V Q L L E S G G G L V Q P G G S L<br>R L S C A A S G F T F S S Y A M N W V R<br>Q A P G K G L E W V S A I S D S G G S T<br>Y Y A D S V K G R F T I S R D N S K N T<br>L Y L Q M N S L R A E D T A V Y Y C A R<br>Y W P M D I W G Q G T L V T V S S G G G<br>G S G G G G S G G G G S E I V L T Q S P<br>G T L S L S P G E R A T L S C R A S Q S<br>V S S S Y L A W Y Q Q K P G Q A P R L L<br>M Y D A S I R A T G I P D R F S G S G S<br>G T D F T L T I S R L E P E D F A V Y Y<br>C Q Q Y G S W P L T F G Q G T K V E I K<br>G S G G G G S C P Y S N P S L C S G G G<br>G S C P Y S N P S L C S G G G G S T T T<br>P A P R P P T P A P T I A S Q P L S L R<br>P E A C R P A A G G A V H T R G L D F A<br>C D I Y I W A P L A G T C G V L L L S L<br>V I T L Y C K R G R K K L L Y I F K Q P<br>F M R P V Q T T Q E E D G C S C R F P E<br>E E E G G C E L R V K F S R S A D A P A<br>Y Q Q G Q N Q L Y N E L N L G R R E E Y<br>D V L D K R R G R D P E M G G K P R R K<br>N P Q E G L Y N E L Q K D K M A E A Y S<br>E I G M K G E R R R G K G H D G L Y Q G<br>L S T A T K D T Y D A L H M Q A L P P R) | 142 |

In some embodiments, the CAR-immune cell (e.g., CAR-T cell) of the disclosure comprises a polynucleotide encoding a suicide polypeptide, such as for example RQR8. See, e.g., WO2013153391A, which is hereby incorporated by reference in its entirety. In some embodiments, a suicide polypeptide is expressed on the surface of the cell. In some embodiments, a suicide polypeptide is included in the CAR construct. In some embodiments, a suicide polypeptide is not part of the CAR construct.

In some embodiments, the extracellular domain of any one of CARs disclosed herein may comprise one or more epitopes specific for (specifically recognized by) a monoclonal antibody. These epitopes are also referred to herein as mAb-specific epitopes. Exemplary mAb-specific epitopes are disclosed in International Patent Publication No. WO 2016/120216, which is incorporated herein in its entirety. In these embodiments, the extracellular domain of the CARs comprise antigen binding domains that specifically bind to a target of interest and one or more epitopes that bind to one or more monoclonal antibodies (mAbs). CARs comprising the mAb-specific epitopes can be single-chain or multichain.

The inclusion of epitopes specific for monoclonal antibodies in the extracellular domain of the CARs described herein allows sorting and depletion of engineered immune cells expressing the CARs. In some embodiments, allowing for depletion provides a safety switch in case of deleterious effects, e.g., upon administration to a subject.

Methods of preparing engineered immune cells for use in immunotherapy are also provided herein. In some embodiments, the methods comprise introducing a CACCR and a CAR into immune cells, and expanding the cells. In some embodiments, the invention relates to a method of engineering an immune cell comprising: providing a cell and expressing a CACCR, and expressing at the surface of the cell at least one CAR. In some embodiments, the method comprises: transfecting the cell with at least one polynucleotide encoding a CACCR, and at least one polynucleotide encoding a CAR, and expressing the polynucleotides in the cell. In some embodiments, the method comprises: transfecting the cell with at least one polynucleotide encoding a CACCR, at least one polynucleotide encoding a CAR, and expressing the polynucleotides in the cell.

In some embodiments, the polynucleotides encoding the CACCR and CAR are present in one or more expression vectors for stable expression in the cells. In some embodiments, the polynucleotides are present in viral vectors for stable expression in the cells. In some embodiments, the viral vectors may be for example, lentiviral vectors or adenoviral vectors.

In some embodiments, polynucleotides encoding polypeptides according to the present disclosure can be mRNA which is introduced directly into the cells, for example by electroporation. In some embodiments, CytoPulse electroporation technology, such as PulseAgile, can be used to transiently permeabilize living cells for delivery of material into the cells (e.g. U.S. Pat. No. 6,078,490; PCT/US2011/000827; and PCT/US2004/005237). Parameters can be modified in order to determine conditions for high transfection efficiency with minimal mortality.

Also provided herein are methods of transfecting an immune cell, e.g a T-cell. In some embodiments, the method comprises: contacting a T-cell with RNA and applying to the T-cell an agile pulse sequence. In some embodiments, a method of transfecting an immune cell (e.g. T-cell) comprising contacting the immune cell with RNA and applying to the cell an agile pulse sequence.

In some embodiments, the method can further comprise a step of genetically modifying a cell by inactivating at least one gene expressing, for example without limitation, a component of the TCR, a target for an immunosuppressive agent, an HLA gene, and/or an immune checkpoint protein such as, for example, PDCD1 or CTLA-4. By inactivating a gene it is intended that the gene of interest is not expressed in a functional protein form. In some embodiments, the gene to be inactivated is selected from the group consisting of, for example without limitation, TCRα, TCRβ, CD52, GR, deoxycytidine kinase (DCK), PD-1, and CTLA-4. In some embodiments the method comprises inactivating one or more genes by introducing into the cells a rare-cutting endonuclease able to selectively inactivate a gene by selective DNA cleavage. In some embodiments the rare-cutting endonuclease can be, for example, a transcription activator-like effector nuclease (TALE-nuclease) or CRISPR-based endonuclease (e.g Cas-9 or Cas12a).

In another aspect, a step of genetically modifying cells can comprise: modifying immune cells (e.g. T-cells) by inactivating at least one gene expressing a target for an immunosuppressive agent, and; expanding the cells, optionally in presence of the immunosuppressive agent.

In some embodiments, the engineered immune cells (e.g. T-cells) provided herein exhibit improved cytotoxicity, increased expansion, and/or increased levels of memory phenotype markers relative to engineered immune cells that do not express the CACCR.

In some embodiments, the engineered immune cells (e.g. T-cells) provided herein exhibit (i) increased in vivo persistence, (ii) increased STAT activation, (iii) increased cytotoxicity, (iv) increased levels of memory phenotype markers, (v) increased expansion (proliferation), or combinations of these functional features constitutively, relative to engineered immune cells that do not express the CACCR. In some embodiments, the improvement in the one or more functional features described herein tunable, dependent upon the mutations/modifications introduced to the CACCR. In some embodiments, STATs activated by the engineered immune cell comprising one or more CACCRs disclosed are STAT1, STAT2, STAT3, STAT4, STAT5, STAT6, or combinations thereof. In one embodiment, memory phenotype markers increased or maintained by the immune cell comprising the CACCR include stem cell memory (Tscm) marker and central memory (Tcm) marker.

In some embodiments, the improvement in one or more functional features exhibited by an engineered immune cell comprising an CACCR provided herein is at least about 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 25 fold, 30 fold, 40 fold, 50 fold, 60 fold, 70 fold, 80 fold, 90 fold, 100 fold, 125 fold, 150 fold, 200 fold, 250 fold, 300 fold, 350 fold, 400 fold, 450 fold, or even about 10500 fold, including values and ranges therebetween, compared to an immune cell that does not express the CACCR.

In some embodiments, the improvement in one or more functional features exhibited by an engineered immune cell comprising a CACCR provided herein is at least about 10%, 20%, 25%, 30%, 35%, 40%, 45%, 50%, 55%, 60%, 70%, 75%, 80%, 90%, 100%, 125%, 150%, 200%, 250%, 300%, 350%, 400%, or even about 80%500%, including values and ranges therebetween, compared to an engineered immune cell that does not express the CACCR.

III. Therapeutic Methods

Provided herein are pharmaceutical compositions comprising cells bearing the CACCRs and CARs of the disclosure.

Engineered CACCR-bearing and CAR-bearing immune cells (e.g. T-cells) obtained by the methods described above, or cell lines derived from such engineered immune cells, can be used as a medicament. In some embodiments, such a medicament can be used for treating a disorder such as for example a viral disease, a bacterial disease, a cancer, an inflammatory disease, an immune disease, or an aging-associated disease. In some embodiments, the cancer is a solid cancer. In some embodiments the cancer is a liquid cancer. The cancer can be selected from the group consisting of gastric cancer, sarcoma, lymphoma, leukemia, head and neck cancer, thymic cancer, epithelial cancer, salivary cancer, liver cancer, stomach cancer, thyroid cancer, lung cancer, ovarian cancer, breast cancer, prostate cancer, esophageal cancer, pancreatic cancer, glioma, leukemia, multiple myeloma, renal cell carcinoma, bladder cancer, cervical cancer, choriocarcinoma, colon cancer, oral cancer, skin cancer, and melanoma. In some embodiments, the subject is a previously treated adult subject with locally advanced or metastatic melanoma, squamous cell head and neck cancer (SCHNC), ovarian carcinoma, sarcoma, or relapsed or refractory classic Hodgkin's Lymphoma (cHL).

In some embodiments, engineered immune cells, or a cell line derived from the engineered immune cells, can be used in the manufacture of a medicament for treatment of a disorder in a subject in need thereof. In some embodiments, the disorder can be, for example, a cancer, an autoimmune disorder, or an infection.

Also provided herein are methods for treating subjects in need of such treatment.

As used herein, the term "subject" refers to any vertebrate including, without limitation, humans and other primates (e.g., chimpanzees, cynomologous monkeys, and other apes and monkey species), farm animals (e.g., cattle, sheep, pigs, goats and horses), domestic mammals (e.g., dogs and cats), laboratory animals (e.g., rabbits, rodents such as mice, rats, and guinea pigs), and birds (e.g., domestic, wild and game birds such as chickens, turkeys and other gallinaceous birds, ducks, geese, and the like). In some embodiments, the subject is a mammal. In exemplary embodiments, the subject is a human.

In some embodiments the method comprises providing immune cells of the disclosure, bearing the CACCRs and CARs described herein to a subject in need thereof.

In some embodiments, CACCR and CAR-bearing T-cells of the invention can undergo robust in vivo T-cell expansion and can persist for an extended amount of time.

Methods of treatment of the invention can be ameliorating, curative or prophylactic. The method of the invention may be either part of an autologous immunotherapy or part of an allogenic immunotherapy treatment.

In another aspect, the invention provides a method of inhibiting tumor growth or progression in a subject who has a tumor, comprising administering to the subject an effective amount of CACCR-expressing and CAR-expressing immune cells as described herein. In another aspect, the invention provides a method of inhibiting or preventing metastasis of cancer cells in a subject, comprising administering to the subject in need thereof an effective amount of engineered immune cells as described herein. In another aspect, the invention provides a method of inducing tumor regression in a subject who has a tumor, comprising administering to the subject an effective amount of engineered immune cells as described herein.

In some embodiments, the engineered T-cells herein can be administered parenterally in a subject.

Also provided is the use of any of the engineered T-cells provided herein in the manufacture of a medicament for the treatment of cancer or for inhibiting tumor growth or progression in a subject in need thereof.

In some embodiments, treatment can be administrated into subjects undergoing an immunosuppressive treatment. Indeed, the invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the subject. The administration of the cells or population of cells according to the invention may be carried out in any convenient manner, including by aerosol inhalation, injection, ingestion, transfusion, implantation or transplantation. The compositions described herein may be administered to a subject subcutaneously, intradermally, intratumorally, intranodally, intramedullary, intramuscularly, by intravenous or intralymphatic injection, or intraperitoneally. Cells bearing the CACCRs and CARs of the disclosure or the pharmaceutical compositions thereof may be administered via one or more of the following routes of administration: intravenous, intraocular, intravitreal, intramuscular, subcutaneous, topical, oral, transdermal, intraperitoneal, intraorbital, by implantation, by inhalation, intrathecal, intraventricular, via the ear, or intranasal.

In some embodiments the administration of the cells or population of cells (bearing the CACCRs and CARs of the disclosure) can comprise administration of, for example, about $10^4$ to about $10^9$ cells per kg body weight including all integer values of cell numbers within those ranges. In some embodiments the administration of the cells or population of cells can comprise administration of about $10^4$ to $10^5$ cells per kg body weight, $10^5$ to $10^6$ cells per kg body weight, $10^6$ to 10' cells per kg body weight, 10' to $10^8$ cells per kg body weight, or $10^8$ to $10^9$ cells per kg body weight. The cells or population of cells can be administrated in one or more doses. In some embodiments, said effective amount of cells can be administered as a single dose. In some embodiments, said effective amount of cells can be administered as more than one dose over a period time. Timing of administration is within the judgment of managing physician and depends on the clinical condition of the subject. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired. In some embodiments, an effective amount of cells or composition comprising those cells are administrated parenterally. In some embodiments, administration can be an intravenous administration. In some embodiments, administration can be directly done by injection within a tumor.

The methods can further comprise administering one or more agents to a subject prior to administering the engineered immune cells bearing a CAR and a CACCR provided herein. In certain embodiments, the agent is a lymphodepleting (preconditioning) regimen. For example, methods of lymphodepleting a subject in need of such therapy comprise administering to the subject specified beneficial doses of cyclophosphamide (between 200 mg/m²/day and 2000 mg/m²/day, about 100 mg/m²/day and about 2000 mg/m²/day; e.g., about 100 mg/m²/day, about 200 mg/m²/day, about 300 mg/m²/day, about 400 mg/m²/day, about 500 mg/m²/day, about 600 mg/m²/day, about 700 mg/m²/day, about 800 mg/m²/day, about 900 mg/m²/day, about 1000 mg/m²/day, about 1500 mg/m²/day or about 2000 mg/m²/day) and specified doses of fludarabine (between 20 mg/m²/day and 900 mg/m²/day, between about 10 mg/m²/day and about 900 mg/m²/day; e.g., about 10 mg/m²/day, about 20 mg/m²/day, about 30 mg/m²/day, about 40 mg/m²/day, about 40 mg/m²/day, about 50 mg/m²/day, about 60 mg/m²/day, about 70 mg/m²/day, about 80 mg/m²/day, about 90 mg/m²/day, about 100 mg/m²/day, about 500 mg/m²/day or about 900 mg/m²/day). An exemplary dosing regimen involves treating a subject comprising administering daily to the patient about 300 mg/m²/day of cyclophosphamide in combination or before or after administering about 30 mg/m²/day of fludarabine for three days prior to administration of a therapeutically effective amount of engineered immune cells to the patient.

In some embodiments, notably in the case when the engineered cells provided herein have been gene edited to eliminate or minimize surface expression of CD52, lymphodepletion further comprises administration of an anti-CD52 antibody, such as alemtuzumab. In some embodiments, the CD52 antibody is administered at a dose of about 1-20 mg/day IV, e.g., about 13 mg/day IV for 1, 2, 3 or more days. The antibody can be administered in combination with, before, or after administration of other elements of a lymphodepletion regime (e.g., cyclophosphamide and/or fludarabine).

In certain embodiments, compositions comprising CACCR and CAR-expressing immune effector cells disclosed herein may be administered in conjunction with any number of chemotherapeutic agents.

IV. Kits and Articles of Manufacture

The present disclosure provides kits comprising any one or more of the CACCRs and CAR-bearing cells described herein, and pharmaceutical compositions thereof. The present disclosure also provides articles of manufacture comprising any one or more of the CACCRs and CAR-bearing CAR-I cells described herein, pharmaceutical compositions thereof, and kits described herein.

The following examples are included for illustrative purposes and are not intend to limit the scope of the disclosure.

All patent and non-patent documents referenced throughout this disclosure are incorporated by reference herein in their entirety for all purposes

EXAMPLES

Example 1

Identification of TpoR TM Mutants that Constitutively Activate Cytokine Signaling A prototypic constitutively active chimeric cytokine receptor (CACCR) was designed, using sequences from the thrombopoietin receptor (TpoR). TpoR is capable of activating the JAK-Stat signaling pathway and signals as homodimeric receptor. Single point mutations (amino acid substitutions) in TpoR activity have been shown to modulate receptor activity (Proc Natl Acad Sci USA. 2013 Feb. 12; 110(7):2540-5; FASEB J. 2011 July; 25(7):2234-44; J Biol Chem. 2016 Feb. 5; 291(6):2974-87). In this example, a constitutively active chimeric cytokine receptor was engineered from a naturally occurring TpoR receptor: the extracellular domain of the natural TpoR receptor was removed, so it no longer has ligand-binding ability; 1-3 mutations were introduced into its transmembrane domain; and the TpoR cytotail was substituted with that of the desired/described cytokine receptor. FIG. 1 shows a schematic of the engineered constitutively active chimeric cytokine receptor.

To demonstrate the utility of the constitutively active chimeric cytokine receptor in the context of CAR-T-cells, each TpoR transmembrane (TM) variant was cloned into a lentiviral vector encoding a second generation EGFRvIII-specific CAR (2173 scFv; described in Sci Transl Med. 2015 Feb. 18; 7(275): 275ra22). To permit stoichiometric co-expression of the cytokine receptor and the CAR, both genes were linked via a P2A peptide. To facilitate the detection of transduced cells, a v5 epitope tag (KPIPNPLLGLDST) SEQ ID NO: 144) was inserted between the scFv and CD8 hinge domain.

FIG. 2 shows a schematic of the lentiviral vector used to co-express the constitutively active chimeric cytokine receptor and the CAR.

Table 4 shows sequences relating to the constructs used.

A HEK293T-cell reporter assay was used to screen for TpoR TM variants capable of constitutive cytokine signaling. Briefly, 20,000 HEK293T-cells were plated into each well of a poly-L-lysine-coated 96-well flat-bottom plate and allowed to adhere overnight. A cytokine receptor-CAR construct (2.5 ng), a Stat response element that drives Firefly Luciferase (100 ng; Promega) and Renilla Luciferase control reporter vector (1 ng; Promega) were mixed in a final volume of 5 uL in Opti-MEM (Gibco) ("DNA mix"). As a negative control, cells were transfected with a BFP CAR construct that lacks all cytokine signaling domains. As a positive control, cells were transfected with a vector encoding full-length human EpoR (an erythropoietin receptor in place of the cytokine receptor-CAR construct) so that Stat5 signaling could be induced by the addition of exogenous recombinant human Epo. 0.3 uL Lipofectamine 2000 (Invitrogen) in 5 uL Opti-MEM was incubated at room temperature for 5 minutes and then added to the DNA mix. The mixture was incubated at room temperature for 20 minutes and the total volume of 10 uL was added to each well containing HEK-293T. 48 hours after transfection, Stat5 reporter activity was evaluated using the Dual-Glo Luciferase Assay System (Promega). Fold induction of Stat5 reporter activity was normalized to that of HEK293T-cells transfected with all vectors except for the cytokine receptor and that were left untreated.

Figure 3A:
FIGS. 3A-3B show the identification of TpoR transmembrane (TM) mutants that constitutively activate cytokine receptor signaling.
Figure 3B:
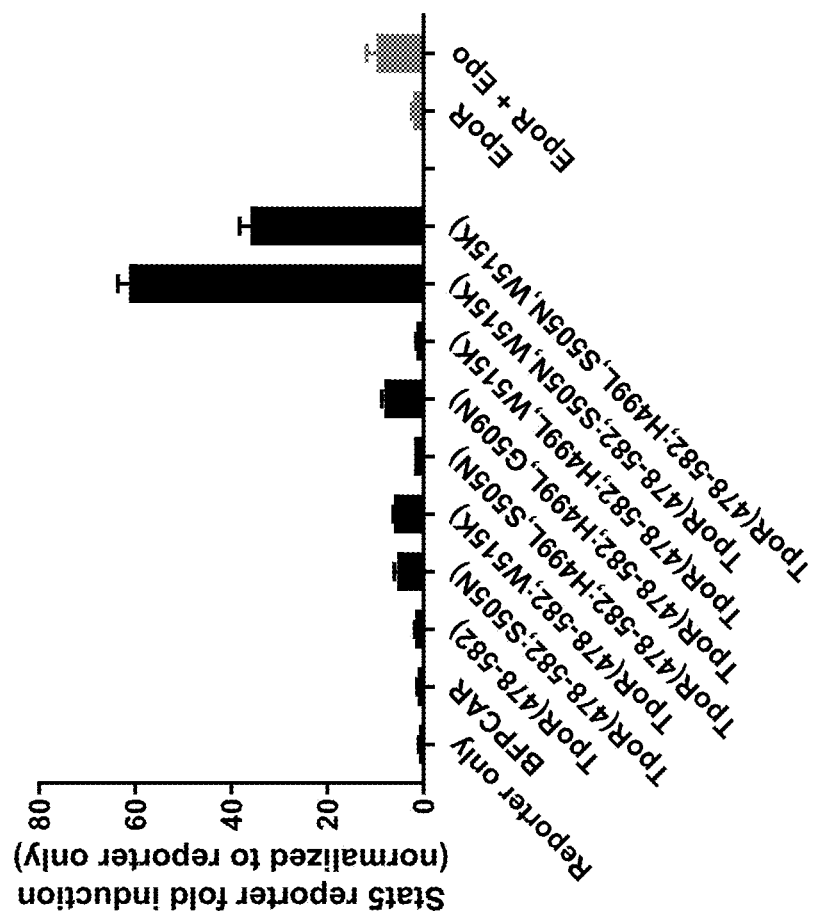

FIGS. 3a and 3b show the identification of TpoR TM mutants that constitutively activate cytokine receptor signaling. FIG. 3a shows a schematic of the lentiviral vector used. It bears the IL7R(316-459) cytotail to mimic IL7 signaling in CAR-T-cells. FIG. 3b shows Stat5 reporter activity as determined by the Dual-Glo luciferase assay. The cytokine receptor bearing the wildtype TpoR TM domain (TpoR(478-582)) did not spontaneously activate Stat5. The TpoR(478-582;S505N), TpoR(478-582;W515K) and TpoR (478-582;H499L,G509N) mutants led to weak Stat5 activation. The TpoR(478-582;H499L,S505N,W515K) permitted a moderate Stat5 activity, while the TpoR(478-582; S505N, W515K) generated the strongest Stat5 signal.

Example 2

Generation of CAR-T-Cells Expressing Constitutively Active Chimeric Cytokine Receptors We next tested whether these cytokine receptors signaled in the context of primary human CAR-T-cells. To make lentivirus encoding cytokine receptor-CARs, HEK293T-cells were plated at 0.45 million cells per mL in 2 mL of DMEM (Gibco) supplemented with 10% FBS (Hyclone) per well of a 6-well plate the day before transfection. On the day of transfection, the lentivirus was prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM was incubated at room temperature for 5 minutes and then added to the DNA mix. The mixture was incubated at room temperature for 20 minutes and the total volume of 500 uL was slowly added to the sides of the wells containing HEK293T. 1 day post-transfection, the media from each well of HEK293T-cells in the 6-well plate was replaced with 2 mL per well of T-cell transduction media, i.e., X-Vivo-15 supplemented with 10% FBS. 2 days post-transfection, The lentiviral supernatants from HEK293T-cells were harvested and passed through a 0.45 micron filter (EMD Millipore) to remove cell debris, concentrated 25-folds using the Lenti-X Concentrator (Takara Bio) according to manufacturer's instructions and flash-frozen in aliquots. Lentiviral titers were determined by thawing an aliquot of the frozen lentivirus, making 4-fold serial dilutions and performing limiting dilution titration on JurkaT-cells (Clone E6-1; ATCC). On Day 0, purified T-cells were activated in X-Vivo-15 medium (Lonza) supplemented with 100 IU/mL human IL-2 (Miltenyi Biotec), 10% FBS (Hyclone), and human T TransAct (Miltenyi Biotec, Cat# 130-111-160, 1:100 dilution) in a Grex-24 plate (Wilson Wolf, cat# 80192M). On Day2, T-cells were resuspended at 0.5 million cells per mL in T-cell transduction media, transduced with the respective lentiviral stocks at MOI=5 along with 100 IU/mL human IL-2 in a Grex-24 plate. On Day 5 when transduction was complete, cells were harvested and washed to remove residual IL-2. They were then resuspended in T-cell expansion media, i.e., X-Vivo-15 supplemented with 5% human AB serum (Gemini Bio), and each sample was divided equally into 2 parts, with one part receiving 100 IU/mL human IL-2 as per standard protocol, and the other receiving a lower concentration of 25 IU/mL human IL-2. Cells were expanded into larger G-Rex vessels (Wilson Wolf) as needed using T-cell expansion media and the respective concentrations of human IL-2. On Days 5, 9 and 14, the absolute number of T-cells in each sample was counted, and transduction efficiency was determined by detecting the percentage of T-cells that bound a FITC-conjugated v5 tag monoclonal antibody (Thermo Fisher) using flow cytometry. On Day 14 or 15, the CAR-T-cell products were cryopreserved and thawed as needed for further assays.

Figure 4A:
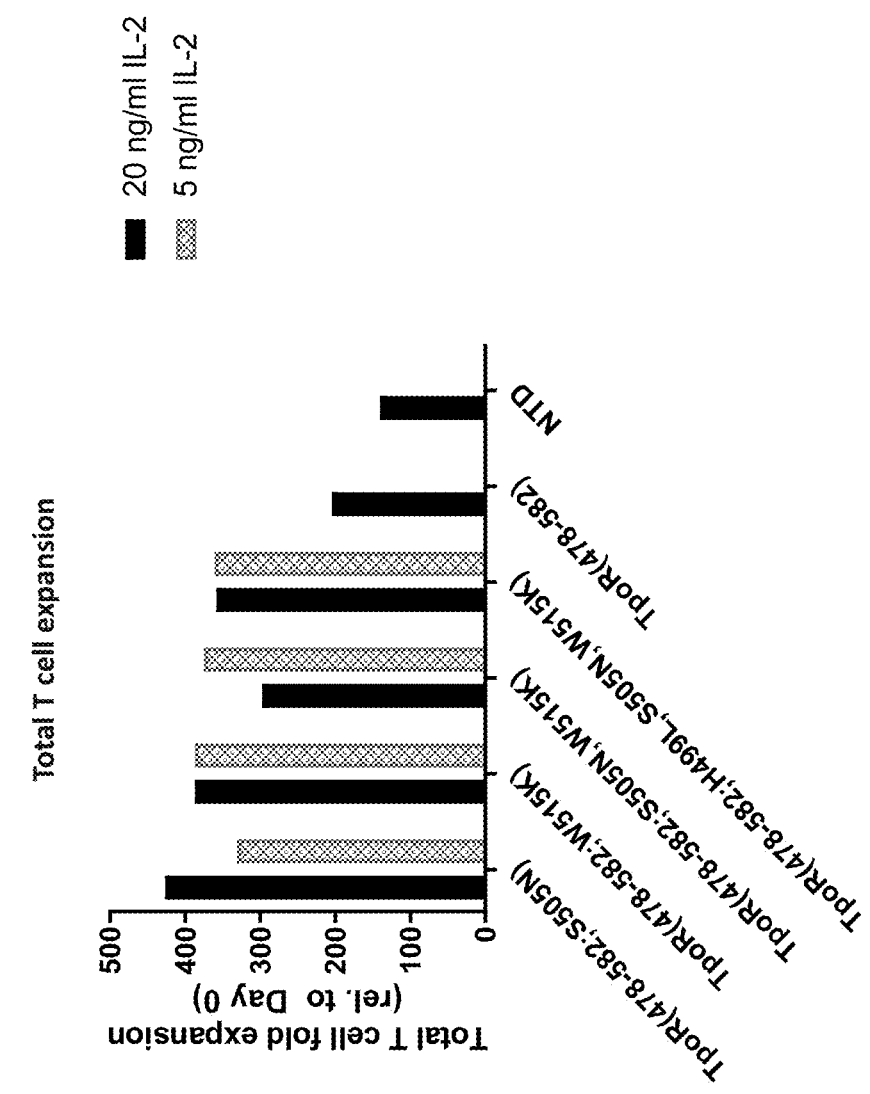
FIGS. 4A-4C show results for the expansion of CAR-T-cells coexpressing a constitutively active chimeric cytokine receptor.
Figure 4B:
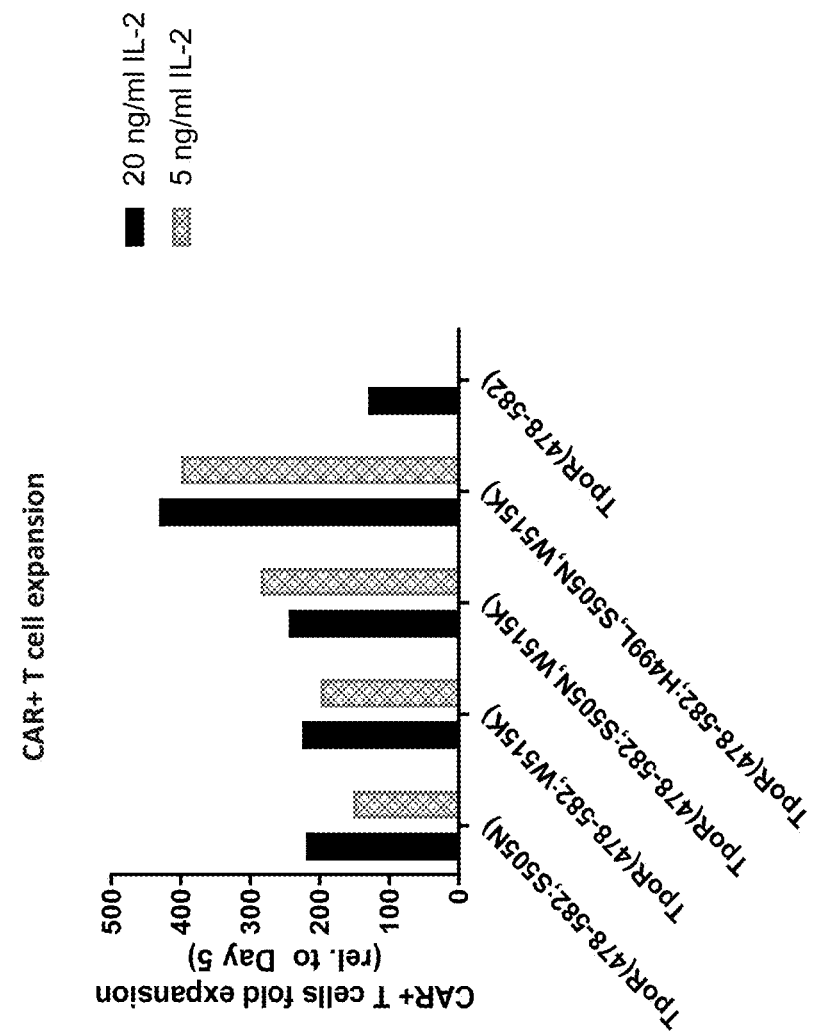
Figure 4C:
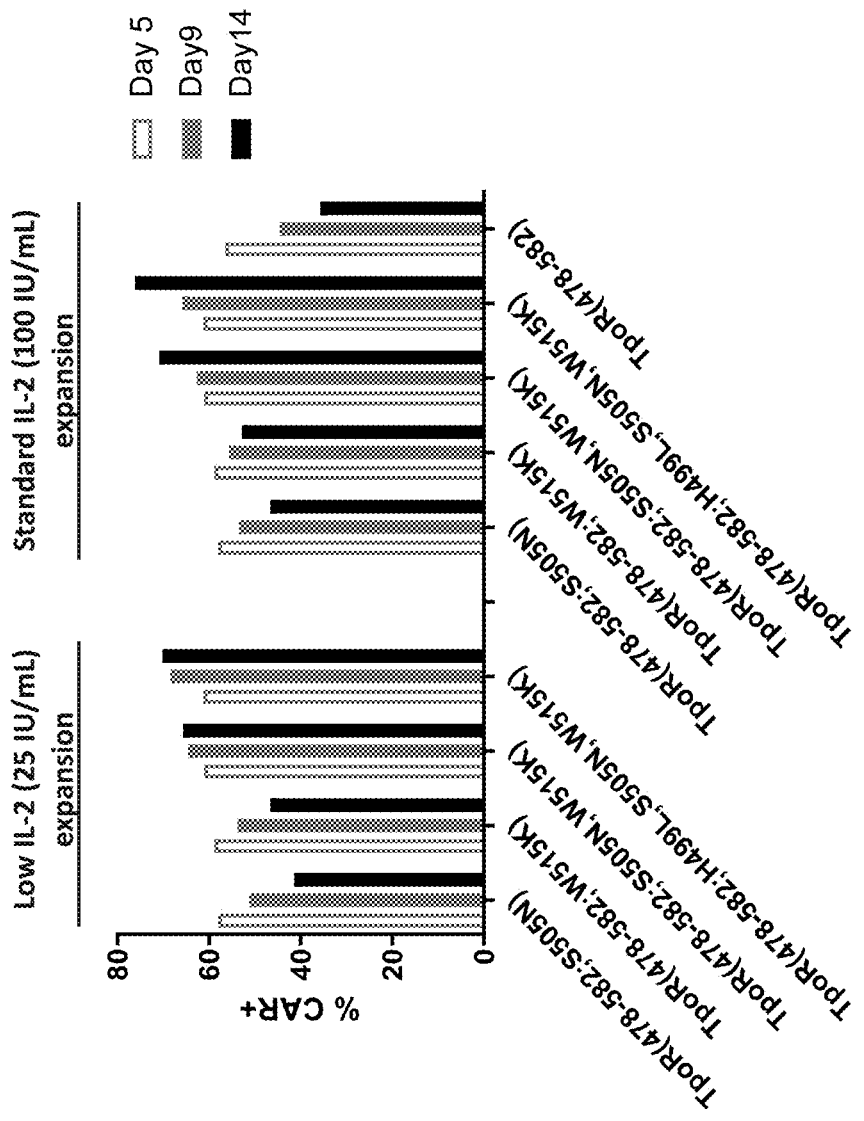

FIGS. 4a-4c show results for the generation of CAR-T-cells coexpressing a constitutively active chimeric cytokine receptor. Compared to CAR-T-cell cultures with the wild-type TpoR TM cytokine receptor (TpoR(478-582)), CAR-T-cell cultures bearing TpoR TM mutants underwent more robust expansion in terms of both total T-cell numbers (FIG. 4a) and CAR-T-cell numbers (FIG. 4b). FIGS. 4a-4c show that transduction efficiencies of TpoR TM mutants was equal or more better than their wildtype TpoR(478-582) counterparts. TpoR TM mutants permit a greater yield of CAR-T-cell product. Furthermore, expanding TpoR TM mutants in lower IL-2 concentrations did not impact CAR-T-cell expansion or yield (FIG. 4c).

On Day 14 of CAR-T-cell production, the memory phenotype of CAR-T-cells were determined. Briefly, samples were washed with PBS, Fc blocked, then stained with the following antibody cocktail diluted in PBS+1%BSA: BUV395-conjugated anti-human CD3, BV510-conjugated anti-human CD8, BV605-conjugated human CD4 and FITC-conjugated v5 tag (for CAR detection), PE/Cy7-conjugated anti-human CD62L (Biolegend) and BV785-conjugated anti-human CD45RO (Biolegend). Finally, samples were washed in PBS and cell pellets were resuspended in 130 uL PBS+1%BSA for FACS analysis.

Figure 5:
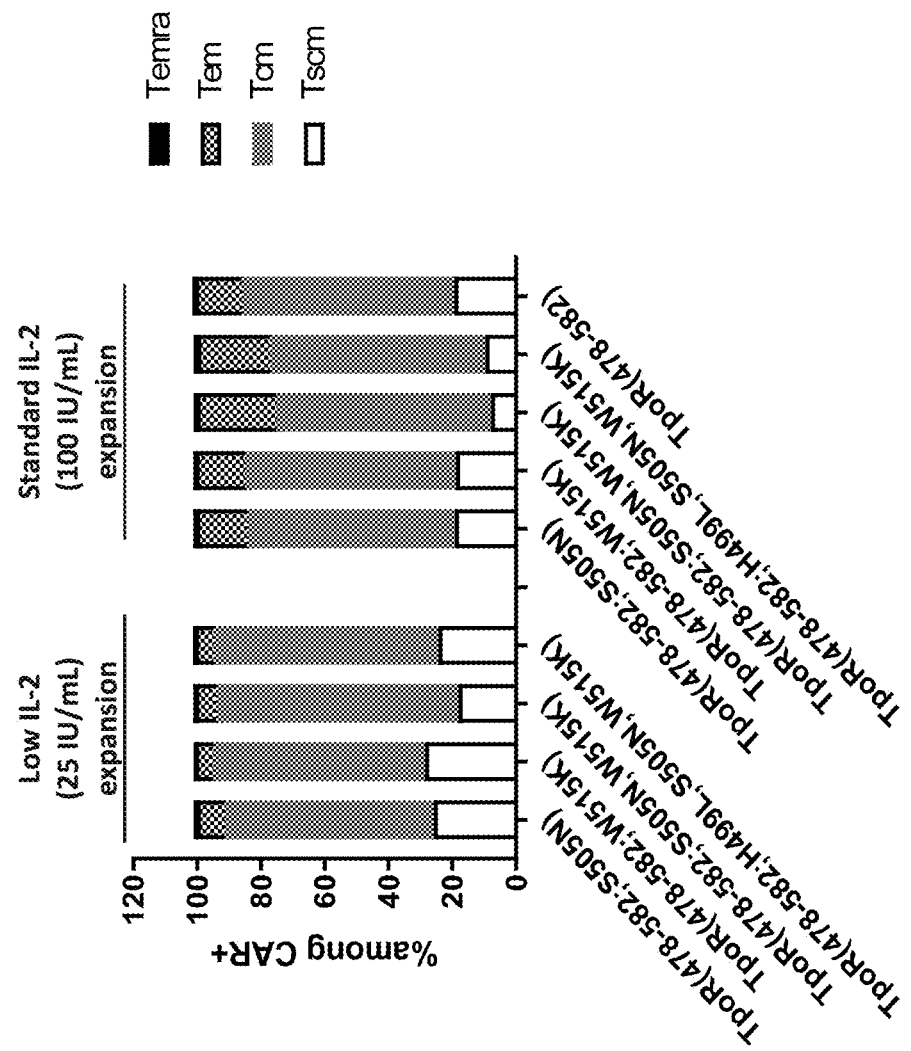
FIG. 5 shows differentiation and the memory T-cell subset distribution in the CAR-T-cell product, under different IL-2 conditions.

FIG. 5 shows the memory T-cell subset distribution in the CAR-T-cell product. Compared to their wildtype TpoR(478-582) counterpart, TpoR(478-582;W515K) and TpoR(478-582;H499L,G509N) mutants showed greater differentiation when expanded in the standard 100 IU/mL IL-2 conditions. Expansion in low IL-2 conditions ameliorated differentiation. In concert with standard concentrations of IL-2, the stronger Stat5 signaling induced by the TpoR(478-582; W515K) and TpoR(478-582;H499L,G509N) mutants may lead to accelerated CAR-T-cell differentiation, and that expansion in low IL-2 conditions may be more favorable in the context of CAR-T-cell expressing constitutive cytokine receptors.

Example 3

TpoR TM Mutants Constitutively Activate Cytokine Signaling in Human CAR-T-Cells

To determine strength of cytokine signaling mediated by TpoR TM mutants, CAR-T-cells bearing TpoR TM cytokine receptor variants were serum starved in 100 uL serum-free RPMI (Corning) for 4 hours in humidified incubator at 37° C. with 5% $CO_2$. As a positive control, exogenous recombinant human IL-7 (10 ng/mL; Miltenyi) was added during the last 30 minutes of the 4-hour serum starvation. After 4 hours, an antibody cocktail comprising BUV395-conjugated anti-human CD3 (Biolegend) and FITC-conjugated v5 tag monoclonal antibody (Thermo Fisher) were added to the cells and allowed to incubate for the final 20 minutes. Cells were then fixed by adding 35 uL of 16% paraformaldehyde to each 100 uL sample and allowed to incubate for 15 minutes at 37° C. Cells were then washed three times with PBS, and permeabilized in 100% cold methanol for 1 or 2 nights at −20° C. On the day of FACS analysis, cells were washed three times with PBS, Fc-blocked, and stained with AlexaFluor647-conjugated anti-mouse/human Stat5 (pY694) (BD Biosciences) diluted in PBS+1%BSA. After a 1 hour incubation at room temperature in the dark, cells were washed three times before FACS analysis.

Figure 6A:
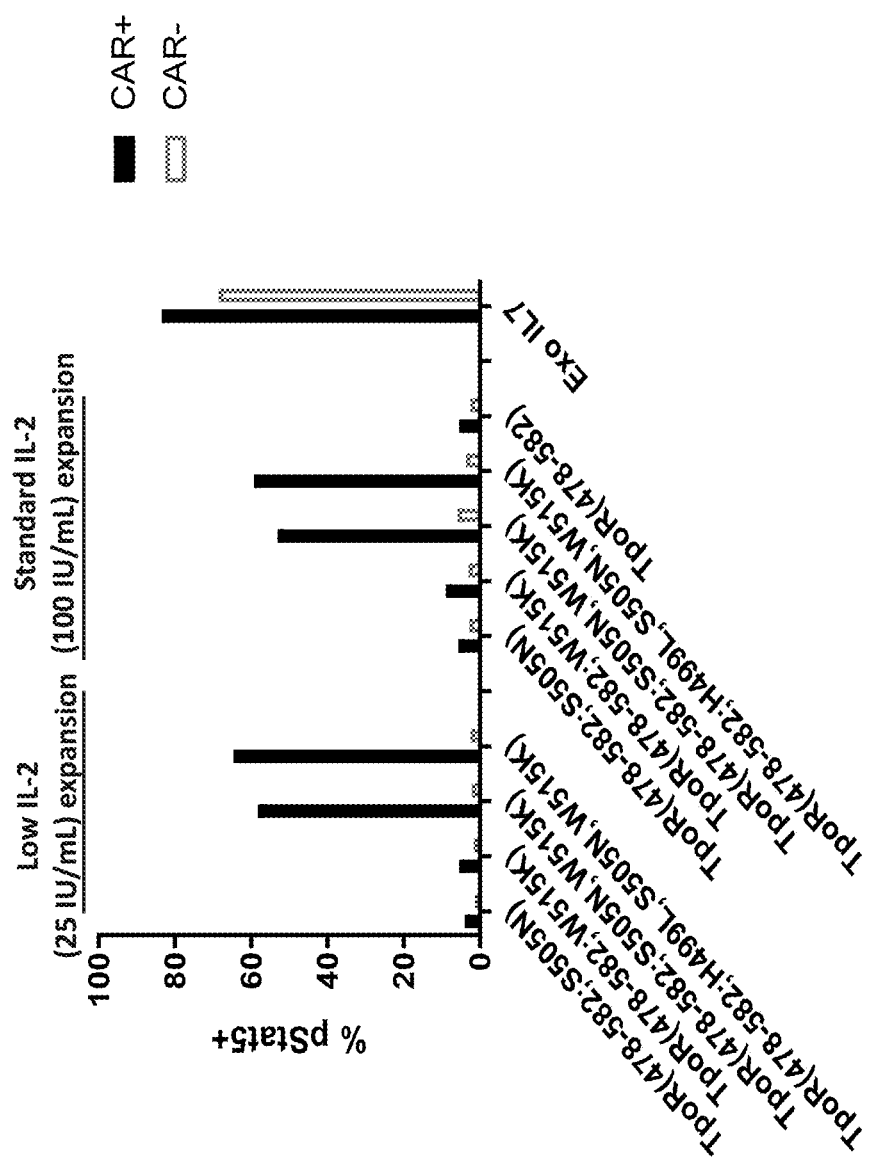
FIGS. 6A-6B show the extent of constitutive cytokine signaling mediated by each TpoR TM variant.
Figure 6B:
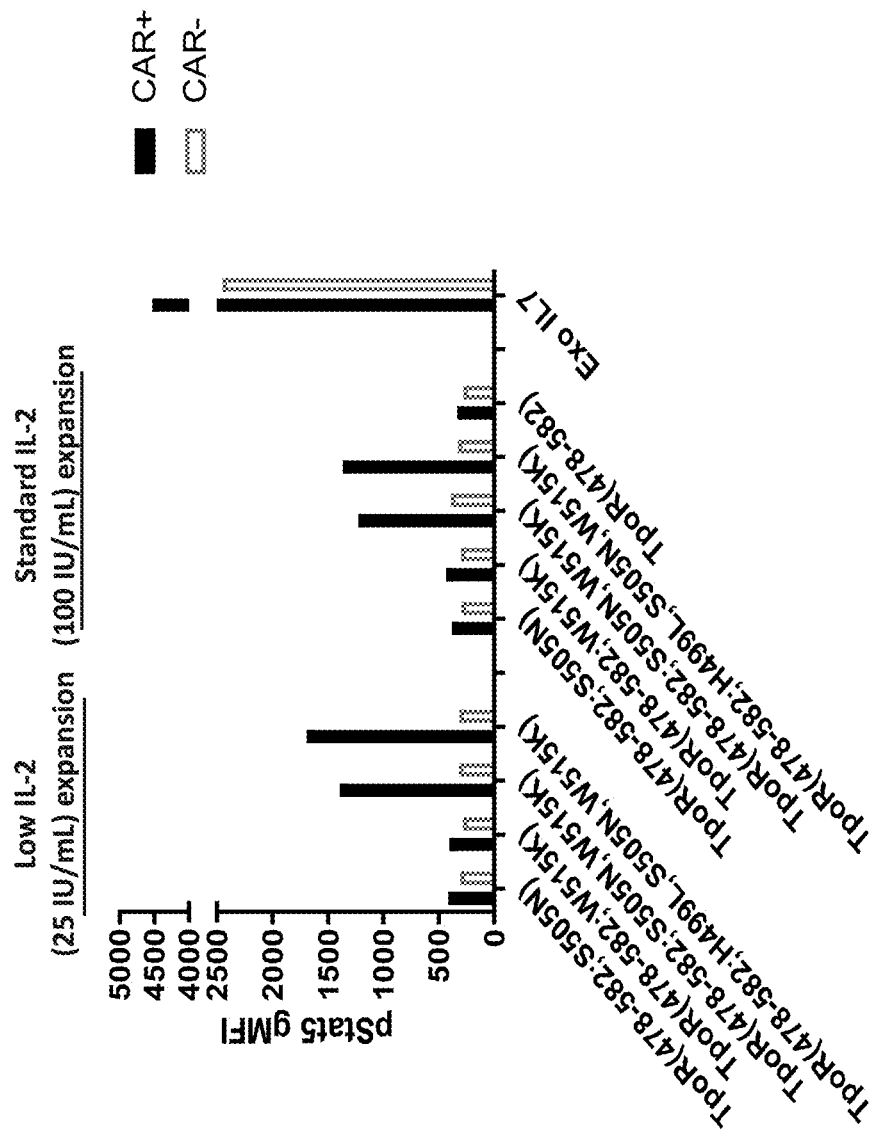

FIGS. 6a-6b show the extent of constitutive cytokine signaling mediated by each TpoR TM variant, as reflected by the percentage of pStat5+ cells (FIG. 6a) and geometric mean fluorescence intensity (gMFI) of pStat5 staining (FIG. 6b). While the TpoR TM single mutants (TpoR(478-582; S505N) and TpoR(478-582;W515K)) did not induce appreciable Stat5 activation, the TpoR TM double mutant (TpoR (478-582;S505N,W515K) and triple mutant (TpoR(478-582;H499L,S505N,W515K)) induced comparably strong constitutive Stat5 activation. CAR-T-cells that were expanded in low IL-2 and standard IL-2 concentrations generated comparable Stat activation profiles. As Stat5 was activated only CAR bearing T-cells (CAR+), and T-cells not bearing a CAR (CAR−) in the same culture, demonstrating that cytokine signaling was CAR-T-cell-specific.

Example 4

Constitutive Cytokine Receptor Enhanced CAR-T-Cell Cytotoxic Potency and Prolonged Durability of Response To test whether constitutive cytokine receptor signaling enhanced the cytotoxic activity of CAR-T-cells, we used U87KO-EGFRvIII-nucGFP as target cells. U87KO-EGFRvIII is a kind gift from Cellectis SA (Paris, France). U87KO-EGFRvIII was derived from the parental cell line, U87MG (ATCC), by first knocking out endogenous wildtype EGFR using Transcription Activator-Like Effector Nucleases (TALEN), and then stably overexpressing full-length human EGFRvIII via lentiviral transduction. To facilitate targeT-cell imaging via the IncuCyte Live Cell Analysis Imaging System, U87KO-EGFRvIII-nucGFP target cells were derived from U87KO-EGFRvIII by a second lentiviral transduction with IncuCyte NucLight Green Lentivirus Reagent (Sartorius). 5,000 U87KO-EGFRvIII-nucGFP target cells were seeded and allowed to attach in 96-well plates with black walls and flat clear bottom in 50 uL RPMI containing 10% FBS (Hyclone), non-essential amino acids, sodium pyruvate and 20-25 mM HEPES. EGFRvIII CAR (2173 scFv) T-cells bearing TpoR TM variant cytokine receptors were thawed and added to plated target cells at Effector:Target (E:T) ratios of 1:8 and 1:2. For comparison, wildtype TpoR(478-582) CAR-T-cells with and without the addition of exogenous recombinant human IL-7 were included in the assay. Where applicable, CAR-T-cells were rechallenged at the indicated timepoint by transferring suspension cells from the original plate to a fresh plate of target cells. Duplicate wells were set up for each condition. Cytotoxicity was determined by enumerating the number of live target cells at each timepoint using the IncuCyte Live Cell Analysis Imaging System.

Figure 7C:
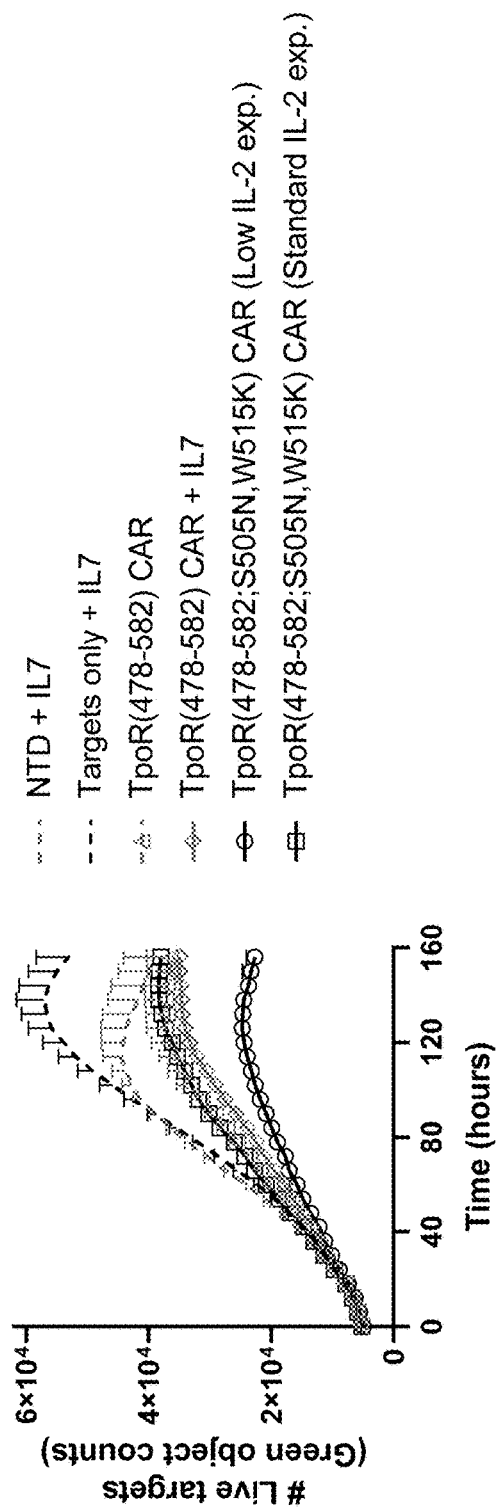
Figure 7D:
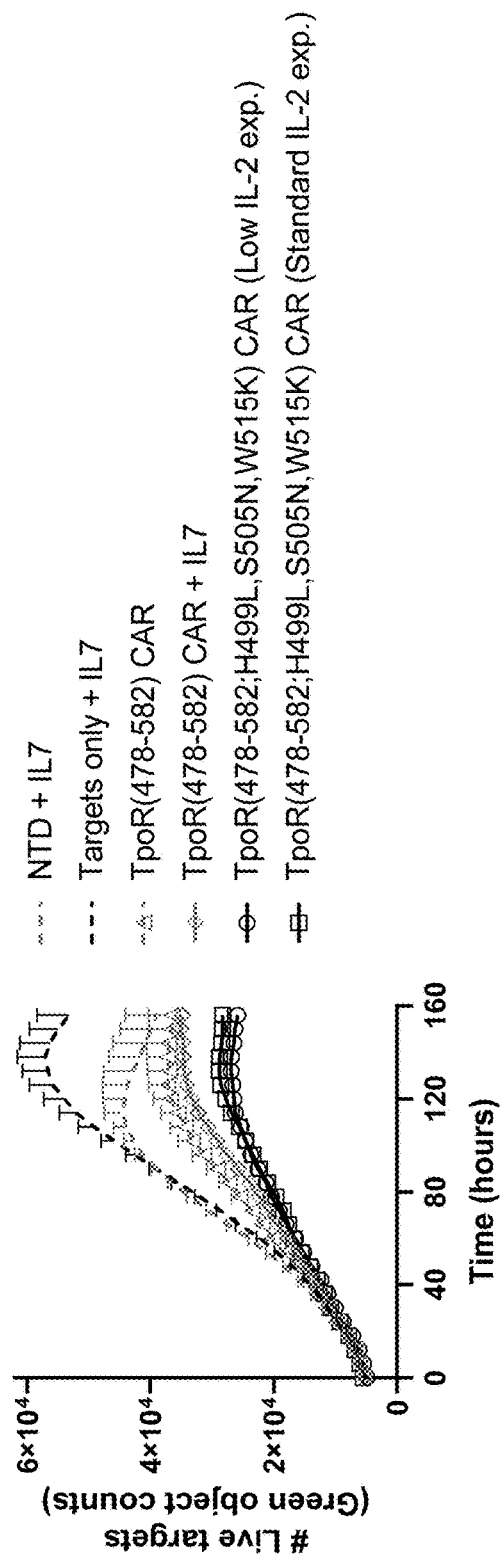

FIGS. 7a-7d shows the cytotoxic activity of TpoR TM mutants at an E:T ratio of 1:8. Consistent with their inability to effectively activate Stat5 (FIGS. 6a-6b), single TpoR TM mutants TpoR(478-582;S505N) (FIG. 7a) and TpoR(478-582;W515KN) (FIG. 7b) did not display functional enhancements compared to their counterparts bearing the wildtype TpoR(478-582) control. FIG. 7c shows that TpoR double mutant CAR-T-cells expanded in standard IL-2 concentrations were not enhanced; whereas TpoR double mutant CAR-T-cells expanded in low IL-2 conditions were more potent at target cell lysis. FIG. 7d shows that TpoR triple mutant CAR-T-cells were more potent at target cell lysis, regardless of the IL-2 concentration during CAR-T-cell production. This indicates that constitutive cytokine receptor signaling enhances CAR-T-cell potency.

Figure 8A:
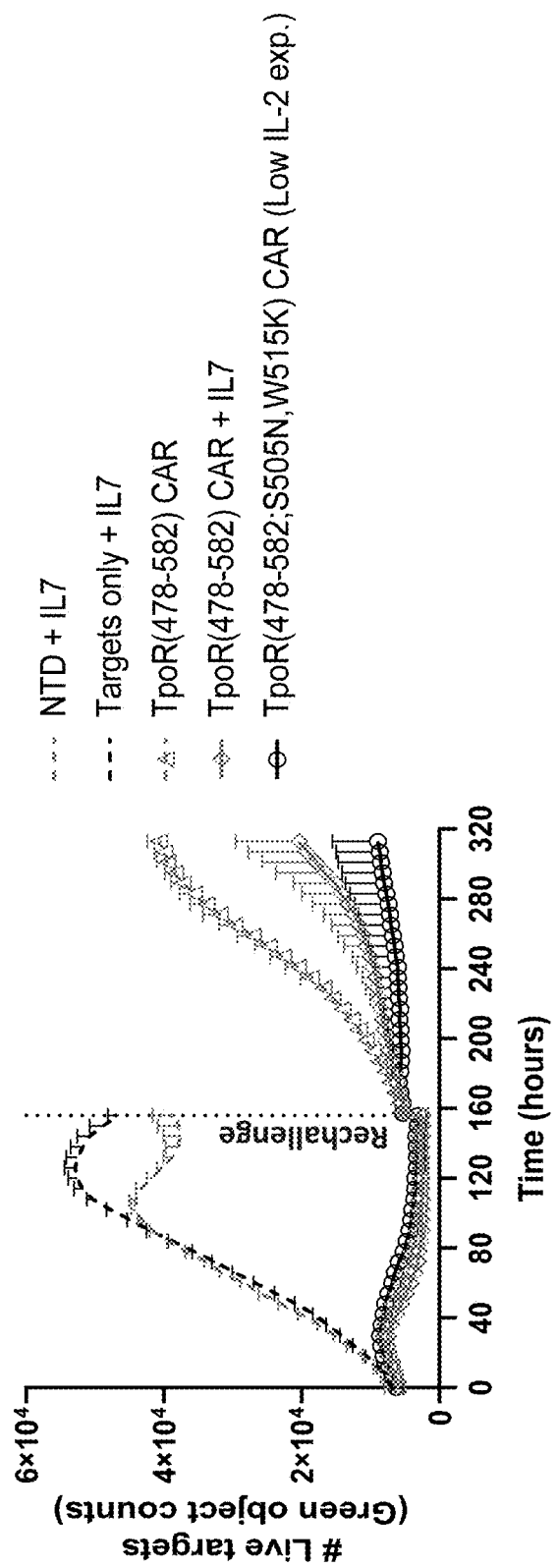
FIGS. 8A-8B show the cytotoxic activity and durability of TpoR TM mutants.
Figure 8B:
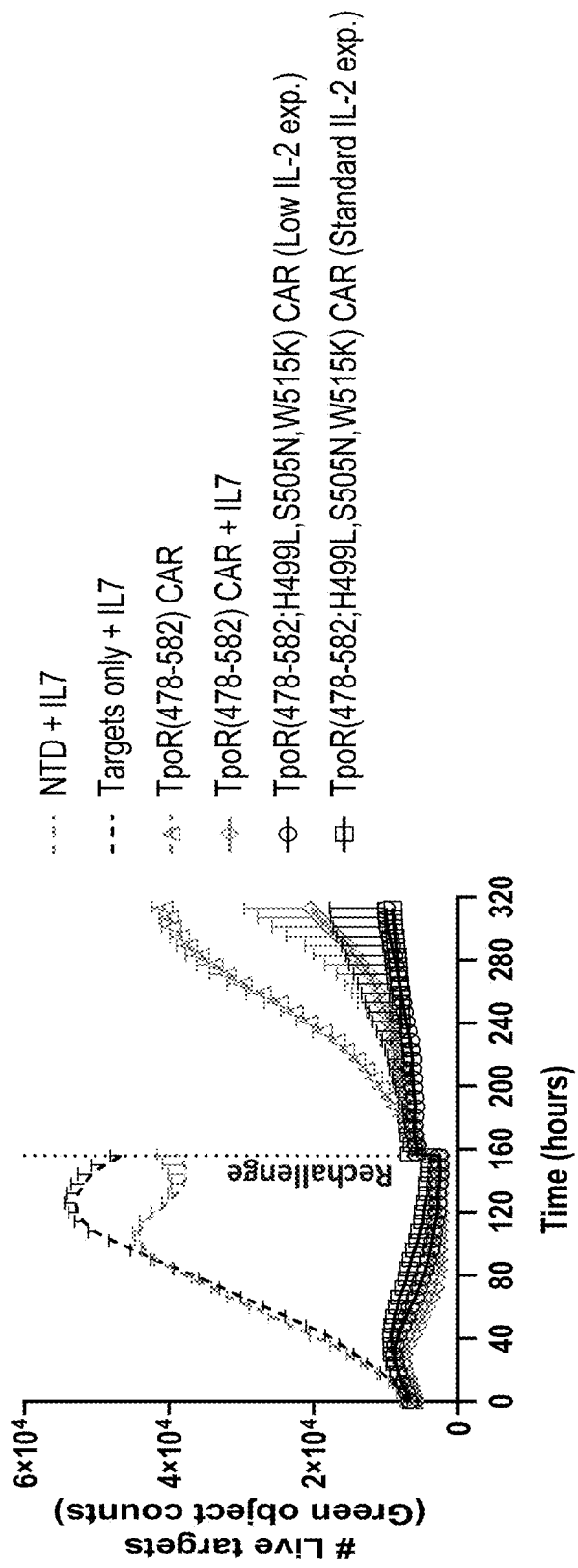

FIGS. 8a-8b show the cytotoxic activity of TpoR TM double (FIG. 8a) and triple mutants (FIG. 8b) at an E:T ratio of 1:2. During the primary response, CAR-T-cells eliminated target ells equally effectively regardless of cytokine receptor activity. However, when re-challenged with fresh targets, only CAR-T-cells expressing constitutively active chimeric cytokine receptors remained functional, indicating that constitutive cytokine receptor signaling enhances the durability of CAR-T-cell responses.

Example 5

Constitutive Cytokine Receptor Enhanced CAR-T-Cell Persistence and Promoted CAR+ Tscm Expansion To see the enhancing effects of constitutive cytokine receptor signaling on CAR-T-cell persistence in the absence of targets or exogenous cytokines, a growth factor-independent assay was performed. Briefly, the percentage of CAR-T-cells across all samples were normalized to the sample with the lowest transduction efficiency (35.7%) by the addition of non-transduced (NTD) T-cells. $0.25 \times 10^6$ CAR bearing T-cells cells/mL in 4 mL RPMI containing 10% FBS (Hyclone), non-essential amino acids, sodium pyruvate and 20-25 mM HEPES. Cells were then seeded in T25 tissue culture flasks. As positive controls, exogenous human IL-7

(10 ng/mL; Miltenyi) were added to CAR-T-cells that lacked constitutive cytokine receptor signaling (the wildtype TpoR (478-582).) On the indicated days, duplicate samples of 200 uL were harvested from each condition, and stained using the Zombie NIR Fixable Viability Kit (Biolegend). Samples were washed with PBS, Fc-blocked, then stained with the following antibody cocktail diluted in PBS+1% BSA: BUV395-conjugated anti-human CD3, BV510-conjugated anti-human CD8, BV605-conjugated human CD4 and FITC-conjugated v5 tag (for CAR detection), PE/Cy7-conjugated anti-human CD62L (Biolegend) and BV785-conjugated anti-human CD45RO (Biolegend). Finally, samples were washed in PBS and cell pellets were resuspended in 130 uL PBS+1%BSA containing 123count eBeads counting beads (Thermo Fisher) (10 uL counting beads in 120 uL PBS+1%BSA) prior to FACS analysis.

Figure 9:
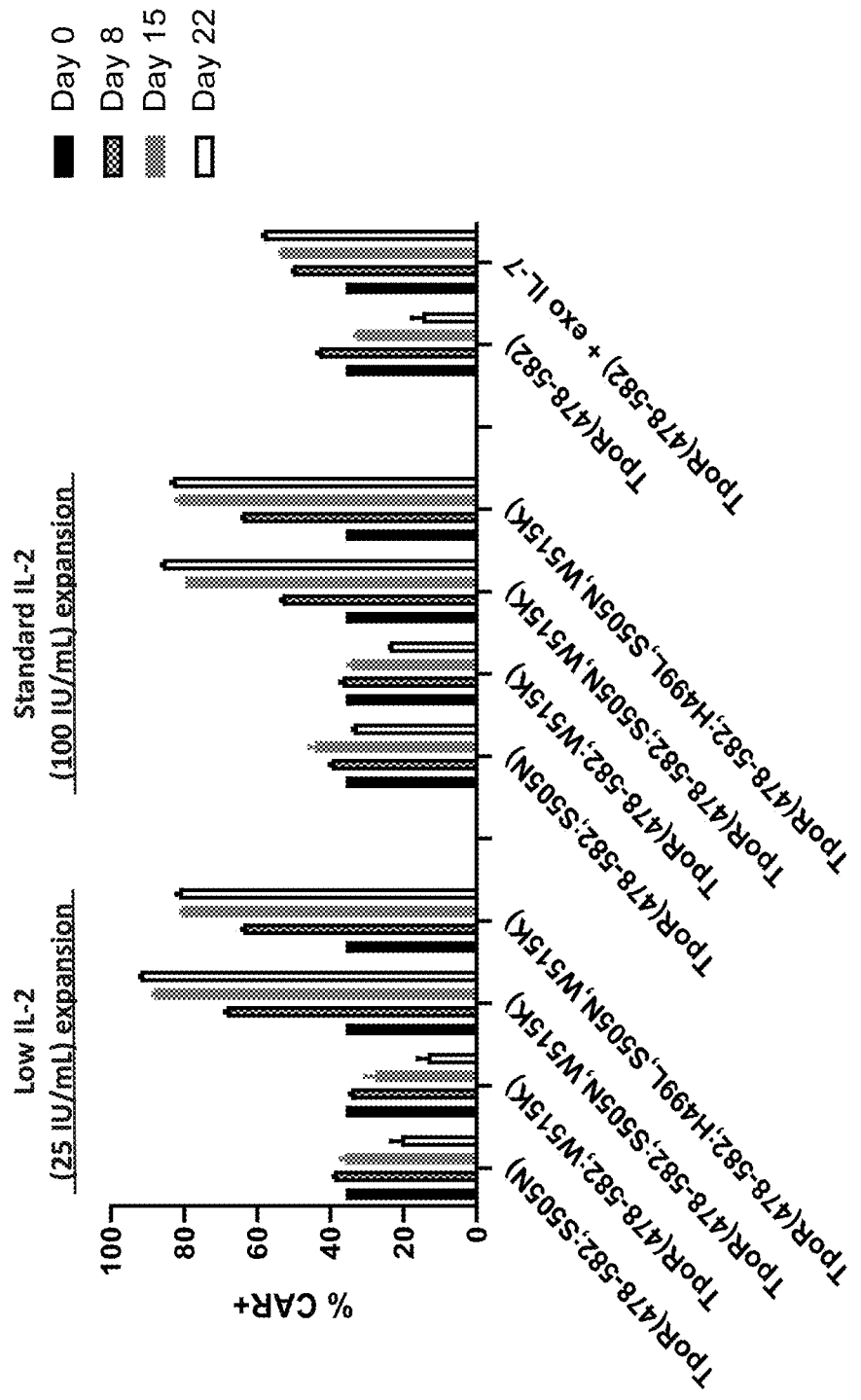
FIG. 9 shows the enrichment of CAR-T-cells over time in a growth factor-independent assay.

FIG. 9 shows the enrichment of CAR-T-cells over time in the growth factor-independent assay. While CAR-T-cells bearing the wildtype TpoR TM (TpoR(478-582) and TpoR TM single mutants (TpoR(478-582;S505N) and TpoR(478-582;W515KN)) did not enrich, CAR-T-cells bearing the TpoR TM double mutant and triple mutants enriched over time, indicating that CAR bearing T-cells that received constitutive cytokine receptor signaling preferentially survived.

FIGS. 10a-10b shows the fold expansion of CAR-T-cells over time in the growth factor-independent assay. Fold expansion was determined by normalizing the absolute number of CAR-T-cells at each timepoint to the number of CAR-T-cells on Day 0 of the assay. FIG. 10a shows that TpoR TM single mutants that were unable to productively activate cytokine receptor signaling declined at the same rate as CAR-T-cells bearing the wildtype TpoR TM (TpoR(478-582). In contrast, FIG. 10b shows that CAR-T-cells bearing the TpoR TM double mutant or the triple mutant had prolonged survival in the absence of targets and exogenous cytokines. TpoR TM double mutant CAR-T-cells expanded in low IL-2 conditions showed increased persistence, compared to their counterparts that were expanded in standard IL-2 conditions. TpoR TM triple mutant CAR-T-cells manufactured in low and standard IL-2 conditions showed comparable, intermediate enhancement in persistence. Notably, although TpoR double and triple mutant CAR-T-cells persisted longer, they eventually declined, indicating that constitutive cytokine receptor signaling unlikely resulted in CAR-T-cell immortalization or transformation.

Figure 11:
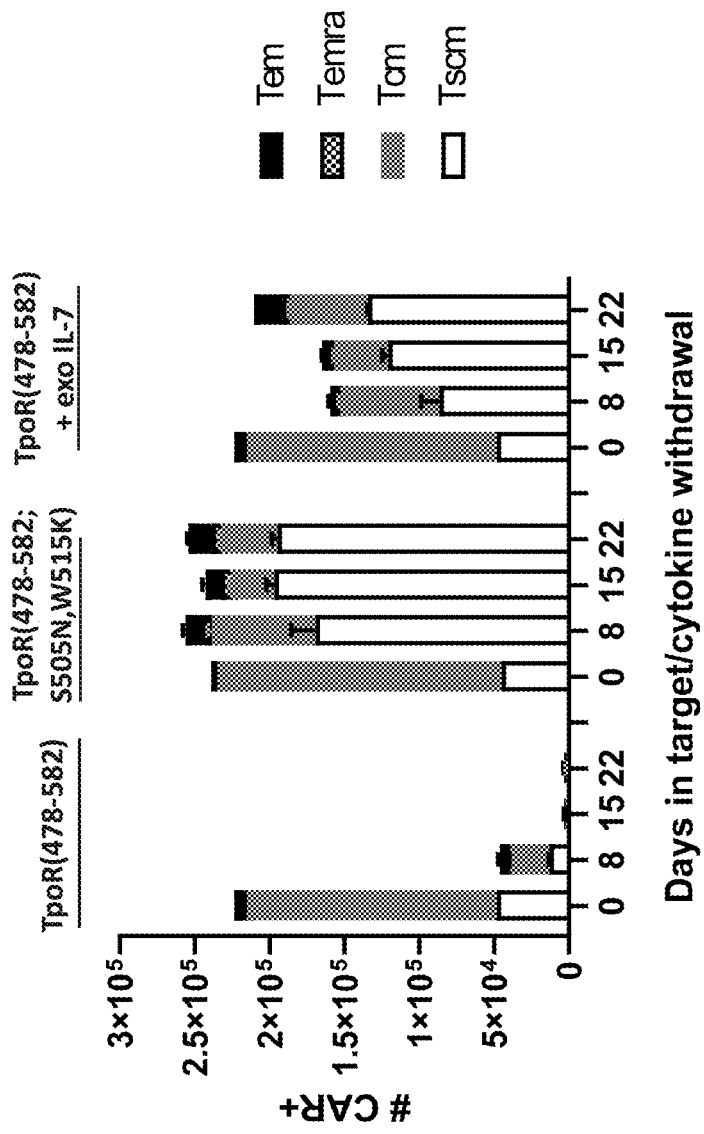
FIG. 11 shows the memory T-cell subset distribution among CAR+ T-cells over time in a growth factor-independent assay.

FIG. 11 shows the memory T-cell subset distribution among CAR+ T-cells over time in the growth factor-independent assay. Compared to the wildtype TpoR TM (TpoR (478-582), CAR-T-cells bearing a constitutively-active cytokine receptor (shown in this case is the TpoR TM triple mutant expanded in low IL-2 conditions) showed an expansion in the absolute numbers of stem cell memory T-cell (Tscm), which is the subset that mediates long-lived anti-tumor immunity. Notably, constitutive signaling from the TpoR TM triple mutant was more effective than exogenous human IL-7 supplementation at expanding Tscm CAR-T-cells.

Example 6

Constitutive Cytotails can be Tailored to Activate Signaling Pathways of Interest The ability of cytokines to regulate CAR-T cell fate and function stems from their ability to elicit different downstream signaling pathways. For instance, IL-7/IL-2/IL-15-mediated STAT5 activation enhances T cell survival and expansion, whereas IL-12-mediated STAT4 activation drives terminal differentiation to short-lived effectors. Designing recruiting domains (i.e., cytotail) that can mimic a broader range of cytokine signals would offer the flexibility for user-programmable signaling outcomes, thereby conferring control over CAR-T cell fate and function.

To interrogate if CACCRs can transmit signals mediated through additional cytokine receptors, the IL7Ra(316-459) cytotail from FIG. 3 was substituted with alternative cytotails derived from the intracellular signaling domains of IL2Rb or IL12Rb2. A HEK293T cell reporter assay was then used to evaluate the signaling capacity of these chimeras. Briefly, 20,000 HEK293T cells were plated into each well of a poly-L-lysine-coated 96-well flat-bottom plate and allowed to adhere overnight. A cytokine receptor-CAR construct (2.5 ng), a Stat response element that drives Firefly Luciferase (100 ng; Promega) and Renilla Luciferase control reporter vector (1 ng; Promega) were mixed in a final volume of 5 uL in Opti-MEM (Gibco) ("DNA mix"). As a negative control, cells were transfected with either a BFP-CAR construct that lacks all cytokine signaling domains, or a TpoR(478-582),IL7Ra(316-459) construct that lacks the transmembrane mutations and therefore cannot constitutively signal. 0.3 uL Lipofectamine 2000 (Invitrogen) in 5 uL Opti-MEM was incubated at room temperature for 5 minutes and then added to the DNA mix. The mixture was incubated at room temperature for 20 minutes and the total volume of 10 uL was added to each well containing HEK-293T. 48 hours after transfection, activity of the respective Stat reporters was evaluated using the Dual-Glo Luciferase Assay System (Promega). Fold induction of Stat5 reporter activity was normalized to that of HEK293T cells transfected with the control BFP-CAR construct.

Figure 12:
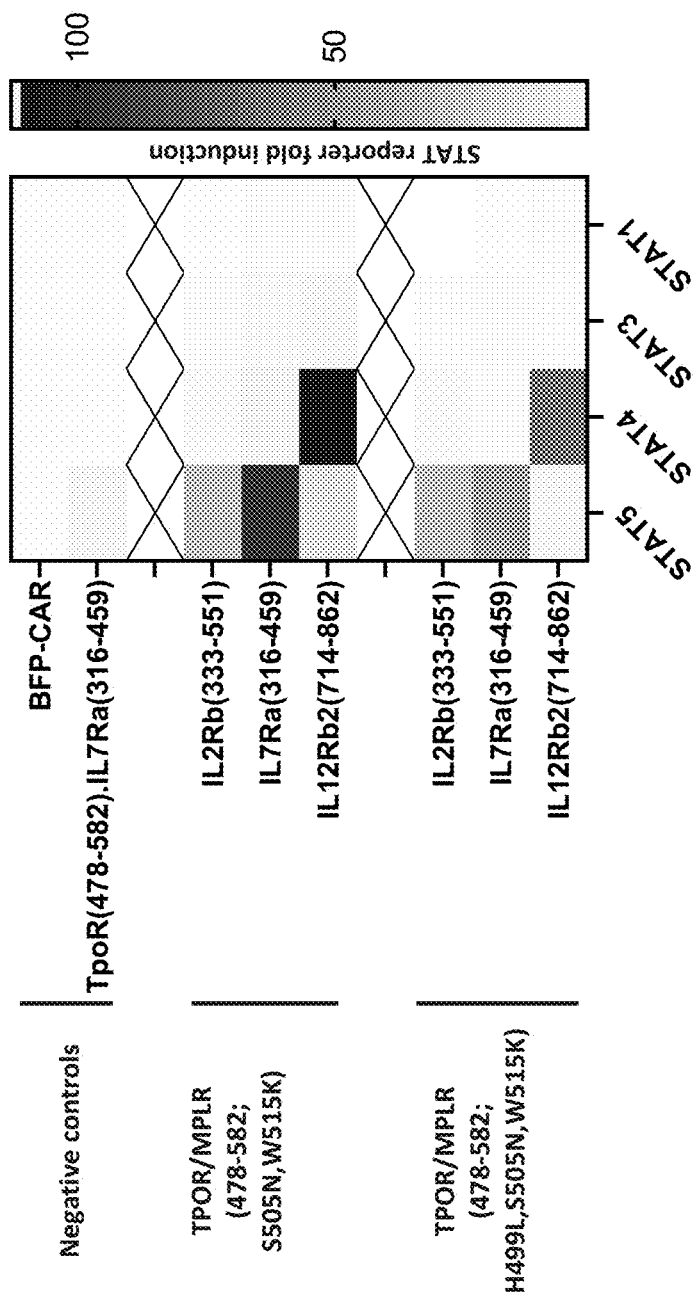
FIG. 12 shows activation of STAT signaling pathways by CAR-T cells co-expressing indicated CACCR.

FIG. 12 shows that construct bearing different signaling domains preferentially activate different STAT pathways. Specifically, IL2Rb(333-551) and IL7Ra(316-459) activated STAT5, while IL12Rb2(714-862) activated STAT4, mirroring signaling expected of the respective parental receptors. This demonstrates that CACCRs can be programmed to activate desired signaling pathways by fusion with the signaling domain of interest. Furthermore, consistent with FIG. 3, CACCRs bearing the TpoR(478-582;S505N, W515K) dimerization domain effected stronger signaling than their TpoR(478-582;H499L,S505N,W515K) counterpart. The strength of CACCR signaling outputs can therefore be further tuned by fusion with either of these dimerization domains.

Example 7

CACCR Signaling Domain can be Optimized to Modulate Signal Strength while Reducing Vector Cargo Size Currently, viral-based gene delivery methods (e.g. lentiviral- and retroviral-mediated gene transfers) are routinely used for CAR-T cell manufacturing. As cargo size increases, transduction efficiency and CAR-T cell yield decreases. Reducing the size of the cargo would therefore be beneficial to ensure manufacturing success. The recruiting/signaling domain of CACCR optimization offers a means to this end for two reasons. First, as in the case of the IL2Rb(333-551), cytokine receptor-derived signaling domains can reach over 200 amino acids in length and represent over 650 basepairs in the transfer vector. Secondly, while tyrosine residues within signaling domains are important for initiating and propagating downstream signal transduction, some of them can also participate in negative feedback loops that limit signaling duration and strength. Trimming the cytotail signaling domain therefore not only allows vector cargo to be reduced in size, but also provides the opportunity for cytotail signaling to be modulated. To this end, we identified tyrosine residues within the full-length IL12Rb2(714-862) and IL2Rb(331-551) tails and generated variants to identify truncated constructs capable of mediating cytotail signaling.

The full-length IL12Rb2(714-862) contains two phosphorylable tyrosine residues, Y767 and Y800, that may participate in downstream signaling. We generated a truncated IL12Rb2(775-825) tail containing only Y800, and evaluated its ability to activate STAT4 using a HEK293T cell reporter assay. Briefly, 20,000 HEK293T cells were plated into each well of a poly-L-lysine-coated 96-well flat-bottom plate and allowed to adhere overnight. A CACCR-CAR construct (2.5 ng), a Stat response element that drives Firefly Luciferase (100 ng; Promega) and Renilla Luciferase control reporter vector (1 ng; Promega) were mixed in a final volume of 5 uL in Opti-MEM (Gibco) ("DNA mix"). As a negative control, cells were transfected with a BFP-CAR construct that lacks all cytokine signaling domains. 0.3 uL Lipofectamine 2000 (Invitrogen) in 5 uL Opti-MEM was incubated at room temperature for 5 minutes and then added to the DNA mix. The mixture was incubated at room temperature for 20 minutes and the total volume of 10 uL was added to each well containing HEK-293T. 48 hours after transfection, activity of the Stat4 reporter was evaluated using the Dual-Glo Luciferase Assay System (Promega). Fold induction of Stat4 reporter activity was normalized to that of HEK293T cells transfected with the control BFP-CAR construct.

Figure 13A:
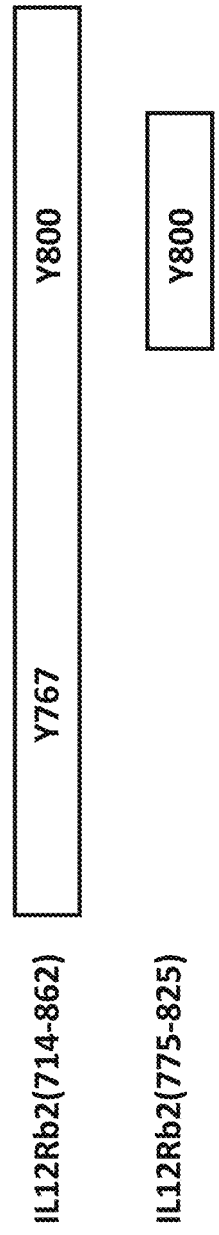
Figure 13B:
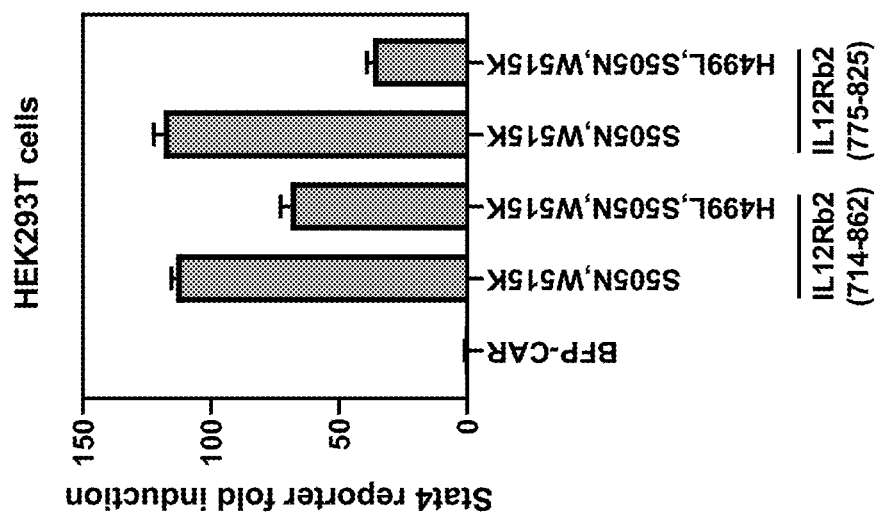

FIGS. 13A-B show the identification of a truncated IL12Rb2(775-825) cytotail capable of STAT4 activation comparable to the full-length IL12Rb2(714-862) cytotail. FIG. 13A shows a schematic diagram of the full-length IL12Rb(714-862) tail and truncated IL12Rb(775-825) cytotail. The positions of tyrosine residues (Y) included in each tail are as indicated. FIG. 13B shows that when fused to the stronger TpoR(478-582;S505N,W515K) dimerization domain, the truncated IL12Rb2(775-825) cytotail fully recapitulated the STAT4 signaling strength of the full-length IL12Rb2(714-862) cytotail. When fused to the weaker TpoR (478-582;H499L,S505N,W515K) dimerization domain, the truncated IL12Rb2(775-825) cytotail partially recapitulated the STAT4 signaling strength of the full-length IL12Rb2 (714-862) cytotail.

The full-length IL2Rb(333-551) cytotail contains six tyrosine residues that may participate in downstream signaling. Of these, Y364 (the tyrosine residue closest to the transmembrane domain of the receptor) has been reported to activate PI3K to promote T cell differentiation and proliferation, as well as cytoskeletal reorganization to induce receptor internalization; therefore, while Y364 can promote T cell effector functions, it can also limit IL2Rb signaling strength and duration. We generated truncated IL2Rb cytotails containing three (Y364, Y418 and Y436) out of six tyrosine residues, or two (Y418 and Y436) out of six tyrosine residues, and evaluated their capacity to activate STAT5 using a HEK293T cell reporter assay. Briefly, 20,000 HEK293T cells were plated into each well of a poly-L-lysine-coated 96-well flat-bottom plate and allowed to adhere overnight. A CACCR-CAR construct (2.5 ng), a Stat response element that drives Firefly Luciferase (100 ng; Promega) and Renilla Luciferase control reporter vector (1 ng; Promega) were mixed in a final volume of 5 uL in Opti-MEM (Gibco) ("DNA mix"). As a negative control, cells were transfected with a BFP-CAR construct that lacks all cytokine signaling domains. 0.3 uL Lipofectamine 2000 (Invitrogen) in 5 uL Opti-MEM was incubated at room temperature for 5 minutes and then added to the DNA mix. The mixture was incubated at room temperature for 20 minutes and the total volume of 10 uL was added to each well containing HEK-293T. 48 hours after transfection, activity of the Stat5 reporter was evaluated using the Dual-Glo Luciferase Assay System (Promega). Fold induction of Stat5 reporter activity was normalized to that of HEK293T cells transfected with the control BFP-CAR construct.

Figure 14B:
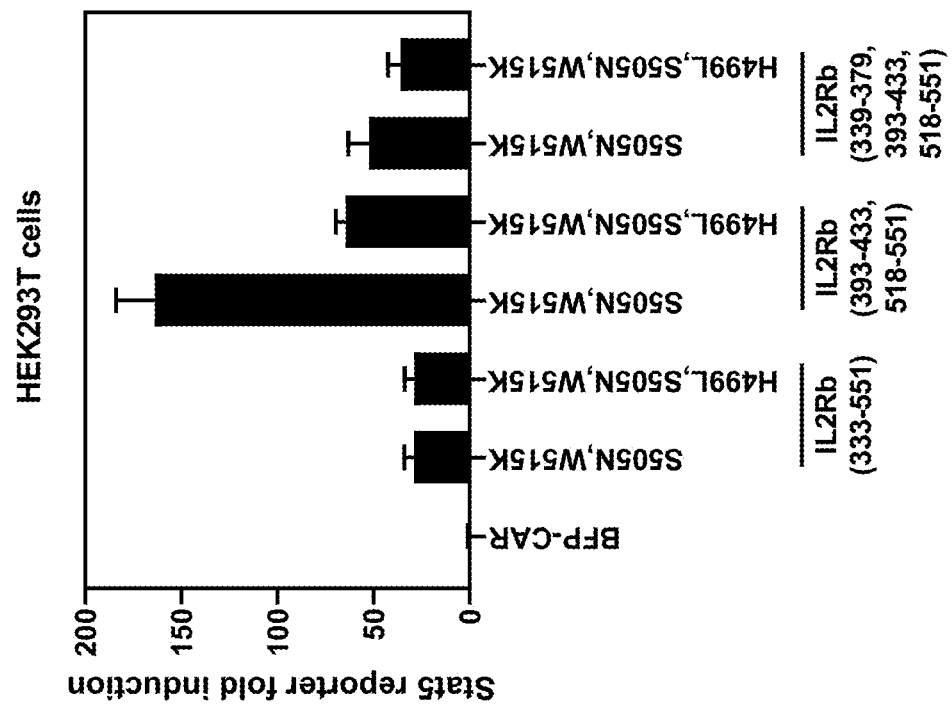

FIGS. 14A-B shows identification of truncated IL2Rb tails capable of equal or better STAT5 activation relative to the full-length IL2Rb(333-551) tail. FIG. 14A shows a schematic of the full-length IL2Rb(333-551) tail and two truncated IL2Rb tails. The positions of tyrosine residues (Y) included in each tail are as indicated. Dotted lines represent interjoining regions in the full-length IL2Rb(333-551) tail that have been removed from the truncated tails. FIG. 14B shows results from a HEK293T cell reporter assay, in which STAT5 signaling of the full-length IL2Rb(333-551) was fully recapitulated by the TpoR(478-582;H499L,S505N,W515K)IL2Rb(339-379,393-433,518-551) cytotail that contained Y364, Y418 and Y536. In the TpoR(478-582; S505N,W515K),IL2Rb(393-433,518-551) cytotail, the additional removal of Y364 that mediates receptor internalization resulted in dramatically improved STAT5 signaling strength.

The HEK293T cell assay is a short-term assay whose readout is measured within 48 hours of cytotail transfection. While it provides an efficient screening platform for cytotail activity, the limited duration of this assay does not reflect the complexities of negative feedback loops that are triggered following long-term constitutive cytokine and cytotail signaling. To more accurately evaluate the long-term signaling activity of reduced IL2Rb tail variants, we generated CACCR CAR-T cells using a 2-week production process and assessed STAT5 activation by intracellular flow cytometry. To this end, CACCR CAR-T cells were serum starved in 100 uL serum-free RPMI (Corning) for 4 hours in humidified incubator at 37° C. with 5% CO$_2$. As a positive control, exogenous recombinant human IL-2 (10 ng/mL; Miltenyi) was added during the last 30 minutes of the 4-hour serum starvation. After 4 hours, an antibody cocktail comprising BUV395-conjugated anti-human CD3 (Biolegend) and FITC-conjugated v5 tag monoclonal antibody (Thermo Fisher) were added to the cells and allowed to incubate for the final 20 minutes. Cells were then fixed by adding 35 uL of 16% paraformaldehyde to each 100 uL sample and allowed to incubate for 15 minutes at 37° C. Cells were then washed three times with PBS, and permeabilized in 100% cold methanol for 1 or 2 nights at −20° C. On the day of FACS analysis, cells were washed three times with PBS, Fc-blocked, and stained with AlexaFluor647-conjugated anti-mouse/human Stat5 (pY694) (BD Biosciences) diluted in PBS+1%BSA. After a 1 hour incubation at room temperature in the dark, cells were washed three times before FACS analysis.

Figure 15:
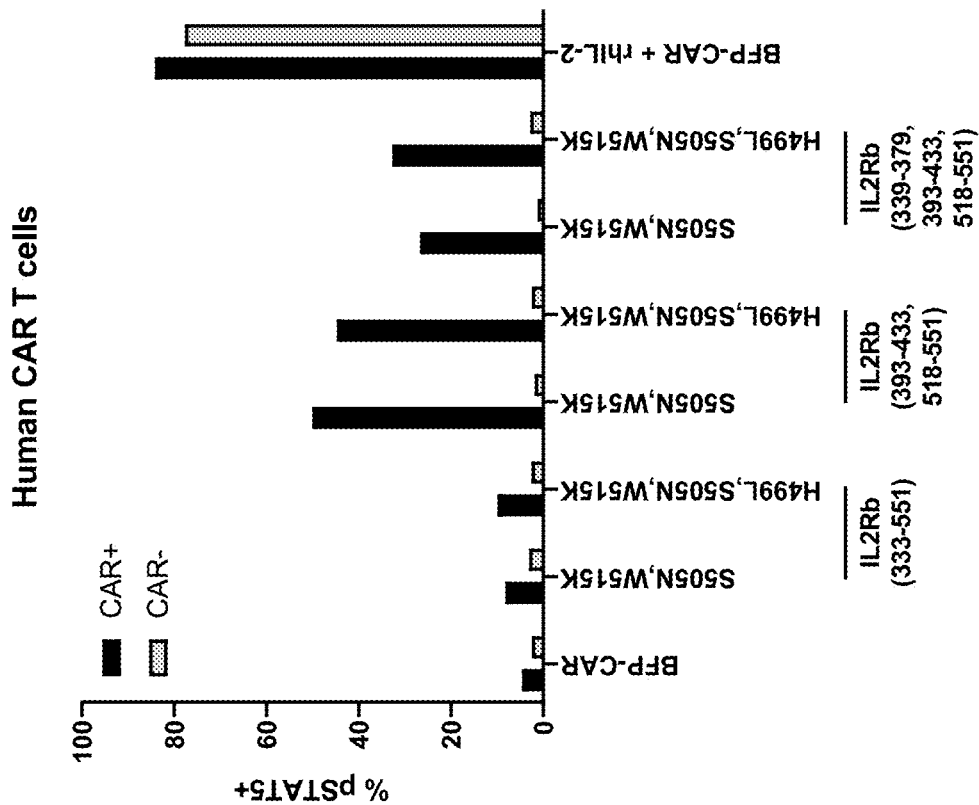
FIG. 15 shows optimization of CACCR signaling strength shown in primary CAR-T cells co-expressing full-length or truncated cytotails.

FIG. 15 shows STAT5 activation in primary CACCR CAR-T cells bearing the full-length or truncated IL2Rb cytotails. The greatest STAT5 activation was elicited by CACCR CAR-T cells bearing the truncated IL2Rb(393-433, 518-551) cytotail that lacked the Y364 internalization motif. Intermediate STAT5 activation was observed in CACCR CAR-T cells bearing the truncated IL2Rb(339-379,393-433, 518-551) cytotail. No STAT5 activation was observed in CAR-negative populations within the same culture, demonstrating the CAR-T cell-specific nature of cytotail signaling. Notably, little to no STAT5 activity was detected in CACCR CAR-T cells bearing the full-length IL2Rb(333-551) cytotail; this may be due to the three other tyrosine residues present in the full-length IL2Rb(333-551) cytotail that may induce long-term, negative regulation. Optimization of cytotail signaling domains to eliminate such negative regulatory motifs is therefore beneficial to ensure that constitutive and productive signaling is maintained in the long-term. As strong cytotails may elicit strong negative feedback response, a weak cytotail may be preferred for long-term stimulation.

Example 7

Optimized IL2Rb-Derived Cytotails More Closely Mimic Signaling of IL-15, rather than IL-2

IL-2 and IL-15 are two cytokines that naturally signal through a heterodimeric cytokine receptor comprised of the common-gamma chain and IL2Rb. In spite of sharing the same native receptors, IL-2 and IL-15 exert different effects on T cell differentiation and persistence. Whereas IL-2 induces short-lived effector differentiation, IL-15 promotes the generation of long-lived memory T cells. Furthermore, increased serum concentrations of IL-15 has been shown to correlate positively with patient response to CAR-T cell therapy. Cytotails that mimic the signaling and effects of IL-15, rather than IL-2, are therefore preferred. We sought to determine if the reduced IL2Rb cytotails more closely mimicked IL-2 or IL-15 signaling.

To this end, we utilized CAR-T cells comprising an exemplary CAR bearing the P5A2 scFv directed towards BCMA, coupled to rituximab mimotopes, 4-1BB and CD3z signaling domains (see U.S. Pat. No. 10,294,304, incorporated herein by reference). BCMA specific CAR-T cells co-expressing the truncated IL2Rb tails were generated, and their gene expression profiles compared to control CAR-T cells that had been exposed to exogenous recombinant human IL-2 or IL-15. To make lentivirus encoding CACCR and CARs, HEK293T cells were plated at 0.45 million cells per mL in 2 mL of DMEM (Gibco) supplemented with 10% FBS (Hyclone) per well of a 6-well plate the day before transfection. On the day of transfection, the lentivirus was prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM was incubated at room temperature for 5 minutes and then added to the DNA mix. The mixture was incubated at room temperature for 20 minutes and the total volume of 500 uL was slowly added to the sides of the wells containing HEK293T. One day post-transfection, the media from each well of HEK293T cells in the 6-well plate was replaced with 2 mL per well of T cell transduction media, i.e., X-Vivo-15 supplemented with 10% FBS. Two days post-transfection, the lentiviral supernatants from HEK293T cells were harvested and passed through a 0.45 micron filter (EMD Millipore) to remove cell debris, and crude lentiviral supernatants were used directly for T cell transduction. On Day 0, purified T cells were activated in X-Vivo-15 medium (Lonza) supplemented with 100 IU/mL human IL-2 (Miltenyi Biotec), 10% FBS (Hyclone), and human T TransAct (Miltenyi Biotec, Cat# 130-111-160, 1:100 dilution) in a Grex-24 plate (Wilson Wolf, cat# 80192M). On Day 2, T cells were resuspended at 0.5 million cells per mL in T cell transduction media, transduced with an equal volume of crude lentiviral supernatant along with 100 IU/mL human IL-2 in a Grex-24 plate. On Day 5, cytotail expressing CAR-T cells were fed by replacing the spent media with T cell expansion media, i.e., X-Vivo-15 supplemented with 5% human AB serum (Gemini Bio), along with 100 IU/mL human IL-2. At this time, control CAR-T cells lacking cytotails were expanded in either 100 U/mL human IL-2 only, or 100 U/mL human IL-2 and 10 ng/mL human IL-15 (Miltenyi Biotec). Cells were expanded into larger G-Rex vessels (Wilson Wolf) as needed using T cell expansion media and the respective concentrations of recombinant cytokines. On Day 13, cells were stained with the Zombie NIR Fixable Viability Kit (Biolegend), labelled with a BUV395-conjugated CD3 antibody (Biolegend) and an anti-idiotype antibody specific for the P5A2 scFv, then FACS-sorted to enrich for CAR+ T cells. Sorted CAR+ T cells were then cultured in Grex-24 plates for a further 2 days in T cell expansion media, with CACCR CAR+ T cells left in the absence of exogenous cytokines, and with sorted control CAR+ T cells either left in the absence of exogenous cytokines, treated with 100 U/mL human IL-2, or treated with 10 ng/mL human IL-15. On Day 15, live CAR+ T cells were enriched using the Easy Sep Dead Cell Removal Kit (StemCell Technologies), and cell pellets were snap-frozen for subsequent RNA extraction and NanoString gene expression analysis (Human CAR-T Panel; NanoString Technologies).

Figure 16A:
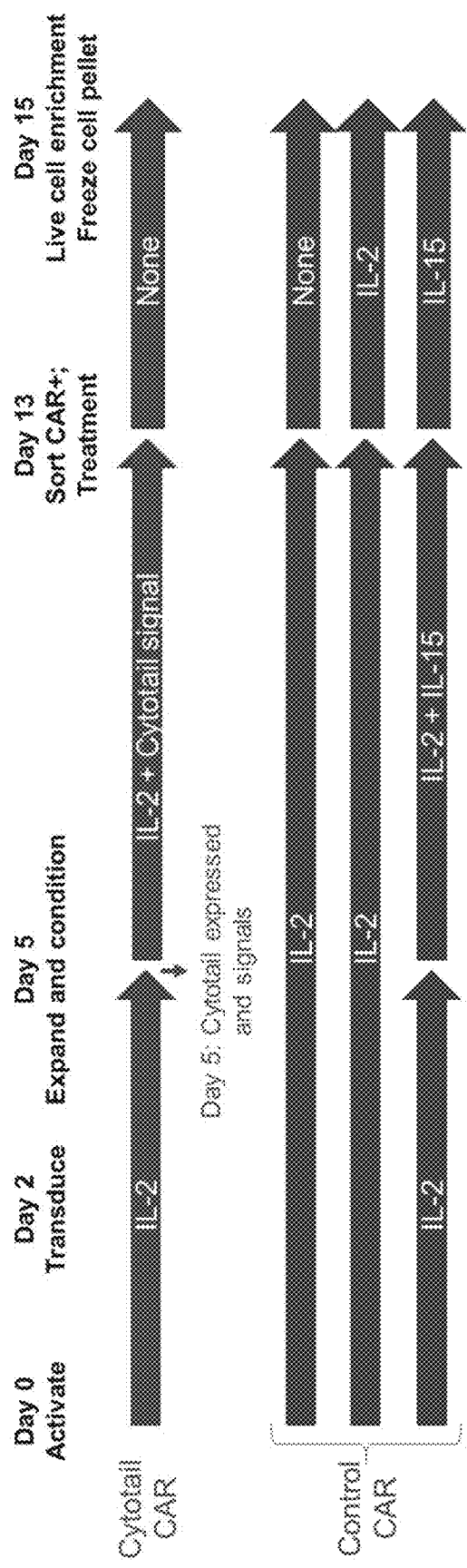
FIGS. 16A-16C show that CACCR CAR-T cells bearing truncated IL2Rb cytotails more closely mimic IL-15, rather than IL-2, signaling.
Figure 16B:
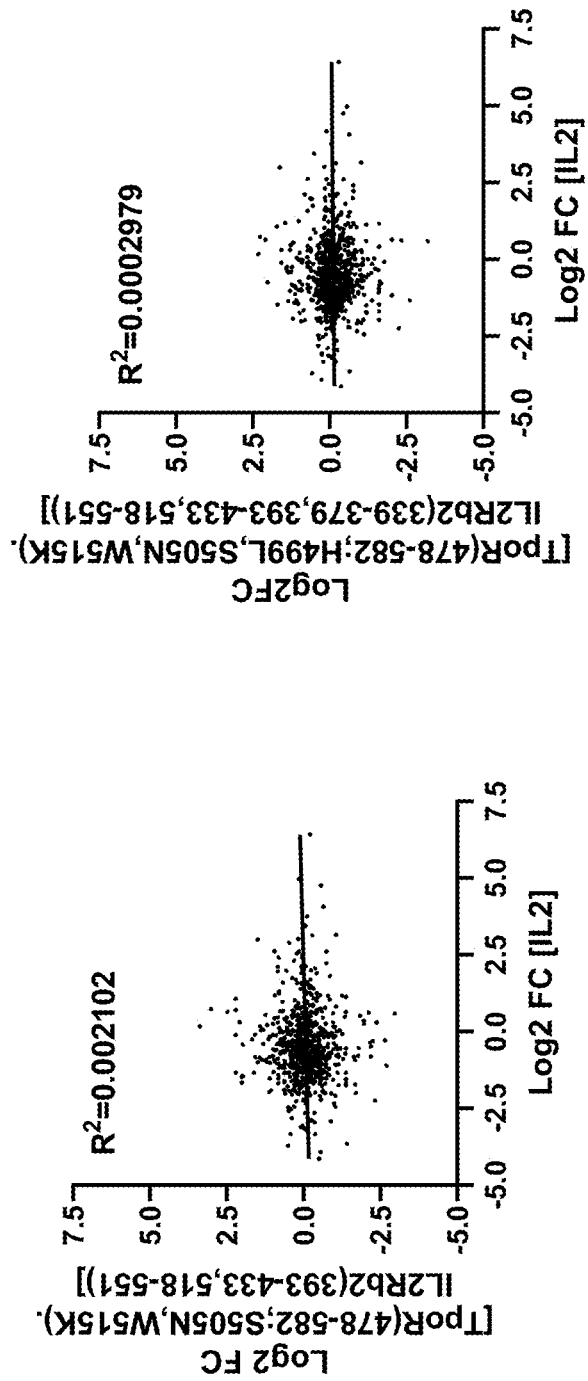
Figure 16C:
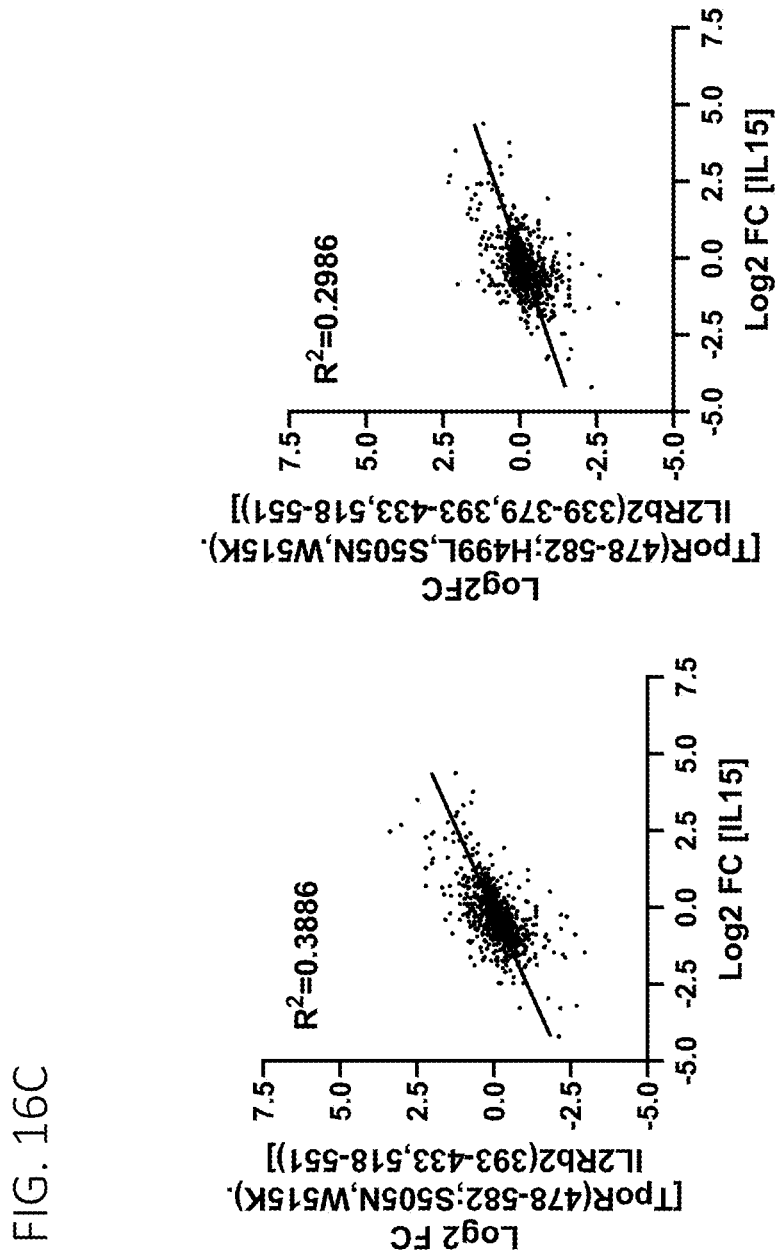

The data show that CACCR CAR-T cells bearing truncated IL2Rb tails more closely mimic IL-15, rather than IL-2, signaling. As an example, we tested the cytotails TpoR(478-582;S505N,W515K),IL2Rb(393-433,518-551) and TpoR(478-582;H499L,S505N,W515K). IL2Rb(339-379,393-433,518-551). FIG. 16A is a schematic diagram of the experimental design and workflow for sample preparation. FIG. 16B shows the gene expression profile of CACCR CAR-T cells compared to that of control CAR-T cells treated with IL-2 from Days 13-15. FIG. 16 C shows the gene expression profile of CACCR CAR-T cells compared to that of control CAR-T cells treated with IL-15 from Days 13-15. Log2 fold change (FC) of each sample was calculated by normalization to control CAR-T cells that were left untreated from Days 13-15. The $R^2$ values and best-fit line (solid line) as determined by linear regression analysis are shown on each graph. Data shown is one representative of two donors. While the gene expression profiles of CACCR CAR-T cells showed no correlation with IL-2-treated samples (FIG. 16B), they correlated positively with IL-15-treated samples (FIG. 16C). These suggest that cytotails bearing the truncated IL2Rb tails more closely mimic the downstream signaling and transcriptional responses of IL-15, instead of IL-2.

Example 9

Constitutive Cytotails can be Programmed for Combinatorial Signaling Outputs

As shown in FIG. 12, CACCRs bearing signaling domains derived from various cytokine receptors can activate signaling reminiscent of the parental receptor. We hypothesized that cytotails can be designed to mimic simultaneous signaling from multiple parental receptors by fusing more than one cytotail in tandem, allowing combinatorial signaling outcomes to be achieved. To test combinatorial signaling outputs from tandem cytotails, we generated a constitutive 7.12tail by fusing the IL7Ra(316-459) cytotail with the truncated IL12Rb2(775-825) cytotail and evaluated signaling using the HEK293T cell reporter assay.

Figure 17A:
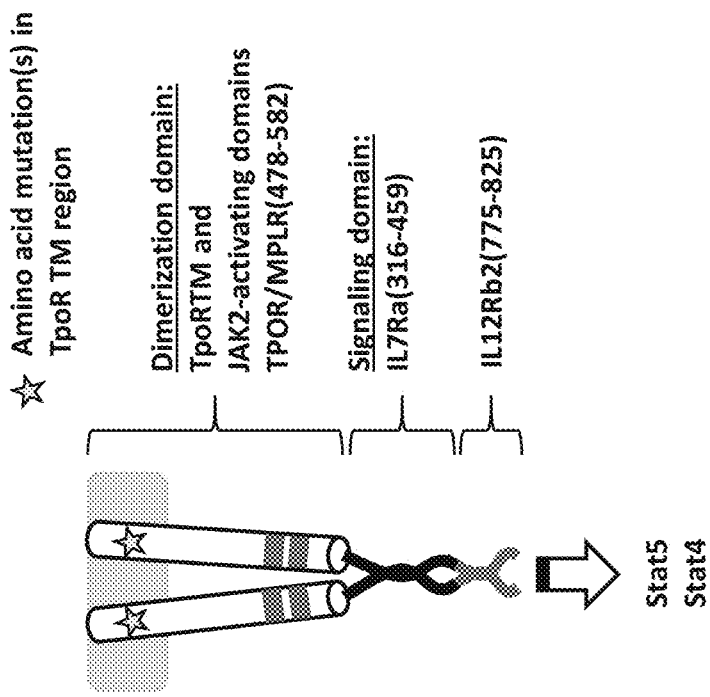
FIGS. 17A-17D show combinatorial signal outputs of different cytotail fused in tandem.
Figure 17B:
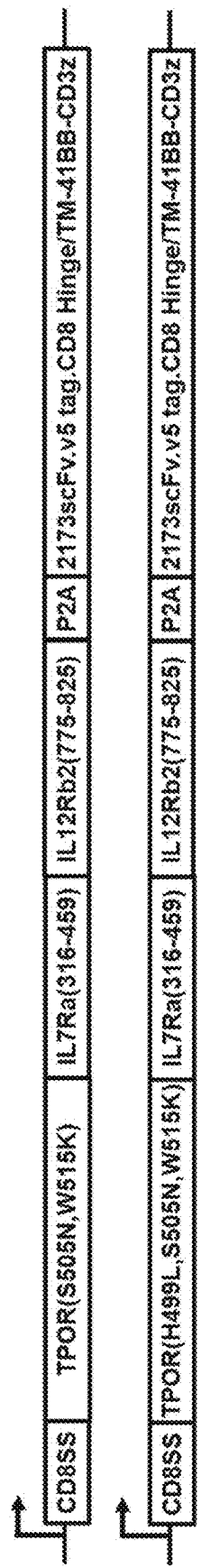
Figure 17C:
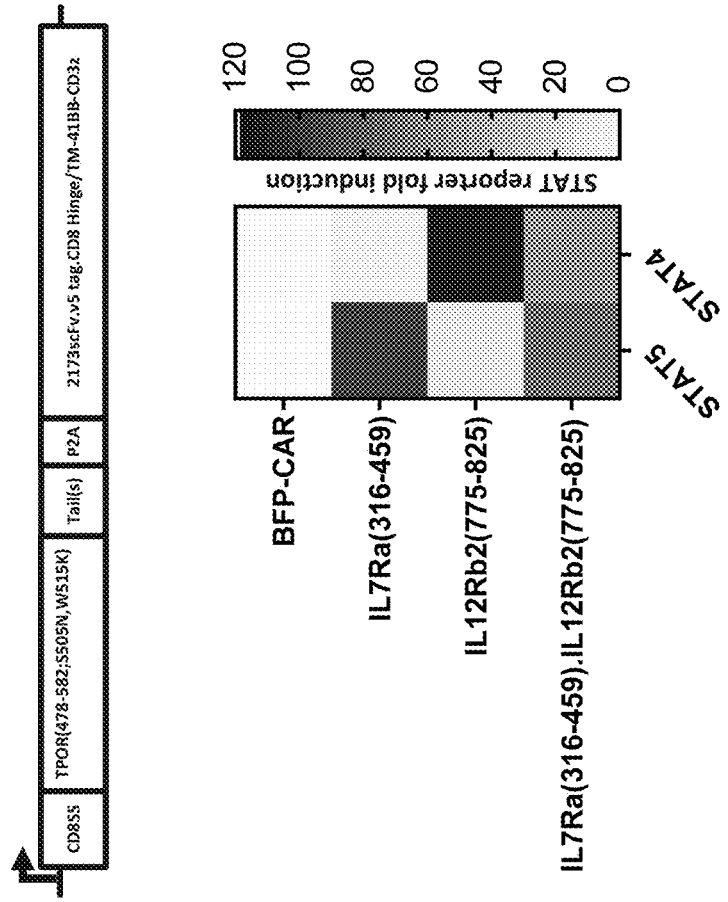
Figure 17D:
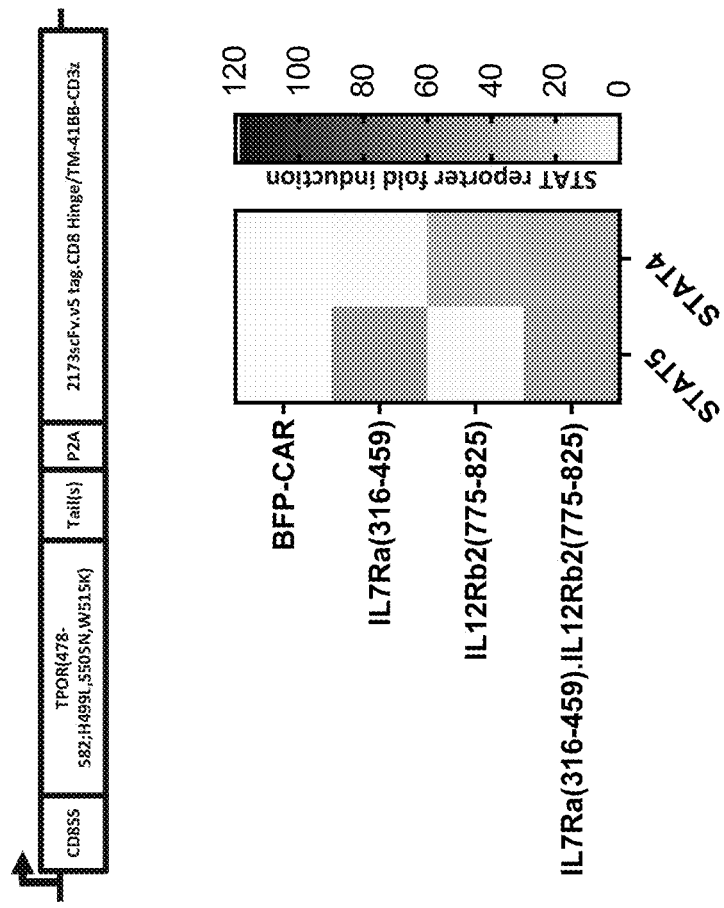

FIGS. 17A-D show the design and signaling capacity of constitutive tandem cytotails, as exemplified by the 7.12tail. FIG. 17A shows a schematic of the constitutive 7.12 tail. FIG. 17B shows a schematic of the lentiviral vectors, differing only in their TpoR(478-582) dimerization/JAK-binding domains, used to co-express the 7.12tail variants and a CAR. FIGS. 17C-D show STAT reporter activity for constructs bearing the TpoR(478-582;S505N;W515K) and TpoR(478-582;H499L;S505N;W515K) dimerization/JAK-binding domains, respectively, fused to the indicated cytotails. While the IL7Ra(316-459) cytotail strongly activated STAT5, the IL12Rb2(775-825) cytotail strongly activated STAT4. However, as observed in the IL7Ra(316-459). IL12Rb2(775-825) cytotail, fusing both cytotails in tandem resulted in simultaneous and combinatorial activation of both STAT5 and STAT4. This demonstrates that multiple signaling pathways that would usually require two or more distinct native cytokine receptors can be achieved with a single cytotail.

Example 10

Constitutive Cytotails can be Tailored with Single or Multiple Outputs to Direct CAR-T Cell Phenotype and Function We next determined if constitutive cytotails bearing different signaling outputs can differentially impact the phenotype and function of primary human CAR-T cells. Unlike IL-7 that drives T cell survival and memory maintenance, IL12 is a proinflammatory cytokine that promotes T cell differentiation. We therefore sought to interrogate if signaling through the IL7Ra- or IL12Rb-derived cytotails can differentially direct these divergent phenotypes, and to assess the net combinatorial effect of fusing both tails in tandem.

To this end, we generated human primary CAR-T cells that co-expressed either the 7tail (i.e. IL7Ra(316-459)) or variants of 12tails (i.e. IL12Rb2(775-825) or IL12Rb2(714-862)). See FIG. 13A. To make lentivirus encoding CACCR and CARs, HEK293T cells were plated at 0.45 million cells per mL in 2 mL of DMEM (Gibco) supplemented with 10% FBS (Hyclone) per well of a 6-well plate the day before transfection. On the day of transfection, the lentivirus was prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM was incubated at room temperature for 5 minutes and then added to the DNA mix. The mixture was incubated at room temperature for 20 minutes and the total volume of 500 uL was slowly added to the sides of the wells containing HEK293T. 1 day post-transfection, the media from each well of HEK293T cells in the 6-well plate was replaced with 2 mL per well of T cell transduction media, i.e., X-Vivo-15 supplemented with 10% FBS. 2 days post-transfection, the lentiviral supernatants from HEK293T cells were harvested and passed through a 0.45 micron filter (EMD Millipore) to remove cell debris, and crude lentiviral supernatants were used directly for T cell transduction. On Day 0, purified T cells were activated in X-Vivo-15 medium (Lonza) supplemented with 100 IU/mL human IL-2 (Miltenyi Biotec), 10% FBS (Hyclone), and human T TransAct (Miltenyi Biotec, Cat# 130-111-160, 1:100 dilution) in a Grex-24 plate (Wilson Wolf, cat# 80192M). On Day2, T cells were resuspended at 0.5 million cells per mL in T cell transduction media, transduced with an equal volume of crude lentiviral supernatant along with 100 IU/mL human IL-2 in a Grex-24 plate. On Day 5, cells were fed by replacing the spent media with T cell expansion media, i.e., X-Vivo-15 supplemented with 5% human AB serum (Gemini Bio), along with 100 IU/mL human IL-2. Cells were expanded into larger G-Rex vessels (Wilson Wolf) as needed using T cell expansion media and the respective concentrations of human IL-2. On Day 14, memory phenotyping of the CAR-T cell products was performed by detecting CAR-transduced cells using a FITC-conjugated v5 tag monoclonal antibody (Thermo Fisher), together with co-staining with a PE/Cy7-conjugated CD62L antibody (Biolegend) and a BV785-conjugated CD45RO antibody (Biolegend) by flow cytometry. As negative controls that lacked CACCR signaling, CAR-T cells co-expressing BFP or the wildtype TpoR(478-582) transmembrane domain coupled to a 7tail were generated in parallel.

Figure 18A:
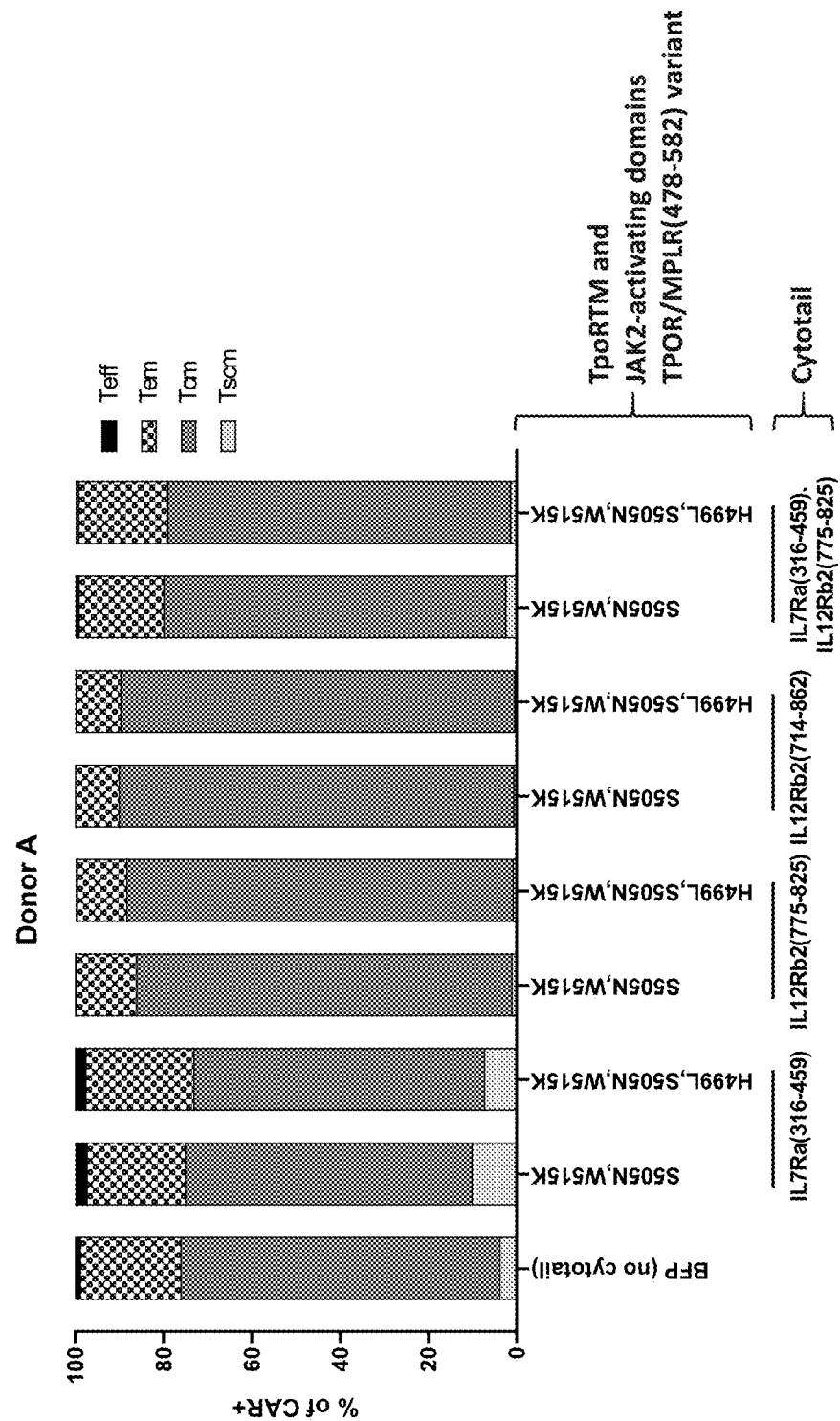
FIGS. 18A-18B depict the effects of CACCRs on memory differentiation of CAR-T cells.
Figure 18B:
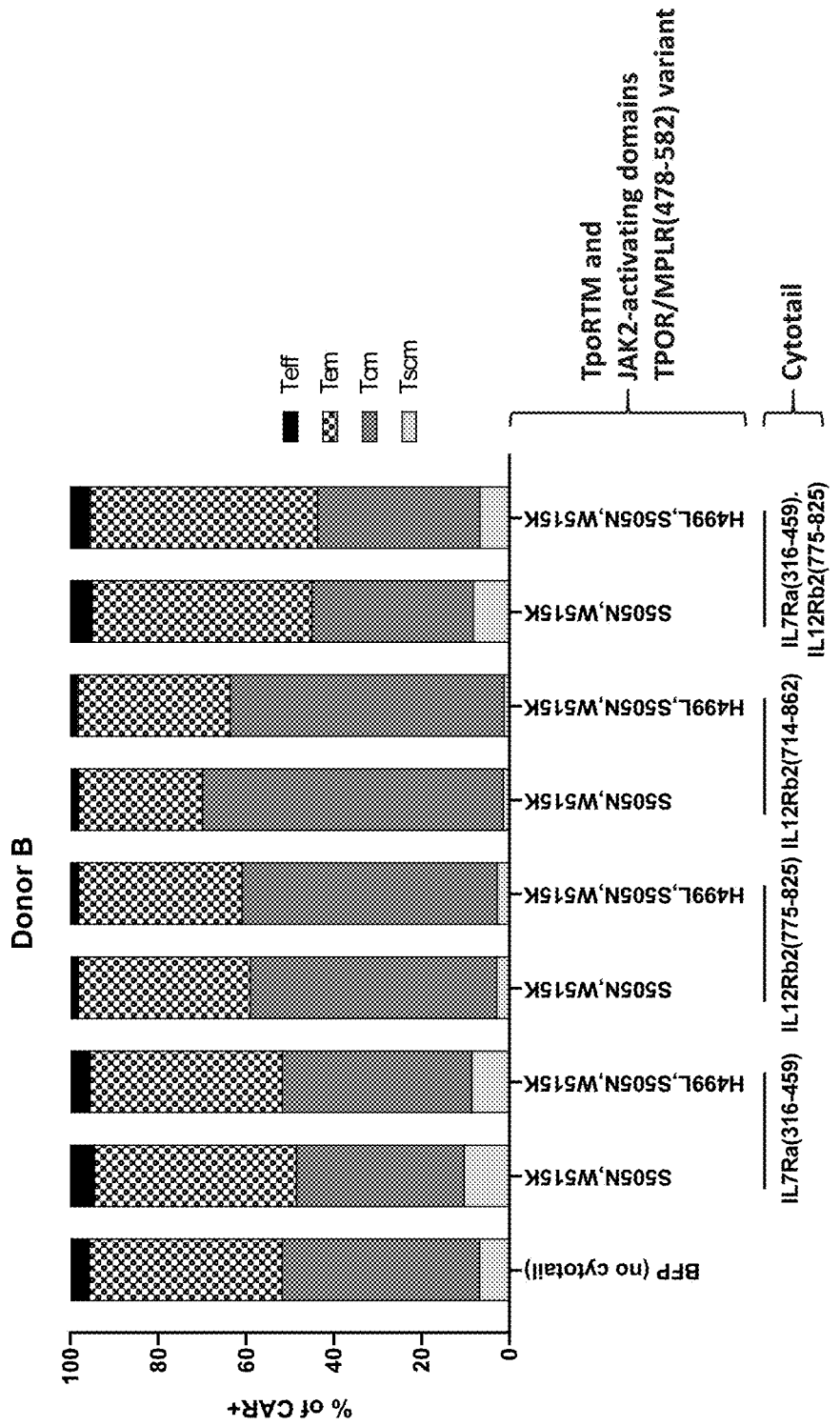

FIG. 18 depicts the impact of cytotails on memory differentiation of CAR-T cell products. The memory phenotype of Day 14 CACCR CAR-T cell products generated from 2 healthy donors is shown. While CAR-T cells co-expressing the IL7Ra(316-459) cytotail retained a stem cell memory (Tscm) population, CAR-T cells bearing IL12Rb2-derived cytotails showed marked reductions in the Tscm population accompanied by an increased central memory (Tcm) population. These suggested that in the absence of CAR engagement, constitutive IL12-like signaling through IL12Rb2-derived cytotails drive progressive differentiation from Tscm to Tcm. Furthermore, CAR-T cells co-expressing the tandem IL7Ra(316-459). IL12Rb2(775-825) cytotail showed a recovery of the Tscm population and mimicked the phenotype of CAR-T cells bearing the single IL7Ra(316-459) cytotail, indicating that negative effects of single cytotails can be mitigated through combinatorial signaling of tandem cytotails.

We further investigated if CACCR signaling could direct CAR-T cell functional outcomes, including survival and cytotoxicity. Compared to IL-7 signaling that promotes long-term T cell survival, IL-12 signaling instead drives differentiation into short-lived terminal effectors. In support of this, the Tscm population, which is capable of long-term survival and is believed to mediate prolonged CAR-T cell persistence, was scarce in CAR-T cells bearing IL12Rb2-derived tails. To interrogate if signaling through different cytotails could program CAR-T cell survival and differentiation, we performed a growth factor-independent assay in which CACCR coexpressing CAR-T cells were cultured in the absence of target cells or exogenously supplemented cytokines. Under these conditions, CAR-T cell numbers and memory differentiation were monitored over time.

Briefly, cryopreserved CAR-T cells were thawed, counted, and the percentage of CAR-T cells across all samples were normalized to the sample with the lowest transduction efficiency by the addition of non-transduced (NTD) T cells. As a control, CAR-T cells co-expressing BFP (BFP CAR) in place of a cytotail was used. $0.25 \times 10^6$ CAR+ T cells/mL in 1.5 mL RPMI containing 10% FBS (Hyclone), non-essential amino acids, sodium pyruvate and 20-25 mM HEPES con were then seeded in 24-well tissue culture plates. On the indicated days, duplicate samples of 100 uL was harvested from each condition, and stained using the Zombie NIR Fixable Viability Kit (Biolegend). Samples were washed with PBS, Fc-blocked, then stained with the following antibody cocktail diluted in PBS+1%BSA: BUV395-conjugated anti-human CD3, BV510-conjugated anti-human CD8, BV605-conjugated human CD4 and FITC-conjugated v5 tag (for CAR detection), PE/Cy7-conjugated anti-human CD62L (Biolegend) and BV785-conjugated anti-human CD45RO (Biolegend). Finally, samples were washed in PBS and cell pellets were resuspended in 130 uL PBS+1%BSA containing 123count eBeads counting beads (Thermo Fisher) (10 uL counting beads in 120 uL PBS+1%BSA) prior to FACS analysis.

Figure 19A:
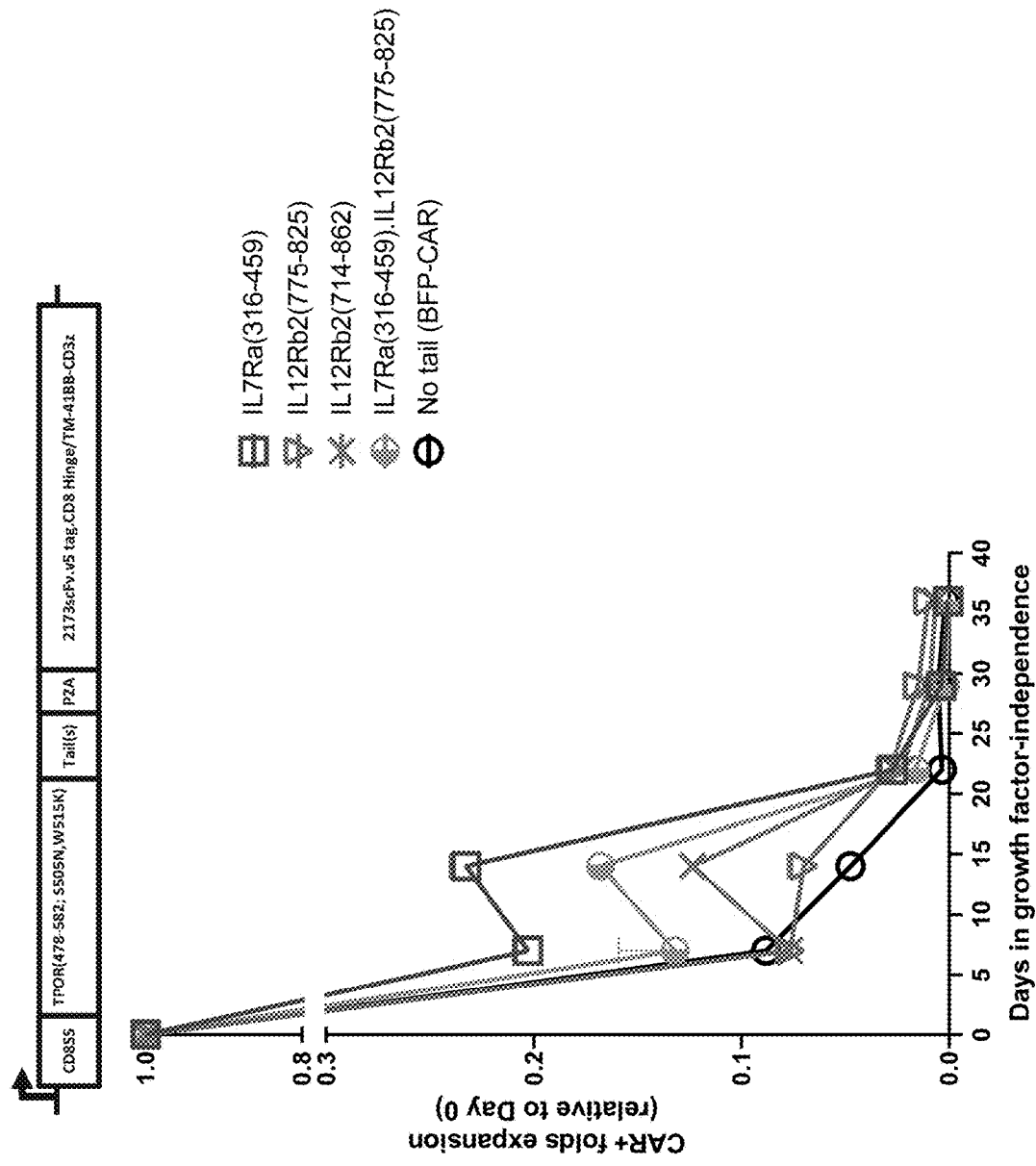
FIGS. 19A-19D depict the impact of CACCRs on CAR-T cell survival and memory differentiation under growth factor-independent conditions.
Figure 19B:
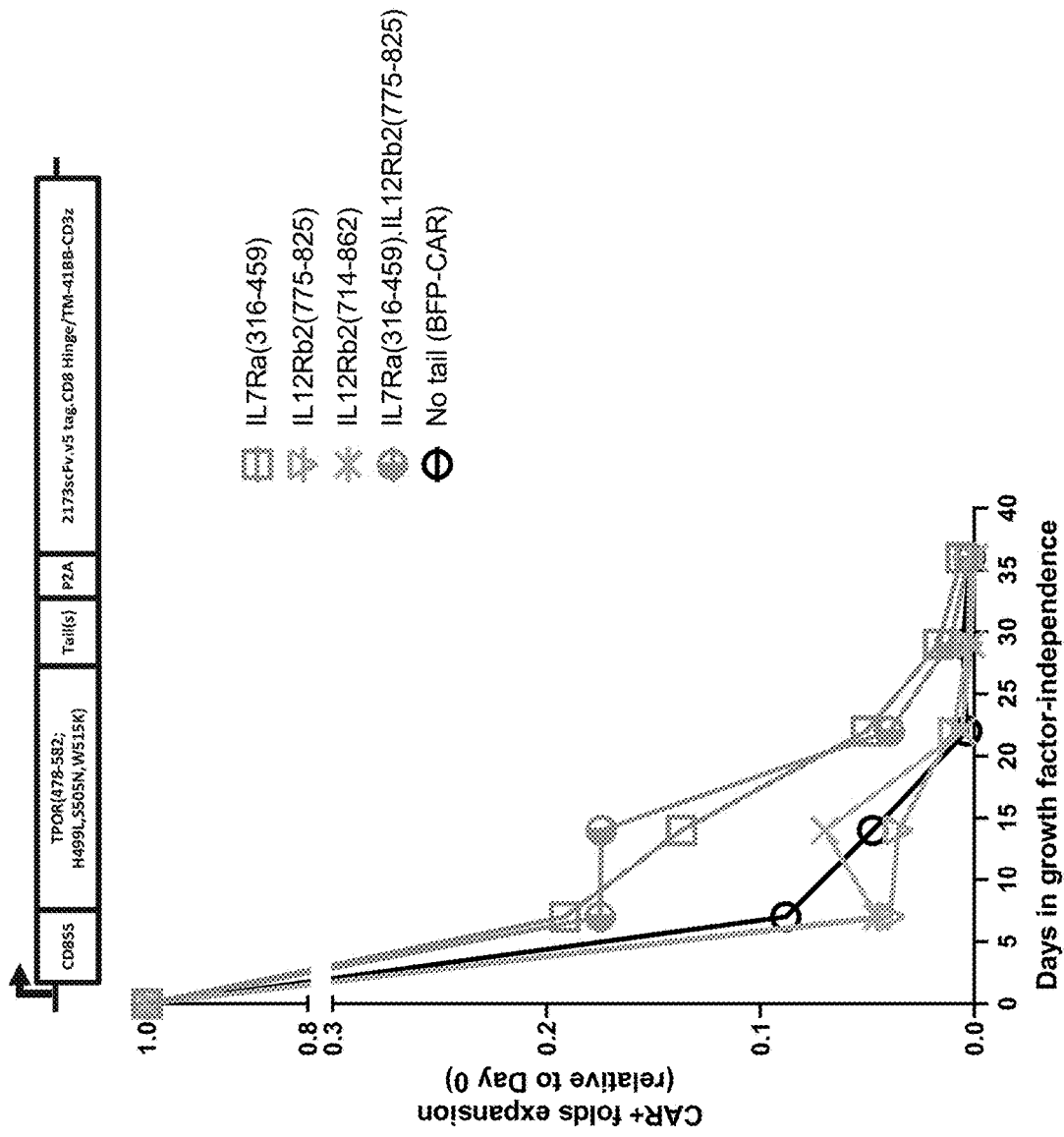
Figure 19C:
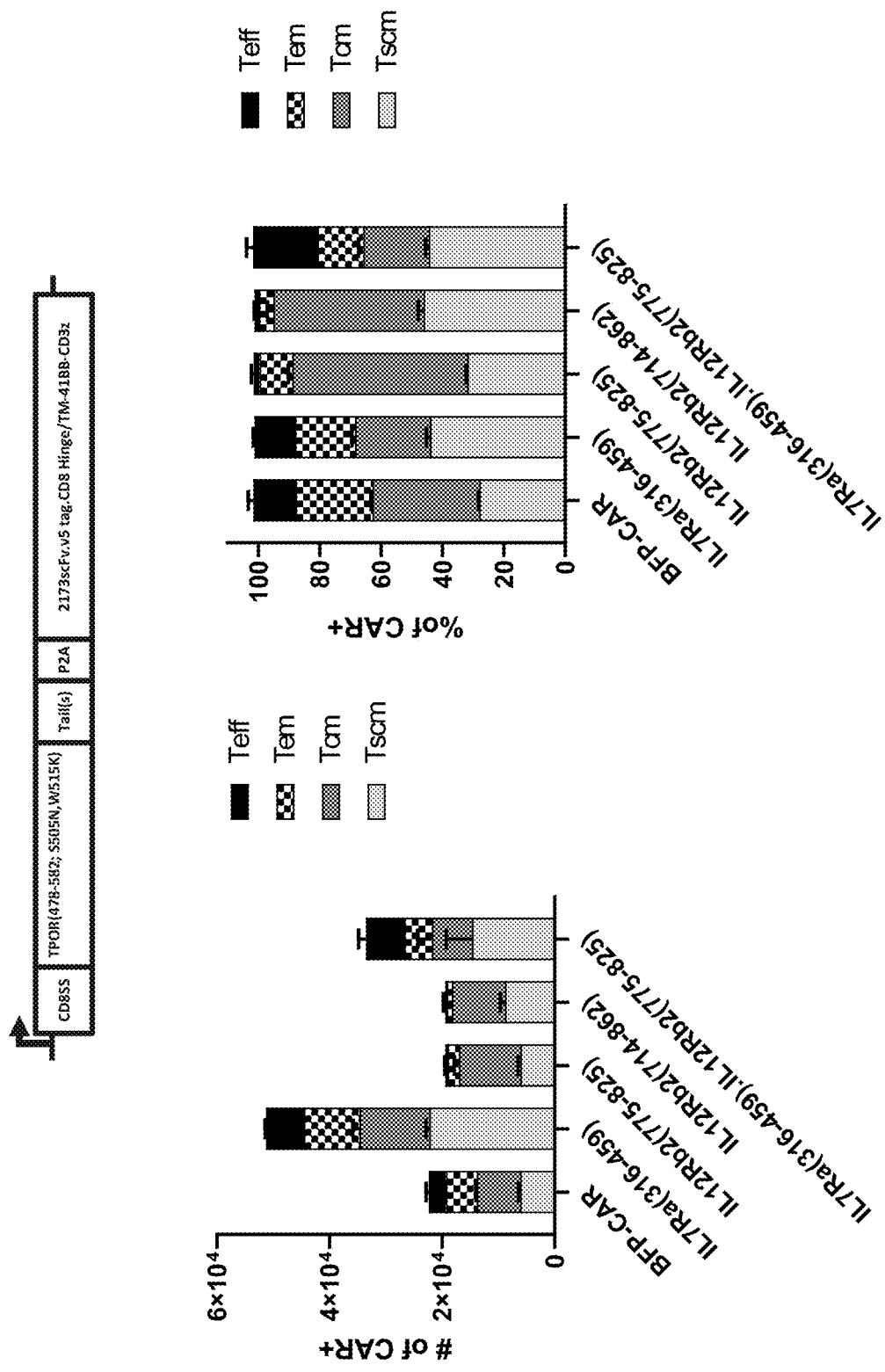
Figure 19D:
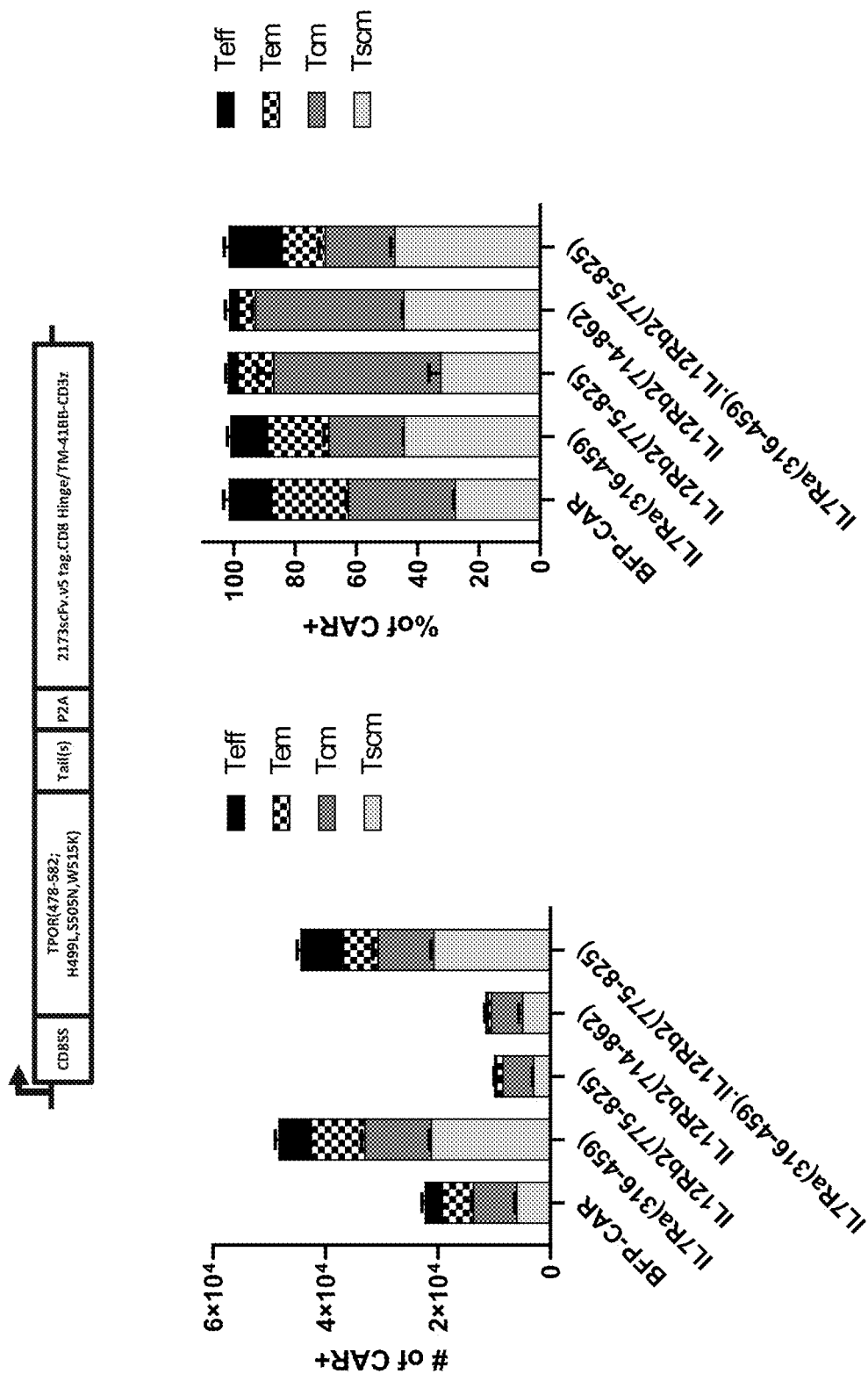

FIGS. 19A-B show representative data of cells from 2 donors. FIG. 19A and FIG. 19B show fold expansion of CAR-T cells relative to the input at the start of the assay (Day 0) for constructs bearing the TpoR(478-582;S505N;W515K) and TpoR(478-582;H499L;S505N;W515K) dimerization/JAK-binding domains, respectively, fused to the indicated cytotails. Compared to the control BFP CAR-T cells, CAR-T cells bearing the IL7Ra(316-459) cytotail declined at a slower rate, indicating that the constitutive signaling through the IL7Ra(316-459) cytotail improved CAR-T cells survival. In contrast, CAR-T cells bearing IL12Rb2-derived cytotails declined at a rate more comparable to BFP CAR-T cells, suggesting the lack of a survival benefit. Notably, CAR-T cells bearing the tandem IL7Ra(316-459),IL12Rb2(775-825) cytotail conferred a survival benefit more comparable to that of the IL7Ra(316-459) cytotail. FIGS. 19C-D show CAR-T cell differentiation on Day 7 of the growth factor-independent assay for constructs bearing the TpoR(478-582;S505N;W515K) and TpoR(478-582;H499L;S505N;W515K) dimerization/JAK-binding domains, respectively, fused to the indicated cytotails. Compared to control BFP CAR-T cells and CAR-T cells bearing IL12Rb2-derived cytotails, CAR-T cells bearing the IL7Ra(316-459) cytotail were not only more abundant, but were also more enriched in the Tscm population. See FIGS. 19C-D. CAR-T cells bearing the tandem IL7Ra(316-459) IL12Rb2(775-825) cytotail improved Tscm enrichment. Without being limited to any particular mechanisms, the results suggest that fusion with the IL7Ra(316-459) cytotail have overridden the phenotype of the single IL12Rb2(775-825) cytotail. Together, these data reiterate the combinatorial functional effects of tandem cytotail signaling and demonstrate tunability of different cytotail constructs.

CAR-T cell products enriched in the Tscm population are associated with improved expansion, persistence and activity. However, terminally-differentiated CAR-T cells are short-lived and have limited proliferative potential, leading to reduced efficacy. Given that these characteristics were differentially influenced by the IL7Ra(316-459) and IL12Rb2-derived cytotails, we evaluated the ability of these cytotails to impact CAR-T cell cytotoxicity.

To this end, 5,000 U87KO-EGFRvIII-nucGFP target cells were seeded and allowed to attach in 96-well plates with black walls and flat clear bottom in 50 uL RPMI containing 10% FBS (Hyclone), non-essential amino acids, sodium pyruvate and 20-25 mM HEPES. EGFRvIII CAR (2173 scFv) T cells bearing either the IL7Ra(316-459) or IL12Rb-derived cytotails were thawed and added to plated target cells at an E:T ratio of 1:3. Since target cells outnumber CAR-T cells, control of target cell growth would require CAR-T cells to kill repeatedly or serially. As a control, CAR-T cells co-expressing the BFP CAR in place of a cytotail was used. The number of live target cells over time was monitored via the IncuCyte Live Cell Analysis Imaging System.

Figure 20A:
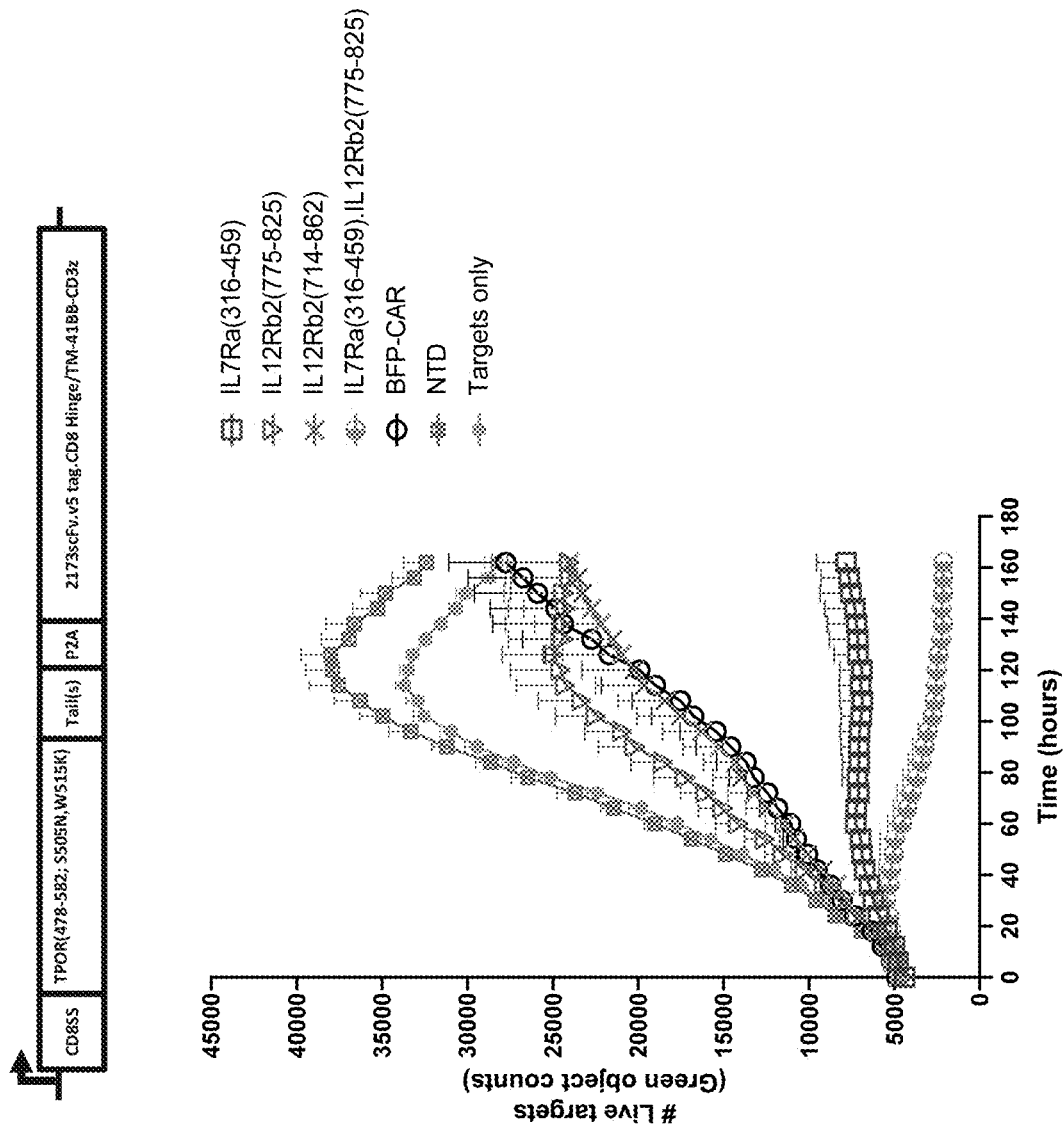
FIGS. 20A-20B depict cytotoxic activity of CAR-T cells co-expressing various CACCRs.
Figure 20B:
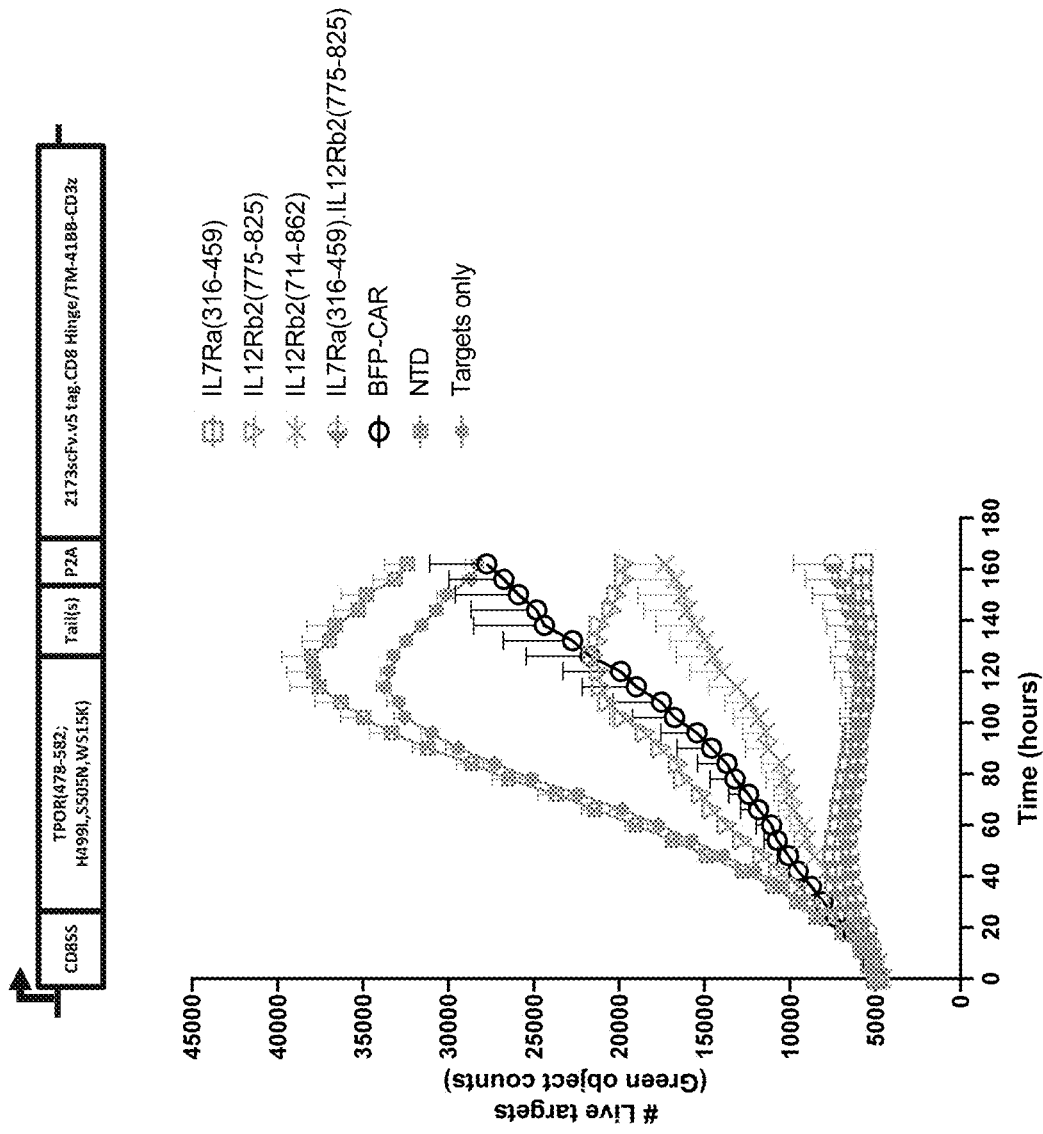

FIGS. 20A-B depict cytotoxic activity of CAR-T cells co-expressing various CACCRs. FIGS. 20A-B show target cell clearance by CACCR CAR-T cells bearing the TpoR (478-582;S505N;W515K) and TpoR(478-582;H499L; S505N;W515K) dimerization/JAK-binding domains, respectively, fused to the indicated cytotails. Compared to BFP CAR-T cells, CAR-T cells bearing IL12Rb2-derived cytotails showed some to no improvement in serial killing activity in vitro, likely due to their limited proliferative potential and short life-span. In contrast, CAR-T cells bearing the IL7Ra(316-459) cytotail exhibited improved serial killing activity, likely due to enhanced proliferation and persistence. Notably, CAR-T cells bearing the tandem IL7Ra(316-459),IL12Rb2(775-825) cytotail showed equal or better serial killing activity than the IL7Ra(316-459) cytotail, suggesting that combining the pro-persistence IL7Ra(316-459) signaling domain and the pro-effector IL12Rb2(775-825) signaling domain in a single cytotail may simultaneously enhance CAR-T cell longevity, expansion and immediate effector functions.

Example 11

Constitutive Cytokine Receptors Enhance the In Vitro Cytotoxicity of CARs Directed Towards a Liquid Tumor Target We have demonstrated that CACCRs can enhance the activity of a CAR directed towards EGFRvIII, a target for solid tumor, e.g., glioblastoma. To determine if CACCRs are broadly applicable across a different scFv for a hematological tumor target, we additionally cloned the CACCRs into CAR construct directed towards a marker for a hematological malignancy (i.e. BCMA) and evaluated the long-term cytotoxicity against the BCMA positive target cell line.

Target cells stably expressing the firefly luciferase and GFP reporters were generated by lentiviral transduction. 10,000 Luc-GFP-labelled target cells were plated in 100 uL per well in a white flat-bottomed 96-well tissue culture plate. Cryopreserved CAR-T cells were thawed, counted, and the percentage of CAR-T cells across all samples were normalized to the sample with the lowest transduction efficiency by the addition of non-transduced (NTD) T cells. CAR-T cells in a volume of 100 uL were then added to each well of target cells at the indicated Effector:Target (E:T) ratios in triplicates. As a "Targets only" negative control, 100 uL of media, instead of T cells, was added to target cells. After two or three days, wells were mixed by gentle pipetting, and 100 uL of each T cell-containing well was transferred to a new white flat-bottomed 96-well tissue culture plate containing 10,000 freshly-plated Luc-GFP-labelled target cells in 100 uL. "Targets only" wells received fresh media in place of T cells. The new plate was incubated at 37° C., while the number of live target cells remaining in the old 96-well plate was determined using the ONE-Glo Luciferase Assay System (Promega) according to manufacturer's instructions. The percentage of live target cells was calculated by normalizing the luciferase signal of to that of "Targets only" wells, and percentage cytotoxicity was calculated as 100%–% live target cells. Serial transfers to fresh target cells and luciferase readouts were performed every two or three days until all cytotoxic activity has ceased.

Figure 21:
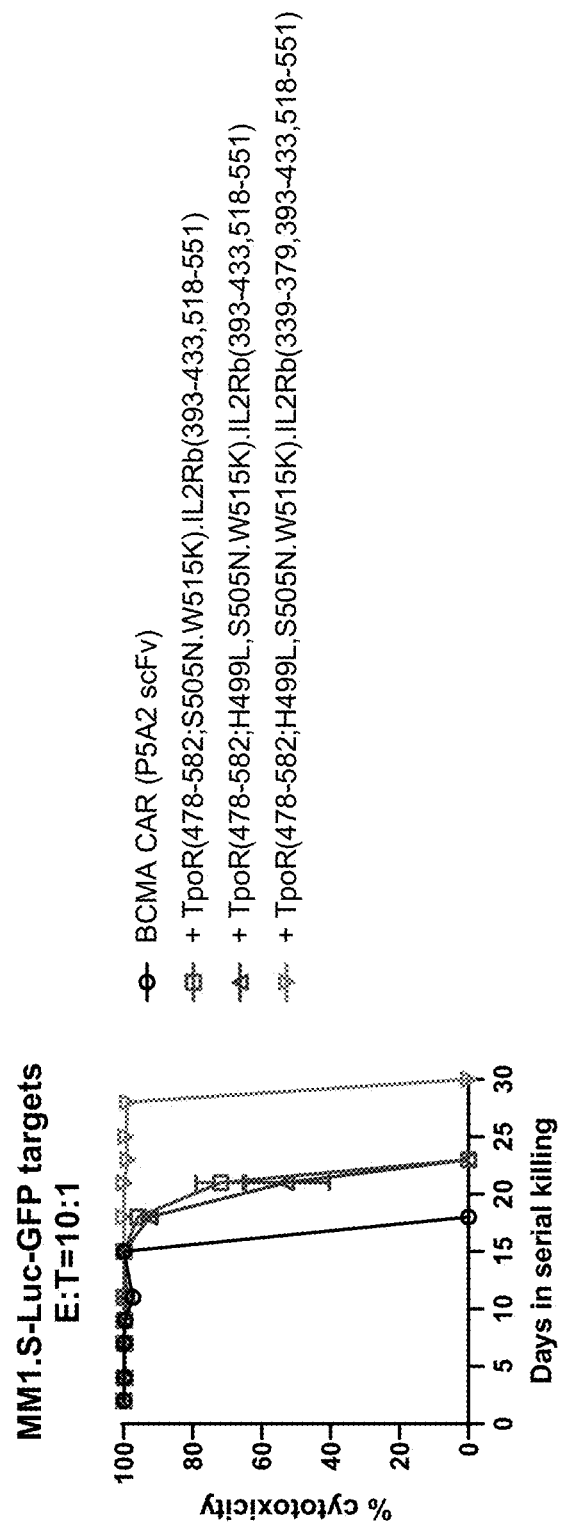
FIG. 21 shows that CACCRs improved the cytotoxic activity of CAR-T cells directed towards a liquid tumor target BCMA.

FIG. 21 shows that CACCRs improved the cytotoxic activity of CAR-T cells directed towards BCMA, a liquid tumor target. FIG. 21 shows the cytotoxicity of a BCMA CAR (P5A2 scFv) against the MM1.S multiple myeloma cell line at an E:T=10:1, indicating co-expression of a CACCR increased the long-term cytotoxicity of CAR-T cells.

Example 12

CACCRs Enhance the In Vivo Activity of CAR-T Cells

CAR-T cell therapies, such as those targeting CD19 and BCMA, have attained unprecedented clinical success in the treatment of hematological malignancies. While a high rate of complete responses has been achieved, this is transient as most patients eventually relapse. Furthermore, CAR-T cells have attained more limited success for the treatment of solid tumors. Among the reasons for relapse and the lack of response include insufficient CAR-T cell expansion and persistence, as well as CAR-T cell functional inhibition by immune-suppressive microenvironments. Since our in vitro characterization of CACCR CAR-T cells revealed improvements in target-driven proliferation, persistence, potency and exhaustion profiles, we next investigated whether these functional enhancements translated into improved anti-tumor activity in vivo.

To interrogate the in vivo activity of CACCR CAR-T cells in the context of hematological malignancies, we utilized CAR-T cells bearing the BCMA-specific P5A2 scFv coupled to 4-1BB and CD3ζ signaling domains in an orthotopic xenograft model of multiple myeloma. T cell receptor (TCR)-deficient BCMA CAR-T cells were generated by Transcription Activator-Like Effector Nucleases (TALEN)-mediated knockout to avoid potential confoundance from TCR-driven xenoreactivity. 8-10 week old female NSG mice were irradiated with 1 Gy one day prior to intravenous inoculation of $5 \times 10^6$ MM1.S-Luc-GFP. 14 days after tumor implantation, mice were randomized based on tumor burden, and dosed intravenously with either $1 \times 10^6$ or $3 \times 10^6$ of the indicated CAR-T cells (n=10 per group). Tumor progression was monitored by bioluminescent imaging. On Day 30 post T cell dose, mice that had received $3 \times 10^6$ CAR-T cells were bled for the enumeration of BCMA CAR-T cells in the periphery. Specifically, 50 uL of whole blood from each mouse was subjected to red blood cell lysis using ACK Lysing Buffer (Gibco), Fc-blocked and stained with the following antibody cocktail diluted in PBS+1% BSA: FITC-conjugated anti-mouse CD45 (Biolegend), BV421-conjugated anti-human CD45 (Biolegend) and an anti-idiotype antibody specific for the P5A2 scFv. Finally, samples were washed in PBS and cell pellets were resuspended in 130 uL PBS+1%BSA containing 123 count eBeads counting beads (Thermo Fisher) (10 uL counting beads in 120 uL PBS+1% BSA) prior to FACS analysis.

Figure 22B:
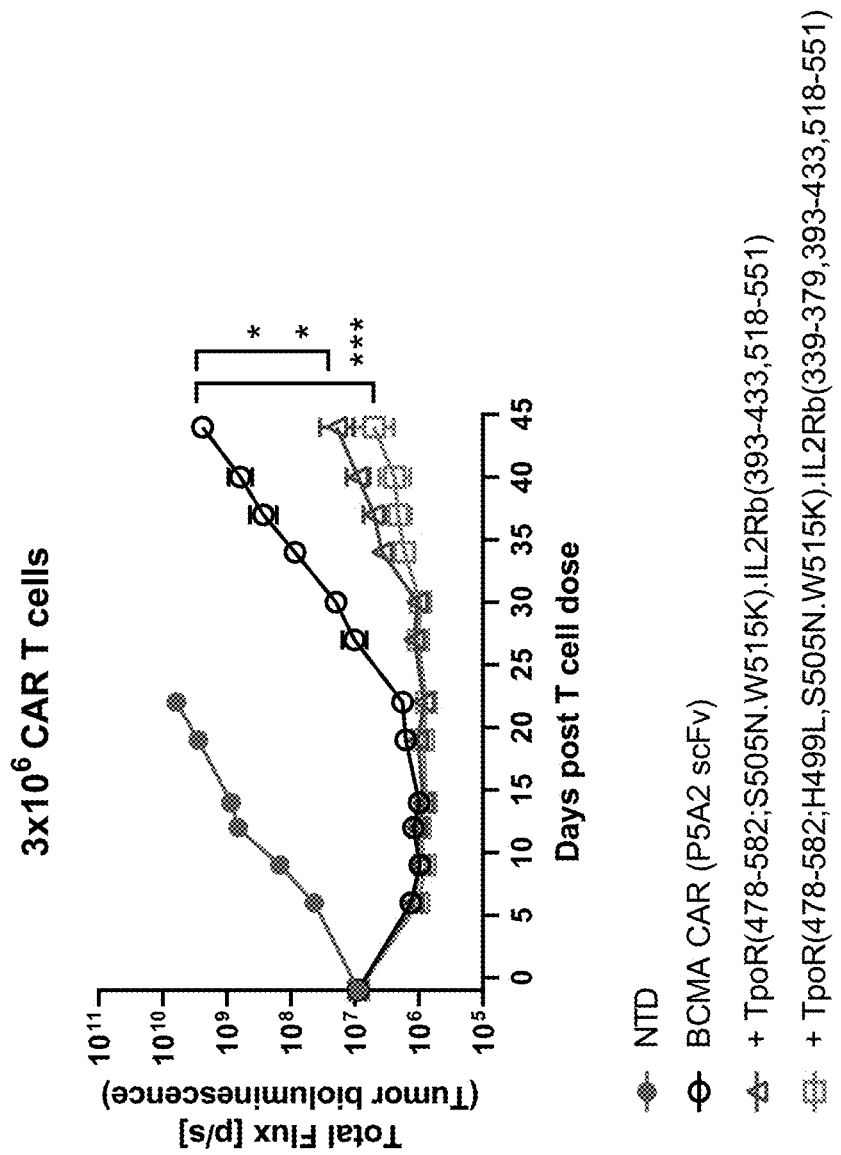
Figure 22C:
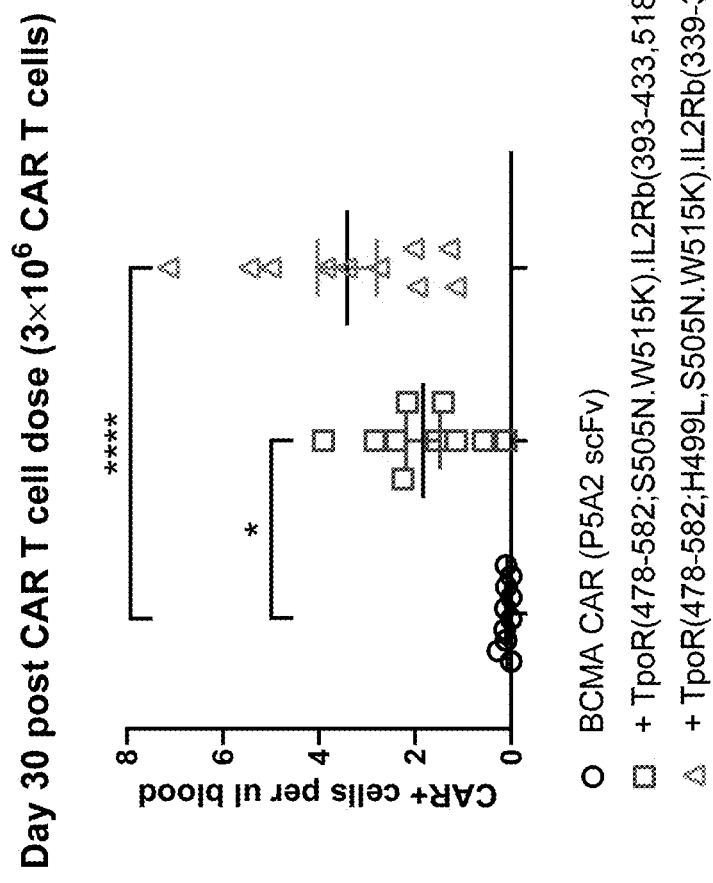

FIGS. 22A-C show that CACCRs improved the in vivo anti-tumor activity and persistence of BCMA CAR-T cells against orthotopic multiple myeloma. FIGS. 24A-B show tumor progression in response to treatment with either $1 \times 10^6$ or $3 \times 10^6$ of the indicated CAR-T cells, respectively. Although control BCMA CAR-T cells were able to mediate initial tumor regression, this response was short-lived as tumors relapsed 22 days after cell infusion. However, CACCR coexpressing CAR-T cells significantly delayed tumor relapse and improved the durability of response. Statistics in FIGS. 24A-B represent  $p<0.01$ and *$p<0.001$ based on repeated measures one-way ANOVA with Tukey's multiple comparisons from Days 6-34 for FIG. 22A and Days 6-44 for FIG. 22B. FIG. 22C shows the number of BCMA CAR-T cells present in the peripheral blood of mice treated with $3 \times 10^6$ CAR-T cells 30 days after T cell infusion. Coincident with tumor relapse observed in mice treated with control BCMA CAR-T cells, control BCMA CAR-T cells could no longer be detected in the periphery. In contrast, CACCR BCMA CAR-T cells that were superior at preventing tumor relapse were also more significantly abundant in vivo. Statistics in FIG. 24C represent *$p<0.05$ and ****$p<0.0001$ based on ordinary one-way ANOVA with Tukey's multiple comparisons. These suggest that improved CACCR CAR-T cell persistence in part mediated enhanced long-term tumor control and prolonged the durability of response.

We additionally assessed the impact on CACCRs on CAR-T cell activity in the context of solid tumors known to resist CAR-T cell therapy, such as glioblastoma. To this end, we utilized a EGFRvIII-specific CAR bearing the 2173 scFv coupled to 4-1BB and CD3ζ signaling domains, as well as the LN229 human glioblastoma cell line stably over-expressing EGFRvIII (LN229-EGFRvIII). 8-10 week old female NSG mice were subcutaneously implanted with $3 \times 10^6$ LN229-EGFRvIII. 25 days later when tumors were established, mice were randomized based on tumor burden and dosed intravenously with either $1.5 \times 10^6$ or $3 \times 10^6$ of the indicated CAR-T cells (n=8-10 per group). Tumor progression was monitored twice a week by caliper measurements.

Figure 23:
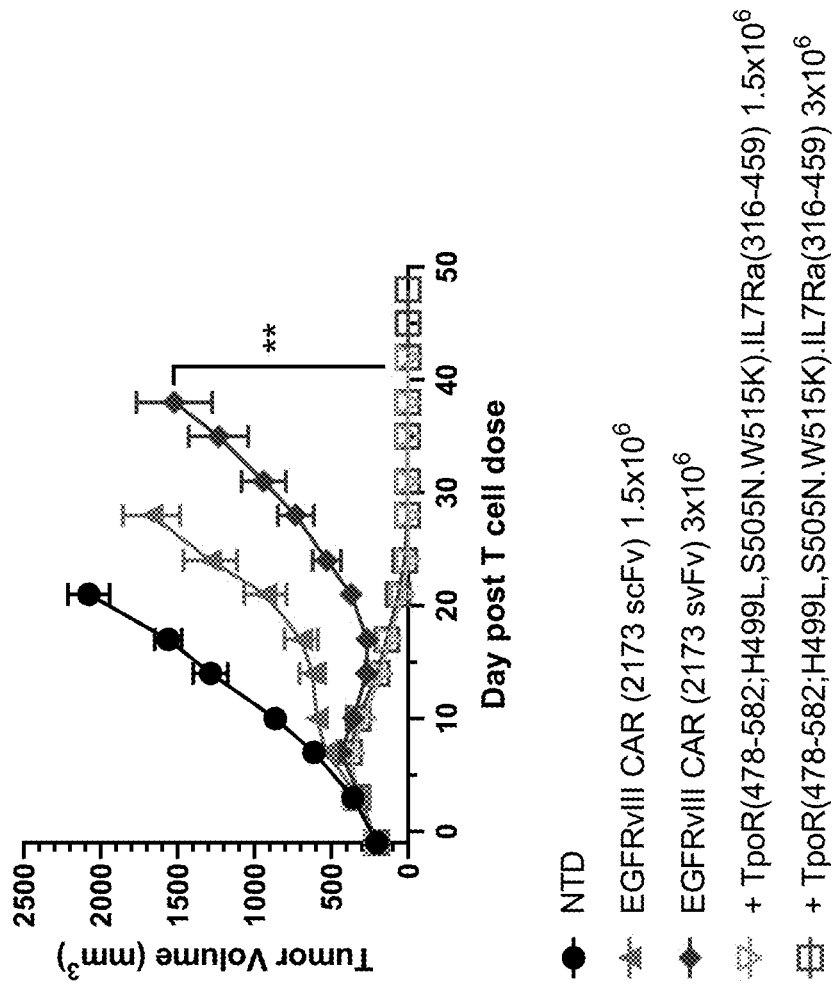
FIG. 23 shows that CACCRs improved the anti-tumor activity of CAR-T cells against established solid tumors.

FIG. 23 shows that CACCR improved the anti-tumor activity of CAR-T cells against established solid tumors. Although treatment with control EGFRvIII CAR-T cells could retard the growth of LN229-EGFRvIII tumors, the response was transient and sub-optimal as tumors eventually progressed. In contrast, treatment with CACCR CAR-T cells resulted in complete tumor regression. Notably, even a low dose of $1.5 \times 10^6$ CACCR CAR-T cells was sufficient for tumor elimination. Statistics represent **$p<0.01$ compared to treatment with $3 \times 10^6$ control CAR-T cells based on repeated measures one-way ANOVA with Tukey's multiple comparisons from Days 3-38. These results reiterate the ability of CACCRs to synergize non-redundantly with signaling domains in CAR-T cells to confer improved activity.

What is claimed is:

1. A constitutively active chimeric cytokine receptor (CACCR) composed of two monomers, each monomer comprising:
   a. a transmembrane domain;
   b. a Janus Kinase (JAK)-binding domain; and
   c. a recruiting domain,
   wherein the monomers are constitutively dimerized and wherein the transmembrane domain and JAK-binding domain comprises amino acids 478-582 of SEQ ID NO: 6 and comprises amino acid substitutions S505N and W515K.

2. The CACCR of claim 1, wherein the JAK-binding domain comprises a JAK1-binding domain, a JAK2-binding domain, a JAK3-binding domain or a TYK2-binding domain.

3. The CACCR of claim 1, wherein the recruiting domain comprises a STAT-recruiting domain from at least one receptor.

4. The CACCR of claim 3, wherein the STAT-recruiting domain is from IL2Rb.

5. The CACCR of claim 1, wherein amino acids 478-582 of SEQ ID NO: 6 further comprise an amino acid substitution H499L.

6. The CACCR of claim 5, wherein the transmembrane domain comprises SEQ ID NO: 12.

7. The CACCR of claim 1, wherein amino acids 478-582 of SEQ ID NO: 6 further comprise an amino acid substitution G509N.

8. The CACCR of claim 1, wherein amino acids 478-582 of SEQ ID NO: 6 further comprise amino acid substitutions H499L and G509N.

9. The CACCR of claim 1, wherein the transmembrane domain comprises SEQ ID NO: 13.

10. The CACCR of claim 1, wherein the monomers are identical.

11. The CACCR of claim 1, wherein the monomers are different.

12. The CACCR of claim 1, wherein the recruiting domain comprises a STAT-recruiting domain from a cytokine receptor.

13. The CACCR of claim 1, wherein the recruiting domain comprises a STAT-recruiting domain from a receptor selected from BLNK, IL2RG, EGFR, EpoR, GHR, IFNAR1, IFNAR2, IFNAR1/2, IFNLR1, IL10R1, IL12Rb1, IL12Rb2, IL21R, IL2Rb, IL2small, IL7R, IL7Ra, IL9R, IL15R, and IL21R.

14. The CACCR of claim 1, wherein the recruiting domain comprises the amino acid sequence of one or more of the receptor sequences selected from SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 106, and SEQ ID NO: 143.

15. The CACCR of claim 1, wherein the recruiting domain comprises a STAT-recruiting domain from IL7Ra.

16. The CACCR of claim 1, wherein the recruiting domain comprises SEQ ID NO: 46.

17. The CACCR of claim 1, wherein the recruiting domain comprises a STAT-recruiting domain from IL2Rb.

18. The CACCR of claim 1, wherein the recruiting domain comprises (i) amino acid residues 1 to 41 of SEQ ID NO: 73, (ii) SEQ ID NO: 74, (iii) SEQ ID NO: 77, or (iv) SEQ ID NO: 78.

19. The CACCR of claim 1, wherein the recruiting domain comprises a STAT-recruiting domain from IL12Rb2.

20. The CACCR of claim 1, wherein the recruiting domain comprises SEQ ID NO: 86 or 67.

21. The CACCR of claim 1, wherein the recruiting domain comprises STAT-recruiting domains from two receptors.

22. The CACCR of claim 1, wherein the recruiting domain comprises STAT-recruiting domains from two cytokine receptors.

23. The CACCR of claim 22, wherein the two cytokine receptors are selected from the group consisting of IL7Ra, IL2Rb, and IL12Rb2.

24. The CACCR of claim 1, wherein the recruiting domain comprises SEQ ID NO: 77.

25. The CACCR of claim 1, wherein the recruiting domain comprises SEQ ID NO: 78.

26. A polynucleotide encoding the CACCR of claim 1.

27. An expression vector comprising the polynucleotide of claim 26.

28. The expression vector of claim 27 further comprising a polynucleotide expressing a chimeric antigen receptor (CAR).

29. The expression vector of claim 27, wherein the vector is a lentiviral vector.

30. An engineered immune cell comprising the expression vector of claim 27.

31. The engineered immune cell of claim 30, wherein the immune cell is a T-cell.

32. An engineered immune cell comprising a chimeric antigen receptor (CAR) and at least one CACCR of claim 1.

33. The engineered immune cell of claim 32, wherein the CAR and the CACCR are expressed in stoichiometrically equal amounts.

34. The engineered immune cell of claim 33, wherein the immune cell is a T-cell.

35. A method of preparing an engineered immune cell, the method comprising introducing the polynucleotide of claim 26 into an immune cell.

36. A pharmaceutical composition comprising the engineered immune cell of claim 30.

37. A kit comprising the engineered immune cell of claim 30.

38. A method of treating a cancer in a subject, comprising administering to the subject a therapeutically effective amount of the engineered immune cell of claim 30.

39. The method of claim 38, wherein the cancer comprises a solid tumor or a liquid tumor.

* * * * *

SEQUENCE LISTING

```
<160> NUMBER OF SEQ ID NOS: 144

<210> SEQ ID NO 1
<211> LENGTH: 508
<212> TYPE: PRT
<213> ORGANISM: Homo sapiens

<400> SEQUENCE: 1

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Pro Asn Leu Pro Asp
```

```
                20                  25                  30
Pro Lys Phe Glu Ser Lys Ala Ala Leu Leu Ala Ala Arg Gly Pro Glu
            35                  40                  45

Glu Leu Leu Cys Phe Thr Arg Leu Glu Asp Leu Val Cys Phe Trp
        50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
                100                 105                 110

Asp Thr Ser Ser Phe Val Pro Leu Glu Leu Arg Val Thr Ala Ala Ser
            115                 120                 125

Gly Ala Pro Arg Tyr His Arg Val Ile His Ile Asn Glu Val Val Leu
                130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
                180                 185                 190

Val Gln Arg Val Glu Ile Leu Glu Gly Arg Thr Glu Cys Val Leu Ser
                195                 200                 205

Asn Leu Arg Gly Arg Thr Arg Tyr Thr Phe Ala Val Arg Ala Arg Met
            210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
                260                 265                 270

Ser His Arg Arg Ala Leu Lys Gln Lys Ile Trp Pro Gly Ile Pro Ser
            275                 280                 285

Pro Glu Ser Glu Phe Glu Gly Leu Phe Thr Thr His Lys Gly Asn Phe
                290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
            340                 345                 350

Gly Pro Leu Leu Glu Pro Val Gly Ser Glu His Ala Gln Asp Thr Tyr
                355                 360                 365

Leu Val Leu Asp Lys Trp Leu Leu Pro Arg Asn Pro Pro Ser Glu Asp
            370                 375                 380

Leu Pro Gly Pro Gly Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
                405                 410                 415

Glu Gly Ala Ser Ala Ala Ser Phe Glu Tyr Thr Ile Leu Asp Pro Ser
                420                 425                 430

Ser Gln Leu Leu Arg Pro Trp Thr Leu Cys Pro Glu Leu Pro Pro Thr
            435                 440                 445
```

-continued

Pro Pro His Leu Lys Tyr Leu Tyr Leu Val Val Ser Asp Ser Gly Ile
    450                 455                 460

Ser Thr Asp Tyr Ser Ser Gly Asp Ser Gln Gly Ala Gln Gly Gly Leu
465                 470                 475                 480

Ser Asp Gly Pro Tyr Ser Asn Pro Tyr Glu Asn Ser Leu Ile Pro Ala
                485                 490                 495

Ala Glu Pro Leu Pro Pro Ser Tyr Val Ala Cys Ser
                500                 505

<210> SEQ ID NO 2
<211> LENGTH: 918
<212> TYPE: PRT
<213> ORGANISM: Homo sapiens

<400> SEQUENCE: 2

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Arg Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile

-continued

```
              305                 310                 315                 320
          Thr Tyr Glu Asp Arg Pro Ser Lys Ala Pro Ser Phe Trp Tyr Lys Ile
                          325                 330                 335

Asp Pro Ser His Thr Gln Gly Tyr Arg Thr Val Gln Leu Val Trp Lys
                          340                 345                 350

Thr Leu Pro Pro Phe Glu Ala Asn Gly Lys Ile Leu Asp Tyr Glu Val
                          355                 360                 365

Thr Leu Thr Arg Trp Lys Ser His Leu Gln Asn Tyr Thr Val Asn Ala
                          370                 375                 380

Thr Lys Leu Thr Val Asn Leu Thr Asn Asp Arg Tyr Val Ala Thr Leu
          385                 390                 395                 400

Thr Val Arg Asn Leu Val Gly Lys Ser Asp Ala Ala Val Leu Thr Ile
                          405                 410                 415

Pro Ala Cys Asp Phe Gln Ala Thr His Pro Val Met Asp Leu Lys Ala
                          420                 425                 430

Phe Pro Lys Asp Asn Met Leu Trp Val Glu Trp Thr Thr Pro Arg Glu
                          435                 440                 445

Ser Val Lys Lys Tyr Ile Leu Glu Trp Cys Val Leu Ser Asp Lys Ala
                          450                 455                 460

Pro Cys Ile Thr Asp Trp Gln Gln Glu Asp Gly Thr Val His Arg Thr
          465                 470                 475                 480

Tyr Leu Arg Gly Asn Leu Ala Glu Ser Lys Cys Tyr Leu Ile Thr Val
                          485                 490                 495

Thr Pro Val Tyr Ala Asp Gly Pro Gly Ser Pro Glu Ser Ile Lys Ala
                          500                 505                 510

Tyr Leu Lys Gln Ala Pro Pro Ser Lys Gly Pro Thr Val Arg Thr Lys
                          515                 520                 525

Lys Val Gly Lys Asn Glu Ala Val Leu Glu Trp Asp Gln Leu Pro Val
                          530                 535                 540

Asp Val Gln Asn Gly Phe Ile Arg Asn Tyr Thr Ile Phe Tyr Arg Thr
          545                 550                 555                 560

Ile Ile Gly Asn Glu Thr Ala Val Asn Val Asp Ser Ser His Thr Glu
                          565                 570                 575

Tyr Thr Leu Ser Ser Leu Thr Ser Asp Thr Leu Tyr Met Val Arg Met
                          580                 585                 590

Ala Ala Tyr Thr Asp Glu Gly Gly Lys Asp Gly Pro Glu Phe Thr Phe
                          595                 600                 605

Thr Thr Pro Lys Phe Ala Gln Gly Glu Ile Glu Ala Ile Val Val Pro
                          610                 615                 620

Val Cys Leu Ala Phe Leu Leu Thr Thr Leu Leu Gly Val Leu Phe Cys
          625                 630                 635                 640

Phe Asn Lys Arg Asp Leu Ile Lys Lys His Ile Trp Pro Asn Val Pro
                          645                 650                 655

Asp Pro Ser Lys Ser His Ile Ala Gln Trp Ser Pro His Thr Pro Pro
                          660                 665                 670

Arg His Asn Phe Asn Ser Lys Asp Gln Met Tyr Ser Asp Gly Asn Phe
                          675                 680                 685

Thr Asp Val Ser Val Val Glu Ile Glu Ala Asn Asp Lys Lys Pro Phe
                          690                 695                 700

Pro Glu Asp Leu Lys Ser Leu Asp Leu Phe Lys Lys Glu Lys Ile Asn
          705                 710                 715                 720

Thr Glu Gly His Ser Ser Gly Ile Gly Gly Ser Ser Cys Met Ser Ser
                          725                 730                 735
```

```
Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
            755                 760                 765

His Gln Val Pro Ser Val Gln Val Phe Ser Arg Ser Glu Ser Thr Gln
            770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Pro Asp Ile Ser His Phe Glu
            820                 825                 830

Arg Ser Lys Gln Val Ser Ser Val Asn Glu Glu Asp Phe Val Arg Leu
            835                 840                 845

Lys Gln Gln Ile Ser Asp His Ile Ser Gln Ser Cys Gly Ser Gly Gln
850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
            885                 890                 895

Thr Asp Glu Gly Met Pro Lys Ser Tyr Leu Pro Gln Thr Val Arg Gln
            900                 905                 910

Gly Gly Tyr Met Pro Gln
            915

<210> SEQ ID NO 3
<211> LENGTH: 622
<212> TYPE: PRT
<213> ORGANISM: Homo sapiens

<400> SEQUENCE: 3

Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
            35                  40                  45

Arg Pro Gly Thr Asp Gly Gly Leu Pro Thr Asn Tyr Ser Leu Thr Tyr
            50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
            115                 120                 125

Pro Pro Leu Glu Leu Ala Val Glu Val Lys Gln Pro Glu Asp Arg Lys
            130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
```

-continued

```
                180                 185                 190
Ile Leu Ser Leu His Pro Gly Gln Lys Tyr Leu Val Gln Val Arg Cys
            195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
            245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
        290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Met Lys Pro Thr Tyr Leu Asp Pro Asp Thr Asp Ser Gly Arg Gly
            340                 345                 350

Ser Cys Asp Ser Pro Ser Leu Leu Ser Glu Lys Cys Glu Glu Pro Gln
        355                 360                 365

Ala Asn Pro Ser Thr Phe Tyr Asp Pro Glu Val Ile Glu Lys Pro Glu
    370                 375                 380

Asn Pro Glu Thr Thr His Thr Trp Asp Pro Gln Cys Ile Ser Met Glu
385                 390                 395                 400

Gly Lys Ile Pro Tyr Phe His Ala Gly Gly Ser Lys Cys Ser Thr Trp
                405                 410                 415

Pro Leu Pro Gln Pro Ser Gln His Asn Pro Arg Ser Ser Tyr His Asn
            420                 425                 430

Ile Thr Asp Val Cys Glu Leu Ala Val Gly Pro Ala Gly Ala Pro Ala
        435                 440                 445

Thr Leu Leu Asn Glu Ala Gly Lys Asp Ala Leu Lys Ser Ser Gln Thr
    450                 455                 460

Ile Lys Ser Arg Glu Glu Gly Lys Ala Thr Gln Gln Arg Glu Val Glu
465                 470                 475                 480

Ser Phe His Ser Glu Thr Asp Gln Asp Thr Pro Trp Leu Leu Pro Gln
                485                 490                 495

Glu Lys Thr Pro Phe Gly Ser Ala Lys Pro Leu Asp Tyr Val Glu Ile
            500                 505                 510

His Lys Val Asn Lys Asp Gly Ala Leu Ser Leu Leu Pro Lys Gln Arg
        515                 520                 525

Glu Asn Ser Gly Lys Pro Lys Pro Gly Thr Pro Glu Asn Asn Lys
    530                 535                 540

Glu Tyr Ala Lys Val Ser Gly Val Met Asp Asn Asn Ile Leu Val Leu
545                 550                 555                 560

Val Pro Asp Pro His Ala Lys Asn Val Ala Cys Phe Glu Glu Ser Ala
                565                 570                 575

Lys Glu Ala Pro Pro Ser Leu Glu Gln Asn Gln Ala Glu Lys Ala Leu
            580                 585                 590

Ala Asn Phe Thr Ala Thr Ser Ser Lys Cys Arg Leu Gln Leu Gly Gly
        595                 600                 605
```

```
Leu Asp Tyr Leu Asp Pro Ala Cys Phe Thr His Ser Phe His
        610                 615                 620

<210> SEQ ID NO 4
<211> LENGTH: 638
<212> TYPE: PRT
<213> ORGANISM: Homo sapiens

<400> SEQUENCE: 4

Met Asp Leu Trp Gln Leu Leu Thr Leu Ala Leu Ala Gly Ser Ser
 1               5                  10                  15

Asp Ala Phe Ser Gly Ser Glu Ala Thr Ala Ala Ile Leu Ser Arg Ala
                20                  25                  30

Pro Trp Ser Leu Gln Ser Val Asn Pro Gly Leu Lys Thr Asn Ser Ser
                35                  40                  45

Lys Glu Pro Lys Phe Thr Lys Cys Arg Ser Pro Glu Arg Glu Thr Phe
        50                  55                  60

Ser Cys His Trp Thr Asp Glu Val His Gly Thr Lys Asn Leu Gly
 65                  70                  75                  80

Pro Ile Gln Leu Phe Tyr Thr Arg Arg Asn Thr Gln Glu Trp Thr Gln
                        85                  90                  95

Glu Trp Lys Glu Cys Pro Asp Tyr Val Ser Ala Gly Glu Asn Ser Cys
                100                 105                 110

Tyr Phe Asn Ser Ser Phe Thr Ser Ile Trp Ile Pro Tyr Cys Ile Lys
                115                 120                 125

Leu Thr Ser Asn Gly Gly Thr Val Asp Glu Lys Cys Phe Ser Val Asp
130                 135                 140

Glu Ile Val Gln Pro Asp Pro Pro Ile Ala Leu Asn Trp Thr Leu Leu
145                 150                 155                 160

Asn Val Ser Leu Thr Gly Ile His Ala Asp Ile Gln Val Arg Trp Glu
                165                 170                 175

Ala Pro Arg Asn Ala Asp Ile Gln Lys Gly Trp Met Val Leu Glu Tyr
                180                 185                 190

Glu Leu Gln Tyr Lys Glu Val Asn Glu Thr Lys Trp Lys Met Met Asp
                195                 200                 205

Pro Ile Leu Thr Thr Ser Val Pro Val Tyr Ser Leu Lys Val Asp Lys
        210                 215                 220

Glu Tyr Glu Val Arg Val Arg Ser Lys Gln Arg Asn Ser Gly Asn Tyr
225                 230                 235                 240

Gly Glu Phe Ser Glu Val Leu Tyr Val Thr Leu Pro Gln Met Ser Gln
                245                 250                 255

Phe Thr Cys Glu Glu Asp Phe Tyr Phe Pro Trp Leu Leu Ile Ile Ile
                260                 265                 270

Phe Gly Ile Phe Gly Leu Thr Val Met Leu Phe Val Phe Leu Phe Ser
                275                 280                 285

Lys Gln Gln Arg Ile Lys Met Leu Ile Leu Pro Pro Val Pro Val Pro
        290                 295                 300

Lys Ile Lys Gly Ile Asp Pro Asp Leu Leu Lys Glu Gly Lys Leu Glu
305                 310                 315                 320

Glu Val Asn Thr Ile Leu Ala Ile His Asp Ser Tyr Lys Pro Glu Phe
                325                 330                 335

His Ser Asp Asp Ser Trp Val Glu Phe Ile Glu Leu Asp Ile Asp Glu
                340                 345                 350

Pro Asp Glu Lys Thr Glu Glu Ser Asp Thr Asp Arg Leu Leu Ser Ser
```

```
            355                 360                 365
Asp His Glu Lys Ser His Ser Asn Leu Gly Val Lys Asp Gly Asp Ser
    370                 375                 380

Gly Arg Thr Ser Cys Cys Glu Pro Asp Ile Leu Glu Thr Asp Phe Asn
385                 390                 395                 400

Ala Asn Asp Ile His Glu Gly Thr Ser Glu Val Ala Gln Pro Gln Arg
                405                 410                 415

Leu Lys Gly Glu Ala Asp Leu Leu Cys Leu Asp Gln Lys Asn Gln Asn
            420                 425                 430

Asn Ser Pro Tyr His Asp Ala Cys Pro Ala Thr Gln Gln Pro Ser Val
        435                 440                 445

Ile Gln Ala Glu Lys Asn Lys Pro Gln Pro Leu Pro Thr Glu Gly Ala
    450                 455                 460

Glu Ser Thr His Gln Ala Ala His Ile Gln Leu Ser Asn Pro Ser Ser
465                 470                 475                 480

Leu Ser Asn Ile Asp Phe Tyr Ala Gln Val Ser Asp Ile Thr Pro Ala
                485                 490                 495

Gly Ser Val Val Leu Ser Pro Gly Gln Lys Asn Lys Ala Gly Met Ser
            500                 505                 510

Gln Cys Asp Met His Pro Glu Met Val Ser Leu Cys Gln Glu Asn Phe
        515                 520                 525

Leu Met Asp Asn Ala Tyr Phe Cys Glu Ala Asp Ala Lys Lys Cys Ile
    530                 535                 540

Pro Val Ala Pro His Ile Lys Val Glu Ser His Ile Gln Pro Ser Leu
545                 550                 555                 560

Asn Gln Glu Asp Ile Tyr Ile Thr Thr Glu Ser Leu Thr Thr Ala Ala
                565                 570                 575

Gly Arg Pro Gly Thr Gly Glu His Val Pro Gly Ser Glu Met Pro Val
            580                 585                 590

Pro Asp Tyr Thr Ser Ile His Ile Val Gln Ser Pro Gln Gly Leu Ile
        595                 600                 605

Leu Asn Ala Thr Ala Leu Pro Leu Pro Asp Lys Glu Phe Leu Ser Ser
    610                 615                 620

Cys Gly Tyr Val Ser Thr Asp Gln Leu Asn Lys Ile Met Pro
625                 630                 635

<210> SEQ ID NO 5
<211> LENGTH: 863
<212> TYPE: PRT
<213> ORGANISM: Homo sapiens

<400> SEQUENCE: 5

Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
            20                  25                  30

Ala Pro Ile Val His Leu Gly Asp Pro Ile Thr Ala Ser Cys Ile Ile
        35                  40                  45

Lys Gln Asn Cys Ser His Leu Asp Pro Glu Pro Gln Ile Leu Trp Arg
    50                  55                  60

Leu Gly Ala Glu Leu Gln Pro Gly Gly Arg Gln Gln Arg Leu Ser Asp
65                  70                  75                  80

Gly Thr Gln Glu Ser Ile Ile Thr Leu Pro His Leu Asn His Thr Gln
                85                  90                  95
```

```
Ala Phe Leu Ser Cys Cys Leu Asn Trp Gly Asn Ser Leu Gln Ile Leu
                100                 105                 110

Asp Gln Val Glu Leu Arg Ala Gly Tyr Pro Pro Ala Ile Pro His Asn
            115                 120                 125

Leu Ser Cys Leu Met Asn Leu Thr Thr Ser Ser Leu Ile Cys Gln Trp
        130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
                165                 170                 175

Cys Val Pro Lys Asp Gly Gln Ser His Cys Cys Ile Pro Arg Lys His
            180                 185                 190

Leu Leu Leu Tyr Gln Asn Met Gly Ile Trp Val Gln Ala Glu Asn Ala
        195                 200                 205

Leu Gly Thr Ser Met Ser Pro Gln Leu Cys Leu Asp Pro Met Asp Val
    210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
                245                 250                 255

Gln Pro Gly Leu His Ile Asn Gln Lys Cys Glu Leu Arg His Lys Pro
            260                 265                 270

Gln Arg Gly Glu Ala Ser Trp Ala Leu Val Gly Pro Leu Pro Leu Glu
        275                 280                 285

Ala Leu Gln Tyr Glu Leu Cys Gly Leu Leu Pro Ala Thr Ala Tyr Thr
    290                 295                 300

Leu Gln Ile Arg Cys Ile Arg Trp Pro Leu Pro Gly His Trp Ser Asp
305                 310                 315                 320

Trp Ser Pro Ser Leu Glu Leu Arg Thr Thr Glu Arg Ala Pro Thr Val
                325                 330                 335

Arg Leu Asp Thr Trp Trp Arg Gln Arg Gln Leu Asp Pro Arg Thr Val
            340                 345                 350

Gln Leu Phe Trp Lys Pro Val Pro Leu Glu Glu Asp Ser Gly Arg Ile
        355                 360                 365

Gln Gly Tyr Val Val Ser Trp Arg Pro Ser Gly Gln Ala Gly Ala Ile
    370                 375                 380

Leu Pro Leu Cys Asn Thr Thr Glu Leu Ser Cys Thr Phe His Leu Pro
385                 390                 395                 400

Ser Glu Ala Gln Glu Val Ala Leu Val Ala Tyr Asn Ser Ala Gly Thr
                405                 410                 415

Ser Arg Pro Thr Pro Val Val Phe Ser Glu Ser Arg Gly Pro Ala Leu
            420                 425                 430

Thr Arg Leu His Ala Met Ala Arg Asp Pro His Ser Leu Trp Val Gly
        435                 440                 445

Trp Glu Pro Pro Asn Pro Trp Pro Gln Gly Tyr Val Ile Glu Trp Gly
    450                 455                 460

Leu Gly Pro Pro Ser Ala Ser Asn Ser Asn Lys Thr Trp Arg Met Glu
465                 470                 475                 480

Gln Asn Gly Arg Ala Thr Gly Phe Leu Leu Lys Glu Asn Ile Arg Pro
                485                 490                 495

Phe Gln Leu Tyr Glu Ile Ile Val Thr Pro Leu Tyr Gln Asp Thr Met
            500                 505                 510

Gly Pro Ser Gln His Val Tyr Ala Tyr Ser Gln Glu Met Ala Pro Ser
```

```
            515                 520                 525
His Ala Pro Glu Leu His Leu Lys His Ile Gly Lys Thr Trp Ala Gln
530                 535                 540

Leu Glu Trp Val Pro Glu Pro Glu Leu Gly Lys Ser Pro Leu Thr
545                 550                 555                 560

His Tyr Thr Ile Phe Trp Asn Ala Gln Asn Ser Phe Ser Ala
                    565                 570                 575

Ile Leu Asn Ala Ser Ser Arg Gly Phe Val Leu His Gly Leu Glu Pro
                580                 585                 590

Ala Ser Leu Tyr His Ile His Leu Met Ala Ala Ser Gln Ala Gly Ala
            595                 600                 605

Thr Asn Ser Thr Val Leu Thr Leu Met Thr Leu Thr Pro Glu Gly Ser
610                 615                 620

Glu Leu His Ile Ile Leu Gly Leu Phe Gly Leu Leu Leu Leu Leu Thr
625                 630                 635                 640

Cys Leu Cys Gly Thr Ala Trp Leu Cys Cys Ser Pro Asn Arg Lys Asn
                645                 650                 655

Pro Leu Trp Pro Ser Val Pro Asp Pro Ala His Ser Ser Leu Gly Ser
                660                 665                 670

Trp Val Pro Thr Ile Met Glu Glu Leu Pro Gly Pro Arg Gln Gly Gln
                675                 680                 685

Trp Leu Gly Gln Thr Ser Glu Met Ser Arg Ala Leu Thr Pro His Pro
690                 695                 700

Cys Val Gln Asp Ala Phe Gln Leu Pro Gly Leu Gly Thr Pro Ile
705                 710                 715                 720

Thr Lys Leu Thr Val Leu Glu Glu Asp Glu Lys Lys Pro Val Pro Trp
                725                 730                 735

Glu Ser His Asn Ser Ser Glu Thr Cys Gly Leu Pro Thr Leu Val Gln
                740                 745                 750

Thr Tyr Val Leu Gln Gly Asp Pro Arg Ala Val Ser Thr Gln Pro Gln
                755                 760                 765

Ser Gln Ser Gly Thr Ser Asp Gln Val Leu Tyr Gly Gln Leu Leu Gly
                770                 775                 780

Ser Pro Thr Ser Pro Gly Pro Gly His Tyr Leu Arg Cys Asp Ser Thr
785                 790                 795                 800

Gln Pro Leu Leu Ala Gly Leu Thr Pro Ser Pro Lys Ser Tyr Glu Asn
                805                 810                 815

Leu Trp Phe Gln Ala Ser Pro Leu Gly Thr Leu Val Thr Pro Ala Pro
                820                 825                 830

Ser Gln Glu Asp Asp Cys Val Phe Gly Pro Leu Leu Asn Phe Pro Leu
                835                 840                 845

Leu Gln Gly Ile Arg Val His Gly Met Glu Ala Leu Gly Ser Phe
                850                 855                 860

<210> SEQ ID NO 6
<211> LENGTH: 635
<212> TYPE: PRT
<213> ORGANISM: Homo sapiens

<400> SEQUENCE: 6

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
                20                  25                  30
```

-continued

Ser Asp Ser Glu Pro Leu Lys Cys Phe Ser Arg Thr Phe Glu Asp Leu
         35                  40                  45

Thr Cys Phe Trp Asp Glu Glu Ala Ala Pro Ser Gly Thr Tyr Gln
 50                  55                  60

Leu Leu Tyr Ala Tyr Pro Arg Glu Lys Pro Arg Ala Cys Pro Leu Ser
 65                  70                  75                  80

Ser Gln Ser Met Pro His Phe Gly Thr Arg Tyr Val Cys Gln Phe Pro
                 85                  90                  95

Asp Gln Glu Glu Val Arg Leu Phe Phe Pro Leu His Leu Trp Val Lys
             100                 105                 110

Asn Val Phe Leu Asn Gln Thr Arg Thr Gln Arg Val Leu Phe Val Asp
             115                 120                 125

Ser Val Gly Leu Pro Ala Pro Pro Ser Ile Ile Lys Ala Met Gly Gly
         130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                 165                 170                 175

Lys Asn Ser Thr Gly Pro Thr Val Ile Gln Leu Ile Ala Thr Glu Thr
             180                 185                 190

Cys Cys Pro Ala Leu Gln Arg Pro His Ser Ala Ser Ala Leu Asp Gln
         195                 200                 205

Ser Pro Cys Ala Gln Pro Thr Met Pro Trp Gln Asp Gly Pro Lys Gln
210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                 245                 250                 255

Arg Ser Glu Pro Asp Gly Ile Ser Leu Gly Gly Ser Trp Gly Ser Trp
             260                 265                 270

Ser Leu Pro Val Thr Val Asp Leu Pro Gly Asp Ala Val Ala Leu Gly
         275                 280                 285

Leu Gln Cys Phe Thr Leu Asp Leu Lys Asn Val Thr Cys Gln Trp Gln
         290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                 325                 330                 335

Glu Glu Lys Thr Asn Pro Gly Leu Gln Thr Pro Gln Phe Ser Arg Cys
             340                 345                 350

His Phe Lys Ser Arg Asn Asp Ser Ile Ile His Ile Leu Val Glu Val
         355                 360                 365

Thr Thr Ala Pro Gly Thr Val His Ser Tyr Leu Gly Ser Pro Phe Trp
370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                 405                 410                 415

Ala Ala Gln Glu Thr Cys Tyr Gln Leu Arg Tyr Thr Gly Glu Gly His
             420                 425                 430

Gln Asp Trp Lys Val Leu Glu Pro Pro Leu Gly Ala Arg Gly Gly Thr
         435                 440                 445

Leu Glu Leu Arg Pro Arg Ser Arg Tyr Arg Leu Gln Leu Arg Ala Arg

```
                     450                 455                 460
Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
            500                 505                 510

Leu Arg Trp Gln Phe Pro Ala His Tyr Arg Arg Leu Arg His Ala Leu
        515                 520                 525

Trp Pro Ser Leu Pro Asp Leu His Arg Val Leu Gly Gln Tyr Leu Arg
    530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
                565                 570                 575

Arg Thr Pro Leu Pro Leu Cys Ser Ser Gln Ala Gln Met Asp Tyr Arg
            580                 585                 590

Arg Leu Gln Pro Ser Cys Leu Gly Thr Met Pro Leu Ser Val Cys Pro
        595                 600                 605

Pro Met Ala Glu Ser Gly Ser Cys Cys Thr Thr His Ile Ala Asn His
    610                 615                 620

Ser Tyr Leu Pro Leu Ser Tyr Trp Gln Gln Pro
625                 630                 635

<210> SEQ ID NO 7
<211> LENGTH: 105
<212> TYPE: PRT
<213> ORGANISM: Homo sapiens

<400> SEQUENCE: 7

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105

<210> SEQ ID NO 8
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
```

```
                    20                  25                  30

Leu Leu Leu Leu Arg Trp Gln Phe Pro Ala His Tyr Arg Arg Leu Arg
            35                  40                  45

His Ala Leu Trp Pro Ser Leu Pro Asp Leu His Arg Val Leu Gly Gln
 50                  55                  60

Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
                100                 105

<210> SEQ ID NO 9
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser Asp Pro Thr Arg Val Glu Thr Ala Thr Glu Thr Ala Trp Ile Ser
 1                   5                  10                  15

Leu Val Thr Ala Leu His Leu Val Leu Gly Leu Asn Ala Val Leu Gly
                20                  25                  30

Leu Leu Leu Leu Arg Trp Gln Phe Pro Ala His Tyr Arg Arg Leu Arg
            35                  40                  45

His Ala Leu Trp Pro Ser Leu Pro Asp Leu His Arg Val Leu Gly Gln
 50                  55                  60

Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
                100                 105

<210> SEQ ID NO 10
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Asp Pro Thr Arg Val Glu Thr Ala Thr Glu Thr Ala Trp Ile Ser
 1                   5                  10                  15

Leu Val Thr Ala Leu Leu Leu Val Leu Gly Leu Ser Ala Val Leu Gly
                20                  25                  30

Leu Leu Leu Leu Arg Lys Gln Phe Pro Ala His Tyr Arg Arg Leu Arg
            35                  40                  45

His Ala Leu Trp Pro Ser Leu Pro Asp Leu His Arg Val Leu Gly Gln
 50                  55                  60

Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
```

```
                100             105

<210> SEQ ID NO 11
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100             105

<210> SEQ ID NO 12
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100             105

<210> SEQ ID NO 13
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Asp Pro Thr Arg Val Glu Thr Ala Thr Glu Thr Ala Trp Ile Ser
1               5                   10                  15
```

```
Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
            35                  40                  45

His Ala Leu Trp Pro Ser Leu Pro Asp Leu His Arg Val Leu Gly Gln
 50                  55                  60

Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                 85                  90                  95

Ser Ser Glu Arg Thr Pro Leu Pro Leu
            100                 105

<210> SEQ ID NO 14
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Asp Pro Thr Arg Val Glu Thr Ala Thr Glu Thr Ala Trp Ile Ser
 1               5                  10                  15

Leu Val Thr Ala Leu Leu Leu Val Gly Leu Ser Ala Val Leu Asn
            20                  25                  30

Leu Leu Leu Leu Arg Trp Gln Phe Pro Ala His Tyr Arg Arg Leu Arg
            35                  40                  45

His Ala Leu Trp Pro Ser Leu Pro Asp Leu His Arg Val Leu Gly Gln
 50                  55                  60

Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                 85                  90                  95

Ser Ser Glu Arg Thr Pro Leu Pro Leu
            100                 105

<210> SEQ ID NO 15
<211> LENGTH: 97
<212> TYPE: PRT
<213> ORGANISM: Unknown
<220> FEATURE:
<223> OTHER INFORMATION: Description of Unknown:
      GCSFR(614-710) sequence

<400> SEQUENCE: 15

Leu Thr Leu Met Thr Leu Thr Pro Glu Gly Ser Glu Leu His Ile Ile
 1               5                  10                  15

Leu Gly Leu Phe Gly Leu Leu Leu Leu Thr Cys Leu Cys Gly Thr
            20                  25                  30

Ala Trp Leu Cys Cys Ser Pro Asn Arg Lys Asn Pro Leu Trp Pro Ser
            35                  40                  45

Val Pro Asp Pro Ala His Ser Ser Leu Gly Ser Trp Val Pro Thr Ile
 50                  55                  60

Met Glu Glu Asp Ala Phe Gln Leu Pro Gly Leu Gly Thr Pro Pro Ile
 65                  70                  75                  80

Thr Lys Leu Thr Val Leu Glu Glu Asp Glu Lys Lys Pro Val Pro Trp
                 85                  90                  95
```

Glu

```
<210> SEQ ID NO 16
<211> LENGTH: 92
<212> TYPE: PRT
<213> ORGANISM: Homo sapiens

<400> SEQUENCE: 16

Thr Thr Pro Lys Phe Ala Gln Gly Glu Ile Glu Ala Ile Val Val Pro
1               5                   10                  15

Val Cys Leu Ala Phe Leu Leu Thr Thr Leu Leu Gly Val Leu Phe Cys
                20                  25                  30

Phe Asn Lys Arg Asp Leu Ile Lys Lys His Ile Trp Pro Asn Val Pro
            35                  40                  45

Asp Pro Ser Lys Ser His Ile Ala Gln Trp Ser Pro His Thr Pro Pro
        50                  55                  60

Arg His Asn Phe Asn Ser Lys Asp Gln Met Tyr Ser Asp Gly Asn Phe
65                  70                  75                  80

Thr Asp Val Ser Val Val Glu Ile Glu Ala Asn Asp
                85                  90

<210> SEQ ID NO 17
<211> LENGTH: 105
<212> TYPE: PRT
<213> ORGANISM: Homo sapiens

<400> SEQUENCE: 17

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
                20                  25                  30

Leu Leu Leu Leu Arg Trp Gln Phe Pro Ala His Tyr Arg Arg Leu Arg
            35                  40                  45

His Ala Leu Trp Pro Ser Leu Pro Asp Leu His Arg Val Leu Gly Gln
        50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
                100                 105

<210> SEQ ID NO 18
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser Asp Pro Thr Arg Val Glu Thr Ala Thr Glu Thr Trp Ile Ser Leu
1               5                   10                  15

Val Thr Ala Leu His Leu Val Leu Gly Leu Ser Ala Val Leu Gly Leu
                20                  25                  30

Leu Leu Leu Arg Trp Gln Phe Pro Ala His Tyr Arg Arg Leu Arg His
            35                  40                  45

Ala Leu Trp Pro Ser Leu Pro Asp Leu His Arg Val Leu Gly Gln Tyr
```

```
                    50                  55                  60

Leu Arg Asp Thr Ala Ala Leu Ser Pro Pro Lys Ala Thr Val Ser Asp
 65                  70                  75                  80

Thr Cys Glu Glu Val Glu Pro Ser Leu Leu Glu Ile Leu Pro Lys Ser
                    85                  90                  95

Ser Glu Arg Thr Pro Leu Pro Leu
                100

<210> SEQ ID NO 19
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser Asp Pro Thr Arg Val Glu Thr Ala Thr Glu Thr Ile Ser Leu Val
 1               5                  10                  15

Thr Ala Leu His Leu Val Leu Gly Leu Ser Ala Val Leu Gly Leu Leu
                20                  25                  30

Leu Leu Arg Trp Gln Phe Pro Ala His Tyr Arg Arg Leu Arg His Ala
             35                  40                  45

Leu Trp Pro Ser Leu Pro Asp Leu His Arg Val Leu Gly Gln Tyr Leu
 50                  55                  60

Arg Asp Thr Ala Ala Leu Ser Pro Pro Lys Ala Thr Val Ser Asp Thr
 65                  70                  75                  80

Cys Glu Glu Val Glu Pro Ser Leu Leu Glu Ile Leu Pro Lys Ser Ser
                85                  90                  95

Glu Arg Thr Pro Leu Pro Leu
            100

<210> SEQ ID NO 20
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser Asp Pro Thr Arg Val Glu Thr Ala Thr Glu Thr Leu Ile Ser Leu
 1               5                  10                  15

Val Thr Ala Leu His Leu Val Leu Gly Leu Ser Ala Val Leu Gly Leu
                20                  25                  30

Leu Leu Leu Arg Trp Gln Phe Pro Ala His Tyr Arg Arg Leu Arg His
             35                  40                  45

Ala Leu Trp Pro Ser Leu Pro Asp Leu His Arg Val Leu Gly Gln Tyr
 50                  55                  60

Leu Arg Asp Thr Ala Ala Leu Ser Pro Pro Lys Ala Thr Val Ser Asp
 65                  70                  75                  80

Thr Cys Glu Glu Val Glu Pro Ser Leu Leu Glu Ile Leu Pro Lys Ser
                85                  90                  95

Ser Glu Arg Thr Pro Leu Pro Leu
            100

<210> SEQ ID NO 21
<211> LENGTH: 102
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 21

Ser Asp Pro Thr Arg Val Glu Thr Ala Thr Glu Thr Ser Leu Val Thr
1               5                   10                  15

Ala Leu His Leu Val Leu Gly Leu Ser Ala Val Leu Gly Leu Leu Leu
            20                  25                  30

Leu Arg Trp Gln Phe Pro Ala His Tyr Arg Arg Leu Arg His Ala Leu
        35                  40                  45

Trp Pro Ser Leu Pro Asp Leu His Arg Val Leu Gly Gln Tyr Leu Arg
    50                  55                  60

Asp Thr Ala Ala Leu Ser Pro Pro Lys Ala Thr Val Ser Asp Thr Cys
65                  70                  75                  80

Glu Glu Val Glu Pro Ser Leu Leu Glu Ile Leu Pro Lys Ser Ser Glu
                85                  90                  95

Arg Thr Pro Leu Pro Leu
                100

<210> SEQ ID NO 22
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser Asp Pro Thr Arg Val Glu Thr Ala Thr Glu Thr Leu Val Thr Ala
1               5                   10                  15

Leu His Leu Val Leu Gly Leu Ser Ala Val Leu Gly Leu Leu Leu Leu
            20                  25                  30

Arg Trp Gln Phe Pro Ala His Tyr Arg Arg Leu Arg His Ala Leu Trp
        35                  40                  45

Pro Ser Leu Pro Asp Leu His Arg Val Leu Gly Gln Tyr Leu Arg Asp
    50                  55                  60

Thr Ala Ala Leu Ser Pro Pro Lys Ala Thr Val Ser Asp Thr Cys Glu
65                  70                  75                  80

Glu Val Glu Pro Ser Leu Leu Glu Ile Leu Pro Lys Ser Ser Glu Arg
                85                  90                  95

Thr Pro Leu Pro Leu
                100

<210> SEQ ID NO 23
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser Asp Pro Thr Arg Val Glu Thr Ala Thr Glu Thr Ile Leu Val Thr
1               5                   10                  15

Ala Leu His Leu Val Leu Gly Leu Ser Ala Val Leu Gly Leu Leu Leu
            20                  25                  30

Leu Arg Trp Gln Phe Pro Ala His Tyr Arg Arg Leu Arg His Ala Leu
        35                  40                  45
```

```
Trp Pro Ser Leu Pro Asp Leu His Arg Val Leu Gly Gln Tyr Leu Arg
        50                  55                  60

Asp Thr Ala Ala Leu Ser Pro Pro Lys Ala Thr Val Ser Asp Thr Cys
 65                  70                  75                  80

Glu Glu Val Glu Pro Ser Leu Leu Glu Ile Leu Pro Lys Ser Ser Glu
                 85                  90                  95

Arg Thr Pro Leu Pro Leu
            100

<210> SEQ ID NO 24
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser Asp Pro Thr Arg Val Glu Thr Ala Thr Glu Thr Val Thr Ala Leu
 1               5                  10                  15

His Leu Val Leu Gly Leu Ser Ala Val Leu Gly Leu Leu Leu Leu Arg
            20                  25                  30

Trp Gln Phe Pro Ala His Tyr Arg Arg Leu Arg His Ala Leu Trp Pro
        35                  40                  45

Ser Leu Pro Asp Leu His Arg Val Leu Gly Gln Tyr Leu Arg Asp Thr
 50                  55                  60

Ala Ala Leu Ser Pro Pro Lys Ala Thr Val Ser Asp Thr Cys Glu Glu
 65                  70                  75                  80

Val Glu Pro Ser Leu Leu Glu Ile Leu Pro Lys Ser Ser Glu Arg Thr
                 85                  90                  95

Pro Leu Pro Leu
            100

<210> SEQ ID NO 25
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser Asp Pro Thr Arg Val Glu Thr Ala Thr Glu Thr Thr Ala Leu His
 1               5                  10                  15

Leu Val Leu Gly Leu Ser Ala Val Leu Gly Leu Leu Leu Arg Trp
            20                  25                  30

Gln Phe Pro Ala His Tyr Arg Arg Leu Arg His Ala Leu Trp Pro Ser
        35                  40                  45

Leu Pro Asp Leu His Arg Val Leu Gly Gln Tyr Leu Arg Asp Thr Ala
    50                  55                  60

Ala Leu Ser Pro Pro Lys Ala Thr Val Ser Asp Thr Cys Glu Glu Val
 65                  70                  75                  80

Glu Pro Ser Leu Leu Glu Ile Leu Pro Lys Ser Ser Glu Arg Thr Pro
                 85                  90                  95

Leu Pro Leu

<210> SEQ ID NO 26
<211> LENGTH: 98
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser Asp Pro Thr Arg Val Glu Thr Ala Thr Glu Thr Ala Leu His Leu
1               5                   10                  15

Val Leu Gly Leu Ser Ala Val Leu Gly Leu Leu Leu Leu Arg Trp Gln
            20                  25                  30

Phe Pro Ala His Tyr Arg Arg Leu Arg His Ala Leu Trp Pro Ser Leu
            35                  40                  45

Pro Asp Leu His Arg Val Leu Gly Gln Tyr Leu Arg Asp Thr Ala Ala
        50                  55                  60

Leu Ser Pro Pro Lys Ala Thr Val Ser Asp Thr Cys Glu Glu Val Glu
65                  70                  75                  80

Pro Ser Leu Leu Glu Ile Leu Pro Lys Ser Ser Glu Arg Thr Pro Leu
                85                  90                  95

Pro Leu

<210> SEQ ID NO 27
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser Asp Pro Thr Arg Val Glu Thr Ala Thr Glu Thr Leu His Leu Val
1               5                   10                  15

Leu Gly Leu Ser Ala Val Leu Gly Leu Leu Leu Arg Trp Gln Phe
            20                  25                  30

Pro Ala His Tyr Arg Arg Leu Arg His Ala Leu Trp Pro Ser Leu Pro
            35                  40                  45

Asp Leu His Arg Val Leu Gly Gln Tyr Leu Arg Asp Thr Ala Ala Leu
        50                  55                  60

Ser Pro Pro Lys Ala Thr Val Ser Asp Thr Cys Glu Glu Val Glu Pro
65                  70                  75                  80

Ser Leu Leu Glu Ile Leu Pro Lys Ser Ser Glu Arg Thr Pro Leu Pro
                85                  90                  95

Leu

<210> SEQ ID NO 28
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser Asp Pro Thr Arg Val Glu Thr Ala Thr Glu Thr His Leu Val Leu
1               5                   10                  15

Gly Leu Ser Ala Val Leu Gly Leu Leu Leu Leu Arg Trp Gln Phe Pro
            20                  25                  30

Ala His Tyr Arg Arg Leu Arg His Ala Leu Trp Pro Ser Leu Pro Asp
            35                  40                  45
```

Leu His Arg Val Leu Gly Gln Tyr Leu Arg Asp Thr Ala Ala Leu Ser
            50                  55                  60

Pro Pro Lys Ala Thr Val Ser Asp Thr Cys Glu Glu Val Glu Pro Ser
65                  70                  75                  80

Leu Leu Glu Ile Leu Pro Lys Ser Ser Glu Arg Thr Pro Leu Pro Leu
                85                  90                  95

<210> SEQ ID NO 29
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser Asp Pro Thr Arg Val Glu Thr Ala Thr Glu Thr Leu Val Leu Gly
1               5                   10                  15

Leu Ser Ala Val Leu Gly Leu Leu Leu Arg Trp Gln Phe Pro Ala
            20                  25                  30

His Tyr Arg Arg Leu Arg His Ala Leu Trp Pro Ser Leu Pro Asp Leu
        35                  40                  45

His Arg Val Leu Gly Gln Tyr Leu Arg Asp Thr Ala Ala Leu Ser Pro
    50                  55                  60

Pro Lys Ala Thr Val Ser Asp Thr Cys Glu Glu Val Glu Pro Ser Leu
65                  70                  75                  80

Leu Glu Ile Leu Pro Lys Ser Ser Glu Arg Thr Pro Leu Pro Leu
                85                  90                  95

<210> SEQ ID NO 30
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser Asp Pro Thr Arg Val Glu Thr Ala Thr Glu Thr Val Leu Gly Leu
1               5                   10                  15

Ser Ala Val Leu Gly Leu Leu Leu Arg Trp Gln Phe Pro Ala His
            20                  25                  30

Tyr Arg Arg Leu Arg His Ala Leu Trp Pro Ser Leu Pro Asp Leu His
        35                  40                  45

Arg Val Leu Gly Gln Tyr Leu Arg Asp Thr Ala Ala Leu Ser Pro Pro
    50                  55                  60

Lys Ala Thr Val Ser Asp Thr Cys Glu Glu Val Glu Pro Ser Leu Leu
65                  70                  75                  80

Glu Ile Leu Pro Lys Ser Ser Glu Arg Thr Pro Leu Pro Leu
                85                  90

<210> SEQ ID NO 31
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser Asp Pro Thr Arg Val Glu Thr Ala Thr Glu Thr Leu Gly Leu Ser

```
                 1               5                  10                  15
Ala Val Leu Gly Leu Leu Leu Arg Trp Gln Phe Pro Ala His Tyr
                20                  25                  30

Arg Arg Leu Arg His Ala Leu Trp Pro Ser Leu Pro Asp Leu His Arg
            35                  40                  45

Val Leu Gly Gln Tyr Leu Arg Asp Thr Ala Ala Leu Ser Pro Pro Lys
    50                  55                  60

Ala Thr Val Ser Asp Thr Cys Glu Glu Val Glu Pro Ser Leu Leu Glu
65                  70                  75                  80

Ile Leu Pro Lys Ser Ser Glu Arg Thr Pro Leu Pro Leu
                85                  90

<210> SEQ ID NO 32
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ser Asp Pro Thr Arg Val Glu Thr Ala Thr Glu Thr Gly Leu Ser Ala
1               5                   10                  15

Val Leu Gly Leu Leu Leu Arg Trp Gln Phe Pro Ala His Tyr Arg
                20                  25                  30

Arg Leu Arg His Ala Leu Trp Pro Ser Leu Pro Asp Leu His Arg Val
            35                  40                  45

Leu Gly Gln Tyr Leu Arg Asp Thr Ala Ala Leu Ser Pro Pro Lys Ala
    50                  55                  60

Thr Val Ser Asp Thr Cys Glu Glu Val Glu Pro Ser Leu Leu Glu Ile
65                  70                  75                  80

Leu Pro Lys Ser Ser Glu Arg Thr Pro Leu Pro Leu
                85                  90

<210> SEQ ID NO 33
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ser Asp Pro Thr Arg Val Glu Thr Ala Thr Glu Thr Leu Ser Ala Val
1               5                   10                  15

Leu Gly Leu Leu Leu Arg Trp Gln Phe Pro Ala His Tyr Arg Arg
                20                  25                  30

Leu Arg His Ala Leu Trp Pro Ser Leu Pro Asp Leu His Arg Val Leu
            35                  40                  45

Gly Gln Tyr Leu Arg Asp Thr Ala Ala Leu Ser Pro Pro Lys Ala Thr
    50                  55                  60

Val Ser Asp Thr Cys Glu Glu Val Glu Pro Ser Leu Leu Glu Ile Leu
65                  70                  75                  80

Pro Lys Ser Ser Glu Arg Thr Pro Leu Pro Leu
                85                  90

<210> SEQ ID NO 34
<211> LENGTH: 90
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 34

Ser Asp Pro Thr Arg Val Glu Thr Ala Thr Glu Thr Ser Ala Val Leu
1               5                   10                  15

Gly Leu Leu Leu Leu Arg Trp Gln Phe Pro Ala His Tyr Arg Arg Leu
            20                  25                  30

Arg His Ala Leu Trp Pro Ser Leu Pro Asp Leu His Arg Val Leu Gly
        35                  40                  45

Gln Tyr Leu Arg Asp Thr Ala Ala Leu Ser Pro Pro Lys Ala Thr Val
    50                  55                  60

Ser Asp Thr Cys Glu Glu Val Glu Pro Ser Leu Leu Glu Ile Leu Pro
65                  70                  75                  80

Lys Ser Ser Glu Arg Thr Pro Leu Pro Leu
                85                  90

<210> SEQ ID NO 35
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ser Asp Pro Thr Arg Val Glu Thr Ala Thr Glu Thr Ala Val Leu Gly
1               5                   10                  15

Leu Leu Leu Leu Arg Trp Gln Phe Pro Ala His Tyr Arg Arg Leu Arg
            20                  25                  30

His Ala Leu Trp Pro Ser Leu Pro Asp Leu His Arg Val Leu Gly Gln
        35                  40                  45

Tyr Leu Arg Asp Thr Ala Ala Leu Ser Pro Pro Lys Ala Thr Val Ser
    50                  55                  60

Asp Thr Cys Glu Glu Val Glu Pro Ser Leu Leu Glu Ile Leu Pro Lys
65                  70                  75                  80

Ser Ser Glu Arg Thr Pro Leu Pro Leu
                85

<210> SEQ ID NO 36
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Asp Pro Thr Arg Val Glu Thr Ala Thr Glu Thr Val Leu Gly Leu
1               5                   10                  15

Leu Leu Leu Arg Trp Gln Phe Pro Ala His Tyr Arg Arg Leu Arg His
            20                  25                  30

Ala Leu Trp Pro Ser Leu Pro Asp Leu His Arg Val Leu Gly Gln Tyr
        35                  40                  45

Leu Arg Asp Thr Ala Ala Leu Ser Pro Pro Lys Ala Thr Val Ser Asp
    50                  55                  60

Thr Cys Glu Glu Val Glu Pro Ser Leu Leu Glu Ile Leu Pro Lys Ser
65                  70                  75                  80

```
Ser Glu Arg Thr Pro Leu Pro Leu
                85

<210> SEQ ID NO 37
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Asp Pro Thr Arg Val Glu Thr Ala Thr Glu Thr Leu Gly Leu Leu
1               5                   10                  15

Leu Leu Arg Trp Gln Phe Pro Ala His Tyr Arg Arg Leu Arg His Ala
                20                  25                  30

Leu Trp Pro Ser Leu Pro Asp Leu His Arg Val Leu Gly Gln Tyr Leu
            35                  40                  45

Arg Asp Thr Ala Ala Leu Ser Pro Pro Lys Ala Thr Val Ser Asp Thr
        50                  55                  60

Cys Glu Glu Val Glu Pro Ser Leu Leu Glu Ile Leu Pro Lys Ser Ser
65                  70                  75                  80

Glu Arg Thr Pro Leu Pro Leu
                85

<210> SEQ ID NO 38
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser Asp Pro Thr Arg Val Glu Thr Ala Thr Glu Thr Ala Trp Leu Ile
1               5                   10                  15

Ser Leu Val Thr Ala Leu His Leu Val Leu Gly Leu Ser Ala Val Leu
                20                  25                  30

Gly Leu Leu Leu Arg Trp Gln Phe Pro Ala His Tyr Arg Arg Leu
            35                  40                  45

Arg His Ala Leu Trp Pro Ser Leu Pro Asp Leu His Arg Val Leu Gly
        50                  55                  60

Gln Tyr Leu Arg Asp Thr Ala Ala Leu Ser Pro Pro Lys Ala Thr Val
65                  70                  75                  80

Ser Asp Thr Cys Glu Glu Val Glu Pro Ser Leu Leu Glu Ile Leu Pro
                85                  90                  95

Lys Ser Ser Glu Arg Thr Pro Leu Pro Leu
                100                 105

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser Asp Pro Thr Arg Val Glu Thr Ala Thr Glu Thr Ala Trp Val Leu
1               5                   10                  15
```

Ile Ser Leu Val Thr Ala Leu His Leu Val Leu Gly Leu Ser Ala Val
            20                  25                  30

Leu Gly Leu Leu Leu Arg Trp Gln Phe Pro Ala His Tyr Arg Arg
        35                  40                  45

Leu Arg His Ala Leu Trp Pro Ser Leu Pro Asp Leu His Arg Val Leu
50                      55                  60

Gly Gln Tyr Leu Arg Asp Thr Ala Ala Leu Ser Pro Pro Lys Ala Thr
65                  70                  75                  80

Val Ser Asp Thr Cys Glu Glu Val Glu Pro Ser Leu Leu Glu Ile Leu
                85                  90                  95

Pro Lys Ser Ser Glu Arg Thr Pro Leu Pro Leu
            100                 105

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Asp Pro Thr Arg Val Glu Thr Ala Thr Glu Thr Ala Trp Leu Val
1               5                   10                  15

Leu Ile Ser Leu Val Thr Ala Leu His Leu Val Leu Gly Leu Ser Ala
            20                  25                  30

Val Leu Gly Leu Leu Leu Arg Trp Gln Phe Pro Ala His Tyr Arg
        35                  40                  45

Arg Leu Arg His Ala Leu Trp Pro Ser Leu Pro Asp Leu His Arg Val
50                      55                  60

Leu Gly Gln Tyr Leu Arg Asp Thr Ala Ala Leu Ser Pro Pro Lys Ala
65                  70                  75                  80

Thr Val Ser Asp Thr Cys Glu Glu Val Glu Pro Ser Leu Leu Glu Ile
                85                  90                  95

Leu Pro Lys Ser Ser Glu Arg Thr Pro Leu Pro Leu
            100                 105

<210> SEQ ID NO 41
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ser Asp Pro Thr Arg Val Glu Thr Ala Thr Glu Thr Ala Trp Ile Leu
1               5                   10                  15

Val Leu Ile Ser Leu Val Thr Ala Leu His Leu Val Leu Gly Leu Ser
            20                  25                  30

Ala Val Leu Gly Leu Leu Leu Arg Trp Gln Phe Pro Ala His Tyr
        35                  40                  45

Arg Arg Leu Arg His Ala Leu Trp Pro Ser Leu Pro Asp Leu His Arg
50                      55                  60

Val Leu Gly Gln Tyr Leu Arg Asp Thr Ala Ala Leu Ser Pro Pro Lys
65                  70                  75                  80

Ala Thr Val Ser Asp Thr Cys Glu Glu Val Glu Pro Ser Leu Leu Glu
                85                  90                  95

Ile Leu Pro Lys Ser Ser Glu Arg Thr Pro Leu Pro Leu
            100                 105

<210> SEQ ID NO 42
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ser Asp Pro Thr Arg Val Glu Thr Ala Thr Glu Thr Ala Trp Leu Ile
1               5                   10                  15

Leu Val Leu Ile Ser Leu Val Thr Ala Leu His Leu Val Leu Gly Leu
            20                  25                  30

Ser Ala Val Leu Gly Leu Leu Leu Arg Trp Gln Phe Pro Ala His
        35                  40                  45

Tyr Arg Arg Leu Arg His Ala Leu Trp Pro Ser Leu Pro Asp Leu His
    50                  55                  60

Arg Val Leu Gly Gln Tyr Leu Arg Asp Thr Ala Ala Leu Ser Pro Pro
65                  70                  75                  80

Lys Ala Thr Val Ser Asp Thr Cys Glu Glu Val Glu Pro Ser Leu Leu
                85                  90                  95

Glu Ile Leu Pro Lys Ser Ser Glu Arg Thr Pro Leu Pro Leu
            100                 105                 110

<210> SEQ ID NO 43
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ser Asp Pro Thr Arg Val Glu Thr Ala Thr Glu Thr Ala Trp Leu Leu
1               5                   10                  15

Ile Leu Val Leu Ile Ser Leu Val Thr Ala Leu His Leu Val Leu Gly
            20                  25                  30

Leu Ser Ala Val Leu Gly Leu Leu Leu Arg Trp Gln Phe Pro Ala
        35                  40                  45

His Tyr Arg Arg Leu Arg His Ala Leu Trp Pro Ser Leu Pro Asp Leu
    50                  55                  60

His Arg Val Leu Gly Gln Tyr Leu Arg Asp Thr Ala Ala Leu Ser Pro
65                  70                  75                  80

Pro Lys Ala Thr Val Ser Asp Thr Cys Glu Glu Val Glu Pro Ser Leu
                85                  90                  95

Leu Glu Ile Leu Pro Lys Ser Ser Glu Arg Thr Pro Leu Pro Leu
            100                 105                 110

<210> SEQ ID NO 44
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser Asp Pro Thr Arg Val Glu Thr Ala Thr Glu Thr Ala Trp Val Leu

```
                 1               5                   10                  15
Leu Ile Leu Val Leu Ile Ser Leu Val Thr Ala Leu His Leu Val Leu
                20                  25                  30

Gly Leu Ser Ala Val Leu Gly Leu Leu Leu Arg Trp Gln Phe Pro
            35                  40                  45

Ala His Tyr Arg Arg Leu Arg His Ala Leu Trp Pro Ser Leu Pro Asp
        50                  55                  60

Leu His Arg Val Leu Gly Gln Tyr Leu Arg Asp Thr Ala Ala Leu Ser
65                  70                  75                  80

Pro Pro Lys Ala Thr Val Ser Asp Thr Cys Glu Glu Val Glu Pro Ser
                85                  90                  95

Leu Leu Glu Ile Leu Pro Lys Ser Ser Glu Arg Thr Pro Leu Pro Leu
                100                 105                 110

<210> SEQ ID NO 45
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ser Asp Pro Thr Arg Val Glu Thr Ala Thr Glu Thr Ala Trp Leu Val
1               5                   10                  15

Leu Leu Ile Leu Val Leu Ile Ser Leu Val Thr Ala Leu His Leu Val
                20                  25                  30

Leu Gly Leu Ser Ala Val Leu Gly Leu Leu Leu Arg Trp Gln Phe
            35                  40                  45

Pro Ala His Tyr Arg Arg Leu Arg His Ala Leu Trp Pro Ser Leu Pro
        50                  55                  60

Asp Leu His Arg Val Leu Gly Gln Tyr Leu Arg Asp Thr Ala Ala Leu
65                  70                  75                  80

Ser Pro Pro Lys Ala Thr Val Ser Asp Thr Cys Glu Glu Val Glu Pro
                85                  90                  95

Ser Leu Leu Glu Ile Leu Pro Lys Ser Ser Glu Arg Thr Pro Leu Pro
                100                 105                 110

Leu

<210> SEQ ID NO 46
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Arg Asp Glu Val Glu Gly Phe Leu Gln Asp Thr Phe Pro Gln Gln
1               5                   10                  15

Leu Glu Glu Ser Glu Lys Gln Arg Leu Gly Gly Asp Val Gln Ser Pro
                20                  25                  30

Asn Cys Pro Ser Glu Asp Val Val Ile Thr Pro Glu Ser Phe Gly Arg
            35                  40                  45

Asp Ser Ser Leu Thr Cys Leu Ala Gly Asn Val Ser Ala Cys Asp Ala
        50                  55                  60

Pro Ile Leu Ser Ser Ser Arg Ser Leu Asp Cys Arg Glu Ser Gly Lys
65                  70                  75                  80
```

Asn Gly Pro His Val Tyr Gln Asp Leu Leu Leu Ser Leu Gly Thr Thr
                85                  90                  95

Asn Ser Thr Leu Pro Pro Pro Phe Ser Leu Gln Ser Gly Ile Leu Thr
            100                 105                 110

Leu Asn Pro Val Ala Gln Gly Gln Pro Ile Leu Thr Ser Leu Gly Ser
        115                 120                 125

Asn Gln Glu Glu Ala Tyr Val Thr Met Ser Ser Phe Tyr Gln Asn Gln
    130                 135                 140

<210> SEQ ID NO 47
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Val Thr Gln Leu Leu Leu Gln Gln Asp Lys Val Pro Glu Pro Ala Ser
1               5                   10                  15

Leu Ser Ser Asn His Ser Leu Thr Ser Cys Phe Thr Asn Gln Gly Tyr
            20                  25                  30

Phe Phe Phe His Leu Pro Asp Ala Leu Glu Ile Glu Ala Cys Gln Val
        35                  40                  45

Tyr Phe Thr Tyr Asp Pro Tyr Ser Glu Glu Asp Pro Asp Glu Gly Val
    50                  55                  60

Ala Gly Ala Pro Thr Gly Ser Ser Pro Gln Pro Leu Gln Pro Leu Ser
65                  70                  75                  80

Gly Glu Asp Asp Ala Tyr Cys Thr Phe Pro Ser Arg Asp Asp Leu Leu
                85                  90                  95

Leu Phe Ser Pro Ser Leu Leu Gly Gly Pro Ser Pro Pro Ser Thr Ala
            100                 105                 110

Pro Gly Gly Ser Gly Ala Gly Glu Glu Arg Met Pro Pro Ser Leu Gln
        115                 120                 125

Glu Arg Val Pro Arg Asp Trp Asp Pro Gln Pro Leu Gly Pro Pro Thr
    130                 135                 140

Pro Gly Val Pro Asp Leu Val Asp Phe Gln Pro Pro Glu Leu Val
145                 150                 155                 160

Leu Arg Glu Ala Gly Glu Glu Val Pro Asp Ala Gly Pro Arg Glu Gly
                165                 170                 175

Val Ser Phe Pro Trp Ser Arg Pro Pro Gly Gln Gly Glu Phe Arg Ala
            180                 185                 190

Leu Asn Ala Arg Leu Pro Leu Asn Thr Asp Ala Tyr Leu Ser Leu Gln
        195                 200                 205

Glu Leu Gln Gly Gln Asp Pro Thr His Leu Val
    210                 215

<210> SEQ ID NO 48
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ile Ser Thr Ile Ala Thr Val Glu Glu Thr Asn Gln Thr Asp Glu Asp
1               5                   10                  15

```
His Lys Lys Tyr Ser Ser Gln Thr Ser Gln Asp Ser Gly Asn Tyr Ser
            20                  25                  30

Asn Glu Asp Glu Ser Glu Ser Lys Thr Ser Glu Glu Leu Gln Gln Asp
        35                  40                  45

Phe Val
    50

<210> SEQ ID NO 49
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Lys Lys Lys Val Trp Asp Tyr Asn Tyr Asp Asp Glu Ser Asp Ser Asp
1               5                   10                  15

Thr Glu Ala Ala Pro Arg Thr Ser Gly Gly Tyr Thr Met His Gly
            20                  25                  30

Leu Thr Val Arg Pro Leu Gly Gln Ala Ser Ala Thr Ser Thr Glu Ser
        35                  40                  45

Gln Leu Ile Asp Pro Glu Ser Glu Glu Pro Asp Leu Pro Glu Val
    50                  55                  60

Asp Val Glu Leu Pro Thr Met Pro Lys Asp Ser Pro Gln Gln Leu Glu
65                  70                  75                  80

Leu Leu Ser Gly Pro Cys Glu Arg Arg Lys Ser Pro Leu Gln Asp Pro
                85                  90                  95

Phe Pro Glu Glu Asp Tyr Ser Ser Thr Glu Gly Ser Gly Gly Arg Ile
            100                 105                 110

Thr Phe Asn Val Asp Leu Asn Ser Val Phe Leu Arg Val Leu Asp Asp
            115                 120                 125

Glu Asp Ser Asp Asp Leu Glu Ala Pro Leu Met Leu Ser Ser His Leu
        130                 135                 140

Glu Glu Met Val Asp Pro Glu Asp Pro Asp Asn Val Gln Ser Asn His
145                 150                 155                 160

Leu Leu Ala Ser Gly Glu Gly Thr Gln Pro Thr Phe Pro Ser Pro Ser
                165                 170                 175

Ser Glu Gly Leu Trp Ser Glu Asp Ala Pro Ser Asp Gln Ser Asp Thr
            180                 185                 190

Ser Glu Ser Asp Val Asp Leu Gly Asp Gly Tyr Ile Met Arg
        195                 200                 205

<210> SEQ ID NO 50
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ile Ser Thr Ile Ala Thr Val Glu Glu Thr Asn Gln Thr Asp Glu Asp
1               5                   10                  15

His Lys Lys Tyr Ser Ser Gln Thr Ser Gln Asp Ser Gly Asn Tyr Ser
            20                  25                  30

Asn Glu Asp Glu Ser Glu Ser Lys Thr Ser Glu Glu Leu Gln Gln Asp
        35                  40                  45
```

```
Phe Val Lys Lys Val Trp Asp Tyr Asn Tyr Asp Asp Glu Ser Asp
    50                  55                  60

Ser Asp Thr Glu Ala Ala Pro Arg Thr Ser Gly Gly Gly Tyr Thr Met
65                  70                  75                  80

His Gly Leu Thr Val Arg Pro Leu Gly Gln Ala Ser Ala Thr Ser Thr
                85                  90                  95

Glu Ser Gln Leu Ile Asp Pro Glu Ser Glu Glu Pro Asp Leu Pro
            100                 105                 110

Glu Val Asp Val Glu Leu Pro Thr Met Pro Lys Asp Ser Pro Gln Gln
        115                 120                 125

Leu Glu Leu Leu Ser Gly Pro Cys Glu Arg Arg Lys Ser Pro Leu Gln
130                 135                 140

Asp Pro Phe Pro Glu Glu Asp Tyr Ser Ser Thr Glu Gly Ser Gly Gly
145                 150                 155                 160

Arg Ile Thr Phe Asn Val Asp Leu Asn Ser Val Phe Leu Arg Val Leu
                165                 170                 175

Asp Asp Glu Asp Ser Asp Asp Leu Glu Ala Pro Leu Met Leu Ser Ser
            180                 185                 190

His Leu Glu Glu Met Val Asp Pro Glu Asp Pro Asp Asn Val Gln Ser
        195                 200                 205

Asn His Leu Leu Ala Ser Gly Glu Gly Thr Gln Pro Thr Phe Pro Ser
210                 215                 220

Pro Ser Ser Glu Gly Leu Trp Ser Glu Asp Ala Pro Ser Asp Gln Ser
225                 230                 235                 240

Asp Thr Ser Glu Ser Asp Val Asp Leu Gly Asp Gly Tyr Ile Met Arg
                245                 250                 255

<210> SEQ ID NO 51
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Arg Gly Val Arg Pro Thr Pro Arg Val Arg Ala Pro Ala Thr Gln Gln
1               5                   10                  15

Thr Arg Trp Lys Lys Asp Leu Ala Glu Asp Glu Glu Glu Asp Glu
            20                  25                  30

Glu Asp Thr Glu Asp Gly Val Ser Phe Gln Pro Tyr Ile Glu Pro Pro
        35                  40                  45

Ser Phe Leu Gly Gln Glu His Gln Ala Pro Gly His Ser Glu Ala Gly
    50                  55                  60

Gly Val Asp Ser Gly Arg Pro Arg Ala Pro Leu Val Pro Ser Glu Gly
65                  70                  75                  80

Ser Ser Ala Trp Asp Ser Ser Asp Arg Ser Trp Ala Ser Thr Val Asp
                85                  90                  95

Ser Ser Trp Asp Arg Ala Gly Ser Ser Gly Tyr Leu Ala Glu Lys Gly
            100                 105                 110

Pro Gly Gln Gly Pro Gly Gly Asp Gly His Gln Glu Ser Leu Pro Pro
        115                 120                 125

Pro Glu Phe Ser Lys Asp Ser Gly Phe Leu Glu Glu Leu Pro Glu Asp
130                 135                 140

Asn Leu Ser Ser Trp Ala Thr Trp Gly Thr Leu Pro Pro Glu Pro Asn
```

```
                145                 150                 155                 160
Leu Val Pro Gly Gly Pro Pro Val Ser Leu Gln Thr Leu Thr Phe Cys
                    165                 170                 175

Trp Glu Ser Ser Pro Glu Glu Glu Ala Arg Glu Ser Glu Ile
                180                 185                 190

Glu Asp Ser Asp Ala Gly Ser Trp Gly Ala Glu Ser Thr Gln Arg Thr
            195                 200                 205

Glu Asp Arg Gly Arg Thr Leu Gly His Tyr Met Ala Arg
    210                 215                 220

<210> SEQ ID NO 52
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ile Pro Pro Lys Gly Gly Ala Leu Gly Glu Gly Pro Gly Ala Ser Pro
1               5                   10                  15

Cys Asn Gln His Ser Pro Tyr Trp Ala Pro Pro Cys Tyr Thr Leu Lys
            20                  25                  30

Pro Glu Thr
        35

<210> SEQ ID NO 53
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Thr Ala Leu Leu Thr Cys Gly Pro Ala Arg Pro Trp Lys Ser Val Ala
1               5                   10                  15

Leu Glu Glu Glu Gln Glu Gly Pro Gly Thr Arg Leu Pro Gly Asn Leu
            20                  25                  30

Ser Ser Glu Asp Val Leu Pro Ala Gly Cys Thr Glu Trp Arg Val Gln
        35                  40                  45

Thr Leu Ala Tyr Leu Pro Gln Glu Asp Trp Ala Pro Thr Ser Leu Thr
    50                  55                  60

Arg Pro Ala Pro Pro Asp Ser Glu Gly Ser Arg Ser Ser Ser Ser Ser
65                  70                  75                  80

Ser Ser Ser Asn Asn Asn Asn Tyr Cys Ala Leu Gly Cys Tyr Gly Gly
                85                  90                  95

Trp His Leu Ser Ala Leu Pro Gly Asn Thr Gln Ser Ser Gly Pro Ile
            100                 105                 110

Pro Ala Leu Ala Cys Gly Leu Ser Cys Asp His Gln Gly Leu Glu Thr
        115                 120                 125

Gln Gln Gly Val Ala Trp Val Leu Ala Gly His Cys Gln Arg Pro Gly
    130                 135                 140

Leu His Glu Asp Leu Gln Gly Met Leu Leu Pro Ser Val Leu Ser Lys
145                 150                 155                 160

Ala Arg Ser Trp Thr Phe
                165
```

```
<210> SEQ ID NO 54
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Pro Arg Ser Pro Ala Lys Arg Leu Gln Leu Thr Glu Leu Gln Glu Pro
1               5                   10                  15

Ala Glu Leu Val Glu Ser Asp Gly Val Pro Lys Pro Ser Phe Trp Pro
            20                  25                  30

Thr Ala Gln Asn Ser Gly Gly Ser Ala Tyr Ser Glu Gly Arg Asp Arg
        35                  40                  45

Pro Tyr Gly Leu Val Ser Ile Asp Thr Val Thr Val Leu Asp Ala Glu
    50                  55                  60

Gly Pro Cys Thr Trp Pro Cys Ser Cys Glu Asp Asp Gly Tyr Pro Ala
65                  70                  75                  80

Leu Asp Leu Asp Ala Gly Leu Glu Pro Ser Pro Gly Leu Glu Asp Pro
                85                  90                  95

Leu Leu Asp Ala Gly Thr Thr Val Leu Ser Cys Gly Cys Val Ser Ala
            100                 105                 110

Gly Ser Pro Gly Leu Gly Gly Pro Leu Gly Ser Leu Leu Asp Arg Leu
        115                 120                 125

Lys Pro Pro Leu Ala Asp Gly Glu Asp Trp Ala Gly Gly Leu Pro Trp
130                 135                 140

Gly Gly Arg Ser Pro Gly Val Ser Glu Ser Glu Ala Gly Ser Pro
145                 150                 155                 160

Leu Ala Gly Leu Asp Met Asp Thr Phe Asp Ser Gly Phe Val Gly Ser
                165                 170                 175

Asp Cys Ser Ser Pro Val Glu Cys Asp Phe Thr Ser Pro Gly Asp Glu
            180                 185                 190

Gly Pro Pro Arg Ser Tyr Leu Arg Gln Trp Val Val Ile Pro Pro Pro
        195                 200                 205

Leu Ser Ser Pro Gly Pro Gln Ala Ser
    210                 215

<210> SEQ ID NO 55
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Pro Asp Glu Lys Thr Glu Glu Ser Asp Thr Asp Arg Leu Leu Ser Ser
1               5                   10                  15

Asp His Glu Lys Ser His Ser Asn Leu Gly Val Lys Asp Gly Asp Ser
            20                  25                  30

Gly Arg Thr Ser Cys Cys Glu Pro Asp Ile Leu Glu Thr Asp Phe Asn
        35                  40                  45

Ala Asn Asp Ile His Glu Gly Thr Ser Glu Val Ala Gln Pro Gln Arg
    50                  55                  60

Leu Lys Gly Glu Ala Asp Leu Leu Cys Leu Asp Gln Lys Asn Gln Asn
65                  70                  75                  80

Asn Ser Pro Tyr His Asp Ala Cys Pro Ala Thr Gln Gln Pro Ser Val
```

```
                    85                  90                  95

Ile Gln Ala Glu Lys Asn Lys Pro Gln Pro Leu Pro Thr Glu Gly Ala
                100                 105                 110

Glu Ser Thr His Gln Ala Ala His Ile Gln Leu Ser Asn Pro Ser Ser
            115                 120                 125

Leu Ser Asn Ile Asp Phe Tyr Ala Gln Val Ser Asp Ile Thr Pro Ala
        130                 135                 140

Gly Ser Val Val Leu Ser Pro Gly Gln Lys Asn Lys Ala Gly Met Ser
145                 150                 155                 160

Gln Cys Asp Met His Pro Glu Met Val Ser Leu Cys Gln Glu Asn Phe
                165                 170                 175

Leu Met Asp Asn Ala Tyr Phe Cys Glu Ala Asp Ala Lys Lys Cys Ile
                180                 185                 190

Pro Val Ala Pro His Ile Lys Val Glu Ser His Ile Gln Pro Ser Leu
            195                 200                 205

Asn Gln Glu Asp Ile Tyr Ile Thr Thr Glu Ser Leu Thr Thr Ala Ala
        210                 215                 220

Gly Arg Pro Gly Thr Gly Glu His Val Pro Gly Ser Glu Met Pro Val
225                 230                 235                 240

Pro Asp Tyr Thr Ser Ile His Ile Val Gln Ser Pro Gln Gly Leu Ile
                245                 250                 255

Leu Asn Ala Thr Ala Leu Pro Leu Pro Asp Lys Glu Phe Leu Ser Ser
                260                 265                 270

Cys Gly Tyr Val Ser Thr Asp Gln Leu Asn Lys Ile Met Pro
            275                 280                 285

<210> SEQ ID NO 56
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Trp Gly Thr Met Gln Ala Val Glu Pro Gly Thr Asp Asp Glu Gly Pro
1               5                   10                  15

Leu Leu Glu Pro Val Gly Ser Glu His Ala Gln Asp Thr Tyr Leu Val
            20                  25                  30

Leu Asp Lys Trp Leu Leu Pro Arg Asn Pro Pro Ser Glu Asp Leu Pro
        35                  40                  45

Gly Pro Gly Gly Ser Val Asp Ile Val Ala Met Asp Glu Gly Ser Glu
    50                  55                  60

Ala Ser Ser Cys Ser Ser Ala Leu Ala Ser Lys Pro Ser Pro Glu Gly
65                  70                  75                  80

Ala Ser Ala Ala Ser Phe Glu Tyr Thr Ile Leu Asp Pro Ser Ser Gln
                85                  90                  95

Leu Leu Arg Pro Trp Thr Leu Cys Pro Glu Leu Pro Pro Thr Pro Pro
                100                 105                 110

His Leu Lys Tyr Leu Tyr Leu Val Val Ser Asp Ser Gly Ile Ser Thr
            115                 120                 125

Asp Tyr Ser Ser Gly Asp Ser Gln Gly Ala Gln Gly Gly Leu Ser Asp
        130                 135                 140

Gly Pro Tyr Ser Asn Pro Tyr Glu Asn Ser Leu Ile Pro Ala Ala Glu
145                 150                 155                 160
```

Pro Leu Pro Pro Ser Tyr Val Ala Cys Ser
                165                 170

<210> SEQ ID NO 57
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Ala Val Gln Leu Leu Leu Gln Lys Asp Ser Ala Pro Leu Pro Ser
1               5                   10                  15

Pro Ser Gly His Ser Gln Ala Ser Cys Phe Thr Asn Gln Gly Tyr Phe
                20                  25                  30

Phe Phe His Leu Pro Asn Ala Leu Glu Ile Glu Ser Cys Gln Val Tyr
                35                  40                  45

Phe Thr Tyr Asp Pro Cys Val Glu Glu Val Glu Glu Asp Gly Ser
        50                  55                  60

Arg Leu Pro Glu Gly Ser Pro His Pro Leu Leu Pro Leu Ala Gly
65                  70                  75                  80

Glu Gln Asp Asp Tyr Cys Ala Phe Pro Pro Arg Asp Asp Leu Leu Leu
                85                  90                  95

Phe Ser Pro Ser Leu Ser Thr Pro Asn Thr Ala Tyr Gly Gly Ser Arg
                100                 105                 110

Ala Pro Glu Glu Arg Ser Pro Leu Ser Leu His Glu Gly Leu Pro Ser
                115                 120                 125

Leu Ala Ser Arg Asp Leu Met Gly Leu Gln Arg Pro Leu Glu Arg Met
        130                 135                 140

Pro Glu Gly Asp Gly Glu Gly Leu Ser Ala Asn Ser Ser Gly Glu Gln
145                 150                 155                 160

Ala Ser Val Pro Glu Gly Asn Leu His Gly Gln Asp Gln Arg Gly
                165                 170                 175

Gln Gly Pro Ile Leu Thr Leu Asn Thr Asp Ala Tyr Leu Ser Leu Gln
                180                 185                 190

Glu Leu Gln Ala Gln Asp Ser Val His Leu Ile
        195                 200

<210> SEQ ID NO 58
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ala Arg Asp Glu Val Glu Ser Phe Leu Pro Asn Asp Leu Pro Ala Gln
1               5                   10                  15

Pro Glu Glu Leu Glu Thr Gln Gly His Arg Ala Ala Val His Ser Ala
                20                  25                  30

Asn Arg Ser Pro Glu Thr Ser Val Ser Pro Glu Thr Val Arg Arg
        35                  40                  45

Glu Ser Pro Leu Arg Cys Leu Ala Arg Asn Leu Ser Thr Cys Asn Ala
        50                  55                  60

Pro Pro Leu Leu Ser Ser Arg Ser Pro Asp Tyr Arg Asp Gly Asp Arg
65                  70                  75                  80

```
Asn Arg Pro Pro Val Tyr Gln Asp Leu Leu Pro Asn Ser Gly Asn Thr
                85                  90                  95

Asn Val Pro Val Pro Val Pro Gln Pro Leu Pro Phe Gln Ser Gly Ile
            100                 105                 110

Leu Ile Pro Val Ser Gln Arg Gln Pro Ile Ser Thr Ser Ser Val Leu
        115                 120                 125

Asn Gln Glu Glu Ala Tyr Val Thr Met Ser Ser Phe Tyr Gln Asn Lys
130                 135                 140
```

<210> SEQ ID NO 59
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Val Ile Gln Gly Asp Glu Arg Met His Leu Pro Ser Pro Thr Asp Ser
1               5                   10                  15

Asn Phe Tyr Arg Ala Leu Met Asp Glu Glu Asp Met Asp Asp Val Val
            20                  25                  30

Asp Ala Asp Glu Tyr Leu Ile Pro Gln Gln Gly Phe Phe Ser Ser Pro
        35                  40                  45

Ser Thr Ser Arg Thr Pro Leu Leu Ser Ser Leu Ser Ala Thr Ser Asn
50                  55                  60

Asn Ser Thr Val Ala Cys Ile Asp Arg Asn Gly Leu Gln Ser Cys Pro
65                  70                  75                  80

Ile Lys Glu Asp Ser Phe Leu Gln Arg Tyr Ser Ser Asp Pro Thr Gly
                85                  90                  95

Ala Leu Thr Glu Asp Ser Ile Asp Thr Phe Leu Pro Val Pro Glu
            100                 105                 110

Tyr Ile Asn Gln Ser Val Pro Lys Arg Pro Ala Gly Ser Val Gln Asn
            115                 120                 125

Pro Val Tyr His Asn Gln Pro Leu Asn Pro Ala Pro Ser Arg Asp Pro
        130                 135                 140

His Tyr Gln Asp Pro His Ser Thr Ala Val Gly Asn Pro Glu Tyr Leu
145                 150                 155                 160

Asn Thr Val Gln Pro Thr Cys Val Asn Ser Thr Phe Asp Ser Pro Ala
                165                 170                 175

His Trp Ala Gln Lys Gly Ser His Gln Ile Ser Leu Asp Asn Pro Asp
            180                 185                 190

Tyr Gln Gln Asp Phe Phe Pro Lys Glu Ala Lys Pro Asn Gly Ile Phe
        195                 200                 205

Lys Gly Ser Thr Ala Glu Asn Ala Glu Tyr Leu Arg Val Ala Pro Gln
    210                 215                 220

Ser Ser Glu Phe Ile Gly Ala
225                 230
```

<210> SEQ ID NO 60
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Val Ile Gln Gly Asp Glu Arg Met His Leu Pro Ser Pro Thr Asp Ser
1               5                   10                  15

Asn Phe Phe Arg Ala Leu Met Asp Glu Asp Met Asp Asp Val Val
                20                  25                  30

Asp Ala Asp Glu Tyr Leu Ile Pro Gln Gln Gly Phe Phe Ser Ser Pro
            35                  40                  45

Ser Thr Ser Arg Thr Pro Leu Leu Ser Ser Leu Ser Ala Thr Ser Asn
50                  55                  60

Asn Ser Thr Val Ala Cys Ile Asp Arg Asn Gly Leu Gln Ser Cys Pro
65                  70                  75                  80

Ile Lys Glu Asp Ser Phe Leu Gln Arg Ile Asp Asp Thr Phe Leu Pro
                85                  90                  95

Val Pro Glu Tyr Ile Asn Gln Ser Val Pro Lys Arg Pro Ala Gly Ser
            100                 105                 110

Val Gln Asn Pro Val Tyr His Asn Gln Pro Leu Asn Pro Ala Pro Ser
            115                 120                 125

Arg Asp Pro His Tyr Gln Asp Pro His Ser Thr Ala Val Gly Asn Pro
        130                 135                 140

Glu Tyr Leu Asn Thr Val Gln Pro Thr Cys Val Asn Ser Thr Phe Asp
145                 150                 155                 160

Ser Pro Ala His Trp Ala Gln Lys Gly Ser His Gln Ile Ser Leu Asp
                165                 170                 175

Asn Pro Asp Tyr Gln Gln Asp Phe Phe Pro Lys Glu Ala Lys Pro Asn
            180                 185                 190

Gly Ile Phe Lys Gly Ser Thr Ala Glu Asn Ala Glu Tyr Leu Arg Val
            195                 200                 205

Ala Pro Gln Ser Ser Glu Phe Ile Gly Ala
        210                 215

<210> SEQ ID NO 61
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Val Ile Gln Gly Asp Glu Arg Met His Leu Pro Ser Pro Thr Asp Ser
1               5                   10                  15

Asn Phe Phe Arg Ala Leu Met Asp Glu Asp Met Asp Asp Val Val
                20                  25                  30

Asp Ala Asp Glu Tyr Leu Ile Pro Gln Gln Gly Phe Phe Ser Ser Pro
            35                  40                  45

Ser Thr Ser Arg Thr Pro
        50

<210> SEQ ID NO 62
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asn Asn Ser Thr Val Ala Cys Ile Asp Arg Asn Gly Leu Gln Ser Cys
1               5                   10                  15
```

```
Pro Ile Lys Glu Asp Ser Phe Leu Gln Arg Ile Asp Asp Thr Phe Leu
            20                  25                  30

Pro Val Pro Glu Tyr Ile Asn Gln Ser Val Pro Lys Arg Pro Ala Gly
        35                  40                  45

Ser Val Gln Asn Pro Val
    50

<210> SEQ ID NO 63
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Lys Glu Asp Ser Phe Leu Gln Arg Ile Asp Asp Thr Phe Leu Pro Val
1               5                   10                  15

Pro Glu Phe Ile Asn Gln Ser Val Pro Lys Arg Pro Ala Gly Ser Val
            20                  25                  30

Gln Asn Pro Val Tyr His Asn Gln Pro Leu Asn Pro Ala Pro Ser Arg
        35                  40                  45

Asp Pro His Phe Gln Asp
    50

<210> SEQ ID NO 64
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Val Pro Glu Phe Ile Asn Gln Ser Val Pro Lys Arg Pro Ala Gly Ser
1               5                   10                  15

Val Gln Asn Pro Val Phe His Asn Gln Pro Leu Asn Pro Ala Pro Ser
            20                  25                  30

Arg Asp Pro His Tyr Gln Asp Pro His Ser Thr Ala Val Gly Asn Pro
        35                  40                  45

Glu Tyr Leu Asn Thr Val
    50

<210> SEQ ID NO 65
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Pro Glu Tyr Leu Asn Thr Val Gln Pro Thr Cys Val Asn Ser Thr Phe
1               5                   10                  15

Asp Ser Pro Ala His Trp Ala Gln Lys Gly Ser His Gln Ile Ser Leu
            20                  25                  30

Asp Asn Pro Asp Tyr Gln Gln Asp Phe Phe Pro Lys Glu Ala Lys Pro
        35                  40                  45

Asn Gly Ile Phe Lys Gly
    50
```

```
<210> SEQ ID NO 66
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Trp Ala Gln Lys Gly Ser His Gln Ile Ser Leu Asp Asn Pro Asp Phe
1               5                   10                  15

Gln Gln Asp Phe Phe Pro Lys Glu Ala Lys Pro Asn Gly Ile Phe Lys
            20                  25                  30

Gly Ser Thr Ala Glu Asn Ala Glu Tyr Leu Arg Val Ala Pro Gln Ser
        35                  40                  45

Ser Glu Phe Ile Gly Ala
    50

<210> SEQ ID NO 67
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ser Asp Pro Lys Pro Glu Asn Pro Ala Cys Pro Trp Thr Val Leu Pro
1               5                   10                  15

Ala Gly Asp Leu Pro Thr His Asp Gly Tyr Leu Pro Ser Asn Ile Asp
            20                  25                  30

Asp Leu Pro Ser His Glu Ala Pro Leu Ala Asp Ser Leu Glu Glu Leu
        35                  40                  45

Glu Pro Gln
    50

<210> SEQ ID NO 68
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Cys Asp Ala Pro Ile Leu Ser Ser Ser Arg Ser Leu Asp Cys Arg
1               5                   10                  15

Glu Ser Gly Lys Asn Gly Pro His Val Tyr Gln Asp Leu Leu Leu Ser
            20                  25                  30

Leu Gly Thr Thr Asn Ser Thr Leu Pro
        35                  40

<210> SEQ ID NO 69
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Ile Leu Thr Leu Asn Pro Val Ala Gln Gly Gln Pro Ile Leu Thr
1               5                   10                  15
```

```
Ser Leu Gly Ser Asn Gln Glu Glu Ala Tyr Val Thr Met Ser Ser Phe
            20                  25                  30

Tyr Gln Asn Gln
        35

<210> SEQ ID NO 70
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Cys Asp Ala Pro Ile Leu Ser Ser Ser Arg Ser Leu Asp Cys Arg
1               5                   10                  15

Glu Ser Gly Lys Asn Gly Pro His Val Tyr Gln Asp Leu Leu Leu Ser
            20                  25                  30

Leu Gly Thr Thr Asn Ser Thr Leu Pro Gln Gly Gln Pro Ile Leu Thr
        35                  40                  45

Ser Leu Gly Ser Asn Gln Glu Glu Ala Tyr Val Thr Met Ser Ser Phe
    50                  55                  60

Tyr Gln Asn Gln
65

<210> SEQ ID NO 71
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Ile Leu Thr Leu Asn Pro Val Ala Gln Gly Gln Pro Ile Leu Thr
1               5                   10                  15

Ser Leu Gly Ser Asn Gln Glu Glu Ala Tyr Val Thr Met Ser Ser Phe
            20                  25                  30

Phe Gln Asn Gln
        35

<210> SEQ ID NO 72
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ala Cys Asp Ala Pro Ile Leu Ser Ser Ser Arg Ser Leu Asp Cys Arg
1               5                   10                  15

Glu Ser Gly Lys Asn Gly Pro His Val Tyr Gln Asp Leu Leu Leu Ser
            20                  25                  30

Leu Gly Thr Thr Asn Ser Thr Leu Pro Gln Gly Gln Pro Ile Leu Thr
        35                  40                  45

Ser Leu Gly Ser Asn Gln Glu Glu Ala Tyr Val Thr Met Ser Ser Phe
    50                  55                  60

Phe Gln Asn Gln
65
```

```
<210> SEQ ID NO 73
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Glu Gly Val Ala Gly Ala Pro Thr Gly Ser Ser Pro Gln Pro Leu
1               5                   10                  15

Gln Pro Leu Ser Gly Glu Asp Ala Tyr Cys Thr Phe Pro Ser Arg
            20                  25                  30

Asp Asp Leu Leu Leu Phe Ser Pro Ser Gly Gln Gly Glu Phe Arg Ala
            35                  40                  45

Leu Asn Ala Arg Leu Pro Leu Asn Thr Asp Ala Tyr Leu Ser Leu Gln
        50                  55                  60

Glu Leu Gln Gly Gln Asp Pro Thr His Leu Val
65                  70                  75

<210> SEQ ID NO 74
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gly Gln Gly Glu Phe Arg Ala Leu Asn Ala Arg Leu Pro Leu Asn Thr
1               5                   10                  15

Asp Ala Tyr Leu Ser Leu Gln Glu Leu Gln Gly Gln Asp Pro Thr His
            20                  25                  30

Leu Val

<210> SEQ ID NO 75
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Gln Asp Lys Val Pro Glu Pro Ala Ser Leu Ser Ser Asn His Ser
1               5                   10                  15

Leu Thr Ser Cys Phe Thr Asn Gln Gly Tyr Phe Phe Phe His Leu Pro
            20                  25                  30

Asp Ala Leu Glu Ile Glu Ala Cys Gln Asp Glu Gly Val Ala Gly Ala
            35                  40                  45

Pro Thr Gly Ser Ser Pro Gln Pro Leu Gln Pro Leu Ser Gly Glu Asp
        50                  55                  60

Asp Ala Tyr Cys Thr Phe Pro Ser Arg Asp Asp Leu Leu Leu Phe Ser
65                  70                  75                  80

Pro Ser

<210> SEQ ID NO 76
<211> LENGTH: 75
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 76

Gln Gln Asp Lys Val Pro Glu Pro Ala Ser Leu Ser Ser Asn His Ser
1               5                   10                  15

Leu Thr Ser Cys Phe Thr Asn Gln Gly Tyr Phe Phe His Leu Pro
            20                  25                  30

Asp Ala Leu Glu Ile Glu Ala Cys Gln Gly Gln Gly Glu Phe Arg Ala
        35                  40                  45

Leu Asn Ala Arg Leu Pro Leu Asn Thr Asp Ala Tyr Leu Ser Leu Gln
    50                  55                  60

Glu Leu Gln Gly Gln Asp Pro Thr His Leu Val
65                  70                  75

<210> SEQ ID NO 77
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Glu Gly Val Ala Gly Ala Pro Thr Gly Ser Ser Pro Gln Pro Leu
1               5                   10                  15

Gln Pro Leu Ser Gly Glu Asp Asp Ala Tyr Cys Thr Phe Pro Ser Arg
            20                  25                  30

Asp Asp Leu Leu Leu Phe Ser Pro Ser Gly Gln Gly Glu Phe Arg Ala
        35                  40                  45

Leu Asn Ala Arg Leu Pro Leu Asn Thr Asp Ala Tyr Leu Ser Leu Gln
    50                  55                  60

Glu Leu Gln Gly Gln Asp Pro Thr His Leu Val
65                  70                  75

<210> SEQ ID NO 78
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Gln Asp Lys Val Pro Glu Pro Ala Ser Leu Ser Ser Asn His Ser
1               5                   10                  15

Leu Thr Ser Cys Phe Thr Asn Gln Gly Tyr Phe Phe His Leu Pro
            20                  25                  30

Asp Ala Leu Glu Ile Glu Ala Cys Gln Asp Glu Gly Val Ala Gly Ala
        35                  40                  45

Pro Thr Gly Ser Ser Pro Gln Pro Leu Gln Pro Leu Ser Gly Glu Asp
    50                  55                  60

Asp Ala Tyr Cys Thr Phe Pro Ser Arg Asp Asp Leu Leu Leu Phe Ser
65                  70                  75                  80

Pro Ser Gly Gln Gly Glu Phe Arg Ala Leu Asn Ala Arg Leu Pro Leu
            85                  90                  95

Asn Thr Asp Ala Tyr Leu Ser Leu Gln Glu Leu Gln Gly Gln Asp Pro
            100                 105                 110

Thr His Leu Val
            115

<210> SEQ ID NO 79
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Lys Lys Lys Val Trp Asp Tyr Asn Tyr Asp Asp Glu Ser Asp Ser Asp
1               5                   10                  15

Thr Glu Ala Ala Pro Arg Thr Ser Gly Gly Gly Tyr Thr Met His Gly
            20                  25                  30

Leu Thr Val Arg Pro Leu Gly Gln Ala Ser Ala
        35                  40

<210> SEQ ID NO 80
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Gly Leu Trp Ser Glu Asp Ala Pro Ser Gln Ser Asp Thr Ser
1               5                   10                  15

Glu Ser Asp Val Asp Leu Gly Asp Gly Tyr Ile Met Arg
            20                  25

<210> SEQ ID NO 81
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Lys Lys Lys Val Trp Asp Tyr Asn Tyr Asp Asp Glu Ser Asp Ser Asp
1               5                   10                  15

Thr Glu Ala Ala Pro Arg Thr Ser Gly Gly Gly Tyr Thr Met His Gly
            20                  25                  30

Leu Thr Val Arg Pro Leu Gly Gln Ala Ser Ala Glu Gly Leu Trp Ser
        35                  40                  45

Glu Asp Ala Pro Ser Asp Gln Ser Asp Thr Ser Glu Ser Asp Val Asp
    50                  55                  60

Leu Gly Asp Gly Tyr Ile Met Arg
65                  70

<210> SEQ ID NO 82
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ala Ser Glu Ser Pro Ala Asp Glu Glu Glu Gln Trp Ser Asp Asp Phe
1               5                   10                  15

Asp Ser Asp Tyr Glu Asn Pro Asp Glu His Ser Asp Ser Glu Met Tyr

```
                20                  25                  30
Val Met Pro Ala Glu Glu Asn Ala Asp Asp Ser Tyr Glu Pro Pro Pro
            35                  40                  45

Val Glu Gln Glu Thr Arg Pro Val His Pro Ala Leu Pro Phe Ala Arg
 50                  55                  60

Gly Glu Tyr Ile Asp Asn Arg Ser Ser Gln Arg His Ser Pro Pro Phe
 65                  70                  75                  80

Ser Lys Thr Leu Pro Ser Lys Pro Ser Trp Pro Ser Glu Lys Ala Arg
                85                  90                  95

Leu Thr Ser Thr Leu Pro Ala Leu Thr Ala Leu Gln Lys Pro Gln Val
               100                 105                 110

Pro Pro Lys Pro Lys Gly Leu Leu Glu Asp Glu Ala Asp Tyr Val Val
               115                 120                 125

Pro Val Glu Asp Asn Asp Glu Asn Tyr Ile His Pro Thr Glu Ser Ser
           130                 135                 140

Ser Pro Pro Pro Glu Lys Ala Pro Met Val Asn Arg
145                 150                 155
```

<210> SEQ ID NO 83
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

```
Ala Ser Glu Ser Pro Ala Asp Glu Glu Glu Gln Trp Ser Asp Asp Phe
 1               5                  10                  15

Asp Ser Asp Phe Glu Asn Pro Asp Glu His Ser Asp Ser Glu Met Tyr
                20                  25                  30

Val Met Pro Ala Glu Glu Asn Ala Asp Asp Ser Tyr Glu Pro Pro Pro
            35                  40                  45

Val Glu Gln Glu Thr Arg Pro Val His Pro Ala Leu Pro Phe Ala Arg
 50                  55                  60

Gly Glu Tyr Ile Asp Asn Arg Ser Ser Gln Arg His Ser Pro Pro Phe
 65                  70                  75                  80

Ser Lys Thr Leu Pro Ser Lys Pro Ser Trp Pro Ser Glu Lys Ala Arg
                85                  90                  95

Leu Thr Ser Thr Leu Pro Ala Leu Thr Ala Leu Gln Lys Pro Gln Val
               100                 105                 110

Pro Pro Lys Pro Lys Gly Leu Leu Glu Asp Glu Ala Asp Tyr Val Val
               115                 120                 125

Pro Val Glu Asp Asn Asp Glu Asn Tyr Ile His Pro Thr Glu Ser Ser
           130                 135                 140

Ser Pro Pro Pro Glu Lys Ala Pro Met Val Asn Arg
145                 150                 155
```

<210> SEQ ID NO 84
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ala Ser Glu Ser Pro Ala Asp Glu Glu Glu Gln Trp Ser Asp Asp Phe

```
            1               5                  10                 15
Asp Ser Asp Phe Glu Asn Pro Asp Glu His Ser Asp Ser Glu Met Tyr
            20                 25                 30

Val Met Pro Ala Glu Glu Asn Ala Asp Asp Ser Phe Glu Pro Pro Pro
            35                 40                 45

Val Glu Gln Glu Thr Arg Pro Val His Pro Ala Leu Pro Phe Ala Arg
            50                 55                 60

Gly Glu Tyr Ile Asp Asn Arg Ser Ser Gln Arg His Ser Pro Pro Phe
65                 70                 75                 80

Ser Lys Thr Leu Pro Ser Lys Pro Ser Trp Pro Ser Glu Lys Ala Arg
            85                 90                 95

Leu Thr Ser Thr Leu Pro Ala Leu Thr Ala Leu Gln Lys Pro Gln Val
            100                105                110

Pro Pro Lys Pro Lys Gly Leu Leu Glu Asp Ala Asp Tyr Val Val
            115                120                125

Pro Val Glu Asp Asn Asp Glu Asn Tyr Ile His Pro Thr Glu Ser Ser
            130                135                140

Ser Pro Pro Pro Glu Lys Ala Pro Met Val Asn Arg
145                150                155
```

<210> SEQ ID NO 85
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Trp Gly Thr Met Gln Ala Val Glu Pro Gly Thr Asp Asp Glu Gly Pro
1               5                  10                 15

Leu Leu Glu Pro Val Gly Ser Glu His Ala Gln Asp Thr Tyr Leu Val
            20                 25                 30

Leu Asp Lys Trp Leu Leu Pro Arg Asn Pro Pro Ser Glu Asp Leu Pro
            35                 40                 45

Gly Pro Gly Gly Ser Val Asp Ile Val Ala Met Asp Glu Gly Ser Glu
            50                 55                 60

Ala Ser Ser Cys Ser Ser Ala Leu Ala Ser Lys Pro Ser Pro Glu Gly
65                 70                 75                 80

Ala Ser Ala Ala Ser Phe Glu Tyr Thr Ile Leu Asp Pro Ser Ser Gln
            85                 90                 95

Leu Leu Arg Pro Trp Thr Leu Cys Pro Glu Leu Pro Pro Thr Pro Pro
            100                105                110

His Leu Lys Tyr Leu Tyr Leu Val Val Ser Asp Ser Gly Ile Ser Thr
            115                120                125

Asp Tyr Ser Ser Gly Asp Ser Gln Gly Ala Gln Gly Gly Leu Ser Asp
            130                135                140

Gly Pro Tyr Ser Asn Pro Tyr Glu Asn Ser Leu Ile Pro Ala Ala Glu
145                150                155                160

Pro Leu Pro Pro Ser Tyr Val Ala Cys Ser
                165                170
```

<210> SEQ ID NO 86
<211> LENGTH: 149
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 86

Val Thr Pro Val Phe Arg His Pro Pro Cys Ser Asn Trp Pro Gln Arg
1               5                   10                  15

Glu Lys Gly Ile Gln Gly His Gln Ala Ser Glu Lys Asp Met Met His
            20                  25                  30

Ser Ala Ser Pro Pro Pro Arg Ala Leu Gln Ala Glu Ser Arg
        35                  40                  45

Gln Leu Val Asp Leu Tyr Lys Val Leu Glu Ser Arg Gly Ser Asp Pro
    50                  55                  60

Lys Pro Glu Asn Pro Ala Cys Pro Trp Thr Val Leu Pro Ala Gly Asp
65                  70                  75                  80

Leu Pro Thr His Asp Gly Tyr Leu Pro Ser Asn Ile Asp Leu Pro
                85                  90                  95

Ser His Glu Ala Pro Leu Ala Asp Ser Leu Glu Glu Leu Glu Pro Gln
            100                 105                 110

His Ile Ser Leu Ser Val Phe Pro Ser Ser Leu His Pro Leu Thr
        115                 120                 125

Phe Ser Cys Gly Asp Lys Leu Thr Leu Asp Gln Leu Lys Met Arg Cys
130                 135                 140

Asp Ser Leu Met Leu
145

<210> SEQ ID NO 87
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Trp Asp Lys Gly Glu Arg Thr Glu Pro Leu Glu Lys Thr Glu Leu Pro
1               5                   10                  15

Glu Gly Ala Pro Glu Leu Ala Leu Asp Thr Gly Leu Ser Leu Glu Asp
            20                  25                  30

Gly Asp Arg Cys Lys Ala Lys Met
        35                  40

<210> SEQ ID NO 88
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Val Ser Pro Glu Leu Lys Asn Leu Asp Leu His Gly Ser Thr Asp Ser
1               5                   10                  15

Gly Phe Gly Ser Thr Lys Pro Ser Leu Gln Thr Glu Pro Gln Phe
            20                  25                  30

Leu Leu Pro Asp Pro His Pro Gln Ala Asp Arg Thr Leu Gly Asn Arg
        35                  40                  45

Glu Pro Pro Val Leu Gly Asp Ser Cys Ser Ser Gly Ser Ser Asn Ser
    50                  55                  60

Thr Asp Ser Gly Ile Cys Leu Gln Glu Pro Ser Leu Ser Pro Ser Thr

```
                65                  70                  75                  80
Gly Pro Thr Trp Glu Gln Gln Val Gly Ser Asn Ser Arg Gly Gln Asp
                85                  90                  95

Asp Ser Gly Ile Asp Leu Val Gln Asn Ser Glu Gly Arg Ala Gly Asp
            100                 105                 110

Thr Gln Gly Gly Ser Ala Leu Gly His His Ser Pro Glu Pro Glu
        115                 120                 125

Val Pro Gly Glu Glu Asp Pro Ala Ala Val Ala Phe Gln Gly Tyr Leu
130                 135                 140

Arg Gln Thr Arg Cys Ala Glu Glu Lys Ala Thr Lys Thr Gly Cys Leu
145                 150                 155                 160

Glu Glu Glu Ser Pro Leu Thr Asp Gly Leu Gly Pro Lys Phe Gly Arg
                165                 170                 175

Cys Leu Val Asp Glu Ala Gly Leu His Pro Ala Leu Ala Lys Gly
            180                 185                 190

Tyr Leu Lys Gln Asp Pro Leu Glu Met Thr Leu Ala Ser Ser Gly Ala
        195                 200                 205

Pro Thr Gly Gln Trp Asn Gln Pro Thr Glu Glu Trp Ser Leu Leu Ala
    210                 215                 220

Leu Ser Ser Cys Ser Asp Leu Gly Ile Ser Asp Trp Ser Phe Ala His
225                 230                 235                 240

Asp Leu Ala Pro Leu Gly Cys Val Ala Pro Gly Gly Leu Leu Gly
                245                 250                 255

Ser Phe Asn Ser Asp Leu Val Thr Leu Pro Leu Ile Ser Ser Leu Gln
            260                 265                 270

Ser Ser Glu
    275

<210> SEQ ID NO 89
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Met Ala Leu Pro Val Thr Ala Leu Leu Leu Pro Leu Ala Leu Leu Leu
1               5                   10                  15

His Ala Ala Arg Pro
            20

<210> SEQ ID NO 90
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
```

```
                50                  55                  60
Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                 85                  90                  95

Ser Ser Glu Arg Thr Pro Leu Pro Leu Ala Arg Asp Glu Val Glu Gly
                100                 105                 110

Phe Leu Gln Asp Thr Phe Pro Gln Gln Leu Glu Glu Ser Glu Lys Gln
                115                 120                 125

Arg Leu Gly Gly Asp Val Gln Ser Pro Asn Cys Pro Ser Glu Asp Val
            130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
                180                 185                 190

Asp Leu Leu Leu Ser Leu Gly Thr Thr Asn Ser Thr Leu Pro Pro Pro
            195                 200                 205

Phe Ser Leu Gln Ser Gly Ile Leu Thr Leu Asn Pro Val Ala Gln Gly
            210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245

<210> SEQ ID NO 91
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Ser Asp Pro Thr Arg Val Glu Thr Ala Thr Glu Thr Ala Trp Ile Ser
 1                   5                  10                  15

Leu Val Thr Ala Leu Leu Leu Val Leu Gly Leu Asn Ala Val Leu Gly
                 20                  25                  30

Leu Leu Leu Leu Arg Trp Gln Phe Pro Ala His Tyr Arg Arg Leu Arg
             35                  40                  45

His Ala Leu Trp Pro Ser Leu Pro Asp Leu His Arg Val Leu Gly Gln
         50                  55                  60

Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                 85                  90                  95

Ser Ser Glu Arg Thr Pro Leu Pro Leu Ala Arg Asp Glu Val Glu Gly
                100                 105                 110

Phe Leu Gln Asp Thr Phe Pro Gln Gln Leu Glu Glu Ser Glu Lys Gln
                115                 120                 125

Arg Leu Gly Gly Asp Val Gln Ser Pro Asn Cys Pro Ser Glu Asp Val
            130                 135                 140

Val Ile Thr Pro Glu Ser Phe Gly Arg Asp Ser Ser Leu Thr Cys Leu
145                 150                 155                 160
```

```
Ala Gly Asn Val Ser Ala Cys Asp Ala Pro Ile Leu Ser Ser Ser Arg
            165                 170                 175

Ser Leu Asp Cys Arg Glu Ser Gly Lys Asn Gly Pro His Val Tyr Gln
        180                 185                 190

Asp Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Ala Tyr Val
225                 230                 235                 240

Thr Met Ser Ser Phe Tyr Gln Asn Gln
            245
```

<210> SEQ ID NO 92
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Ala Tyr Val
225                 230                 235                 240

Thr Met Ser Ser Phe Tyr Gln Asn Gln
            245
```

<210> SEQ ID NO 93

<211> LENGTH: 249
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 93

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Ser Ala Val Leu Gly
                20                  25                  30

Leu Leu Leu Leu Arg Lys Gln Phe Pro Ala His Tyr Arg Arg Leu Arg
            35                  40                  45

His Ala Leu Trp Pro Ser Leu Pro Asp Leu His Arg Val Leu Gly Gln
        50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245

<210> SEQ ID NO 94
<211> LENGTH: 249
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 94

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
                20                  25                  30

Leu Leu Leu Leu Arg Lys Gln Phe Pro Ala His Tyr Arg Arg Leu Arg
            35                  40                  45

His Ala Leu Trp Pro Ser Leu Pro Asp Leu His Arg Val Leu Gly Gln
        50                  55                  60

```
Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                 85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
            115                 120                 125

Arg Leu Gly Gly Asp Val Gln Ser Pro Asn Cys Pro Ser Glu Asp Val
130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Ser Leu Gly Thr Thr Asn Ser Thr Leu Pro Pro Pro
            195                 200                 205

Phe Ser Leu Gln Ser Gly Ile Leu Thr Leu Asn Pro Val Ala Gln Gly
            210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245

<210> SEQ ID NO 95
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ser Asp Pro Thr Arg Val Glu Thr Ala Thr Glu Thr Ala Trp Ile Ser
 1               5                  10                  15

Leu Val Thr Ala Leu Leu Leu Val Leu Gly Leu Asn Ala Val Leu Gly
                20                  25                  30

Leu Leu Leu Leu Arg Lys Gln Phe Pro Ala His Tyr Arg Arg Leu Arg
            35                  40                  45

His Ala Leu Trp Pro Ser Leu Pro Asp Leu His Arg Val Leu Gly Gln
 50                 55                  60

Tyr Leu Arg Asp Thr Ala Ala Leu Ser Pro Pro Lys Ala Thr Val Ser
 65                 70                  75                  80

Asp Thr Cys Glu Glu Val Glu Pro Ser Leu Leu Glu Ile Leu Pro Lys
                 85                 90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
            115                 120                 125

Arg Leu Gly Gly Asp Val Gln Ser Pro Asn Cys Pro Ser Glu Asp Val
130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
```

```
                    165                 170                 175
Ser Leu Asp Cys Arg Glu Ser Gly Lys Asn Gly Pro His Val Tyr Gln
                180                 185                 190

Asp Leu Leu Ser Leu Gly Thr Thr Asn Ser Thr Leu Pro Pro Pro
            195                 200                 205

Phe Ser Leu Gln Ser Gly Ile Leu Thr Leu Asn Pro Val Ala Gln Gly
        210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245

<210> SEQ ID NO 96
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
                20                  25                  30

Leu Leu Leu Leu Arg Lys Gln Phe Pro Ala His Tyr Arg Arg Leu Arg
            35                  40                  45

His Ala Leu Trp Pro Ser Leu Pro Asp Leu His Arg Val Leu Gly Gln
        50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245

<210> SEQ ID NO 97
<211> LENGTH: 249
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Ser Ala Val Leu Asn
                20                  25                  30

Leu Leu Leu Leu Arg Trp Gln Phe Pro Ala His Tyr Arg Arg Leu Arg
            35                  40                  45

His Ala Leu Trp Pro Ser Leu Pro Asp Leu His Arg Val Leu Gly Gln
        50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
                100                 105                 110

Phe Leu Gln Asp Thr Phe Pro Gln Gln Leu Glu Glu Ser Glu Lys Gln
            115                 120                 125

Arg Leu Gly Gly Asp Val Gln Ser Pro Asn Cys Pro Ser Glu Asp Val
130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245

<210> SEQ ID NO 98
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
                20                  25                  30

Leu Leu Leu Leu Arg Trp Gln Phe Pro Ala His Tyr Arg Arg Leu Arg
            35                  40                  45

His Ala Leu Trp Pro Ser Leu Pro Asp Leu His Arg Val Leu Gly Gln
        50                  55                  60
```

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Pro Asn Pro Leu Leu Gly Leu Asp Ser Thr
1               5                   10

<210> SEQ ID NO 100
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
            20                  25                  30

Tyr Ile His Trp Val Arg Gln Met Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

```
Ala Phe Arg Gly Gly Val Tyr Trp Gly Gln Gly Thr Thr Val Thr Val
                100                 105                 110

Ser Ser Gly Gly Gly Gly Ser Gly Gly Gly Ser Gly Gly Gly
        115                 120                 125

Ser Gly Gly Gly Gly Ser Asp Val Val Met Thr Gln Ser Pro Asp Ser
        130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
                180                 185                 190

Leu Asp Ser Gly Val Pro Asp Arg Phe Ser Gly Ser Gly Ser Gly Thr
                195                 200                 205

Asp Phe Thr Leu Thr Ile Ser Ser Leu Gln Ala Glu Asp Val Ala Val
                210                 215                 220

Tyr Tyr Cys Trp Gln Gly Thr His Phe Pro Gly Thr Phe Gly Gly Gly
225                 230                 235                 240

Thr Lys Val Glu Ile Lys
                245

<210> SEQ ID NO 101
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 102
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 103
<211> LENGTH: 112
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 104
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Ser Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Thr Ser
            115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ile Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asn Glu
        195                 200                 205

-continued

```
Thr Tyr Val Glu Gln His Glu Val Ala Val Ala Arg Tyr Cys Asp Leu
    210                 215                 220
Pro Ser Lys Leu Gly His Lys Leu Asn
225                 230

<210> SEQ ID NO 105
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Ser Gly Ala Thr Asn Phe Ser Leu Leu Lys Gln Ala Gly Asp Val
1               5                   10                  15
Glu Glu Asn Pro Gly Pro
            20

<210> SEQ ID NO 106
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Val Thr Gln Leu Leu Leu Gln Gln Asp Lys Val Pro Glu Pro Ala Ser
1               5                   10                  15
Leu Ser Ser Asn His Ser Leu Thr Ser Cys Phe Thr Asn Gln Gly Tyr
            20                  25                  30
Phe Phe Phe His Leu Pro Asp Ala Leu Glu Ile Glu Ala Cys Gln Val
        35                  40                  45
Ser Phe Thr Ser Asp Pro Ser Ser Glu Glu Asp Pro Asp Glu Gly Val
    50                  55                  60
Ala Gly Ala Pro Thr Gly Ser Ser Pro Gln Pro Leu Gln Pro Leu Ser
65                  70                  75                  80
Gly Glu Asp Asp Ala Tyr Cys Thr Phe Pro Ser Arg Asp Asp Leu Leu
                85                  90                  95
Leu Phe Ser Pro Ser Leu Leu Gly Gly Pro Ser Pro Pro Ser Thr Ala
            100                 105                 110
Pro Gly Gly Ser Gly Ala Gly Glu Glu Arg Met Pro Pro Ser Leu Gln
        115                 120                 125
Glu Arg Val Pro Arg Asp Trp Asp Pro Gln Pro Leu Gly Pro Pro Thr
130                 135                 140
Pro Gly Val Pro Asp Leu Val Asp Phe Gln Pro Pro Pro Glu Leu Val
145                 150                 155                 160
Leu Arg Glu Ala Gly Glu Glu Val Pro Asp Ala Gly Pro Arg Glu Gly
                165                 170                 175
Val Ser Phe Pro Trp Ser Arg Pro Pro Gly Gln Gly Glu Phe Arg Ala
            180                 185                 190
Leu Asn Ala Arg Leu Pro Leu Asn Thr Asp Ala Tyr Leu Ser Leu Gln
        195                 200                 205
Glu Leu Gln Gly Gln Asp Pro Thr His Leu Val
    210                 215

<210> SEQ ID NO 107
<211> LENGTH: 275
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu His Leu Val Leu Gly Leu
        35                  40                  45

Asn Ala Val Leu Gly Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Val Glu Pro Ser Leu Leu
                100                 105                 110

Glu Ile Leu Pro Lys Ser Ser Glu Arg Thr Pro Leu Pro Leu Val Thr
            115                 120                 125

Pro Val Phe Arg His Pro Pro Cys Ser Asn Trp Pro Gln Arg Glu Lys
        130                 135                 140

Gly Ile Gln Gly His Gln Ala Ser Glu Lys Asp Met Met His Ser Ala
145                 150                 155                 160

Ser Ser Pro Pro Pro Arg Ala Leu Gln Ala Glu Ser Arg Gln Leu
                165                 170                 175

Val Asp Leu Tyr Lys Val Leu Glu Ser Arg Gly Ser Asp Pro Lys Pro
            180                 185                 190

Glu Asn Pro Ala Cys Pro Trp Thr Val Leu Pro Ala Gly Asp Leu Pro
        195                 200                 205

Thr His Asp Gly Tyr Leu Pro Ser Asn Ile Asp Asp Leu Pro Ser His
    210                 215                 220

Glu Ala Pro Leu Ala Asp Ser Leu Glu Glu Leu Gly Pro Gln His Ile
225                 230                 235                 240

Ser Leu Ser Val Phe Pro Ser Ser Leu His Pro Leu Thr Phe Ser
                245                 250                 255

Cys Gly Asp Lys Leu Thr Leu Asp Gln Leu Lys Met Arg Cys Asp Ser
            260                 265                 270

Leu Met Leu
        275

<210> SEQ ID NO 108
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu Leu Val Leu Gly Leu
                35                  40                  45

Asn Ala Val Leu Gly Leu Leu Leu Arg Lys Gln Phe Pro Ala His
 50                  55                  60

Tyr Arg Arg Leu Arg His Ala Leu Trp Pro Ser Leu Pro Asp Leu His
 65                  70                  75                  80

Arg Val Leu Gly Gln Tyr Leu Arg Asp Thr Ala Ala Leu Ser Pro Pro
                 85                  90                  95

Lys Ala Thr Val Ser Asp Thr Cys Glu Val Glu Pro Ser Leu Leu
                100                 105                 110

Glu Ile Leu Pro Lys Ser Ser Glu Arg Thr Pro Leu Pro Leu Val Thr
                115                 120                 125

Pro Val Phe Arg His Pro Pro Cys Ser Asn Trp Pro Gln Arg Glu Lys
130                 135                 140

Gly Ile Gln Gly His Gln Ala Ser Glu Lys Asp Met Met His Ser Ala
145                 150                 155                 160

Ser Ser Pro Pro Pro Arg Ala Leu Gln Ala Glu Ser Arg Gln Leu
                165                 170                 175

Val Asp Leu Tyr Lys Val Leu Glu Ser Arg Gly Ser Asp Pro Lys Pro
                180                 185                 190

Glu Asn Pro Ala Cys Pro Trp Thr Val Leu Pro Ala Gly Asp Leu Pro
                195                 200                 205

Thr His Asp Gly Tyr Leu Pro Ser Asn Ile Asp Asp Leu Pro Ser His
                210                 215                 220

Glu Ala Pro Leu Ala Asp Ser Leu Glu Glu Leu Glu Pro Gln His Ile
225                 230                 235                 240

Ser Leu Ser Val Phe Pro Ser Ser Ser Leu His Pro Leu Thr Phe Ser
                245                 250                 255

Cys Gly Asp Lys Leu Thr Leu Asp Gln Leu Lys Met Arg Cys Asp Ser
                260                 265                 270

Leu Met Leu
        275

<210> SEQ ID NO 109
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Met Ala Leu Pro Val Thr Ala Leu Leu Leu Pro Leu Ala Leu Leu Leu
 1               5                   10                  15

His Ala Ala Arg Pro Ser Asp Pro Thr Arg Val Glu Thr Ala Thr Glu
                20                  25                  30

Thr Ala Trp Ile Ser Leu Val Thr Ala Leu His Leu Val Leu Gly Leu
                35                  40                  45

Asn Ala Val Leu Gly Leu Leu Leu Arg Lys Gln Phe Pro Ala His
 50                  55                  60

Tyr Arg Arg Leu Arg His Ala Leu Trp Pro Ser Leu Pro Asp Leu His
 65                  70                  75                  80

Arg Val Leu Gly Gln Tyr Leu Arg Asp Thr Ala Ala Leu Ser Pro Pro
                 85                  90                  95

Lys Ala Thr Val Ser Asp Thr Cys Glu Glu Val Glu Pro Ser Leu Leu
                100                 105                 110

```
Glu Ile Leu Pro Lys Ser Ser Glu Arg Thr Pro Leu Pro Leu Ser Asp
            115                 120                 125

Pro Lys Pro Glu Asn Pro Ala Cys Pro Trp Thr Val Leu Pro Ala Gly
        130                 135                 140

Asp Leu Pro Thr His Asp Gly Tyr Leu Pro Ser Asn Ile Asp Asp Leu
145                 150                 155                 160

Pro Ser His Glu Ala Pro Leu Ala Asp Ser Leu Glu Glu Leu Glu Pro
                165                 170                 175

Gln

<210> SEQ ID NO 110
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu Leu Val Leu Gly Leu
        35                  40                  45

Asn Ala Val Leu Gly Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Ser Asp
            115                 120                 125

Pro Lys Pro Glu Asn Pro Ala Cys Pro Trp Thr Val Leu Pro Ala Gly
        130                 135                 140

Asp Leu Pro Thr His Asp Gly Tyr Leu Pro Ser Asn Ile Asp Asp Leu
145                 150                 155                 160

Pro Ser His Glu Ala Pro Leu Ala Asp Ser Leu Glu Glu Leu Glu Pro
                165                 170                 175

Gln

<210> SEQ ID NO 111
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu His Leu Val Leu Gly Leu
```

```
              35                  40                  45
Asn Ala Val Leu Gly Leu Leu Leu Arg Lys Gln Phe Pro Ala His
 50                  55                  60
Tyr Arg Arg Leu Arg His Ala Leu Trp Pro Ser Leu Pro Asp Leu His
 65                  70                  75                  80
Arg Val Leu Gly Gln Tyr Leu Arg Asp Thr Ala Ala Leu Ser Pro Pro
                     85                  90                  95
Lys Ala Thr Val Ser Asp Thr Cys Glu Val Glu Pro Ser Leu Leu
                100                 105                 110
Glu Ile Leu Pro Lys Ser Ser Glu Arg Thr Pro Leu Pro Leu Val Thr
            115                 120                 125
Gln Leu Leu Leu Gln Gln Asp Lys Val Pro Glu Pro Ala Ser Leu Ser
            130                 135                 140
Ser Asn His Ser Leu Thr Ser Cys Phe Thr Asn Gln Gly Tyr Phe Phe
145                 150                 155                 160
Phe His Leu Pro Asp Ala Leu Glu Ile Glu Ala Cys Gln Val Tyr Phe
                165                 170                 175
Thr Tyr Asp Pro Tyr Ser Glu Glu Asp Pro Asp Glu Gly Val Ala Gly
                180                 185                 190
Ala Pro Thr Gly Ser Ser Pro Gln Pro Leu Gln Pro Leu Ser Gly Glu
                195                 200                 205
Asp Asp Ala Tyr Cys Thr Phe Pro Ser Arg Asp Asp Leu Leu Leu Phe
210                 215                 220
Ser Pro Ser Leu Leu Gly Gly Pro Ser Pro Ser Thr Ala Pro Gly
225                 230                 235                 240
Gly Ser Gly Ala Gly Glu Arg Met Pro Pro Ser Leu Gln Glu Arg
                245                 250                 255
Val Pro Arg Asp Trp Asp Pro Gln Pro Leu Gly Pro Pro Thr Pro Gly
                260                 265                 270
Val Pro Asp Leu Val Asp Phe Gln Pro Pro Glu Leu Val Leu Arg
                275                 280                 285
Glu Ala Gly Glu Glu Val Pro Asp Ala Gly Pro Arg Glu Gly Val Ser
290                 295                 300
Phe Pro Trp Ser Arg Pro Pro Gly Gln Gly Glu Phe Arg Ala Leu Asn
305                 310                 315                 320
Ala Arg Leu Pro Leu Asn Thr Asp Ala Tyr Leu Ser Leu Gln Glu Leu
                325                 330                 335
Gln Gly Gln Asp Pro Thr His Leu Val
                340                 345

<210> SEQ ID NO 112
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Ala Leu Pro Val Thr Ala Leu Leu Leu Pro Leu Ala Leu Leu Leu
 1               5                  10                  15
His Ala Ala Arg Pro Ser Asp Pro Thr Arg Val Glu Thr Ala Thr Glu
                 20                  25                  30
Thr Ala Trp Ile Ser Leu Val Thr Ala Leu Leu Leu Val Leu Gly Leu
             35                  40                  45
```

```
Asn Ala Val Leu Gly Leu Leu Leu Arg Lys Gln Phe Pro Ala His
 50                  55                  60

Tyr Arg Arg Leu Arg His Ala Leu Trp Pro Ser Leu Pro Asp Leu His
 65                  70                  75                  80

Arg Val Leu Gly Gln Tyr Leu Arg Asp Thr Ala Ala Leu Ser Pro Pro
                 85                  90                  95

Lys Ala Thr Val Ser Asp Thr Cys Glu Glu Val Glu Pro Ser Leu Leu
                100                 105                 110

Glu Ile Leu Pro Lys Ser Ser Glu Arg Thr Pro Leu Pro Leu Val Thr
            115                 120                 125

Gln Leu Leu Leu Gln Gln Asp Lys Val Pro Glu Pro Ala Ser Leu Ser
130                 135                 140

Ser Asn His Ser Leu Thr Ser Cys Phe Thr Asn Gln Gly Tyr Phe Phe
145                 150                 155                 160

Phe His Leu Pro Asp Ala Leu Glu Ile Glu Ala Cys Gln Val Tyr Phe
                165                 170                 175

Thr Tyr Asp Pro Tyr Ser Glu Glu Asp Pro Asp Glu Gly Val Ala Gly
            180                 185                 190

Ala Pro Thr Gly Ser Ser Pro Gln Pro Leu Gln Pro Leu Ser Gly Glu
            195                 200                 205

Asp Asp Ala Tyr Cys Thr Phe Pro Ser Arg Asp Asp Leu Leu Leu Phe
210                 215                 220

Ser Pro Ser Leu Leu Gly Pro Ser Pro Ser Thr Ala Pro Gly
225                 230                 235                 240

Gly Ser Gly Ala Gly Glu Glu Arg Met Pro Pro Ser Leu Gln Glu Arg
                245                 250                 255

Val Pro Arg Asp Trp Asp Pro Gln Pro Leu Gly Pro Pro Thr Pro Gly
            260                 265                 270

Val Pro Asp Leu Val Asp Phe Gln Pro Pro Glu Leu Val Leu Arg
            275                 280                 285

Glu Ala Gly Glu Glu Val Pro Asp Ala Gly Pro Arg Glu Gly Val Ser
290                 295                 300

Phe Pro Trp Ser Arg Pro Pro Gly Gln Gly Glu Phe Arg Ala Leu Asn
305                 310                 315                 320

Ala Arg Leu Pro Leu Asn Thr Asp Ala Tyr Leu Ser Leu Gln Glu Leu
                325                 330                 335

Gln Gly Gln Asp Pro Thr His Leu Val
            340                 345

<210> SEQ ID NO 113
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Ala Leu Pro Val Thr Ala Leu Leu Leu Pro Leu Ala Leu Leu Leu
 1               5                  10                  15

His Ala Ala Arg Pro Ser Asp Pro Thr Arg Val Glu Thr Ala Thr Glu
                20                  25                  30

Thr Ala Trp Ile Ser Leu Val Thr Ala Leu His Leu Val Leu Gly Leu
            35                  40                  45

Asn Ala Val Leu Gly Leu Leu Leu Arg Lys Gln Phe Pro Ala His
 50                  55                  60
```

```
Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Asp Glu
            115                 120                 125

Gly Val Ala Gly Ala Pro Thr Gly Ser Ser Pro Gln Pro Leu Gln Pro
            130                 135                 140

Leu Ser Gly Glu Asp Asp Ala Tyr Cys Thr Phe Pro Ser Arg Asp Asp
145                 150                 155                 160

Leu Leu Leu Phe Ser Pro Ser Gly Gln Gly Glu Phe Arg Ala Leu Asn
                165                 170                 175

Ala Arg Leu Pro Leu Asn Thr Asp Ala Tyr Leu Ser Leu Gln Glu Leu
            180                 185                 190

Gln Gly Gln Asp Pro Thr His Leu Val
            195                 200

<210> SEQ ID NO 114
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu Leu Val Leu Gly Leu
            35                  40                  45

Asn Ala Val Leu Gly Leu Leu Leu Leu Arg Lys Gln Phe Pro Ala His
50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Asp Glu
            115                 120                 125

Gly Val Ala Gly Ala Pro Thr Gly Ser Ser Pro Gln Pro Leu Gln Pro
            130                 135                 140

Leu Ser Gly Glu Asp Asp Ala Tyr Cys Thr Phe Pro Ser Arg Asp Asp
145                 150                 155                 160

Leu Leu Leu Phe Ser Pro Ser Gly Gln Gly Glu Phe Arg Ala Leu Asn
                165                 170                 175

Ala Arg Leu Pro Leu Asn Thr Asp Ala Tyr Leu Ser Leu Gln Glu Leu
            180                 185                 190

Gln Gly Gln Asp Pro Thr His Leu Val
            195                 200
```

```
<210> SEQ ID NO 115
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu His Leu Val Leu Gly Leu
        35                  40                  45

Asn Ala Val Leu Gly Leu Leu Leu Arg Lys Gln Phe Pro Ala His
    50                  55                  60

Tyr Arg Arg Leu Arg His Ala Leu Trp Pro Ser Leu Pro Asp Leu His
65              70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Gln Gln
        115                 120                 125

Asp Lys Val Pro Glu Pro Ala Ser Leu Ser Ser Asn His Ser Leu Thr
    130                 135                 140

Ser Cys Phe Thr Asn Gln Gly Tyr Phe Phe His Leu Pro Asp Ala
145                 150                 155                 160

Leu Glu Ile Glu Ala Cys Gln Asp Glu Gly Val Ala Gly Ala Pro Thr
                165                 170                 175

Gly Ser Ser Pro Gln Pro Leu Gln Pro Leu Ser Gly Glu Asp Asp Ala
            180                 185                 190

Tyr Cys Thr Phe Pro Ser Arg Asp Asp Leu Leu Leu Phe Ser Pro Ser
        195                 200                 205

Gly Gln Gly Glu Phe Arg Ala Leu Asn Ala Arg Leu Pro Leu Asn Thr
    210                 215                 220

Asp Ala Tyr Leu Ser Leu Gln Glu Leu Gln Gly Gln Asp Pro Thr His
225                 230                 235                 240

Leu Val

<210> SEQ ID NO 116
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu Leu Leu Val Leu Gly Leu
        35                  40                  45

Asn Ala Val Leu Gly Leu Leu Leu Leu Arg Lys Gln Phe Pro Ala His
    50                  55                  60
```

```
Tyr Arg Arg Leu Arg His Ala Leu Trp Pro Ser Leu Pro Asp Leu His
 65                  70                  75                  80

Arg Val Leu Gly Gln Tyr Leu Arg Asp Thr Ala Ala Leu Ser Pro Pro
                 85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Gln Gln
        115                 120                 125

Asp Lys Val Pro Glu Pro Ala Ser Leu Ser Ser Asn His Ser Leu Thr
130                 135                 140

Ser Cys Phe Thr Asn Gln Gly Tyr Phe Phe His Leu Pro Asp Ala
145                 150                 155                 160

Leu Glu Ile Glu Ala Cys Gln Asp Glu Gly Val Ala Gly Ala Pro Thr
                165                 170                 175

Gly Ser Ser Pro Gln Pro Leu Gln Pro Leu Ser Gly Glu Asp Asp Ala
            180                 185                 190

Tyr Cys Thr Phe Pro Ser Arg Asp Asp Leu Leu Leu Phe Ser Pro Ser
        195                 200                 205

Gly Gln Gly Glu Phe Arg Ala Leu Asn Ala Arg Leu Pro Leu Asn Thr
210                 215                 220

Asp Ala Tyr Leu Ser Leu Gln Glu Leu Gln Gly Gln Asp Pro Thr His
225                 230                 235                 240

Leu Val

<210> SEQ ID NO 117
<211> LENGTH: 321
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
                20                  25                  30

Thr Ala Trp Ile Ser Leu Val Thr Ala Leu His Leu Val Leu Gly Leu
            35                  40                  45

Asn Ala Val Leu Gly Leu Leu Leu Leu Arg Lys Gln Phe Pro Ala His
        50                  55                  60

Tyr Arg Arg Leu Arg His Ala Leu Trp Pro Ser Leu Pro Asp Leu His
 65                  70                  75                  80

Arg Val Leu Gly Gln Tyr Leu Arg Asp Thr Ala Ala Leu Ser Pro Pro
                 85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Ala Arg
        115                 120                 125

Asp Glu Val Glu Gly Phe Leu Gln Asp Thr Phe Pro Gln Gln Leu Glu
130                 135                 140

Glu Ser Glu Lys Gln Arg Leu Gly Gly Asp Val Gln Ser Pro Asn Cys
145                 150                 155                 160

Pro Ser Glu Asp Val Val Ile Thr Pro Glu Ser Phe Gly Arg Asp Ser
                165                 170                 175
```

```
Ser Leu Thr Cys Leu Ala Gly Asn Val Ser Ala Cys Asp Ala Pro Ile
            180                 185                 190

Leu Ser Ser Ser Arg Ser Leu Asp Cys Arg Glu Ser Gly Lys Asn Gly
            195                 200                 205

Pro His Val Tyr Gln Asp Leu Leu Ser Leu Gly Thr Thr Asn Ser
    210                 215                 220

Thr Leu Pro Pro Pro Phe Ser Leu Gln Ser Gly Ile Leu Thr Leu Asn
225                 230                 235                 240

Pro Val Ala Gln Gly Gln Pro Ile Leu Thr Ser Leu Gly Ser Asn Gln
                245                 250                 255

Glu Glu Ala Tyr Val Thr Met Ser Ser Phe Tyr Gln Asn Gln Ser Asp
                260                 265                 270

Pro Lys Pro Glu Asn Pro Ala Cys Pro Trp Thr Val Leu Pro Ala Gly
            275                 280                 285

Asp Leu Pro Thr His Asp Gly Tyr Leu Pro Ser Asn Ile Asp Asp Leu
    290                 295                 300

Pro Ser His Glu Ala Pro Leu Ala Asp Ser Leu Glu Glu Leu Glu Pro
305                 310                 315                 320

Gln

<210> SEQ ID NO 118
<211> LENGTH: 321
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu Leu Val Leu Gly Leu
        35                  40                  45

Asn Ala Val Leu Gly Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
                100                 105                 110

Glu Ile Leu Pro Lys Ser Ser Glu Arg Thr Pro Leu Pro Leu Ala Arg
            115                 120                 125

Asp Glu Val Glu Gly Phe Leu Gln Asp Thr Phe Pro Gln Gln Leu Glu
    130                 135                 140

Glu Ser Glu Lys Gln Arg Leu Gly Gly Asp Val Gln Ser Pro Asn Cys
145                 150                 155                 160

Pro Ser Glu Asp Val Val Ile Thr Pro Glu Ser Phe Gly Arg Asp Ser
                165                 170                 175

Ser Leu Thr Cys Leu Ala Gly Asn Val Ser Ala Cys Asp Ala Pro Ile
            180                 185                 190

Leu Ser Ser Ser Arg Ser Leu Asp Cys Arg Glu Ser Gly Lys Asn Gly
            195                 200                 205
```

```
Pro His Val Tyr Gln Asp Leu Leu Leu Ser Leu Gly Thr Thr Asn Ser
    210                 215                 220

Thr Leu Pro Pro Pro Phe Ser Leu Gln Ser Gly Ile Leu Thr Leu Asn
225                 230                 235                 240

Pro Val Ala Gln Gly Gln Pro Ile Leu Thr Ser Leu Gly Ser Asn Gln
                245                 250                 255

Glu Glu Ala Tyr Val Thr Met Ser Ser Phe Tyr Gln Asn Gln Ser Asp
                260                 265                 270

Pro Lys Pro Glu Asn Pro Ala Cys Pro Trp Thr Val Leu Pro Ala Gly
            275                 280                 285

Asp Leu Pro Thr His Asp Gly Tyr Leu Pro Ser Asn Ile Asp Asp Leu
            290                 295                 300

Pro Ser His Glu Ala Pro Leu Ala Asp Ser Leu Glu Glu Leu Glu Pro
305                 310                 315                 320

Gln

<210> SEQ ID NO 119
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
                20                  25                  30

Leu Leu Leu Leu Arg Trp Gln Phe Pro Ala His Tyr Arg Arg Leu Arg
            35                  40                  45

His Ala Leu Trp Pro Ser Leu Pro Asp Leu His Arg Val Leu Gly Gln
        50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
                100                 105                 110

Glu Gly Phe Leu Gln Asp Thr Phe Pro Gln Gln Leu Glu Glu Ser Glu
            115                 120                 125

Lys Gln Arg Leu Gly Gly Asp Val Gln Ser Pro Asn Cys Pro Ser Glu
130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240
```

```
Tyr Val Thr Met Ser Ser Phe Tyr Gln Asn Gln
                245                 250
```

<210> SEQ ID NO 120
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Ser Asp Pro Thr Arg Val Glu Thr Ala Thr Glu Thr Ala Trp Ile Ser
1               5                   10                  15

Leu Val Thr Ala Leu Leu Val Leu Gly Leu Asn Ala Val Leu Gly
                20                  25                  30

Leu Leu Leu Leu Arg Trp Gln Phe Pro Ala His Tyr Arg Arg Leu Arg
            35                  40                  45

His Ala Leu Trp Pro Ser Leu Pro Asp Leu His Arg Val Leu Gly Gln
        50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Gln Leu Glu Glu Ser Glu
        115                 120                 125

Lys Gln Arg Leu Gly Gly Asp Val Gln Ser Pro Asn Cys Pro Ser Glu
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln
                245                 250
```

<210> SEQ ID NO 121
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
                20                  25                  30
```

```
Leu Leu Leu Leu Arg Trp Gln Phe Pro Ala His Tyr Arg Arg Leu Arg
            35                  40                  45

His Ala Leu Trp Pro Ser Leu Pro Asp Leu His Arg Val Leu Gly Gln
 50                  55                  60

Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                    85                  90                  95

Ser Ser Glu Arg Thr Pro Leu Pro Leu Leu Glu Ala Arg Asp Glu Val
                100                 105                 110

Glu Gly Phe Leu Gln Asp Thr Phe Pro Gln Gln Leu Glu Glu Ser Glu
            115                 120                 125

Lys Gln Arg Leu Gly Gly Asp Val Gln Ser Pro Asn Cys Pro Ser Glu
130                 135                 140

Asp Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
            195                 200                 205

Pro Pro Phe Ser Leu Gln Ser Gly Ile Leu Thr Leu Asn Pro Val Ala
        210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln
                245                 250
```

<210> SEQ ID NO 122
<211> LENGTH: 251
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 122

```
Ser Asp Pro Thr Arg Val Glu Thr Ala Thr Glu Thr Ala Trp Ile Ser
 1               5                  10                  15

Leu Val Thr Ala Leu Leu Val Leu Gly Leu Ser Ala Val Leu Gly
                20                  25                  30

Leu Leu Leu Leu Arg Lys Gln Phe Pro Ala His Tyr Arg Arg Leu Arg
            35                  40                  45

His Ala Leu Trp Pro Ser Leu Pro Asp Leu His Arg Val Leu Gly Gln
 50                  55                  60

Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                    85                  90                  95

Ser Ser Glu Arg Thr Pro Leu Pro Leu Leu Glu Ala Arg Asp Glu Val
                100                 105                 110

Glu Gly Phe Leu Gln Asp Thr Phe Pro Gln Gln Leu Glu Glu Ser Glu
            115                 120                 125

Lys Gln Arg Leu Gly Gly Asp Val Gln Ser Pro Asn Cys Pro Ser Glu
```

```
            130                 135                 140
Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
                180                 185                 190

Tyr Gln Asp Leu Leu Leu Ser Leu Gly Thr Thr Asn Ser Thr Leu Pro
            195                 200                 205

Pro Pro Phe Ser Leu Gln Ser Gly Ile Leu Thr Leu Asn Pro Val Ala
        210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln
                245                 250
```

<210> SEQ ID NO 123
<211> LENGTH: 251
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 123

```
Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
                20                  25                  30

Leu Leu Leu Leu Arg Lys Gln Phe Pro Ala His Tyr Arg Arg Leu Arg
            35                  40                  45

His Ala Leu Trp Pro Ser Leu Pro Asp Leu His Arg Val Leu Gly Gln
        50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
                100                 105                 110

Glu Gly Phe Leu Gln Asp Thr Phe Pro Gln Gln Leu Glu Glu Ser Glu
            115                 120                 125

Lys Gln Arg Leu Gly Gly Asp Val Gln Ser Pro Asn Cys Pro Ser Glu
        130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
                180                 185                 190

Tyr Gln Asp Leu Leu Leu Ser Leu Gly Thr Thr Asn Ser Thr Leu Pro
            195                 200                 205

Pro Pro Phe Ser Leu Gln Ser Gly Ile Leu Thr Leu Asn Pro Val Ala
        210                 215                 220

Gln Gly Gln Pro Ile Leu Thr Ser Leu Gly Ser Asn Gln Glu Glu Ala
225                 230                 235                 240
```

```
Tyr Val Thr Met Ser Ser Phe Tyr Gln Asn Gln
                245                 250

<210> SEQ ID NO 124
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ser Asp Pro Thr Arg Val Glu Thr Ala Thr Glu Thr Ala Trp Ile Ser
1               5                   10                  15

Leu Val Thr Ala Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Gln Leu Glu Glu Ser Glu
        115                 120                 125

Lys Gln Arg Leu Gly Gly Asp Val Gln Ser Pro Asn Cys Pro Ser Glu
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln
                245                 250

<210> SEQ ID NO 125
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30
```

```
Leu Leu Leu Leu Arg Lys Gln Phe Pro Ala His Tyr Arg Arg Leu Arg
             35                  40                  45

His Ala Leu Trp Pro Ser Leu Pro Asp Leu His Arg Val Leu Gly Gln
         50                  55                  60

Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                 85                  90                  95

Ser Ser Glu Arg Thr Pro Leu Pro Leu Leu Ala Arg Asp Glu Val
                100                 105                 110

Glu Gly Phe Leu Gln Asp Thr Phe Pro Gln Gln Leu Glu Glu Ser Glu
            115                 120                 125

Lys Gln Arg Leu Gly Gly Asp Val Gln Ser Pro Asn Cys Pro Ser Glu
        130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln
                245                 250

<210> SEQ ID NO 126
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ser Asp Pro Thr Arg Val Glu Thr Ala Thr Glu Thr Ala Trp Ile Ser
 1               5                  10                  15

Leu Val Thr Ala Leu Leu Leu Val Leu Gly Leu Ser Ala Val Leu Asn
             20                  25                  30

Leu Leu Leu Leu Arg Trp Gln Phe Pro Ala His Tyr Arg Arg Leu Arg
             35                  40                  45

His Ala Leu Trp Pro Ser Leu Pro Asp Leu His Arg Val Leu Gly Gln
         50                  55                  60

Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                 85                  90                  95

Ser Ser Glu Arg Thr Pro Leu Pro Leu Leu Ala Arg Asp Glu Val
                100                 105                 110

Glu Gly Phe Leu Gln Asp Thr Phe Pro Gln Gln Leu Glu Glu Ser Glu
            115                 120                 125

Lys Gln Arg Leu Gly Gly Asp Val Gln Ser Pro Asn Cys Pro Ser Glu
        130                 135                 140
```

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln
                245                 250

<210> SEQ ID NO 127
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Gln Leu Glu Glu Ser Glu
        115                 120                 125

Lys Gln Arg Leu Gly Gly Asp Val Gln Ser Pro Asn Cys Pro Ser Glu
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln

<210> SEQ ID NO 128
<211> LENGTH: 326
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 128

```
Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Gln Leu Leu
            100                 105                 110

Leu Gln Gln Asp Lys Val Pro Glu Pro Ala Ser Leu Ser Ser Asn His
        115                 120                 125

Ser Leu Thr Ser Cys Phe Thr Asn Gln Gly Tyr Phe Phe His Leu
    130                 135                 140

Pro Asp Ala Leu Glu Ile Glu Ala Cys Gln Val Tyr Phe Thr Tyr Asp
145                 150                 155                 160

Pro Tyr Ser Glu Glu Asp Pro Asp Gly Val Ala Gly Ala Pro Thr
                165                 170                 175

Gly Ser Ser Pro Gln Pro Leu Gln Pro Leu Ser Gly Glu Asp Asp Ala
            180                 185                 190

Tyr Cys Thr Phe Pro Ser Arg Asp Asp Leu Leu Leu Phe Ser Pro Ser
        195                 200                 205

Leu Leu Gly Gly Pro Ser Pro Ser Thr Ala Pro Gly Gly Ser Gly
    210                 215                 220

Ala Gly Glu Glu Arg Met Pro Pro Ser Leu Gln Glu Arg Val Pro Arg
225                 230                 235                 240

Asp Trp Asp Pro Gln Pro Leu Gly Pro Thr Pro Gly Val Pro Asp
                245                 250                 255

Leu Val Asp Phe Gln Pro Pro Glu Leu Val Leu Arg Glu Ala Gly
            260                 265                 270

Glu Glu Val Pro Asp Ala Gly Pro Arg Glu Gly Val Ser Phe Pro Trp
        275                 280                 285

Ser Arg Pro Pro Gly Gln Gly Glu Phe Arg Ala Leu Asn Ala Arg Leu
    290                 295                 300

Pro Leu Asn Thr Asp Ala Tyr Leu Ser Leu Gln Glu Leu Gln Gly Gln
305                 310                 315                 320

Asp Pro Thr His Leu Val
                325
```

<210> SEQ ID NO 129
<211> LENGTH: 256

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Pro Val Phe
            100                 105                 110

Arg His Pro Pro Cys Ser Asn Trp Pro Gln Arg Glu Lys Gly Ile Gln
        115                 120                 125

Gly His Gln Ala Ser Glu Lys Asp Met Met His Ser Ala Ser Ser Pro
    130                 135                 140

Pro Pro Pro Arg Ala Leu Gln Ala Glu Ser Arg Gln Leu Val Asp Leu
145                 150                 155                 160

Tyr Lys Val Leu Glu Ser Arg Gly Ser Asp Pro Lys Pro Glu Asn Pro
                165                 170                 175

Ala Cys Pro Trp Thr Val Leu Pro Ala Gly Asp Leu Pro Thr His Asp
            180                 185                 190

Gly Tyr Leu Pro Ser Asn Ile Asp Asp Leu Pro Ser His Glu Ala Pro
        195                 200                 205

Leu Ala Asp Ser Leu Glu Glu Leu Glu Pro Gln His Ile Ser Leu Ser
    210                 215                 220

Val Phe Pro Ser Ser Ser Leu His Pro Leu Thr Phe Ser Cys Gly Asp
225                 230                 235                 240

Lys Leu Thr Leu Asp Gln Leu Lys Met Arg Cys Asp Ser Leu Met Leu
                245                 250                 255

<210> SEQ ID NO 130
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

```
Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                 85                  90                  95

Ser Ser Glu Arg Thr Pro Leu Pro Leu Leu Glu Val Thr Gln Leu Leu
            100                 105                 110

Leu Gln Gln Asp Lys Val Pro Glu Pro Ala Ser Leu Ser Ser Asn His
        115                 120                 125

Ser Leu Thr Ser Cys Phe Thr Asn Gln Gly Tyr Phe Phe His Leu
130                 135                 140

Pro Asp Ala Leu Glu Ile Glu Ala Cys Gln Val Tyr Phe Thr Tyr Asp
145                 150                 155                 160

Pro Tyr Ser Glu Glu Asp Pro Asp Gly Val Ala Gly Ala Pro Thr
                165                 170                 175

Gly Ser Ser Pro Gln Pro Leu Gln Pro Leu Ser Gly Glu Asp Asp Ala
                180                 185                 190

Tyr Cys Thr Phe Pro Ser Arg Asp Asp Leu Leu Leu Phe Ser Pro Ser
            195                 200                 205

Leu Leu Gly Gly Pro Ser Pro Pro Ser Thr Ala Pro Gly Gly Ser Gly
210                 215                 220

Ala Gly Glu Glu Arg Met Pro Pro Ser Leu Gln Glu Arg Val Pro Arg
225                 230                 235                 240

Asp Trp Asp Pro Gln Pro Leu Gly Pro Pro Thr Pro Gly Val Pro Asp
                245                 250                 255

Leu Val Asp Phe Gln Pro Pro Pro Glu Leu Val Leu Arg Glu Ala Gly
            260                 265                 270

Glu Glu Val Pro Asp Ala Gly Pro Arg Glu Gly Val Ser Phe Pro Trp
        275                 280                 285

Ser Arg Pro Pro Gly Gln Gly Glu Phe Arg Ala Leu Asn Ala Arg Leu
290                 295                 300

Pro Leu Asn Thr Asp Ala Tyr Leu Ser Leu Gln Glu Leu Gln Gly Gln
305                 310                 315                 320

Asp Pro Thr His Leu Val
                325

<210> SEQ ID NO 131
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
                20                  25                  30

Leu Leu Leu Leu Arg Lys Gln Phe Pro Ala His Tyr Arg Arg Leu Arg
            35                  40                  45

His Ala Leu Trp Pro Ser Leu Pro Asp Leu His Arg Val Leu Gly Gln
        50                  55                  60

Tyr Leu Arg Asp Thr Ala Ala Leu Ser Pro Pro Lys Ala Thr Val Ser
 65                  70                  75                  80

Asp Thr Cys Glu Glu Val Glu Pro Ser Leu Leu Glu Ile Leu Pro Lys
                 85                  90                  95
```

Ser Ser Glu Arg Thr Pro Leu Pro Leu Leu Glu Val Thr Pro Val Phe
            100                 105                 110

Arg His Pro Pro Cys Ser Asn Trp Pro Gln Arg Glu Lys Gly Ile Gln
        115                 120                 125

Gly His Gln Ala Ser Glu Lys Asp Met Met His Ser Ala Ser Ser Pro
    130                 135                 140

Pro Pro Pro Arg Ala Leu Gln Ala Glu Ser Arg Gln Leu Val Asp Leu
145                 150                 155                 160

Tyr Lys Val Leu Glu Ser Arg Gly Ser Asp Pro Lys Pro Glu Asn Pro
                165                 170                 175

Ala Cys Pro Trp Thr Val Leu Pro Ala Gly Asp Leu Pro Thr His Asp
            180                 185                 190

Gly Tyr Leu Pro Ser Asn Ile Asp Asp Leu Pro Ser His Glu Ala Pro
        195                 200                 205

Leu Ala Asp Ser Leu Glu Glu Leu Glu Pro Gln His Ile Ser Leu Ser
    210                 215                 220

Val Phe Pro Ser Ser Ser Leu His Pro Leu Thr Phe Ser Cys Gly Asp
225                 230                 235                 240

Lys Leu Thr Leu Asp Gln Leu Lys Met Arg Cys Asp Ser Leu Met Leu
                245                 250                 255

<210> SEQ ID NO 132
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ser Asp Pro Lys Pro
            100                 105                 110

Glu Asn Pro Ala Cys Pro Trp Thr Val Leu Pro Ala Gly Asp Leu Pro
        115                 120                 125

Thr His Asp Gly Tyr Leu Pro Ser Asn Ile Asp Asp Leu Pro Ser His
    130                 135                 140

Glu Ala Pro Leu Ala Asp Ser Leu Glu Glu Leu Glu Pro Gln
145                 150                 155

<210> SEQ ID NO 133
<211> LENGTH: 158
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

```
Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ser Asp Pro Lys Pro
            100                 105                 110

Glu Asn Pro Ala Cys Pro Trp Thr Val Leu Pro Ala Gly Asp Leu Pro
        115                 120                 125

Thr His Asp Gly Tyr Leu Pro Ser Asn Ile Asp Leu Pro Ser His
    130                 135                 140

Glu Ala Pro Leu Ala Asp Ser Leu Glu Glu Leu Glu Pro Gln
145                 150                 155
```

<210> SEQ ID NO 134
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

```
Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Leu Glu Glu Ser Glu
        115                 120                 125

Lys Gln Arg Leu Gly Gly Asp Val Gln Ser Pro Asn Cys Pro Ser Glu
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
```

```
            180                 185                 190
Tyr Gln Asp Leu Leu Leu Ser Leu Gly Thr Thr Asn Ser Thr Leu Pro
            195                 200                 205

Pro Pro Phe Ser Leu Gln Ser Gly Ile Leu Thr Leu Asn Pro Val Ala
        210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln Ser Arg Ser Asp Pro
                245                 250                 255

Lys Pro Glu Asn Pro Ala Cys Pro Trp Thr Val Leu Pro Ala Gly Asp
            260                 265                 270

Leu Pro Thr His Asp Gly Tyr Leu Pro Ser Asn Ile Asp Asp Leu Pro
        275                 280                 285

Ser His Glu Ala Pro Leu Ala Asp Ser Leu Glu Leu Glu Pro Gln
    290                 295                 300

<210> SEQ ID NO 135
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ser Asp Pro Thr Arg Val Glu Thr Ala Thr Glu Thr Ala Trp Ile Ser
1               5                   10                  15

Leu Val Thr Ala Leu Leu Leu Val Gly Leu Asn Ala Val Leu Gly
            20                  25                  30

Leu Leu Leu Leu Arg Lys Gln Phe Pro Ala His Tyr Arg Arg Leu Arg
            35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Gln Leu Glu Glu Ser Glu
        115                 120                 125

Lys Gln Arg Leu Gly Gly Asp Val Gln Ser Pro Asn Cys Pro Ser Glu
130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
        210                 215                 220

Gln Gly Gln Pro Ile Leu Thr Ser Leu Gly Ser Asn Gln Glu Glu Ala
225                 230                 235                 240
```

```
Tyr Val Thr Met Ser Ser Phe Tyr Gln Asn Gln Ser Arg Ser Asp Pro
            245                 250                 255

Lys Pro Glu Asn Pro Ala Cys Pro Trp Thr Val Leu Pro Ala Gly Asp
        260                 265                 270

Leu Pro Thr His Asp Gly Tyr Leu Pro Ser Asn Ile Asp Asp Leu Pro
            275                 280                 285

Ser His Glu Ala Pro Leu Ala Asp Ser Leu Glu Glu Leu Glu Pro Gln
    290                 295                 300

<210> SEQ ID NO 136
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Gln Leu Leu
            100                 105                 110

Leu Gln Gln Asp Lys Val Pro Glu Pro Ala Ser Leu Ser Ser Asn His
        115                 120                 125

Ser Leu Thr Ser Cys Phe Thr Asn Gln Gly Tyr Phe Phe Phe His Leu
    130                 135                 140

Pro Asp Ala Leu Glu Ile Glu Ala Cys Gln Val Ser Phe Thr Ser Asp
145                 150                 155                 160

Pro Ser Ser Glu Glu Asp Pro Asp Glu Gly Val Ala Gly Ala Pro Thr
                165                 170                 175

Gly Ser Ser Pro Gln Pro Leu Gln Pro Leu Ser Gly Glu Asp Asp Ala
            180                 185                 190

Tyr Cys Thr Phe Pro Ser Arg Asp Asp Leu Leu Leu Phe Ser Pro Ser
        195                 200                 205

Leu Leu Gly Gly Pro Ser Pro Ser Thr Ala Pro Gly Gly Ser Gly
    210                 215                 220

Ala Gly Glu Glu Arg Met Pro Pro Ser Leu Gln Glu Arg Val Pro Arg
225                 230                 235                 240

Asp Trp Asp Pro Gln Pro Leu Gly Pro Pro Thr Pro Gly Val Pro Asp
                245                 250                 255

Leu Val Asp Phe Gln Pro Pro Pro Glu Leu Val Leu Arg Glu Ala Gly
            260                 265                 270

Glu Glu Val Pro Asp Ala Gly Pro Arg Glu Gly Val Ser Phe Pro Trp
        275                 280                 285

Ser Arg Pro Pro Gly Gln Gly Glu Phe Arg Ala Leu Asn Ala Arg Leu
    290                 295                 300
```

```
Pro Leu Asn Thr Asp Ala Tyr Leu Ser Leu Gln Glu Leu Gln Gly Gln
305                 310                 315                 320

Asp Pro Thr His Leu Val
                325

<210> SEQ ID NO 137
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ser Asp Pro Thr Arg Val Glu Thr Ala Thr Glu Thr Ala Trp Ile Ser
1               5                   10                  15

Leu Val Thr Ala Leu Leu Val Leu Gly Leu Asn Ala Val Leu Gly
                20                  25                  30

Leu Leu Leu Leu Arg Lys Gln Phe Pro Ala His Tyr Arg Arg Leu Arg
            35                  40                  45

His Ala Leu Trp Pro Ser Leu Pro Asp Leu His Arg Val Leu Gly Gln
        50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Glu Ile Leu Pro Lys
                85                  90                  95

Ser Ser Glu Arg Thr Pro Leu Pro Leu Leu Glu Val Thr Gln Leu Leu
                100                 105                 110

Leu Gln Gln Asp Lys Val Pro Glu Pro Ala Ser Leu Ser Ser Asn His
            115                 120                 125

Ser Leu Thr Ser Cys Phe Thr Asn Gln Gly Tyr Phe Phe Phe His Leu
        130                 135                 140

Pro Asp Ala Leu Glu Ile Glu Ala Cys Gln Val Ser Phe Thr Ser Asp
145                 150                 155                 160

Pro Ser Ser Glu Glu Asp Pro Asp Glu Gly Val Ala Gly Ala Pro Thr
                165                 170                 175

Gly Ser Ser Pro Gln Pro Leu Gln Pro Leu Ser Gly Glu Asp Asp Ala
                180                 185                 190

Tyr Cys Thr Phe Pro Ser Arg Asp Asp Leu Leu Leu Phe Ser Pro Ser
            195                 200                 205

Leu Leu Gly Gly Pro Ser Pro Pro Ser Thr Ala Pro Gly Gly Ser Gly
        210                 215                 220

Ala Gly Glu Glu Arg Met Pro Pro Ser Leu Gln Glu Arg Val Pro Arg
225                 230                 235                 240

Asp Trp Asp Pro Gln Pro Leu Gly Pro Pro Thr Pro Gly Val Pro Asp
                245                 250                 255

Leu Val Asp Phe Gln Pro Pro Pro Glu Leu Val Leu Arg Glu Ala Gly
                260                 265                 270

Glu Glu Val Pro Asp Ala Gly Pro Arg Glu Gly Val Ser Phe Pro Trp
            275                 280                 285

Ser Arg Pro Pro Gly Gln Gly Glu Phe Arg Ala Leu Asn Ala Arg Leu
        290                 295                 300

Pro Leu Asn Thr Asp Ala Tyr Leu Ser Leu Gln Glu Leu Gln Gly Gln
305                 310                 315                 320

Asp Pro Thr His Leu Val
```

<210> SEQ ID NO 138
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Gln Leu Leu
            100                 105                 110

Leu Gln Gln Asp Lys Val Pro Glu Pro Ala Ser Leu Ser Ser Asn His
        115                 120                 125

Ser Leu Thr Ser Cys Phe Thr Asn Gln Gly Ser Phe Phe His Leu
    130                 135                 140

Pro Asp Ala Leu Glu Ile Glu Ala Cys Gln Val Ser Phe Thr Ser Asp
145                 150                 155                 160

Pro Ser Ser Glu Glu Asp Pro Asp Gly Val Ala Gly Ala Pro Thr
                165                 170                 175

Gly Ser Ser Pro Gln Pro Leu Gln Pro Leu Ser Gly Glu Asp Asp Ala
            180                 185                 190

Tyr Cys Thr Phe Pro Ser Arg Asp Asp Leu Leu Leu Phe Ser Pro Ser
        195                 200                 205

Leu Leu Gly Gly Pro Ser Pro Ser Thr Ala Pro Gly Gly Ser Gly
    210                 215                 220

Ala Gly Glu Glu Arg Met Pro Pro Ser Leu Gln Glu Arg Val Pro Arg
225                 230                 235                 240

Asp Trp Asp Pro Gln Pro Leu Gly Pro Thr Pro Gly Val Pro Asp
                245                 250                 255

Leu Val Asp Phe Gln Pro Pro Glu Leu Val Leu Arg Glu Ala Gly
            260                 265                 270

Glu Glu Val Pro Asp Ala Gly Pro Arg Glu Gly Val Ser Phe Pro Trp
        275                 280                 285

Ser Arg Pro Pro Gly Gln Gly Glu Phe Arg Ala Leu Asn Ala Arg Leu
    290                 295                 300

Pro Leu Asn Thr Asp Ala Tyr Leu Ser Leu Gln Glu Leu Gln Gly Gln
305                 310                 315                 320

Asp Pro Thr His Leu Val
                325

<210> SEQ ID NO 139
<211> LENGTH: 326

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
                20                  25                  30

Leu Leu Leu Leu Arg Lys Gln Phe Pro Ala His Tyr Arg Arg Leu Arg
            35                  40                  45

His Ala Leu Trp Pro Ser Leu Pro Asp Leu His Arg Val Leu Gly Gln
        50                  55                  60

Tyr Leu Arg Asp Thr Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Gln Leu Leu
                100                 105                 110

Leu Gln Gln Asp Lys Val Pro Glu Pro Ala Ser Leu Ser Ser Asn His
            115                 120                 125

Ser Leu Thr Ser Cys Phe Thr Asn Gln Gly Ser Phe Phe His Leu
        130                 135                 140

Pro Asp Ala Leu Glu Ile Glu Ala Cys Gln Val Ser Phe Thr Ser Asp
145                 150                 155                 160

Pro Ser Ser Glu Glu Asp Pro Asp Glu Gly Val Ala Gly Ala Pro Thr
                165                 170                 175

Gly Ser Ser Pro Gln Pro Leu Gln Pro Leu Ser Gly Glu Asp Asp Ala
                180                 185                 190

Tyr Cys Thr Phe Pro Ser Arg Asp Asp Leu Leu Leu Phe Ser Pro Ser
            195                 200                 205

Leu Leu Gly Gly Pro Ser Pro Ser Thr Ala Pro Gly Gly Ser Gly
210                 215                 220

Ala Gly Glu Glu Arg Met Pro Pro Ser Leu Gln Glu Arg Val Pro Arg
225                 230                 235                 240

Asp Trp Asp Pro Gln Pro Leu Gly Pro Thr Pro Gly Val Pro Asp
                245                 250                 255

Leu Val Asp Phe Gln Pro Pro Glu Leu Val Leu Arg Glu Ala Gly
                260                 265                 270

Glu Glu Val Pro Asp Ala Gly Pro Arg Glu Gly Val Ser Phe Pro Trp
            275                 280                 285

Ser Arg Pro Pro Gly Gln Gly Glu Phe Arg Ala Leu Asn Ala Arg Leu
290                 295                 300

Pro Leu Asn Thr Asp Ala Tyr Leu Ser Leu Gln Glu Leu Gln Gly Gln
305                 310                 315                 320

Asp Pro Thr His Leu Val
                325

<210> SEQ ID NO 140
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Ala Leu Pro Val Thr Ala Leu Leu Leu Pro Leu Ala Leu Leu Leu
1               5                   10                  15

His Ala Ala Arg Pro Glu Ile Gln Leu Val Gln Ser Gly Ala Glu Val
            20                  25                  30

Lys Lys Pro Gly Glu Ser Leu Arg Ile Ser Cys Lys Gly Ser Gly Phe
        35                  40                  45

Asn Ile Glu Asp Tyr Tyr Ile His Trp Val Arg Gln Met Pro Gly Lys
    50                  55                  60

Gly Leu Glu Trp Met Gly Arg Ile Asp Pro Glu Asn Asp Glu Thr Lys
65                  70                  75                  80

Tyr Gly Pro Ile Phe Gln Gly His Val Thr Ile Ser Ala Asp Thr Ser
                85                  90                  95

Ile Asn Thr Val Tyr Leu Gln Trp Ser Ser Leu Lys Ala Ser Asp Thr
            100                 105                 110

Ala Met Tyr Tyr Cys Ala Phe Arg Gly Gly Val Tyr Trp Gly Gln Gly
        115                 120                 125

Thr Thr Val Thr Val Ser Ser Gly Gly Gly Ser Gly Gly Gly Gly
    130                 135                 140

Ser Gly Gly Gly Gly Ser Gly Gly Gly Gly Ser Asp Val Val Met Thr
145                 150                 155                 160

Gln Ser Pro Asp Ser Leu Ala Val Ser Leu Gly Glu Arg Ala Thr Ile
                165                 170                 175

Asn Cys Lys Ser Ser Gln Ser Leu Leu Asp Ser Asp Gly Lys Thr Tyr
            180                 185                 190

Leu Asn Trp Leu Gln Gln Lys Pro Gly Gln Pro Pro Lys Arg Leu Ile
        195                 200                 205

Ser Leu Val Ser Lys Leu Asp Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Trp Gln Gly Thr His Phe Pro Gly
                245                 250                 255

Thr Phe Gly Gly Gly Thr Lys Val Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg

```
            405                 410                 415
Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
            450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 141
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Ala Ile Ser Asp Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
            100                 105                 110

Val Ser Ser Gly Gly Gly Gly Ser Gly Gly Gly Gly Ser Gly Gly Gly
            115                 120                 125

Gly Ser Glu Ile Val Leu Thr Gln Ser Pro Gly Thr Leu Ser Leu Ser
        130                 135                 140

Pro Gly Glu Arg Ala Thr Leu Ser Cys Arg Ala Ser Gln Ser Val Ser
145                 150                 155                 160

Ser Ser Tyr Leu Ala Trp Tyr Gln Gln Lys Pro Gly Gln Ala Pro Arg
                165                 170                 175

Leu Leu Met Tyr Asp Ala Ser Ile Arg Ala Thr Gly Ile Pro Asp Arg
            180                 185                 190

Phe Ser Gly Ser Gly Ser Gly Thr Asp Phe Thr Leu Thr Ile Ser Arg
            195                 200                 205

Leu Glu Pro Glu Asp Phe Ala Val Tyr Tyr Cys Gln Gln Tyr Gly Ser
        210                 215                 220

Trp Pro Leu Thr Phe Gly Gln Gly Thr Lys Val Glu Ile Lys
225                 230                 235

<210> SEQ ID NO 142
<211> LENGTH: 519
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 142

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Ala Ile Ser Asp Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Tyr Trp Pro Met Asp Ile Trp Gly Gln
        115                 120                 125

Gly Thr Leu Val Thr Val Ser Ser Gly Gly Gly Ser Gly Gly Gly
    130                 135                 140

Gly Ser Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
                165                 170                 175

Ser Gln Ser Val Ser Ser Ser Tyr Leu Ala Trp Tyr Gln Gln Lys Pro
            180                 185                 190

Gly Gln Ala Pro Arg Leu Leu Met Tyr Asp Ala Ser Ile Arg Ala Thr
        195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Tyr Gly Ser Trp Pro Leu Thr Phe Gly Gln Gly Thr Lys Val
                245                 250                 255

Glu Ile Lys Gly Ser Gly Gly Gly Ser Cys Pro Tyr Ser Asn Pro
            260                 265                 270

Ser Leu Cys Ser Gly Gly Gly Ser Cys Pro Tyr Ser Asn Pro Ser
            275                 280                 285

Leu Cys Ser Gly Gly Gly Ser Thr Thr Thr Pro Ala Pro Arg Pro
290                 295                 300

Pro Thr Pro Ala Pro Thr Ile Ala Ser Gln Pro Leu Ser Leu Arg Pro
305                 310                 315                 320

Glu Ala Cys Arg Pro Ala Ala Gly Gly Ala Val His Thr Arg Gly Leu
            325                 330                 335

Asp Phe Ala Cys Asp Ile Tyr Ile Trp Ala Pro Leu Ala Gly Thr Cys
        340                 345                 350

Gly Val Leu Leu Leu Ser Leu Val Ile Thr Leu Tyr Cys Lys Arg Gly
    355                 360                 365

Arg Lys Lys Leu Leu Tyr Ile Phe Lys Gln Pro Phe Met Arg Pro Val
    370                 375                 380

Gln Thr Thr Gln Glu Glu Asp Gly Cys Ser Cys Arg Phe Pro Glu Glu
385                 390                 395                 400
```

```
Glu Glu Gly Gly Cys Glu Leu Arg Val Lys Phe Ser Arg Ser Ala Asp
                405                 410                 415

Ala Pro Ala Tyr Gln Gln Gly Gln Asn Gln Leu Tyr Asn Glu Leu Asn
            420                 425                 430

Leu Gly Arg Arg Glu Glu Tyr Asp Val Leu Asp Lys Arg Arg Gly Arg
        435                 440                 445

Asp Pro Glu Met Gly Gly Lys Pro Arg Arg Lys Asn Pro Gln Glu Gly
    450                 455                 460

Leu Tyr Asn Glu Leu Gln Lys Asp Lys Met Ala Glu Ala Tyr Ser Glu
465                 470                 475                 480

Ile Gly Met Lys Gly Glu Arg Arg Arg Gly Lys Gly His Asp Gly Leu
                485                 490                 495

Tyr Gln Gly Leu Ser Thr Ala Thr Lys Asp Thr Tyr Asp Ala Leu His
            500                 505                 510

Met Gln Ala Leu Pro Pro Arg
        515

<210> SEQ ID NO 143
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Val Thr Gln Leu Leu Leu Gln Gln Asp Lys Val Pro Glu Pro Ala Ser
1               5                   10                  15

Leu Ser Ser Asn His Ser Leu Thr Ser Cys Phe Thr Asn Gln Gly Ser
            20                  25                  30

Phe Phe Phe His Leu Pro Asp Ala Leu Glu Ile Glu Ala Cys Gln Val
        35                  40                  45

Ser Phe Thr Ser Asp Pro Ser Ser Glu Glu Asp Pro Glu Gly Val
    50                  55                  60

Ala Gly Ala Pro Thr Gly Ser Ser Pro Gln Pro Leu Gln Pro Leu Ser
65                  70                  75                  80

Gly Glu Asp Asp Ala Tyr Cys Thr Phe Pro Ser Arg Asp Asp Leu Leu
                85                  90                  95

Leu Phe Ser Pro Ser Leu Leu Gly Gly Pro Ser Pro Ser Thr Ala
            100                 105                 110

Pro Gly Gly Ser Gly Ala Gly Glu Glu Arg Met Pro Pro Ser Leu Gln
        115                 120                 125

Glu Arg Val Pro Arg Asp Trp Asp Pro Gln Pro Leu Gly Pro Pro Thr
    130                 135                 140

Pro Gly Val Pro Asp Leu Val Asp Phe Gln Pro Pro Glu Leu Val
145                 150                 155                 160

Leu Arg Glu Ala Gly Glu Glu Val Pro Asp Ala Gly Pro Arg Glu Gly
                165                 170                 175

Val Ser Phe Pro Trp Ser Arg Pro Pro Gly Gln Gly Glu Phe Arg Ala
            180                 185                 190

Leu Asn Ala Arg Leu Pro Leu Asn Thr Asp Ala Tyr Leu Ser Leu Gln
        195                 200                 205

Glu Leu Gln Gly Gln Asp Pro Thr His Leu Val
    210                 215
```

```
<210> SEQ ID NO 144
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Lys Pro Ile Pro Asn Pro Leu Leu Gly Leu Asp Ser Thr
1               5                   10
```